(12) United States Patent
Hamp et al.

(10) Patent No.: US 11,538,555 B1
(45) Date of Patent: Dec. 27, 2022

(54) PROTEIN STRUCTURE-BASED PROTEIN LANGUAGE MODELS

(71) Applicants: Illumina, Inc., San Diego, CA (US); Illumina Cambridge Limited, Cambridge (GB)

(72) Inventors: Tobias Hamp, Cambridge (GB); Hong Gao, Palo Alto, CA (US); Kai-How Farh, San Mateo, CA (US)

(73) Assignees: Illumina, Inc., San Diego, CA (US); Illumina Cambridge Limited, Cambridge (GB)

( * ) Notice: Subject to any disclaimer, the term of this patent is extended or adjusted under 35 U.S.C. 154(b) by 0 days.

(21) Appl. No.: 17/533,091

(22) Filed: Nov. 22, 2021

Related U.S. Application Data

(60) Provisional application No. 63/281,592, filed on Nov. 19, 2021, provisional application No. 63/281,579, filed on Nov. 19, 2021, provisional application No. 63/253,122, filed on Oct. 6, 2021.

(51) Int. Cl.
| | | |
|---|---|---|
| *G16B 30/00* | (2019.01) | |
| *G16B 20/50* | (2019.01) | |
| *G16B 20/20* | (2019.01) | |
| *G16H 50/20* | (2018.01) | |

(52) U.S. Cl.
CPC ............ *G16B 30/00* (2019.02); *G16B 20/20* (2019.02); *G16B 20/50* (2019.02); *G16H 50/20* (2018.01)

(58) Field of Classification Search
None
See application file for complete search history.

(56) References Cited

U.S. PATENT DOCUMENTS

| | | |
|---|---|---|
| 2013/0110407 A1 | 5/2013 | Baccash et al. |
| 2015/0337388 A1 | 11/2015 | Garner, Jr. et al. |

FOREIGN PATENT DOCUMENTS

| | | |
|---|---|---|
| JP | 2015501974 A | 1/2015 |
| WO | 2015173222 A1 | 11/2015 |
| WO | 2016061396 A1 | 4/2016 |

OTHER PUBLICATIONS

JP 2019-547220—Office Action dated Nov. 15, 2021, 8 pages (IP-1530-JP).
Marquet et al., Embeddings from protein language models predict conservation and variant effects, Research Square, dated Jun. 3, 2021, 25 pages.
Sturmfels et al., Profile Prediction: An Alignment-Based Pre-Training Task for Protein Sequence Models, dated Dec. 1, 2020, 8 pages.
Meier et al., Language models enable zero-shot prediction of the effects of mutations on protein function, dated Jul. 10, 2021, 28 pages.
Nambiar et al., Transforming the Language of Life—Transformer Neural Networks For Protein Prediction Tasks, dated Jun. 16, 2020, 16 pages.
Asgari, Life Language Processing: Deep Learning-based Language-agnostic Processing of Proteomics, Genomics/Metagenomics, and Human Languages, UC Berkeley dated 2019, 256 pages.
Elnaggar et al., ProtTrans: Towards Cracking the Language of Life's Code Through Self-Supervised Learning, IEEE Pattern Analysis and Machine Intelligence, vol. 14, No. 8, dated Aug. 2021, 17 pages.
Pollaris, Protein Secondary Structure Prediction Using Transformer Networks, Faculty of Bioscience Engineering, Ghent University, dated 2019-2020, 94 pages.
Rives et al., Biological structure and function emerge from scaling unsupervised learning to 250 million protein sequences, PNAS, vol. 118, No. 15, dated Dec. 16, 2020, 12 pages.
Clauwaert et al., Explainability in transformer models for functional genomics, Briefings in Bioinformatics, vol. 22, No. 5, dated Jan. 28, 2021, 11 pages.
Eschauzier, ProdBERT: Shopping Basket Completion Using Bidirectional Encoder Representations from Transformers, Erasmus University Rotterdam, dated Jul. 2020, 22 pages.
Wu, Data-Driven Protein Engineering, California Institute of Technology, dated Jun. 25, 2020, 167 pages.
Bioinformatics Group—List of Thesis projects, dated Oct. 21, 2021, 45 pages.
Rao et al., Transformer Protein Language Models are Unsupervised Structure Learners, dated Dec. 15, 2020, 24 pages.
Ofer et al., The language of proteins: NLP, machine learning and protein sequences, Computational and Structural Biotechnology Journal, vol. 19, pp. 1750-1758, dated Mar. 19, 2021, 9 pages.
Gao et al., Deep Learning in Protein Structural Modeling and Design, Patterns, dated Dec. 11, 2020, 23 pages.
Jaganathan et al., Predicting Splicing from Primary Sequence with Deep Learning, Cell 176, dated Jan. 24, 2019, 40 pages.

(Continued)

*Primary Examiner* — John S Brusca
(74) *Attorney, Agent, or Firm* — Keller Preece PLLC

(57) ABSTRACT

The technology disclosed relates to determining pathogenicity of nucleotide variants. In particular, the technology disclosed relates to specifying a particular amino acid at a particular position in a protein as a gap amino acid, and specifying remaining amino acids at remaining positions in the protein as non-gap amino acids. The technology disclosed further relates to generating a gapped spatial representation of the protein that includes spatial configurations of the non-gap amino acids, and excludes a spatial configuration of the gap amino acid, and determining a pathogenicity of a nucleotide variant based at least in part on the gapped spatial representation, and a representation of an alternate amino acid created by the nucleotide variant at the particular position.

30 Claims, 70 Drawing Sheets

(56) References Cited

OTHER PUBLICATIONS

Sundaram et al., Predicting the clinical impact of human mutation with deep neural networks, Nature Genetics, vol. 50, dated Aug. 2018, 15 pages.

Torng, Wen, et al., "3D deep convolutional neural networks for amino acid environment similarity analysis", 2017, 23pages.

Figure 2

Atom Classification 300

| Reference Amino Acid Sequence 202 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | $N^{th}$ |
|---|---|---|---|---|---|---|---|---|---|---|---|---|---|---|---|---|---|---|---|---|---|---|---|---|---|---|---|---|---|
| | F | ⋮ | ⋮ | ⋮ | ⋮ | ⋮ | ⋮ | ⋮ | ⋮ | ⋮ | ⋮ | ⋮ | ⋮ | ⋮ | ⋮ | ⋮ | G | ⋮ | ⋮ | ⋮ | ⋮ | ⋮ | ⋮ | ⋮ | ⋮ | ⋮ | ⋮ | ⋮ | ⋮ |

204

| Amino Acids 302 | 308 $C_\alpha$ Atoms |
|---|---|
| 1. Alanine (A) | 11 |
| 2. Arginine (R) | 35 |
| 3. Asparagine (N) | 40 |
| 4. Aspartic acid (D) | 27 |
| 5. Cysteine (C) | 54 |
| 6. Glutamine (Q) | 25 |
| 7. Glutamic acid (E) | 14 |
| 8. Glycine (G) | 68 |
| 9. Histidine (H) | 90 |
| 10. Isolucine (I) | 25 |
| 11. Methionine (M) | 19 |
| 12. Leucine (L) | 56 |
| 13. Lysine (K) | 76 |
| 14. Phenylalanine (F) | 29 |
| 15. Proline (P) | 44 |
| 16. Serine (S) | 38 |
| 17. Threonine (T) | 56 |
| 18. Tryptophan (W) | 75 |
| 19. Tyrosine (Y) | 24 |
| 20. Valine (V) | 18 |
| 21. GAP (*) | 4 |
| Total | |

Figure 3

Atomic Coordinates Bucketing 400

| | | | | |
|---|---|---|---|---|
| 1. Alanine (A) | 2. Arginine (R) | 3. Asparagine (N) | 4. Aspartic acid (D) | 5. Cysteine (C) |
| $C_\alpha$ Atom Coordinates 402 | $C_\alpha$ Atom Coordinates 404 | $C_\alpha$ Atom Coordinates 406 | $C_\alpha$ Atom Coordinates 408 | $C_\alpha$ Atom Coordinates 410 |
| 1. x, y, z<br>2. x, y, z<br>⋮<br>11. x, y, z | 1. x, y, z<br>2. x, y, z<br>⋮<br>35. x, y, z | 1. x, y, z<br>2. x, y, z<br>⋮<br>40. x, y, z | 1. x, y, z<br>2. x, y, z<br>⋮<br>27. x, y, z | 1. x, y, z<br>2. x, y, z<br>⋮<br>54. x, y, z |
| 6. Glutamine (Q) | 7. Glutamic acid (E) | 8. Glycine (G) | 9. Histidine (H) | 10. Isoleucine (I) |
| $C_\alpha$ Atom Coordinates 412 | $C_\alpha$ Atom Coordinates 414 | $C_\alpha$ Atom Coordinates 416 | $C_\alpha$ Atom Coordinates 418 | $C_\alpha$ Atom Coordinates 420 |
| 1. x, y, z<br>2. x, y, z<br>⋮<br>25. x, y, z | 1. x, y, z<br>2. x, y, z<br>⋮<br>14. x, y, z | 1. x, y, z<br>2. x, y, z<br>⋮<br>68. x, y, z | 1. x, y, z<br>2. x, y, z<br>⋮<br>90. x, y, z | 1. x, y, z<br>2. x, y, z<br>⋮<br>25. x, y, z |
| 11. Methionine (M) | 12. Leucine (L) | 13. Lysine (K) | 14. Phenylalanine (F) | 15. Proline (P) |
| $C_\alpha$ Atom Coordinates 422 | $C_\alpha$ Atom Coordinates 424 | $C_\alpha$ Atom Coordinates 426 | $C_\alpha$ Atom Coordinates 428 | $C_\alpha$ Atom Coordinates 430 |
| 1. x, y, z<br>2. x, y, z<br>⋮<br>19. x, y, z | 1. x, y, z<br>2. x, y, z<br>⋮<br>56. x, y, z | 1. x, y, z<br>2. x, y, z<br>⋮<br>76. x, y, z | 1. x, y, z<br>2. x, y, z<br>⋮<br>29. x, y, z | 1. x, y, z<br>2. x, y, z<br>⋮<br>44. x, y, z |
| 16. Serine (S) | 17. Threonine (T) | 18. Tryptophan (W) | 19. Tyrosine (Y) | 20. Valine (V) |
| $C_\alpha$ Atom Coordinates 432 | $C_\alpha$ Atom Coordinates 434 | $C_\alpha$ Atom Coordinates 436 | $C_\alpha$ Atom Coordinates 438 | $C_\alpha$ Atom Coordinates 440 |
| 1. x, y, z<br>2. x, y, z<br>⋮<br>38. x, y, z | 1. x, y, z<br>2. x, y, z<br>⋮<br>56. x, y, z | 1. x, y, z<br>2. x, y, z<br>⋮<br>75. x, y, z | 1. x, y, z<br>2. x, y, z<br>⋮<br>24. x, y, z | 1. x, y, z<br>2. x, y, z<br>⋮<br>18. x, y, z |
| | | 21. GAP (*) | | |
| | | 1. x, y, z<br>2. x, y, z<br>⋮<br>4. x, y, z | | |

Figure 4

Amino Acid-Wise Distance Channels 600

| Voxels 514 | 1.A | 2.R | 3.N | 4.D | 5.C | 6.Q | 7.E | 8.G | 9.H | 10.I | 11.M | 12.L | 13.K | 14.F | 15.P | 16.S | 17.T | 18.W | 19.Y | 20.V | 21.* |
|---|---|---|---|---|---|---|---|---|---|---|---|---|---|---|---|---|---|---|---|---|---|
| (1, 1) | 1.55 | 0.34 | 3.49 | 0.71 | 2.8 | 4.9 | 0.25 | 0.15 | 0.59 | 1.8 | 2.5 | 3.2 | 4.7 | 0.61 | 2.72 | 5.4 | 1.5 | 2.4 | 0.36 | 2.9 | 4.2 |
| (1, 2) | 2.38 | 4.57 | 0.22 | 1.4 | 3.6 | 2.7 | 0.45 | 0.31 | 0.68 | 4.5 | 1.7 | 5.3 | 0.78 | 0.46 | 4.1 | 7.3 | 5.2 | 4.9 | 1.6 | 3.8 | 4.1 |
| (1, 3) | 5.16 | 1.77 | 0.38 | 0.84 | 1.22 | 2.3 | 0.56 | 0.28 | 0.41 | 3.7 | 1.85 | 4.52 | 0.92 | 3.12 | 1.98 | 5.21 | 3.53 | 1.34 | 0.47 | 5.9 | 3.3 |
| (2, 1) | 1.42 | 2.21 | 3.5 | 0.91 | 3.67 | 5.8 | 0.37 | 0.24 | 3.55 | 0.59 | 3.16 | 0.27 | 2.41 | 3.30 | 5.58 | 4.43 | 1.17 | 2.41 | 2.15 | 1.3 | 1.4 |
| (2, 2) | 4.27 | 0.36 | 1.38 | 4.54 | 3.15 | 4.92 | 1.25 | 2.33 | 0.60 | 1.82 | 2.66 | 3.25 | 2.72 | 5.99 | 4.21 | 1.26 | 1.35 | 3.15 | 3.36 | 2.7 | 1.1 |
| (2, 3) | 5.82 | 3.22 | 2.35 | 5.12 | 2.10 | 3.17 | 0.16 | 5.71 | 5.19 | 0.19 | 5.28 | 4.13 | 1.27 | 0.65 | 0.22 | 2.18 | 2.89 | 1.44 | 1.15 | 1.4 | 0.28 |
| (3, 1) | 2.19 | 4.34 | 1.19 | 3.15 | 1.56 | 2.16 | 1.25 | 3.25 | 4.22 | 1.86 | 5.52 | 3.14 | 0.42 | 4.29 | 1.34 | 3.36 | 3.81 | 0.44 | 0.28 | 4.9 | 1.22 |
| (3, 2) | 3.45 | 5.35 | 2.15 | 4.70 | 5.18 | 4.12 | 2.34 | 2.11 | 3.79 | 4.19 | 3.43 | 5.51 | 4.44 | 1.65 | 0.15 | 4.42 | 2.76 | 5.1 | 0.64 | 1.1 | 2.45 |
| (3, 3) | 1.35 | 2.98 | 1.17 | 0.70 | 3.2 | 3.16 | 3.27 | 5.65 | 1.16 | 5.25 | 2.75 | 2.12 | 1.24 | 0.27 | 1.72 | 5.41 | 1.53 | 1.16 | 0.71 | 0.77 | 3.90 |

Figure 6

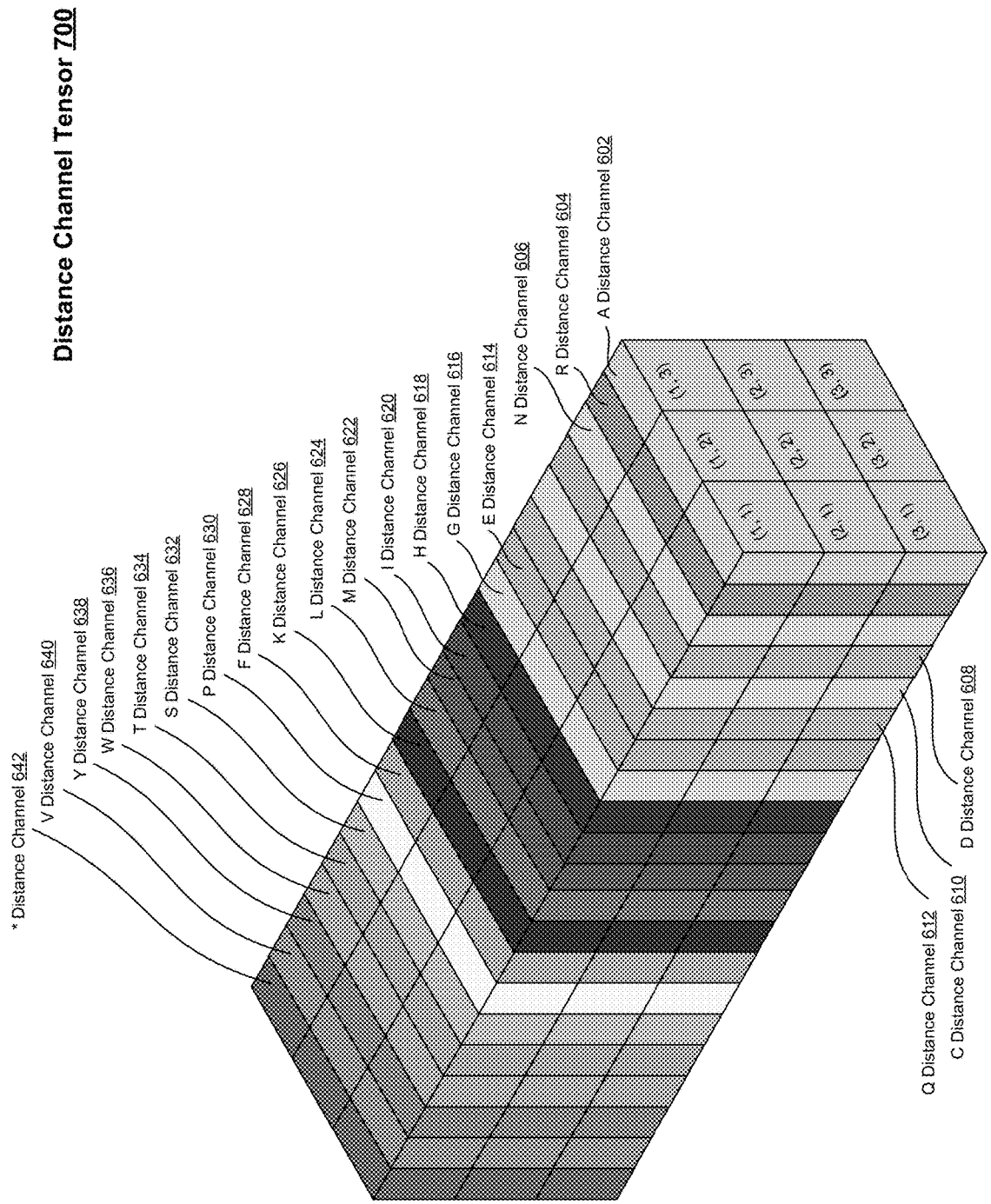

One-Hot Encodings 800

| Amino Acids 302 | One-Hot Encoded Variant-Experiencing Reference Amino Acid 802 | One-Hot Encoded Variant/Alternative Amino Acid 804 |
|---|---|---|
| | G | A |
| 1. Alanine (A) | 0 | 1 |
| 2. Arginine (R) | 0 | 0 |
| 3. Asparagine (N) | 0 | 0 |
| 4. Aspartic acid (D) | 0 | 0 |
| 5. Cysteine (C) | 0 | 0 |
| 6. Glutamine (Q) | 0 | 0 |
| 7. Glutamic acid (E) | 0 | 0 |
| 8. Glycine (G) | 1 | 0 |
| 9. Histidine (H) | 0 | 0 |
| 10. Isolucine (I) | 0 | 0 |
| 11. Methionine (M) | 0 | 0 |
| 12. Leucine (L) | 0 | 0 |
| 13. Lysine (K) | 0 | 0 |
| 14. Phenylalanine (F) | 0 | 0 |
| 15. Proline (P) | 0 | 0 |
| 16. Serine (S) | 0 | 0 |
| 17. Threonine (T) | 0 | 0 |
| 18. Tryptophan (W) | 0 | 0 |
| 19. Tyrosine (Y) | 0 | 0 |
| 20. Valine (V) | 0 | 0 |
| 21. GAP (*) | 0 | 0 |

Figure 8

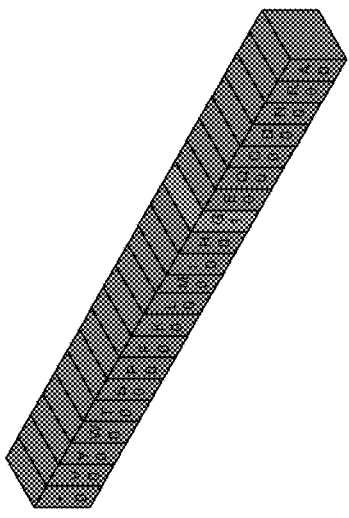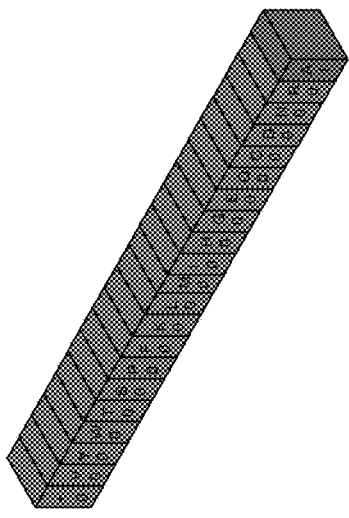
Voxelized One-Hot Encoded Variant-Experiencing Reference Amino Acid 902
Voxelized One-Hot Encoded Variant/Alternative Amino Acid 912
Figure 9

Voxels-to-Nearest Amino Acids Mapping 1300

| Voxels 514 | Nearest Atoms 1302 | Nearest Reference Amino Acids 1312 |
|---|---|---|
| (1, 1) | Carbon$_\alpha$ $^{15}$ | Aspartic acid (D) $^{15}$ |
| (1, 2) | Oxygen $^{27}$ | Arginine (R) $^{27}$ |
| (1, 3) | Hydrogen $^{14}$ | Isolucine (I) $^{14}$ |
| (2, 1) | Carbon$_\beta$ $^{45}$ | Threonine (T) $^{45}$ |
| (2, 2) | Oxygen $^{22}$ | Tyrosine (Y) $^{22}$ |
| (2, 3) | Nitrogen $^{63}$ | Glycine (G) $^{63}$ |
| (3, 1) | Carbon$_\alpha$ $^{38}$ | Tryptophan (W) $^{38}$ |
| (3, 2) | Carbon$_\beta$ $^{5}$ | Valine (V) $^{5}$ |
| (3, 3) | Carbon$_\alpha$ $^{23}$ | Proline (P) $^{23}$ |

Figure 13

Voxels-to-Evolutionary Profiles Mapping 1600

| Voxels 514 | Nearest Atoms 1302 | Corresponding Amino Acids 1312 | Per-Voxel Evolutionary Profiles 1602 |||||||||||||||||||
|---|---|---|---|---|---|---|---|---|---|---|---|---|---|---|---|---|---|---|---|---|
| | | | A | R | N | D | C | Q | E | G | H | I | L | M | K | F | P | S | T | W | Y | V | * |
| (1, 1) | Carbon$_\alpha^{15}$ | Aspartic acid (D)$^{15}$ | 1612 | | | | | | | | | | | | | | | | | | | | |
| (1, 2) | Oxygen$^{27}$ | Arginine (R)$^{27}$ | 1622 | | | | | | | | | | | | | | | | | | | | |
| (1, 3) | Hydrogen$^{14}$ | Isolucine (I)$^{14}$ | 1632 | | | | | | | | | | | | | | | | | | | | |
| (2, 1) | Carbon$_\beta^{45}$ | Threonine (T)$^{45}$ | 1642 | | | | | | | | | | | | | | | | | | | | |
| (2, 2) | Oxygen$^{22}$ | Tyrosine (Y)$^{22}$ | 1652 | | | | | | | | | | | | | | | | | | | | |
| (2, 3) | Nitrogen$^{63}$ | Glycine (G)$^{63}$ | 1662 | 0 | 0 | 0 | 0 | 0 | 0 | .77 | 0 | 0 | 0 | 0 | 0 | 0 | .23 | 0 | 0 | 0 | 0 | 0 | 0 |
| (3, 1) | Carbon$_\alpha^{38}$ | Tryptophan (W)$^{38}$ | 1672 | | | | | | | | | | | | | | | | | | | | |
| (3, 2) | Carbon$_\beta^{5}$ | Valine (V)$^{5}$ | 1682 | | | | | | | | | | | | | | | | | | | | |
| (3, 3) | Carbon$_\alpha^{23}$ | Proline (P)$^{23}$ | 1692 | 0 | 0 | 0 | 0 | 0 | 0 | 0 | 0 | 0 | 0 | .25 | 0 | 0 | .75 | 0 | 0 | 0 | 0 | 0 | 0 |

Figure 16

Evolutionary Profiles Tensor 1800

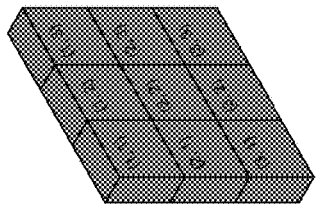
Annotation Channel 2006
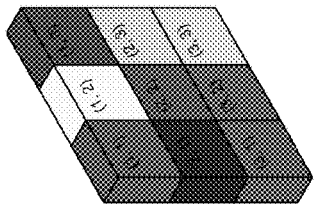
Annotation Channel 2016
Annotation Channel 2004
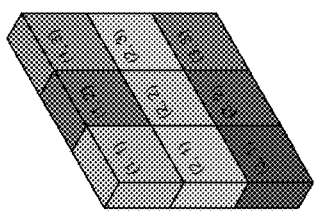
Annotation Channel 2014
Voxelized Annotation Channels 2000
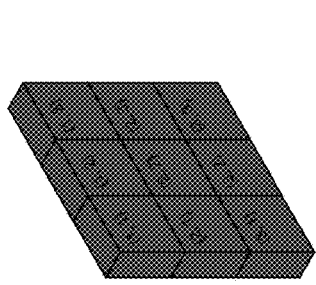
Annotation Channel 2002
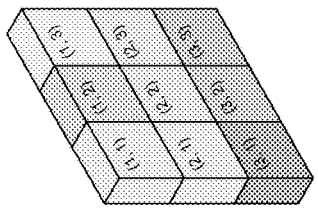
Annotation Channel 2012
Figure 20

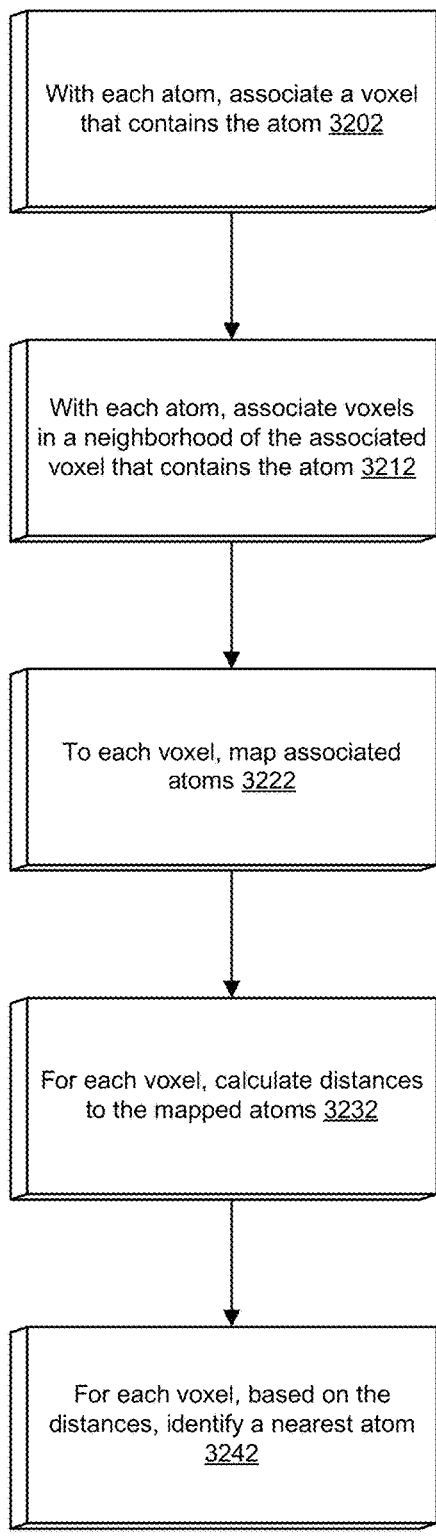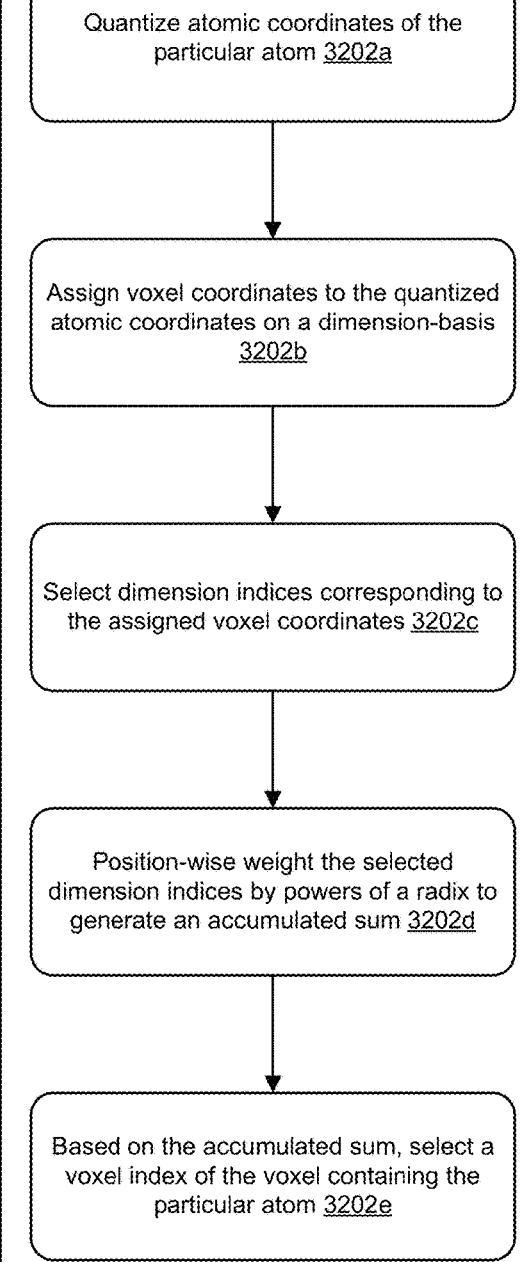
Figure 32A
Figure 32B

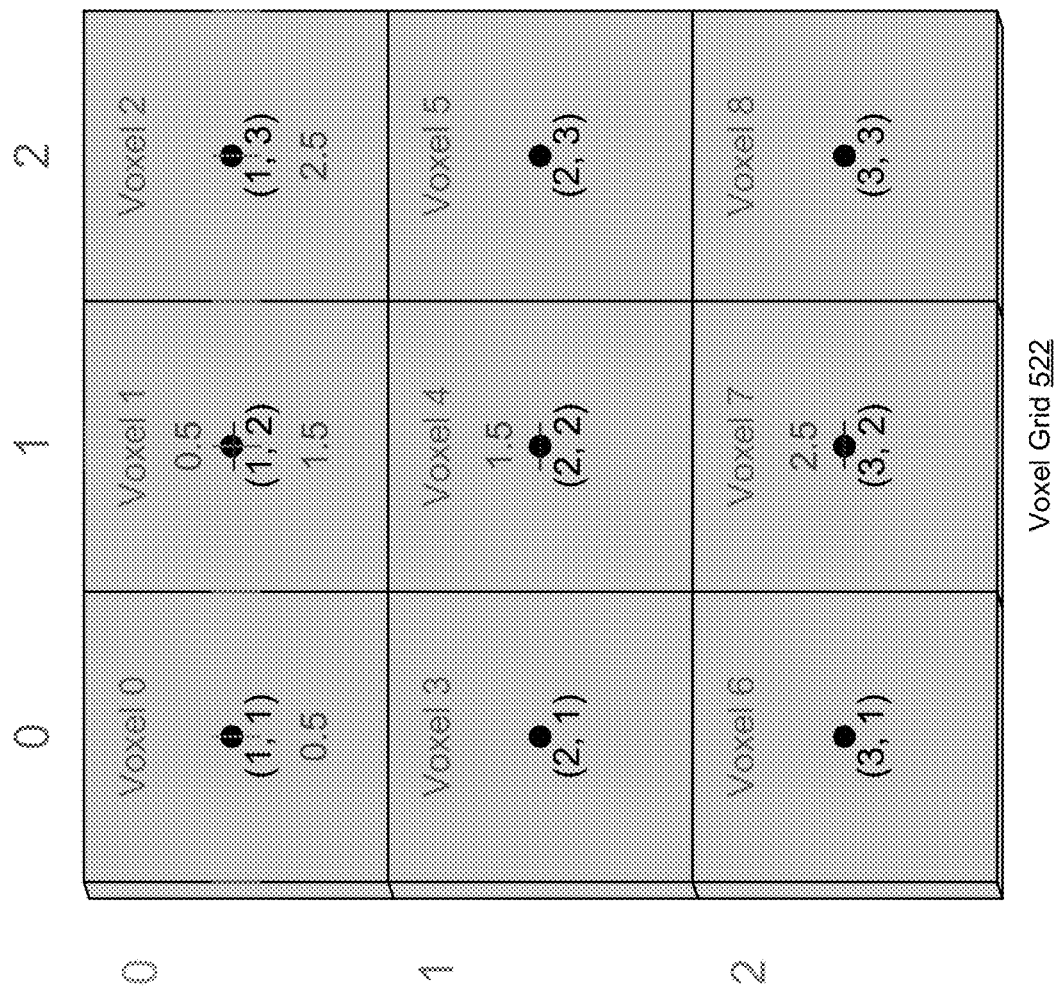
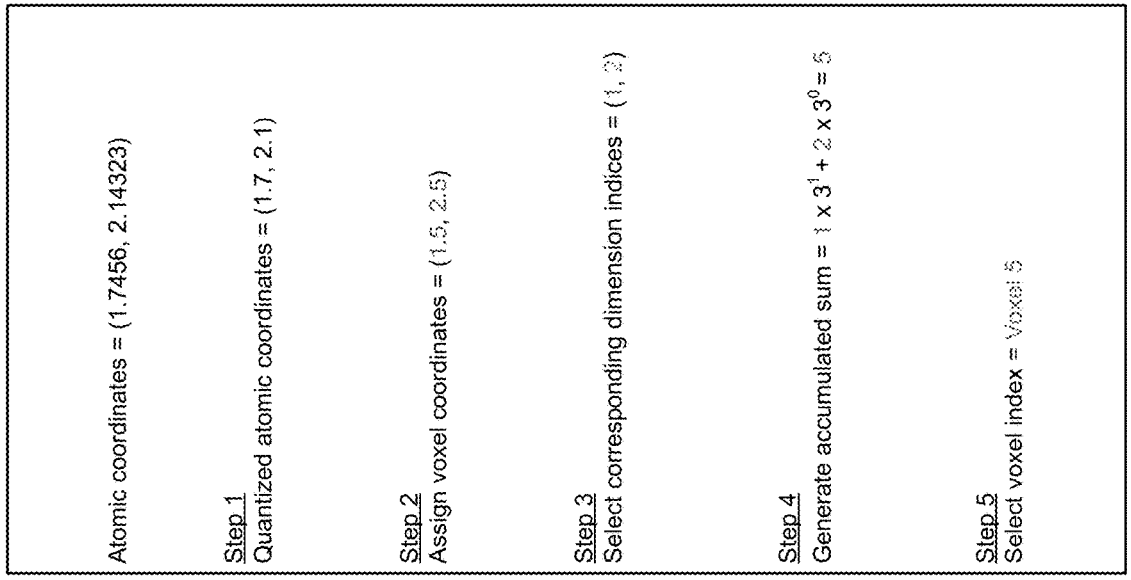
Atomic coordinates = (1.7456, 2.14323)
Step 1
Quantized atomic coordinates = (1.7, 2.1)
Step 2
Assign voxel coordinates = (1.5, 2.5)
Step 3
Select corresponding dimension indices = (1, 2)
Step 4
Generate accumulated sum = $1 \times 3^1 + 2 \times 3^0 = 5$
Step 5
Select voxel index = Voxel 5
Figure 33

| Atom-to-Voxels Mapping 3402 | |
|---|---|
| Atom | Voxels |
| Ca-1 | ... 3404 |
| Ca-2 | ... 3406 |
| ... | ... |
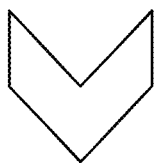
| Voxel-to-Atoms Mapping 3412 | |
|---|---|
| Voxel | Atoms |
| ... | Ca-1, Ca-2, ... 3414 |
| ... | Ca-3, ... 3416 |
| ... | ... |
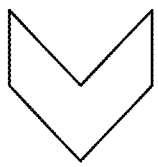
| Voxel-to-Nearest Atom Mapping 3422 | |
|---|---|
| Voxel | Atom |
| ... | Ca-2 3424 |
| ... | Ca-31 3426 |
| ... | ... |
Figure 34

Spatial Representation of Protein 3800

Gaped Spatial Representation of Protein 3900

Masked Amino Acid Classes 4700

Those unreachable alternate amino acid classes that are confined by reachability of single nucleotide polymorphisms (SNPs) to transform a reference codon of a reference amino acid into to alternate amino acids of the unreachable alternate amino acid classes are masked in ground truth labels
4702

The masked amino acid classes result in zero loss and do not contribute to gradient updates
4712

The masked amino acid classes are identified in a lookup table
4722

The lookup table identifies a set of masked amino acids classes for each reference amino acid position
4732

Figure 47

Final Pathogenicity Score Determination 4800

The pathogenicity predictor generates a first pathogenicity score for a first alternate amino acid that is same as a first reference amino acid
4802

↓

The pathogenicity predictor generates a second pathogenicity score for a second alternate amino acid that is different from the first reference amino acid
4812

↓

A final pathogenicity score for the second alternate amino acid is the second pathogenicity score
4822

Alt 1

The final pathogenicity score for the second alternate amino acid is a ratio of the second pathogenicity score over a sum of the first pathogenicity score and the second pathogenicity score
4822a

Alt 2

The final pathogenicity score for the second alternate amino acid is determined by subtracting the first pathogenicity score from the second pathogenicity score
4822b

Figure 48

Ground Truth Label Encoding 5802

| A | C | D | E | F | G | H |
|---|---|---|---|---|---|---|
| 0.1 | 0.03 | 0 | 0 | 0.8 | 0 | 0 |

Ground Truth Label Encoding 5812

| A | C | D | E | F | G | H |
|---|---|---|---|---|---|---|
| 0.1 | 0.03 | 0 | 0 | 0 | 0 | 0 |

Ground Truth Label Encoding 5822

| A | C | D | E | F | G | H |
|---|---|---|---|---|---|---|
| 1 | 1 | 0 | 0 | 1 | 0 | 0 |

Ground Truth Label Encoding 5832

| A | C | D | E | F | G | H |
|---|---|---|---|---|---|---|
| 1 | 1 | 0 | 0 | 0 | 0 | 0 |

Figure 58

Position-Specific Frequency Matrix (PSFM) 5900

| REF | Position 1 | Position 2 | Position 3 | ... | Position L |
|---|---|---|---|---|---|
| AA 1 | [[0.13357191 | 0.02123407 | 0.05054696 | ... | 0.07456496 0.00546158 0.02382472] |
| AA 2 | [0.14884646 | 0.01372283 | 0.04499814 | ... | 0.04899388 0.00437769 0.0178027 ] |
| AA 3 | [0.09806549 | 0.01243535 | 0.0437023 | ... | 0.05005365 0.00902787 0.0387827 ] |
| ... | | | | | |
| | [0.04893677 | 0.00704114 | 0.05692372 | ... | 0.03935399 0.01199536 0.03443038] |
| | [0.07351513 | 0.0088064 | 0.118982 64 | ... | 0.04019244 0.0038681 0.01772018] |
| AA 20 | [0.06564224 | 0.01080317 | 0.07469432 | ... | 0.04195507 0.00506814 0.02520286]] |

Figure 59

Position-Specific Scoring Matrix (PSSM) 6000

| REF | Position 1 | Position 2 | Position 3 | ••• | Position L |
|---|---|---|---|---|---|
| AA 1 | [[ 0.8016887 | 0.17052507 | -0.09523201 | ... | -1.1914673 |
|      | -0.72639656] | | | | |
| AA 2 | [ 0.95789695 | -0.45870304 | -0.26299095 | ... | -1.5106144 |
|      | -1.1467605 ] | | | | |
| AA 3 | [ 0.35588932 | -0.60140896 | -0.30514717 | ... | -0.4663992 |
|      | -0.02344275] | | | | |
| ••• | ...  | | | | |
|      | [-0.64693713 | -1.42197562 | 0.07617378 | ... | -0.05638027 |
|      | -0.19517422] | | | | |
|      | [-0.05981493 | -1.0992317 | 1.139823 | ... | -1.6891584 |
|      | -1.1534629 ] | | | | |
| AA 20 | [-0.22323179 | -0.80044019 | 0.46814227 | ... | -1.2993279 |
|       | -0.6452689 ]] | | | | |

Figure 60

PSSM 6300

Score(V→H | pos = 1) = -3
Score(V→H | pos = 8) = -4

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| 1 V | -1 | -2 | -3 | -4 | -1 | -2 | -3 | -3 | -3 | 2 | 1 | -2 | 4 | -1 | -3 | -2 | -1 | -3 | -1 | 4 |
| 2 L | -2 | -3 | -4 | -4 | -2 | -3 | -3 | -4 | -3 | 1 | 5 | -3 | 2 | 0 | -3 | -3 | -2 | -2 | -1 | 1 |
| 3 I | -2 | -3 | -4 | -4 | -2 | -3 | -4 | -4 | -4 | 5 | 2 | 3 | 4 | 2 | -3 | -3 | -1 | -3 | -2 | 2 |
| 4 K | -1 | 2 | 0 | -1 | -4 | 1 | 1 | -2 | -1 | -3 | -3 | Different Scores | -3 | -2 | -3 | 0 | -2 | -3 | -2 | -3 |
| 5 E | -1 | 0 | -1 | 1 | -4 | 2 | 6 | -3 | 0 | -3 | -3 | 0 | -3 | -3 | -2 | -4 | -2 | -3 | -2 | -3 |
| 6 F | -2 | -3 | -3 | -4 | -3 | -2 | -3 | -4 | 1 | -1 | -1 | 2 | 5 | 6 | 2 | -2 | -1 | 2 | 6 | -1 |
| 7 R | -2 | 6 | -1 | -2 | -4 | 1 | 0 | -3 | 1 | -3 | -3 | 2 | -2 | -3 | -3 | -1 | -1 | -3 | -2 | -3 |
| 8 V | -1 | -3 | -3 | -4 | -1 | -3 | -3 | -4 | -4 | 4 | 1 | -3 | 1 | -1 | -3 | -2 | -1 | -3 | -2 | -3 |
| 9 V | -1 | -3 | -3 | -3 | -2 | -2 | -2 | -3 | -3 | 2 | 0 | -2 | 0 | -2 | 5 | -2 | -1 | -4 | -2 | 3 |
| 10 L | -2 | -3 | -4 | -4 | -3 | -3 | -3 | -4 | -3 | 1 | 5 | -3 | 3 | 0 | -3 | -3 | -2 | -2 | -1 | 1 |
| 11 P | -1 | -3 | -2 | -2 | -3 | -2 | -1 | -3 | -3 | -3 | -3 | -1 | -3 | -4 | 8 | -1 | -1 | -4 | -3 | -3 |
| 12 C | -1 | -3 | -3 | -4 | 7 | -3 | -4 | -4 | -3 | -1 | -2 | -3 | 0 | -1 | -3 | -2 | -1 | -3 | -2 | 2 |

20 Amino Acid $L_j$

Figure 63

| | Jigsaw 6406 | PrimateAI-3D 6408 |
|---|---|---|
| Voxel input 6412 | Missing central residue 6416 | Full input 6418 |
| Labels 6422 | 1 label missing (out of 20) 6426 | 19 labels missing (out of 20) 6428 |
| #Samples 6432 | ~10M 6436 | ~1M 6438 |

Figure 64

Combined Learning 6500
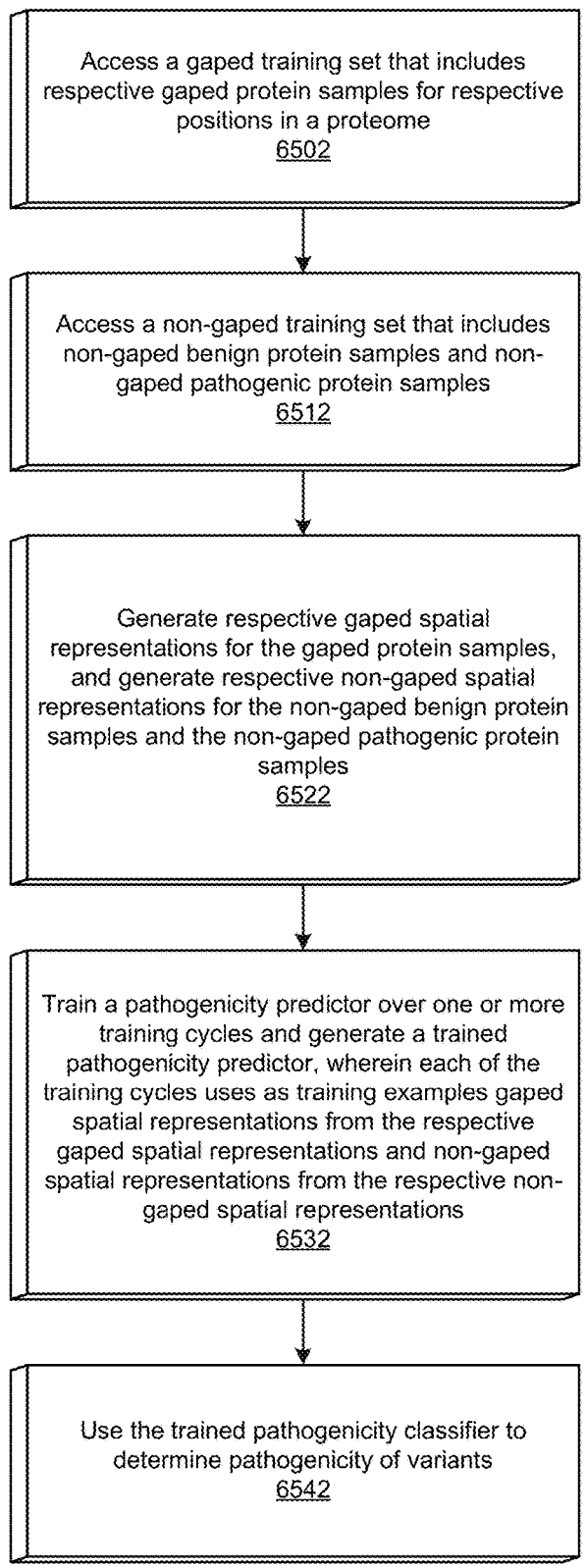
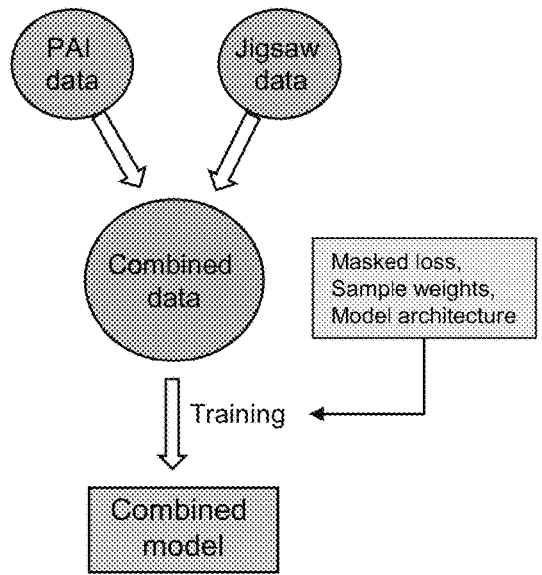
Figure 65B
Figure 65A

Transfer Learning 6600
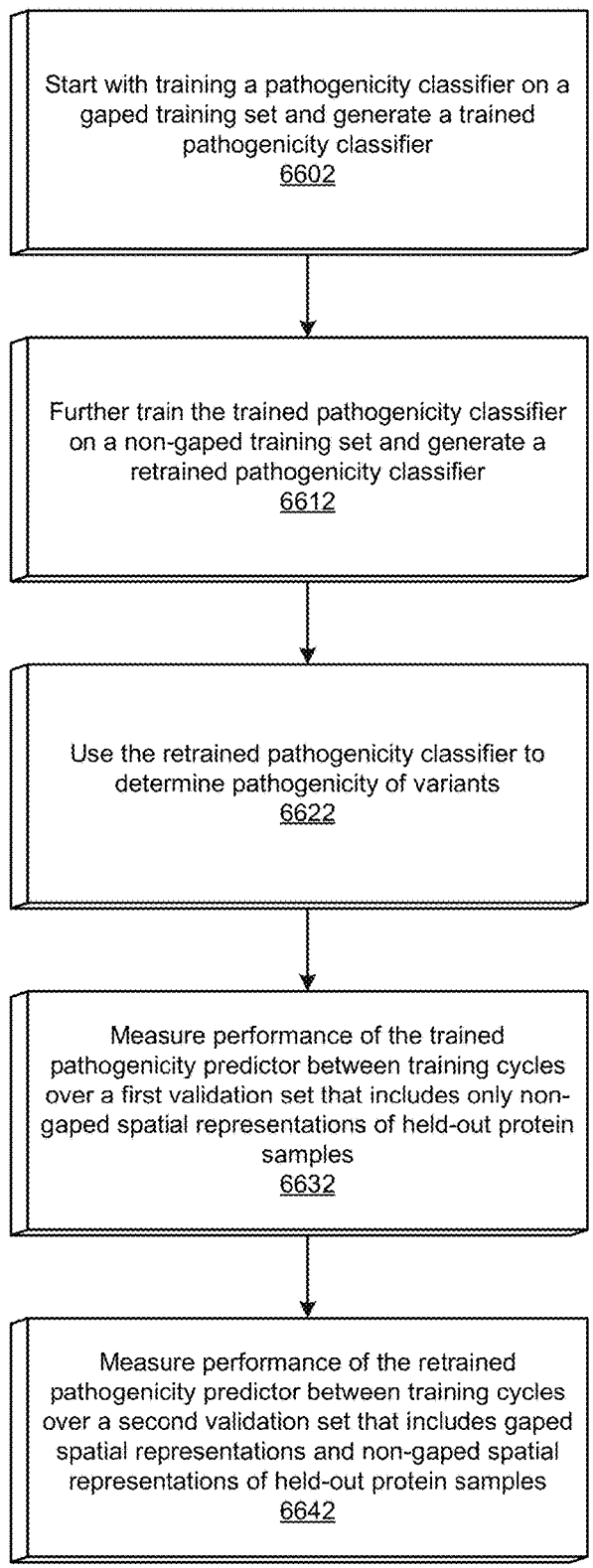
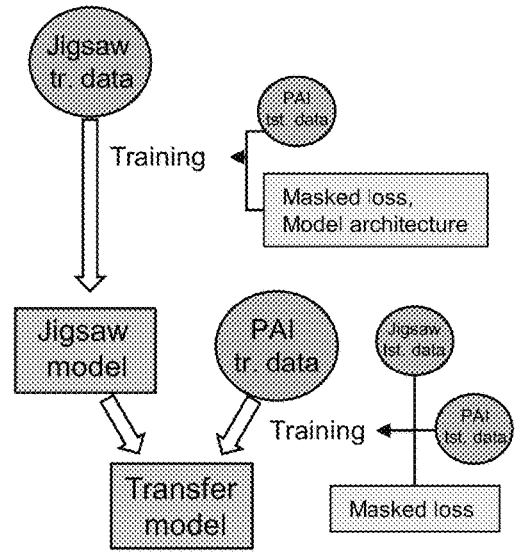
Figure 66B
Figure 66A

Pathogenicity Determination 6800

Access a spatial representation of a protein, wherein the spatial representation of the protein specifies respective spatial configurations of respective amino acids at respective positions in the protein
6802

Remove, from the spatial representation of the protein, a particular spatial configuration of a particular amino acid at a particular position, thereby generate a gapped spatial representation of the protein
6812

Determine a pathogenicity of a nucleotide variant based at least in part on the gapped spatial representation, and a representation of an alternate amino acid created by the nucleotide variant at the particular position
6822

Figure 68

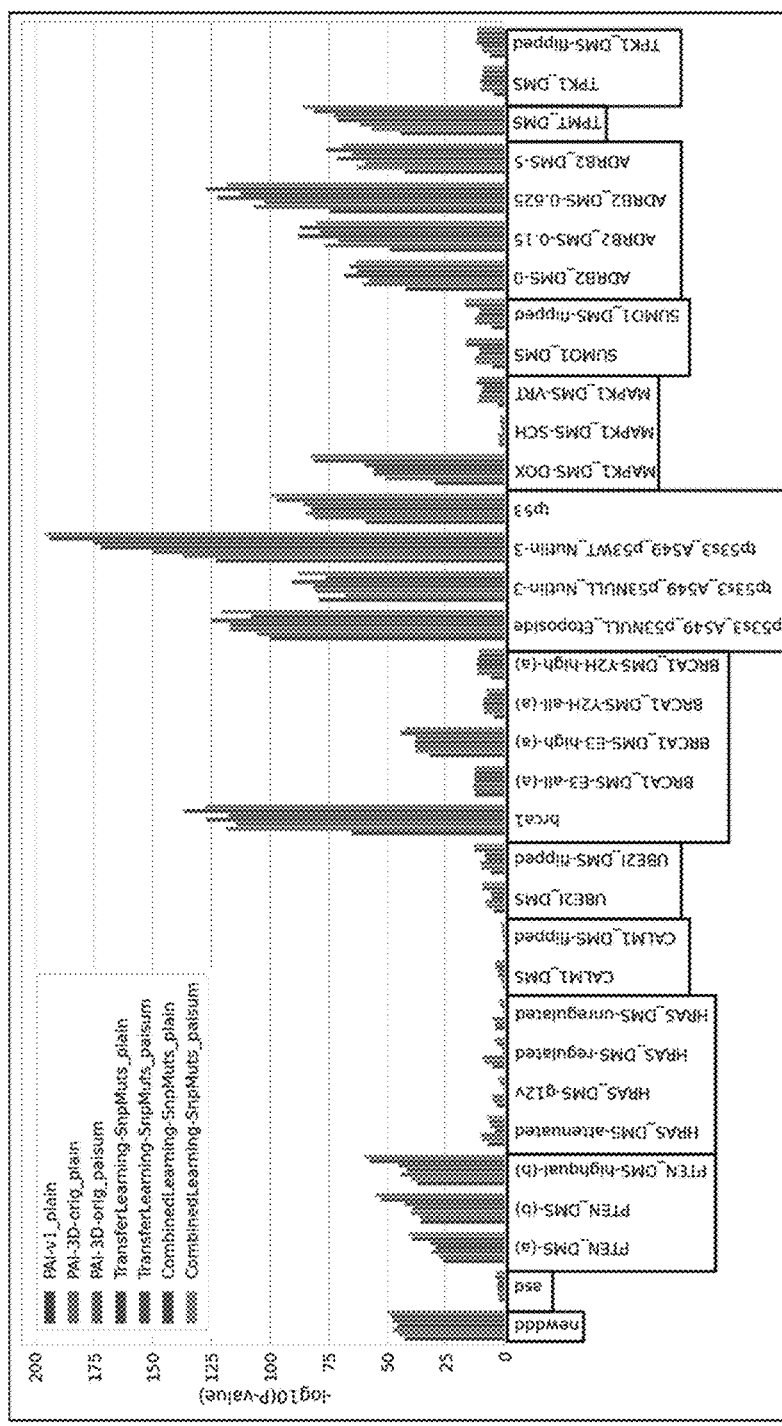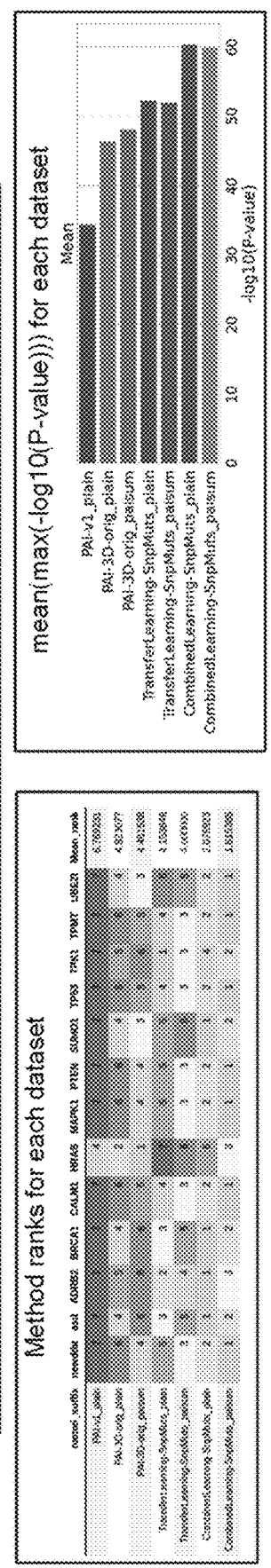
Figure 70

PROTEIN STRUCTURE-BASED PROTEIN LANGUAGE MODELS

PRIORITY APPLICATIONS

This application claims the benefit of U.S. Provisional Patent Application No. 63/253,122, titled "PROTEIN STRUCTURE-BASED PROTEIN LANGUAGE MODELS," filed Oct. 6, 2021. The priority provisional application is hereby incorporated by reference for all purposes.

This application claims the benefit of U.S. Provisional Patent Application No. 63/281,579, titled "PREDICTING VARIANT PATHOGENICITY FROM EVOLUTIONARY CONSERVATION USING THREE-DIMENSIONAL (3D) PROTEIN STRUCTURE VOXELS," filed Nov. 19, 2021. The priority provisional application is hereby incorporated by reference for all purposes.

This application claims the benefit of U.S. Provisional Patent Application No. 63/281,592, titled "COMBINED AND TRANSFER LEARNING OF A VARIANT PATHOGENICITY PREDICTOR USING GAPED AND NON-GAPED PROTEIN SAMPLES," filed Nov. 19, 2021. The priority provisional application is hereby incorporated by reference for all purposes.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep convolutional neural networks to analyze multi-channel voxelized data.

INCORPORATIONS

The following are incorporated by reference for all purposes as if fully set forth herein:

Sundaram, L et al. Predicting the clinical impact of human mutation with deep neural networks. Nat. Genet. 50, 1161-1170 (2018);

Jaganathan, K et al. Predicting splicing from primary sequence with deep learning. Cell 176, 535-548 (2019);

U.S. Patent Application No. 62/573,144, titled "TRAINING A DEEP PATHOGENICITY CLASSIFIER USING LARGE-SCALE BENIGN TRAINING DATA," filed Oct. 16, 2017;

U.S. Patent Application No. 62/573,149, titled "PATHOGENICITY CLASSIFIER BASED ON DEEP CONVOLUTIONAL NEURAL NETWORKS (CNNs)," filed Oct. 16, 2017;

U.S. Patent Application No. 62/573,153, titled "DEEP SEMI-SUPERVISED LEARNING THAT GENERATES LARGE-SCALE PATHOGENIC TRAINING DATA," filed Oct. 16, 2017;

U.S. Patent Application No. 62/582,898, titled "PATHOGENICITY CLASSIFICATION OF GENOMIC DATA USING DEEP CONVOLUTIONAL NEURAL NETWORKS (CNNs)," filed Nov. 7, 2017;

U.S. patent application Ser. No. 16/160,903, titled "DEEP LEARNING-BASED TECHNIQUES FOR TRAINING DEEP CONVOLUTIONAL NEURAL NETWORKS," filed on Oct. 15, 2018;

U.S. patent application Ser. No. 16/160,986, titled "DEEP CONVOLUTIONAL NEURAL NETWORKS FOR VARIANT CLASSIFICATION," filed on Oct. 15, 2018;

U.S. patent application Ser. No. 16/160,968, titled "SEMI-SUPERVISED LEARNING FOR TRAINING AN ENSEMBLE OF DEEP CONVOLUTIONAL NEURAL NETWORKS," filed on Oct. 15, 2018;

U.S. patent application Ser. No. 16/407,149, titled "DEEP LEARNING-BASED TECHNIQUES FOR PRE-TRAINING DEEP CONVOLUTIONAL NEURAL NETWORKS," filed May 8, 2019;

U.S. patent application Ser. No. 17/232,056, titled "DEEP CONVOLUTIONAL NEURAL NETWORKS TO PREDICT VARIANT PATHOGENICITY USING THREE-DIMENSIONAL (3D) PROTEIN STRUCTURES," filed on Apr. 15, 2021;

U.S. Patent Application No. 63/175,495, titled "MULTI-CHANNEL PROTEIN VOXELIZATION TO PREDICT VARIANT PATHOGENICITY USING DEEP CONVOLUTIONAL NEURAL NETWORKS," filed on Apr. 15, 2021;

U.S. Patent Application No. 63/175,767, titled "EFFICIENT VOXELIZATION FOR DEEP LEARNING," filed on Apr. 16, 2021; and U.S. patent application Ser. No. 17/468,411, titled "ARTIFICIAL INTELLIGENCE-BASED ANALYSIS OF PROTEIN THREE-DIMENSIONAL (3D) STRUCTURES," filed on Sep. 7, 2021.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Genomics, in the broad sense, also referred to as functional genomics, aims to characterize the function of every genomic element of an organism by using genome-scale assays such as genome sequencing, transcriptome profiling and proteomics. Genomics arose as a data-driven science— it operates by discovering novel properties from explorations of genome-scale data rather than by testing preconceived models and hypotheses. Applications of genomics include finding associations between genotype and phenotype, discovering biomarkers for patient stratification, predicting the function of genes, and charting biochemically active genomic regions such as transcriptional enhancers.

Genomics data are too large and too complex to be mined solely by visual investigation of pairwise correlations. Instead, analytical tools are required to support the discovery of unanticipated relationships, to derive novel hypotheses and models and to make predictions. Unlike some algorithms, in which assumptions and domain expertise are hard coded, machine learning algorithms are designed to automatically detect patterns in data. Hence, machine learning algorithms are suited to data-driven sciences and, in particular, to genomics. However, the performance of machine learning algorithms can strongly depend on how the data are represented, that is, on how each variable (also called a feature) is computed. For instance, to classify a tumor as malign or benign from a fluorescent microscopy image, a preprocessing algorithm could detect cells, identify the cell type, and generate a list of cell counts for each cell type.

A machine learning model can take the estimated cell counts, which are examples of handcrafted features, as input features to classify the tumor. A central issue is that classification performance depends heavily on the quality and the relevance of these features. For example, relevant visual features such as cell morphology, distances between cells or localization within an organ are not captured in cell counts, and this incomplete representation of the data may reduce classification accuracy.

Deep learning, a subdiscipline of machine learning, addresses this issue by embedding the computation of features into the machine learning model itself to yield end-to-end models. This outcome has been realized through the development of deep neural networks, machine learning models that comprise successive elementary operations, which compute increasingly more complex features by taking the results of preceding operations as input. Deep neural networks are able to improve prediction accuracy by discovering relevant features of high complexity, such as the cell morphology and spatial organization of cells in the above example. The construction and training of deep neural networks have been enabled by the explosion of data, algorithmic advances, and substantial increases in computational capacity, particularly through the use of graphical processing units (GPUs).

The goal of supervised learning is to obtain a model that takes features as input and returns a prediction for a so-called target variable. An example of a supervised learning problem is one that predicts whether an intron is spliced out or not (the target) given features on the RNA such as the presence or absence of the canonical splice site sequence, the location of the splicing branchpoint or intron length. Training a machine learning model refers to learning its parameters, which commonly involves minimizing a loss function on training data with the aim of making accurate predictions on unseen data.

For many supervised learning problems in computational biology, the input data can be represented as a table with multiple columns, or features, each of which contains numerical or categorical data that are potentially useful for making predictions. Some input data are naturally represented as features in a table (such as temperature or time), whereas other input data need to be first transformed (such as deoxyribonucleic acid (DNA) sequence into k-mer counts) using a process called feature extraction to fit a tabular representation. For the intron-splicing prediction problem, the presence or absence of the canonical splice site sequence, the location of the splicing branchpoint and the intron length can be preprocessed features collected in a tabular format. Tabular data are standard for a wide range of supervised machine learning models, ranging from simple linear models, such as logistic regression, to more flexible nonlinear models, such as neural networks and many others.

Logistic regression is a binary classifier, that is, a supervised learning model that predicts a binary target variable. Specifically, logistic regression predicts the probability of the positive class by computing a weighted sum of the input features mapped to the [0,1] interval using the sigmoid function, a type of activation function. The parameters of logistic regression, or other linear classifiers that use different activation functions, are the weights in the weighted sum. Linear classifiers fail when the classes, for instance, that of an intron spliced out or not, cannot be well discriminated with a weighted sum of input features. To improve predictive performance, new input features can be manually added by transforming or combining existing features in new ways, for example, by taking powers or pairwise products.

Neural networks use hidden layers to learn these nonlinear feature transformations automatically. Each hidden layer can be thought of as multiple linear models with their output transformed by a nonlinear activation function, such as the sigmoid function or the more popular rectified-linear unit (ReLU). Together, these layers compose the input features into relevant complex patterns, which facilitates the task of distinguishing two classes.

Deep neural networks use many hidden layers, and a layer is said to be fully-connected when each neuron receives inputs from all neurons of the preceding layer. Neural networks are commonly trained using stochastic gradient descent, an algorithm suited to training models on very large data sets. Implementation of neural networks using modern deep learning frameworks enables rapid prototyping with different architectures and data sets. Fully-connected neural networks can be used for a number of genomics applications, which include predicting the percentage of exons spliced in for a given sequence from sequence features such as the presence of binding motifs of splice factors or sequence conservation; prioritizing potential disease-causing genetic variants; and predicting cis-regulatory elements in a given genomic region using features such as chromatin marks, gene expression and evolutionary conservation.

Local dependencies in spatial and longitudinal data must be considered for effective predictions. For example, shuffling a DNA sequence or the pixels of an image severely disrupts informative patterns. These local dependencies set spatial or longitudinal data apart from tabular data, for which the ordering of the features is arbitrary. Consider the problem of classifying genomic regions as bound versus unbound by a particular transcription factor, in which bound regions are defined as high-confidence binding events in chromatin immunoprecipitation following by sequencing (ChIP-seq) data. Transcription factors bind to DNA by recognizing sequence motifs. A fully-connected layer based on sequence-derived features, such as the number of k-mer instances or the position weight matrix (PWM) matches in the sequence, can be used for this task. As k-mer or PWM instance frequencies are robust to shifting motifs within the sequence, such models could generalize well to sequences with the same motifs located at different positions. However, they would fail to recognize patterns in which transcription factor binding depends on a combination of multiple motifs with well-defined spacing. Furthermore, the number of possible k-mers increases exponentially with k-mer length, which poses both storage and overfitting challenges.

A convolutional layer is a special form of fully-connected layer in which the same fully-connected layer is applied locally, for example, in a 6 bp window, to all sequence positions. This approach can also be viewed as scanning the sequence using multiple PWMs, for example, for transcription factors GATA1 and TAL1. By using the same model parameters across positions, the total number of parameters is drastically reduced, and the network is able to detect a motif at positions not seen during training. Each convolutional layer scans the sequence with several filters by producing a scalar value at every position, which quantifies the match between the filter and the sequence. As in fully-connected neural networks, a nonlinear activation function (commonly ReLU) is applied at each layer. Next, a pooling operation is applied, which aggregates the activations in contiguous bins across the positional axis, commonly taking the maximal or average activation for each channel. Pooling reduces the effective sequence length and coarsens the signal. The subsequent convolutional layer composes the output of the previous layer and is able to detect whether a GATA1 motif and TAL1 motif were present at some distance range. Finally, the output of the convolutional layers can be used as input to a fully-connected neural network to perform the final prediction task. Hence, different types of neural network layers (e.g., fully-connected layers and convolutional layers) can be combined within a single neural network.

Convolutional neural networks (CNNs) can predict various molecular phenotypes on the basis of DNA sequence alone. Applications include classifying transcription factor binding sites and predicting molecular phenotypes such as chromatin features, DNA contact maps, DNA methylation, gene expression, translation efficiency, RBP binding, and microRNA (miRNA) targets. In addition to predicting molecular phenotypes from the sequence, convolutional neural networks can be applied to more technical tasks traditionally addressed by handcrafted bioinformatics pipelines. For example, convolutional neural networks can predict the specificity of guide RNA, denoise ChIP-seq, enhance Hi-C data resolution, predict the laboratory of origin from DNA sequences and call genetic variants. Convolutional neural networks have also been employed to model long-range dependencies in the genome. Although interacting regulatory elements may be distantly located on the unfolded linear DNA sequence, these elements are often proximal in the actual 3D chromatin conformation. Hence, modelling molecular phenotypes from the linear DNA sequence, albeit a crude approximation of the chromatin, can be improved by allowing for long-range dependencies and allowing the model to implicitly learn aspects of the 3D organization, such as promoter-enhancer looping. This is achieved by using dilated convolutions, which have a receptive field of up to 32 kb. Dilated convolutions also allow splice sites to be predicted from sequence using a receptive field of 10 kb, thereby enabling the integration of genetic sequence across distances as long as typical human introns (See Jaganathan, K. et al. Predicting splicing from primary sequence with deep learning. Cell 176, 535-548 (2019)).

Different types of neural network can be characterized by their parameter-sharing schemes. For example, fully-connected layers have no parameter sharing, whereas convolutional layers impose translational invariance by applying the same filters at every position of their input. Recurrent neural networks (RNNs) are an alternative to convolutional neural networks for processing sequential data, such as DNA sequences or time series, that implement a different parameter-sharing scheme. Recurrent neural networks apply the same operation to each sequence element. The operation takes as input the memory of the previous sequence element and the new input. It updates the memory and optionally emits an output, which is either passed on to subsequent layers or is directly used as model predictions. By applying the same model at each sequence element, recurrent neural networks are invariant to the position index in the processed sequence. For example, a recurrent neural network can detect an open reading frame in a DNA sequence regardless of the position in the sequence. This task requires the recognition of a certain series of inputs, such as the start codon followed by an in-frame stop codon.

The main advantage of recurrent neural networks over convolutional neural networks is that they are, in theory, able to carry over information through infinitely long sequences via memory. Furthermore, recurrent neural networks can naturally process sequences of widely varying length, such as mRNA sequences. However, convolutional neural networks combined with various tricks (such as dilated convolutions) can reach comparable or even better performances than recurrent neural networks on sequence-modelling tasks, such as audio synthesis and machine translation. Recurrent neural networks can aggregate the outputs of convolutional neural networks for predicting single-cell DNA methylation states, RBP binding, transcription factor binding, and DNA accessibility. Moreover, because recurrent neural networks apply a sequential operation, they cannot be easily parallelized and are hence much slower to compute than convolutional neural networks.

Each human has a unique genetic code, though a large portion of the human genetic code is common for all humans. In some cases, a human genetic code may include an outlier, called a genetic variant, that may be common among individuals of a relatively small group of the human population. For example, a particular human protein may comprise a specific sequence of amino acids, whereas a variant of that protein may differ by one amino acid in the otherwise same specific sequence.

Genetic variants may be pathogenetic, leading to diseases. Though most of such genetic variants have been depleted from genomes by natural selection, an ability to identify which genetic variants are likely to be pathogenic can help researchers focus on these genetic variants to gain an understanding of the corresponding diseases and their diagnostics, treatments, or cures. The clinical interpretation of millions of human genetic variants remains unclear. Some of the most frequent pathogenic variants are single nucleotide missense mutations that change the amino acid of a protein. However, not all missense mutations are pathogenic.

Models that can predict molecular phenotypes directly from biological sequences can be used as in silico perturbation tools to probe the associations between genetic variation and phenotypic variation and have emerged as new methods for quantitative trait loci identification and variant prioritization. These approaches are of major importance given that the majority of variants identified by genome-wide association studies of complex phenotypes are non-coding, which makes it challenging to estimate their effects and contribution to phenotypes. Moreover, linkage disequilibrium results in blocks of variants being co-inherited, which creates difficulties in pinpointing individual causal variants. Thus, sequence-based deep learning models that can be used as interrogation tools for assessing the impact of such variants offer a promising approach to find potential drivers of complex phenotypes. One example includes predicting the effect of non-coding single-nucleotide variants and short insertions or deletions (indels) indirectly from the difference between two variants in terms of transcription factor binding, chromatin accessibility or gene expression predictions. Another example includes predicting novel splice site creation from sequence or quantitative effects of genetic variants on splicing.

End-to-end deep learning approaches for variant effect predictions are applied to predict the pathogenicity of missense variants from protein sequence and sequence conservation data (See Sundaram, L et al. Predicting the clinical impact of human mutation with deep neural networks. *Nat. Genet.* 50, 1161-1170 (2018), referred to herein as "PrimateAI"). PrimateAI uses deep neural networks trained on variants of known pathogenicity with data augmentation using cross-species information. In particular, PrimateAI uses sequences of wild-type and mutant proteins to compare the difference and decide the pathogenicity of mutations using the trained deep neural networks. Such an approach which utilizes the protein sequences for pathogenicity prediction is promising because it can avoid the circularity problem and overfitting to previous knowledge. However, compared to the adequate number of data to train the deep neural networks effectively, the number of clinical data available in ClinVar is relatively small. To overcome this data scarcity, PrimateAI uses common human variants and variants from primates as benign data while simulated variants based on trinucleotide context were used as unlabeled data.

PrimateAI outperforms prior methods when trained directly upon sequence alignments. PrimateAI learns important protein domains, conserved amino acid positions, and sequence dependencies directly from the training data consisting of about 120,000 human samples. PrimateAI substantially exceeds the performance of other variant pathogenicity prediction tools in differentiating benign and pathogenic de-novo mutations in candidate developmental disorder genes, and in reproducing prior knowledge in ClinVar. These results suggest that PrimateAI is an important step forward for variant classification tools that may lessen the reliance of clinical reporting on prior knowledge.

Central to protein biology is the understanding of how structural elements give rise to observed function. The surfeit of protein structural data enables development of computational methods to systematically derive rules governing structural-functional relationships. However, performance of these methods depends critically on the choice of protein structural representation.

Protein sites are microenvironments within a protein structure, distinguished by their structural or functional role. A site can be defined by a three-dimensional (3D) location and a local neighborhood around this location in which the structure or function exists. Central to rational protein engineering is the understanding of how the structural arrangement of amino acids creates functional characteristics within protein sites. Determination of the structural and functional roles of individual amino acids within a protein provides information to help engineer and alter protein functions. Identifying functionally or structurally important amino acids allows focused engineering efforts such as site-directed mutagenesis for altering targeted protein functional properties. Alternatively, this knowledge can help avoid engineering designs that would abolish a desired function.

Since it has been established that structure is far more conserved than sequence, the increase in protein structural data provides an opportunity to systematically study the underlying pattern governing the structural-functional relationships using data-driven approaches. A fundamental aspect of any computational protein analysis is how protein structural information is represented. The performance of machine learning methods often depends more on the choice of data representation than the machine learning algorithm employed. Good representations efficiently capture the most critical information while poor representations create a noisy distribution with no underlying patterns.

The surfeit of protein structures and the recent success of deep learning algorithms provide an opportunity to develop tools for automatically extracting task specific representations of protein structures. Therefore, an opportunity arises to predict variant pathogenicity using multi-channel voxelized representations of 3D protein structures as input to deep neural networks.

BRIEF DESCRIPTION OF THE DRAWINGS

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which.

FIG. 2 schematically illustrates an example reference amino acid sequence of a protein and an alternative amino acid sequence of the protein, in accordance with one implementation of the technology disclosed.

FIG. 3 illustrates amino acid-wise classification of atoms of amino acids in the reference amino acid sequence of FIG. 2, in accordance with one implementation of the technology disclosed.

FIG. 4 illustrates amino acid-wise attribution of 3D atomic coordinates of the alpha-carbon atoms classified in FIG. 3 on an amino acid-basis, in accordance with one implementation of the technology disclosed.

FIG. 6 shows an example of twenty-one amino acid-wise distance channels, in accordance with one implementation of the technology disclosed.

FIG. 7 is a schematic diagram of a distance channel tensor, in accordance with one implementation of the technology disclosed.

FIG. 8 shows one-hot encodings of the reference amino acid and the alternative amino acid from FIG. 2, in accordance with one implementation of the technology disclosed.

FIG. 9 is a schematic diagram of a voxelized one-hot encoded reference amino acid and a voxelized one-hot encoded variant/alternative amino acid, in accordance with one implementation of the technology disclosed.

FIG. 13 illustrates voxels-to-nearest amino acids, in accordance with one implementation of the technology disclosed.

FIG. 16 shows respective pan-amino acid conservation frequencies determined for respective voxels using the position frequency logic described in FIG. 15, in accordance with one implementation of the technology disclosed.

FIG. 20 shows various examples of voxelized annotation channels that are concatenated with the distance channel tensor, in accordance with one implementation of the technology disclosed.

FIGS. 32A and 32B show the disclosed efficient voxelization process, in accordance with various implementations of the technology disclosed.

FIG. 33 depicts how atoms are associated with voxels that contain the atoms, in accordance with one implementation of the technology disclosed.

FIG. 34 shows generating voxel-to-atoms mapping from atom-to-voxels mapping to identify nearest atoms on a voxel-by-voxel basis, in accordance with one implementation of the technology disclosed.

FIG. 47 shows how certain unreachable amino acid classes are masked during training.

FIG. 48 illustrates one implementation of determining a final pathogenicity score.

FIG. 58 depicts different implementations of ground truth label encodings used to train the evolutionary conservation determiner.

FIG. 59 illustrates an example position-specific frequency matrix (PSFM).

FIG. 60 depicts an example position-specific scoring matrix (PSSM).

FIG. 63 depicts an example PSSM encoding.

FIG. 64 illustrates two datasets on which the models disclosed herein can be trained.

FIGS. 65A-65B illustrate one implementation of combined learning of the models disclosed herein.

FIGS. 66A-66B illustrate one implementation of using transfer learning to train the models disclosed herein using the two datasets shown in FIG. 64.

FIG. 68 illustrates one implementation of a method of determining pathogenicity of nucleotide variants.

FIG. 70 depicts performance results that demonstrate objective indicia of non-obviousness and inventiveness.

DETAILED DESCRIPTION

Figure 1:
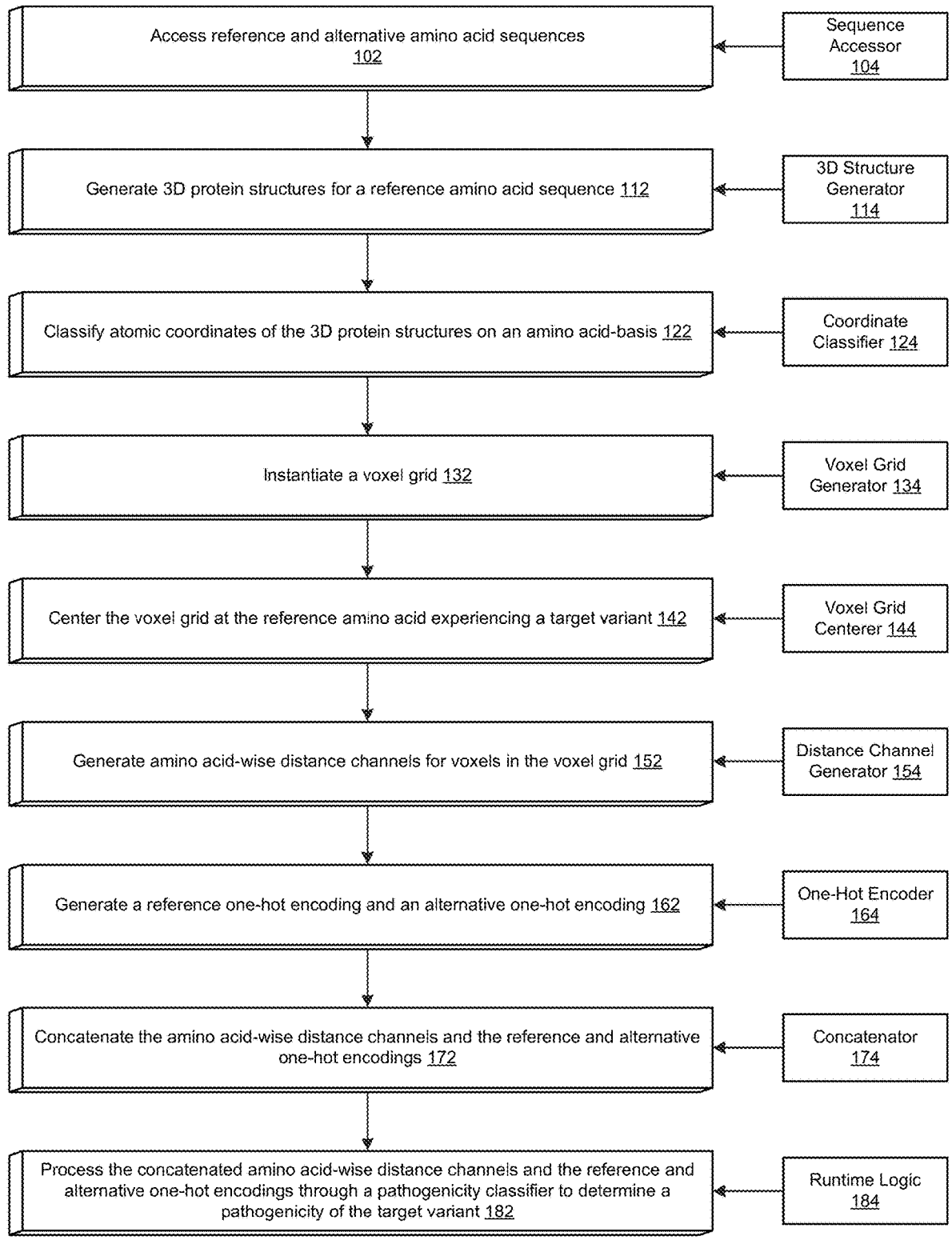
FIG. 1 is a flow diagram that illustrates a process of a system for determining pathogenicity of variants, according to various implementations of the technology disclosed.

The following discussion is presented to enable any person skilled in the art to make and use the technology disclosed and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown but is to be accorded the widest scope consistent with the principles and features disclosed herein.

The detailed description of various implementations will be better understood when read in conjunction with the appended drawings. To the extent that the figures illustrate diagrams of the functional blocks of the various implementations, the functional blocks are not necessarily indicative of the division between hardware circuitry. Thus, for example, one or more of the functional blocks (e.g., modules, processors, or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various implementations are not limited to the arrangements and instrumentality shown in the drawings.

The processing engines and databases of the figures, designated as modules, can be implemented in hardware or software, and need not be divided up in precisely the same blocks as shown in the figures. Some of the modules can also be implemented on different processors, computers, or servers, or spread among a number of different processors, computers, or servers. In addition, it will be appreciated that some of the modules can be combined, operated in parallel or in a different sequence than that shown in the figures without affecting the functions achieved. The modules in the figures can also be thought of as flowchart steps in a method. A module also need not necessarily have all its code disposed contiguously in memory; some parts of the code can be separated from other parts of the code with code from other modules or other functions disposed in between.

Protein Structure-Based Pathogenicity Determination

FIG. 1 is a flow diagram that illustrates a process 100 of a system for determining pathogenicity of variants. At step 102, a sequence accessor 104 of the system accesses reference and alternative amino acid sequences. At 112, a 3D structure generator 114 of the system generates 3D protein structures for a reference amino acid sequence. In some implementations, the 3D protein structures are homology models of human proteins. In one implementation, a so-called SwissModel homology modelling pipeline provides a public repository of predicted human protein structures. In another implementation, a so-called HHpred homology modelling uses a tool called Modeller to predict the structure of a target protein from template structures.

Proteins are represented by a collection of atoms and their coordinates in 3D space. An amino acid can have a variety of atoms, such as carbon atoms, oxygen (O) atoms, nitrogen (N) atoms, and hydrogen (H) atoms. The atoms can be further classified as side chain atoms and backbone atoms. The backbone carbon atoms can include alpha-carbon ($C_\alpha$) atoms and beta-carbon ($C_\beta$) atoms.

At step 122, a coordinate classifier 124 of the system classifies 3D atomic coordinates of the 3D protein structures on an amino acid-basis. In one implementation, the amino acid-wise classification involves attributing the 3D atomic coordinates to the twenty-one amino acid categories (including stop or gap amino acid category). In one example, an amino acid-wise classification of alpha-carbon atoms can respectively list alpha-carbon atoms under each of the twenty-one amino acid categories. In another example, an amino acid-wise classification of beta-carbon atoms can respectively list beta-carbon atoms under each of the twenty-one amino acid categories.

In yet another example, an amino acid-wise classification of oxygen atoms can respectively list oxygen atoms under each of the twenty-one amino acid categories. In yet another example, an amino acid-wise classification of nitrogen atoms can respectively list nitrogen atoms under each of the twenty-one amino acid categories. In yet another example, an amino acid-wise classification of hydrogen atoms can respectively list hydrogen atoms under each of the twenty-one amino acid categories.

A person skilled in the art will appreciate that, in various implementations, the amino acid-wise classification can include a subset of the twenty-one amino acid categories and a subset of the different atomic elements.

At step 132, a voxel grid generator 134 of the system instantiates a voxel grid. The voxel grid can have any resolution, for example, 3×3×3, 5×5×5, 7×7×7, and so on. Voxels in the voxel grid can be of any size, for example, one angstrom (Å) on each side, two Å on each side, three Å on each side, and so on. One skilled in the art will appreciate that these example dimensions refer to cubic dimensions because voxels are cubes. Also, one skilled in the art will appreciate that these example dimensions are non-limiting, and the voxels can have any cubic dimensions.

At step 142, a voxel grid centerer 144 of the system centers the voxel grid at the reference amino acid experiencing a target variant at the amino acid level. In one implementation, the voxel grid is centered at an atomic coordinate of a particular atom of the reference amino acid experiencing the target variant, for example, the 3D atomic coordinate of the alpha-carbon atom of the reference amino acid experiencing the target variant.

Distance Channels

The voxels in the voxel grid can have a plurality of channels (or features). In one implementation, the voxels in the voxel grid have a plurality of distance channels (e.g., twenty-one distance channels for the twenty-one amino acid categories, respectively (including stop or gap amino acid category)). At step 152, a distance channel generator 154 of the system generates amino acid-wise distance channels for the voxels in the voxel grid. The distance channels are independently generated for each of the twenty-one amino acid categories.

Consider, for example, the Alanine (A) amino acid category. Further consider, for example, that the voxel grid is of size 3×3×3 and has twenty-seven voxels. Then, in one implementation, an Alanine distance channel includes twenty-seven distance values for the twenty-seven voxels in the voxel grid, respectively. The twenty-seven distance values in the Alanine distance channel are measured from respective centers of the twenty-seven voxels in the voxel grid to respective nearest atoms in the Alanine amino acid category.

In one example, the Alanine amino acid category includes only alpha-carbon atoms and therefore the nearest atoms are those Alanine alpha-carbon atoms that are most proximate to the twenty-seven voxels in the voxel grid, respectively. In another example, the Alanine amino acid category includes only beta-carbon atoms and therefore the nearest atoms are those Alanine beta-carbon atoms that are most proximate to the twenty-seven voxels in the voxel grid, respectively.

In yet another example, the Alanine amino acid category includes only oxygen atoms and therefore the nearest atoms are those Alanine oxygen atoms that are most proximate to the twenty-seven voxels in the voxel grid, respectively. In yet another example, the Alanine amino acid category includes only nitrogen atoms and therefore the nearest atoms are those Alanine nitrogen atoms that are most proximate to the twenty-seven voxels in the voxel grid, respectively. In yet another example, the Alanine amino acid category includes only hydrogen atoms and therefore the nearest atoms are those Alanine hydrogen atoms that are most proximate to the twenty-seven voxels in the voxel grid, respectively.

Like the Alanine distance channel, the distance channel generator 154 generates a distance channel (i.e., a set of voxel-wise distance values) for each of the remaining amino acid categories. In other implementations, the distance channel generator 154 generates distance channels only for a subset of the twenty-one amino acid categories.

In other implementations, the selection of the nearest atoms is not confined to a particular atom type. That is, within a subject amino acid category, the nearest atom to a particular voxel is selected, irrespective of the atomic element of the nearest atom, and the distance value for the particular voxel calculated for inclusion in the distance channel for the subject amino acid category.

In yet other implementations, the distance channels are generated on an atomic element-basis. Instead of or in addition to having the distance channels for the amino acid categories, distance values can be generated for atom element categories, irrespective of the amino acids to which the atoms belong. Consider, for example, that the atoms of amino acids in the reference amino acid sequence span seven atomic elements: carbon, oxygen, nitrogen, hydrogen, calcium, iodine, and sulfur. Then, the voxels in the voxel grid are configured to have seven distance channels, such that each of the seven distance channels have twenty-seven voxel wise distance values that specify distances to nearest atoms only within a corresponding atomic element category. In other implementations, distance channels for only a subset of the seven atomic elements can be generated. In yet other implementations, the atomic element categories and the distance channel generation can be further stratified into variations of a same atomic element, for example, alpha-carbon ($C_\alpha$) atoms and beta-carbon ($C_\beta$) atoms.

In yet other implementations, the distance channels can be generated on an atom type-basis, for example, distance channels only for side chain atoms and distance channels only for backbone atoms.

The nearest atoms can be searched within a predefined maximum scan radius from the voxel centers (e.g., six angstrom (Å)). Also, multiple atoms can be nearest to a same voxel in the voxel grid.

The distances are calculated between 3D coordinates of the voxel centers and 3D atomic coordinates of the atoms. Also, the distance channels are generated with the voxel grid centered at a same location (e.g., centered at the 3D atomic coordinate of the alpha-carbon atom of the reference amino acid experiencing the target variant).

The distances can be Euclidean distances. Also, the distances can be parameterized by atom size (or atom influence) (e.g., by using Lennard-Jones potential and/or Van der Waals atom radius of the atom in question). Also, the distance values can be normalized by the maximum scan radius, or by a maximum observed distance value of the furthest nearest atom within a subject amino acid category or a subject atomic element category or a subject atom type category. In some implementations, the distances between the voxels and the atoms are calculated based on polar coordinates of the voxels and the atoms. The polar coordinates are parameterized by angles between the voxels and the atoms. In one implementation, this angel information is used to generate an angle channel for the voxels (i.e., independent of the distance channels). In some implementations, angles between a nearest atom and neighboring atoms (e.g., backbone atoms) can be used as features that are encoded with the voxels.

Reference Allele and Alternative Allele Channels

The voxels in the voxel grid can also have reference allele and alternative allele channels. At step 162, a one-hot encoder 164 of the system generates a reference one-hot encoding of a reference amino acid in the reference amino acid sequence and an alternative one-hot encoding of an alternative amino acid in an alternative amino acid sequence. The reference amino acid experiences the target variant. The alternative amino acid is the target variant. The reference amino acid and the alternative amino acid are located at a same position respectively in the reference amino acid sequence and the alternative amino acid sequence. The reference amino acid sequence and the alternative amino acid sequence have the same position-wise amino acid composition with one exception. The exception is the position that has the reference amino acid in the reference amino acid sequence and the alternative amino acid in the alternative amino acid sequence.

At step 172, a concatenator 174 of the system concatenates the amino acid-wise distance channels and the reference and alternative one-hot encodings. In another implementation, the concatenator 174 concatenates the atomic element-wise distance channels and the reference and alternative one-hot encodings. In yet another implementation, the concatenator 174 concatenates the atomic type-wise distance channels and the reference and alternative one-hot encodings.

At step 182, runtime logic 184 of the system processes the concatenated amino acid-wise/atomic element-wise/atomic type-wise distance channels and the reference and alternative one-hot encodings through a pathogenicity classifier (pathogenicity determination engine) to determine a pathogenicity of the target variant, which is in turn inferred as a pathogenicity determination of the underlying nucleotide variant that creates the target variant at the amino acid level. The pathogenicity classifier is trained using labelled datasets of benign and pathogenic variants, for example, using the backpropagation algorithm. Additional details about the labelled datasets of benign and pathogenic variants and example architectures and training of the pathogenicity classifier can be found in commonly owned U.S. patent application Ser. Nos. 16/160,903; 16/160,986; 16/160,968; and Ser. No. 16/407,149.

Figure 2:
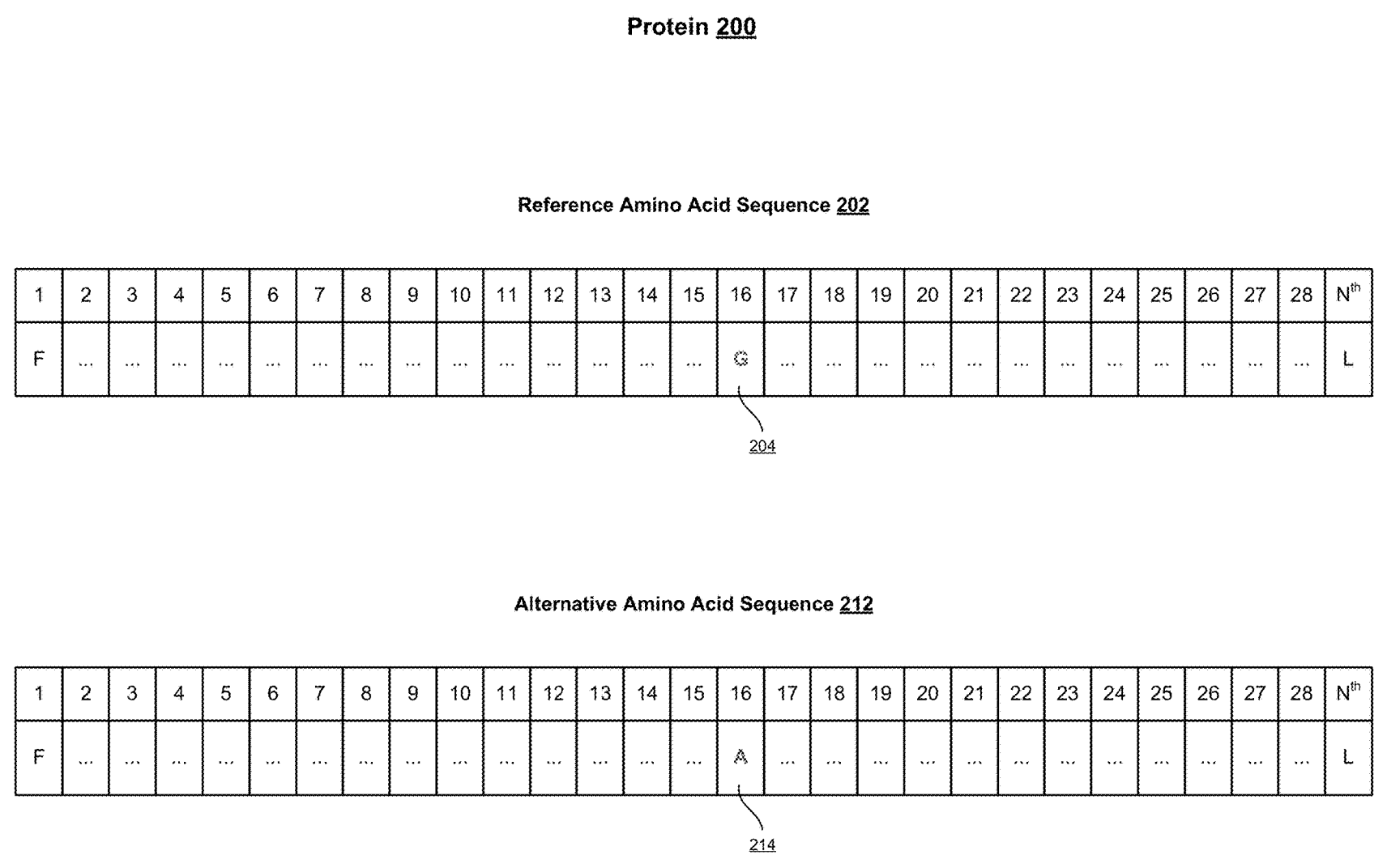

FIG. 2 schematically illustrates a reference amino acid sequence 202 of a protein 200 and an alternative amino acid sequence 212 of the protein 200. The protein 200 comprises N amino acids. Positions of the amino acids in the protein 200 are labelled 1, 2, 3 . . . N. In the illustrated example, position 16 is the location that experiences an amino acid variant 214 (mutation) caused by an underlying nucleotide variant. For example, for the reference amino acid sequence 202, position 1 has reference amino acid Phenylalanine (F), position 16 has reference amino acid Glycine (G) 204, and position N (e.g., the last amino acid of the sequence 202) has reference amino acid Leucine (L). Though not illustrated for clarity, remaining positions in the reference amino acid sequence 202 contain various amino acids in an order that is specific to the protein 200. The alternative amino acid sequence 212 is the same as the reference amino acid sequence 202 except for the variant 214 at position 16, which contains the alternative amino acid Alanine (A) 214 instead of the reference amino acid Glycine (G) 204.

FIG. 3 illustrates amino acid-wise classification of atoms of amino acids in the reference amino acid sequence 202, also referred to herein as "atom classification 300." Specific types of amino acids, among the twenty natural amino acids listed in column 302, may repeat in a protein. That is, a particular type of amino acid may occur more than once in a protein. Proteins may also have some undetermined amino acids that are categorized by a twenty-first stop or gap amino acid category. The right column in FIG. 3 contains counts of alpha-carbon ($C_\alpha$) atoms from different amino acids.

Specifically, FIG. 3 shows amino acid-wise classification of alpha-carbon ($C_\alpha$) atoms of the amino acids in the reference amino acid sequence 202. Column 308 of FIG. 3 lists the total number of alpha-carbon atoms observed for the reference amino acid sequence 202 in each of the twenty-one amino acid categories. For example, column 308 lists eleven alpha-carbon atoms observed for the Alanine (A) amino acid category. Since each amino acid has only one alpha-carbon atom, this means that Alanine occurs 11 times in the reference amino acid sequence 202. In another example, Arginine (R) occurs thirty-five times in the reference amino acid sequence 202. The total number of alpha-carbon atoms across the twenty-one amino acid categories is eight hundred and twenty-eight.

FIG. 4 illustrates amino acid-wise attribution of 3D atomic coordinates of the alpha-carbon atoms of the reference amino acid sequence 202 based on the atom classification 300 in FIG. 3. This is referred to herein as "atomic coordinates bucketing 400." In FIG. 4, lists 404-440 tabulate the 3D atomic coordinates of the alpha-carbon atoms bucketed to each of the twenty-one amino acid categories.

In the illustrated implementation, the bucketing 400 in FIG. 4 follows the classification 300 of FIG. 3. For example, in FIG. 3, the Alanine amino acid category has eleven alpha-carbon atoms, and therefore, in FIG. 4, the Alanine amino acid category has eleven 3D atomic coordinates of the corresponding eleven alpha-carbon atoms from FIG. 3. This classification-to-bucketing logic flows from FIG. 3 to FIG. 4 for other amino acid categories too. However, this classification-to-bucketing logic is only for representational purposes, and in other implementations, the technology disclosed need not perform the classification 300 and the bucketing 400 to locate the voxel-wise nearest atoms, and may perform fewer, additional, or different steps. For example, in some implementations, the technology disclosed can locate the voxel-wise nearest atoms by using a sort and search algorithm that returns the voxel-wise nearest atoms from one or more databases in response to a search query configured to accept query parameters like sort criteria (e.g., amino acid-wise, atomic element-wise, atom type-wise), the predefined maximum scan radius, and the type of distances (e.g., Euclidean, Mahalanobis, normalized, unnormalized). In various implementations of the technology disclosed, a plurality of sort and search algorithms from the current or future technical field can be analogous used by a person skilled in the art to locate the voxel-wise nearest atoms.

In FIG. 4, the 3D atomic coordinates are represented by cartesian coordinates x, y, z, but any type of coordinate system may be used, such as spherical or cylindrical coordinates, and claimed subject matter is not limited in this respect. In some implementations, one or more databases may include information regarding the 3D atomic coordinates of the alpha-carbon atoms and other atoms of amino acids in proteins. Such databases may be searchable by specific proteins.

As discussed above, the voxels and the voxel grid are 3D entities. However, for clarity's sake, the drawings depict, and the description discusses the voxels and the voxel grid in a two-dimensional (2D) format. For example, a 3×3×3 voxel grid of twenty-seven voxels is depicted and described herein as a 3×3 2D pixel grid with nine 2D pixels. A person skilled in the art will appreciate that the 2D format is used only for representational purposes and is intended to cover the 3D counterparts (i.e., 2D pixels represent 3D voxels and 2D pixel grid represents 3D voxel grid). Also, the drawings are also not scale. For example, voxels of size two angstrom (Å) are depicted using a single pixel.

Voxel-Wise Distance Calculation

Figure 5:
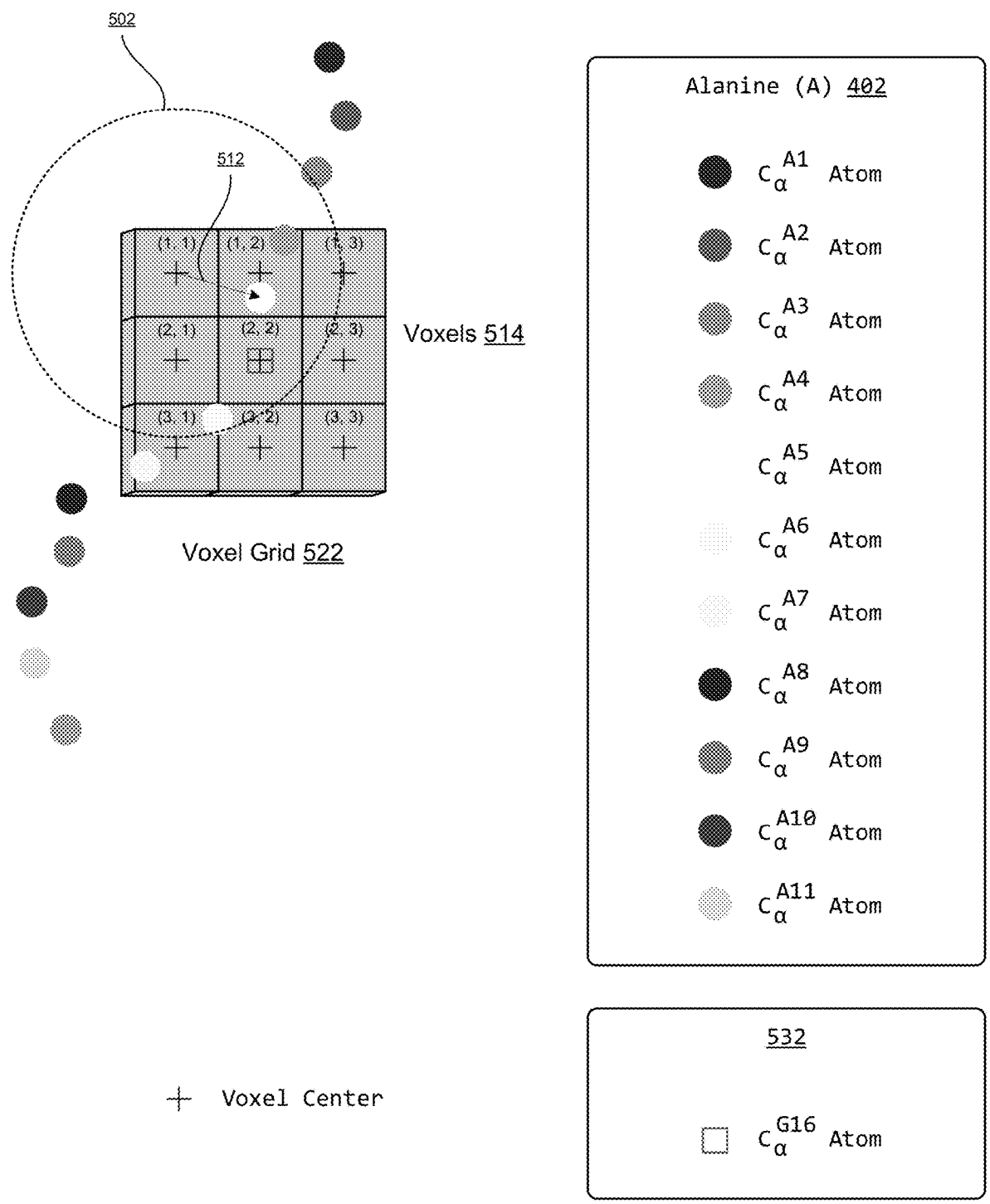
FIG. 5 schematically illustrates a process of determining voxel-wise distance values, in accordance with one implementation of the technology disclosed.

FIG. 5 schematically illustrates a process of determining voxel-wise distance values, also referred to herein as "voxel-wise distance calculation 500." In the illustrated example, the voxel-wise distance values are calculated only for the Alanine (A) distance channel. However, the same distance calculation logic is executed for each of the twenty-one amino acid categories to generate twenty-one amino acid-wise distance channels and can be further expanded to other atom types like beta-carbon atoms and other atomic elements like oxygen, nitrogen, and hydrogen, as discussed above with respect to FIG. 1. In some implementations, the atoms are randomly rotated prior to the distance calculation to make the training of the pathogenicity classifier invariant to atom orientation.

In FIG. 5, a voxel grid 522 has nine voxels 514 identified with indices (1, 1), (1, 2), (1, 3), (2, 1), (2, 2), (2, 3), (3, 1), (3, 2), and (3, 3). The voxel grid 522 is centered, for example, at the 3D atomic coordinate 532 of the alpha-carbon atom of the Glycine (G) amino acid at position 16 in the reference amino acid sequence 202 because, in the alternative amino acid sequence 212, the position 16 experiences the variant that mutates the Glycine (G) amino acid to the Alanine (A) amino acid, as discussed above with respect to FIG. 2. Also, the center of the voxel grid 522 coincides with the center of voxel (2, 2).

The centered voxel grid 522 is used for the voxel-wise distance calculation for each of the twenty-one amino acid-wise distance channels. Starting, for example, with the Alanine (A) distance channel, distances between the 3D coordinates of respective centers of the nine voxels 514 and the 3D atomic coordinates 402 of the eleven Alanine alpha-carbon atoms are measured to locate a nearest Alanine alpha-carbon atom for each of the nine voxels 514. Then, nine distance values for nine distances between the nine voxels 514 and the respective nearest Alanine alpha-carbon atoms are used to construct the Alanine distance channel. The resulting Alanine distance channel arranges the nine Alanine distance values in the same order as the nine voxels 514 in the voxel grid 522.

The above process is executed for each of the twenty-one amino acid categories. For example, the centered voxel grid 522 is similarly used to calculate the Arginine (R) distance channel, such that distances between the 3D coordinates of respective centers of the nine voxels 514 and the 3D atomic coordinates 404 of the thirty-five Arginine alpha-carbon atoms are measured to locate a nearest Arginine alpha-carbon atom for each of the nine voxels 514. Then, nine distance values for nine distances between the nine voxels 514 and the respective nearest Arginine alpha-carbon atoms are used to construct the Arginine distance channel. The resulting Arginine distance channel arranges the nine Arginine distance values in the same order as the nine voxels 514 in the voxel grid 522. The twenty-one amino acid-wise distance channels are voxel-wise encoded to form a distance channel tensor.

Specifically, in the illustrated example, a distance 512 is between the center of voxel (1, 1) of voxel grid 522 and the nearest alpha-carbon ($C_\alpha$) atom, which is the $C\alpha^{45}$ atom in list 402. Accordingly, the value assigned to voxel (1, 1) is the distance 512. In another example, the $C\alpha^{44}$ atom is the nearest $C_\alpha$ atom to the center of voxel (1, 2). Accordingly, the value assigned to voxel (1, 2) is the distance between the center of voxel (1, 2) and the $C\alpha^{44}$ atom. In still another example, the $C\alpha^{46}$ atom is the nearest $C_\alpha$ atom to the center of voxel (2, 1). Accordingly, the value assigned to voxel (2, 1) is the distance between the center of voxel (2, 1) and the $C\alpha^{46}$ atom. In still another example, the $C\alpha^{46}$ atom is also the nearest $C_\alpha$ atom to the center of voxels (3, 2) and (3, 3). Accordingly, the value assigned to voxel (3, 2) is the distance between the center of voxel (3, 2) and the $C\alpha^{46}$ atom and the value assigned to voxel (3, 3) is the distance between the center of voxel (3, 3) and the $C\alpha^{46}$ atom. In some implementations, the distance values assigned to the voxels 514 may be normalized distances. For example, the distance value assigned to voxel (1, 1) may be the distance 512 divided by a maximum distance 502 (predefined maximum scan radius). In some implementations, the nearest-atom distances may be Euclidean distances and the nearest-atom distances may be normalized by dividing the Euclidean distances with a maximum nearest-atom distance (e.g., such as the maximum distance 502).

As described above, for amino acids having alpha-carbon atoms, the distances may be nearest-alpha-carbon atom distances from corresponding voxel centers to nearest alpha-carbon atoms of the corresponding amino acids. Additionally, for amino acids having beta-carbon atoms, the distances may be nearest-beta-carbon atom distances from corresponding voxel centers to nearest beta-carbon atoms of the corresponding amino acids. Similarly, for amino acids having backbone atoms, the distances may be nearest-backbone atom distances from corresponding voxel centers to nearest backbone atoms of the corresponding amino acids. Similarly, for amino acids having sidechain atoms, the distances may be nearest-sidechain atom distances from corresponding voxel centers to nearest sidechain atoms of the corresponding amino acids. In some implementations, the distances additionally/alternatively can include distances to second, third, fourth nearest atoms, and so on.
Amino Acid-Wise Distance Channels FIG. 6 shows an example of twenty-one amino acid-wise distance channels 600. Each column in FIG. 6 corresponds to a respective one of the twenty-one amino acid-wise distance channels 602-642. Each amino acid-wise distance channel comprises a distance value for each of the voxels 514 of the voxel grid 522. For example, the amino acid-wise distance channel 602 for Alanine (A) comprises distance values for respective ones of the voxels 514 of the voxel grid 522. As mentioned above, the voxel grid 522 is 3D grid of volume 3×3×3 and comprises twenty-seven voxels. Likewise, though FIG. 6 illustrates the voxels 514 in two dimensions (e.g., nine voxels of a 3×3 grid), each amino acid-wise distance channel may comprise twenty-seven voxel-wise distance values for the 3×3×3 voxel grid.
Directionality Encoding In some implementations, the technology disclosed uses a directionality parameter to specify the directionality of the reference amino acids in the reference amino acid sequence 202. In some implementations, the technology disclosed uses the directionality parameter to specify the directionality of the alternative amino acids in the alternative amino acid sequence 212. In some implementations, the technology disclosed uses the directionality parameter to specify the position in the protein 200 that experiences the target variant at the amino acid level.

As discussed above, all the distance values in the twenty-one amino acid-wise distance channels 602-642 are measured from respective nearest atoms to the voxels 514 in the voxel grid 522. These nearest atoms originate from one of the reference amino acids in the reference amino acid sequence 202. These originating reference amino acids, which contain the nearest atoms, can be classified into two categories: (1) those originating reference amino acids that precede the variant-experiencing reference amino acid 204 in the reference amino acid sequence 202 and (2) those originating reference amino acids that succeed the variant-experiencing reference amino acid 204 in the reference amino acid sequence 202. The originating reference amino acids in the first category can be called preceding reference amino acids. The originating reference amino acids in the second category can be called succeeding reference amino acids.

The directionality parameter is applied to those distance values in the twenty-one amino acid-wise distance channels 602-642 that are measured from those nearest atoms that originate from the preceding reference amino acids. In one implementation, the directionality parameter is multiplied with such distance values. The directionality parameter can be any number, such as −1.

As a result of the application of the directionality parameter, the twenty-one amino acid-wise distance channels 600 include some distance values that indicate to the pathogenicity classifier which end of the protein 200 is the start terminal and which end is the end terminal. This also allows the pathogenicity classifier to reconstruct a protein sequence from the 3D protein structure information supplied by the distance channels and the reference and allele channels.
Distance Channel Tensor FIG. 7 is a schematic diagram of a distance channel tensor 700. Distance channel tensor 700 is a voxelized representation of the amino acid-wise distance channels 600 from FIG. 6. In the distance channel tensor 700, the twenty-one amino acid-wise distance channels 602-642 are concatenated voxel-wise, like RGB channels of a color image. The voxelized dimensionality of the distance channel tensor 700 is 21×3×3×3 (where 21 denotes the twenty-one amino acid categories and 3×3×3 denotes the 3D voxel grid with twenty-seven voxels); although FIG. 7 is a 2D depiction of dimensionality 21×3×3.

One-Hot Encodings

FIG. 8 shows one-hot encodings 800 of the reference amino acid 204 and the alternative amino acid 214. In FIG. 8, left column is a one-hot encoding 802 of the reference amino acid Glycine (G) 204, with one for the Glycine amino acid category and zeros for all other amino acid categories. In FIG. 8, right column is a one-hot encoding 804 of the variant/alternative amino acid Alanine (A) 214, with one for the Alanine amino acid category and zeros for all other amino acid categories.

FIG. 9 is a schematic diagram of a voxelized one-hot encoded reference amino acid 902 and a voxelized one-hot encoded variant/alternative amino acid 912. The voxelized one-hot encoded reference amino acid 902 is a voxelized representation of the one-hot encoding 802 of the reference amino acid Glycine (G) 204 from FIG. 8. The voxelized one-hot encoded alternative amino acid 912 is a voxelized representation of the one-hot encoding 804 of the variant/alternative amino acid Alanine (A) 214 from FIG. 8. The voxelized dimensionality of the voxelized one-hot encoded reference amino acid 902 is 21×1×1×1 (where 21 denotes the twenty-one amino acid categories); although FIG. 9 is a 2D depiction of dimensionality 21×1×1. Similarly, the voxelized dimensionality of the voxelized one-hot encoded alternative amino acid 912 is 21×1×1×1 (where 21 denotes the twenty-one amino acid categories); although FIG. 9 is a 2D depiction of dimensionality 21×1×1.

Reference Allele Tensor

Figure 10:
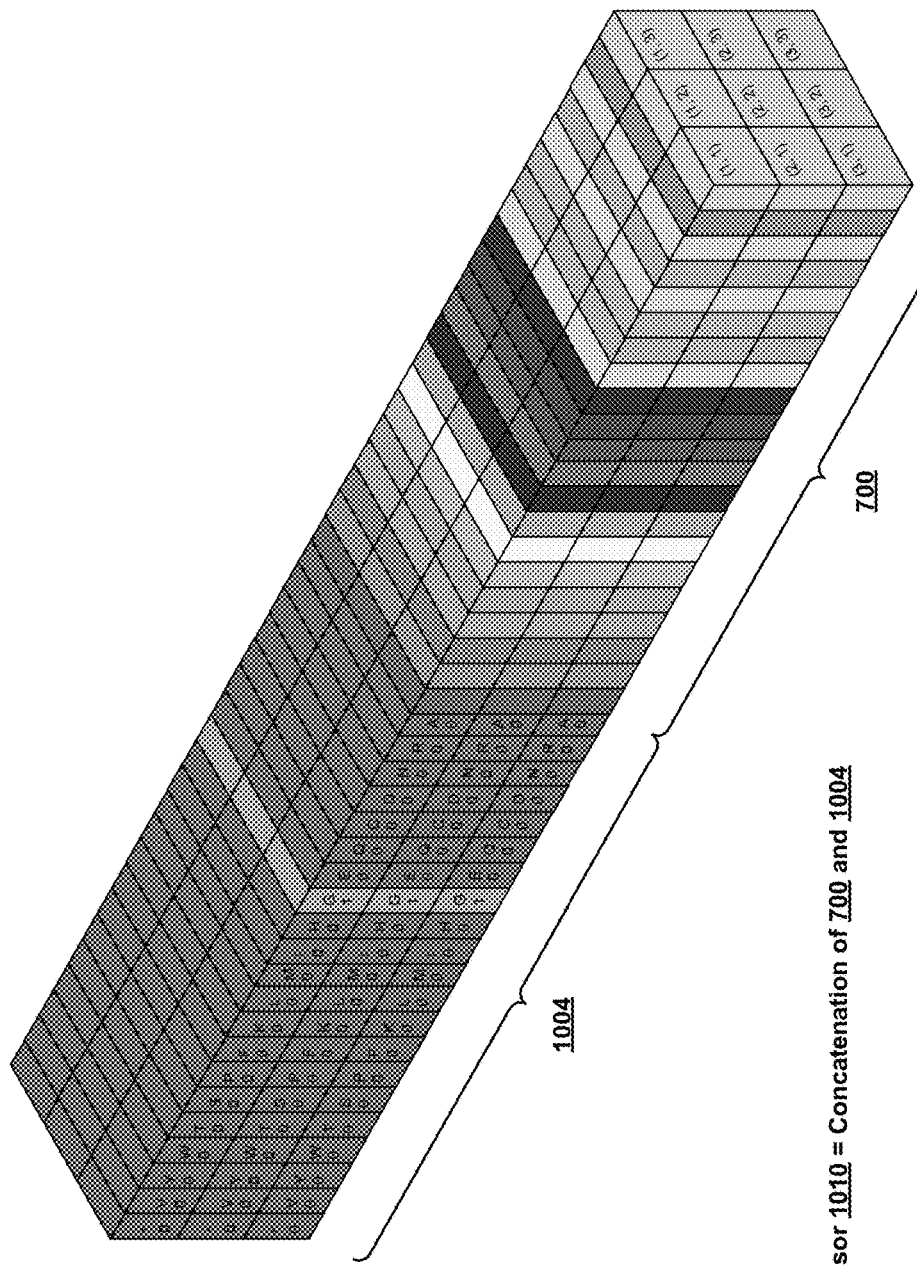
FIG. 10 schematically illustrates a concatenation process that voxel-wise concatenates the distance channel tensor of FIG. 7 and a reference allele tensor, in accordance with one implementation of the technology disclosed.

FIG. 10 schematically illustrates a concatenation process 1000 that voxel-wise concatenates the distance channel tensor 700 of FIG. 7 and a reference allele tensor 1004. The reference allele tensor 1004 is a voxel-wise aggregation (repetition/cloning/replication) of the voxelized one-hot encoded reference amino acid 902 from FIG. 9. That is, multiple copies of the voxelized one-hot encoded reference amino acid 902 are voxel-wise concatenated according with each other to the spatial arrangement of the voxels 514 in the voxel grid 522, such that the reference allele tensor 1004 has a corresponding copy of the voxelized one-hot encoded reference amino acid 910 for each of the voxels 514 in the voxel grid 522.

The concatenation process 1000 produces a concatenated tensor 1010. The voxelized dimensionality of the reference allele tensor 1004 is 21×3×3×3 (where 21 denotes the twenty-one amino acid categories and 3×3×3 denotes the 3D voxel grid with twenty-seven voxels); although FIG. 10 is a 2D depiction of the reference allele tensor 1004 having dimensionality 21×3×3. The voxelized dimensionality of the concatenated tensor 1010 is 42×3×3×3; although FIG. 10 is a 2D depiction of the concatenated tensor 1010 having dimensionality 42×3×3.

Alternative Allele Tensor

Figure 11:
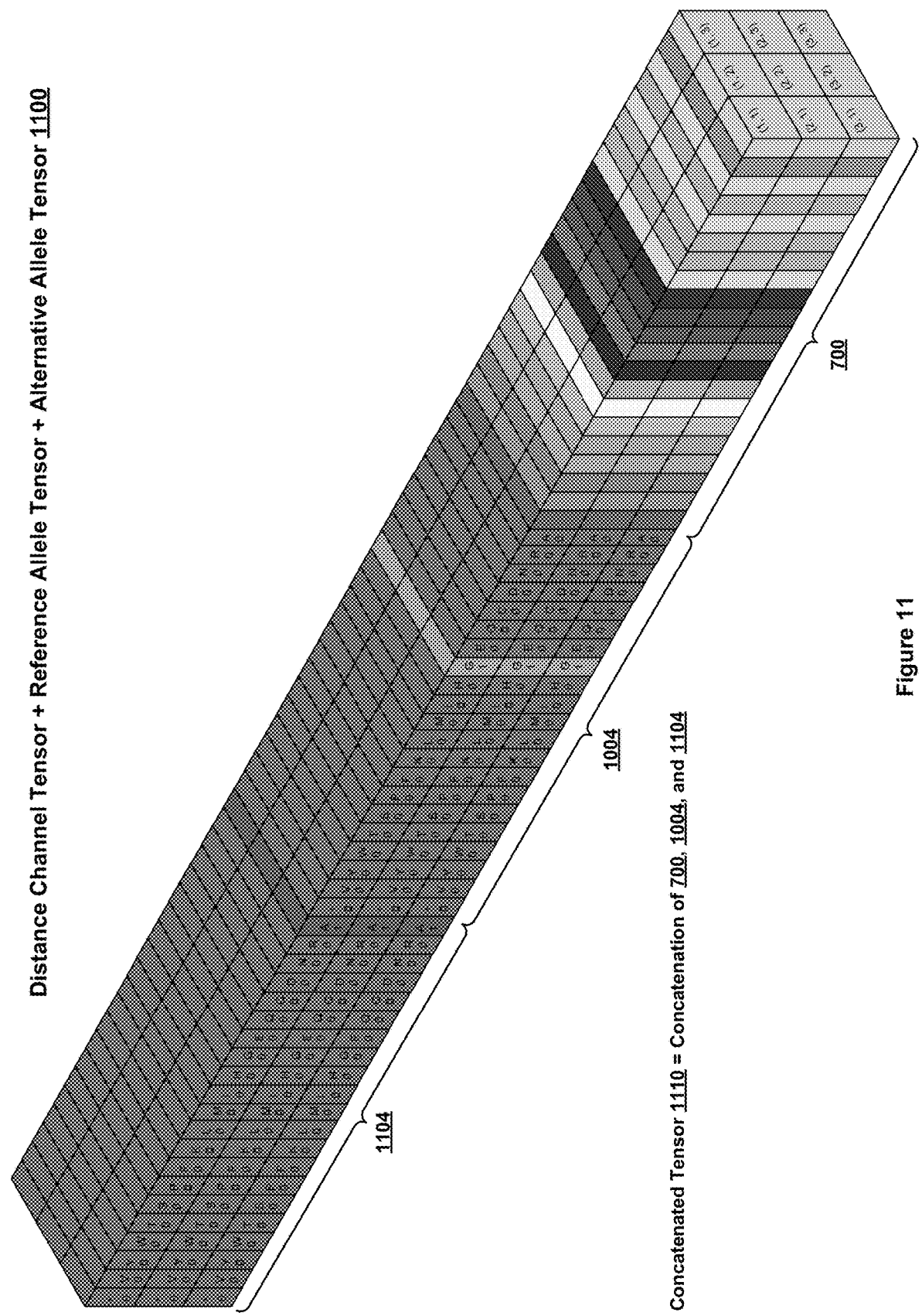
FIG. 11 schematically illustrates a concatenation process that voxel-wise concatenates the distance channel tensor of FIG. 7, the reference allele tensor of FIG. 10, and an alternative allele tensor, in accordance with one implementation of the technology disclosed.

FIG. 11 schematically illustrates a concatenation process 1100 that voxel-wise concatenates the distance channel tensor 700 of FIG. 7, the reference allele tensor 1004 of FIG. 10, and an alternative allele tensor 1104. The alternative allele tensor 1104 is a voxel-wise aggregation (repetition/cloning/replication) of the voxelized one-hot encoded alternative amino acid 912 from FIG. 9. That is, multiple copies of the voxelized one-hot encoded alternative amino acid 912 are voxel-wise concatenated with each other according to the spatial arrangement of the voxels 514 in the voxel grid 522, such that the alternative allele tensor 1104 has a corresponding copy of the voxelized one-hot encoded alternative amino acid 910 for each of the voxels 514 in the voxel grid 522.

The concatenation process 1100 produces a concatenated tensor 1110. The voxelized dimensionality of the alternative allele tensor 1104 is 21×3×3×3 (where 21 denotes the twenty-one amino acid categories and 3×3×3 denotes the 3D voxel grid with twenty-seven voxels); although FIG. 11 is a 2D depiction of the alternative allele tensor 1104 having dimensionality 21×3×3. The voxelized dimensionality of the concatenated tensor 1110 is 63×3×3×3; although FIG. 11 is a 2D depiction of the concatenated tensor 1110 having dimensionality 63×3×3.

In some implementations, the runtime logic 184 processes the concatenated tensor 1110 through the pathogenicity classifier to determine a pathogenicity of the variant/alternative amino acid Alanine (A) 214, which is in turn inferred as a pathogenicity determination of the underlying nucleotide variant that creates the variant/alternative amino acid Alanine (A) 214.

Evolutionary Conservation Channels

Predicting the functional consequences of variants relies at least in part on the assumption that crucial amino acids for protein families are conserved through evolution due to negative selection (i.e., amino acid changes at these sites were deleterious in the past), and that mutations at these sites have an increased likelihood of being pathogenic (causing disease) in humans. In general, homologous sequences of a target protein are collected and aligned, and a metric of conservation is computed based on the weighted frequencies of different amino acids observed in the target position in the alignment.

Accordingly, the technology disclosed concatenates the distance channel tensor 700, the reference allele tensor 1004, and the alternative allele tensor 1004 with evolutionary channels. One example of the evolutionary channels is pan-amino acid conservation frequencies. Another example of the evolutionary channels is per-amino acid conservation frequencies.

In some implementations, the evolutionary channels are constructed using position weight matrices (PWMs). In other implementations, the evolutionary channels are constructed using position specific frequency matrices (PSFMs). In yet other implementations, the evolutionary channels are constructed using computational tools like SIFT, PolyPhen, and PANTHER-PSEC. In yet other implementations, the evolutionary channels are preservation channels based on evolutionary preservation. Preservation is related to conservation, as it also reflects the effect of negative selection that has acted to prevent evolutionary change at a given site in a protein.

Pan-Amino Acid Evolutionary Profiles

Figure 12:
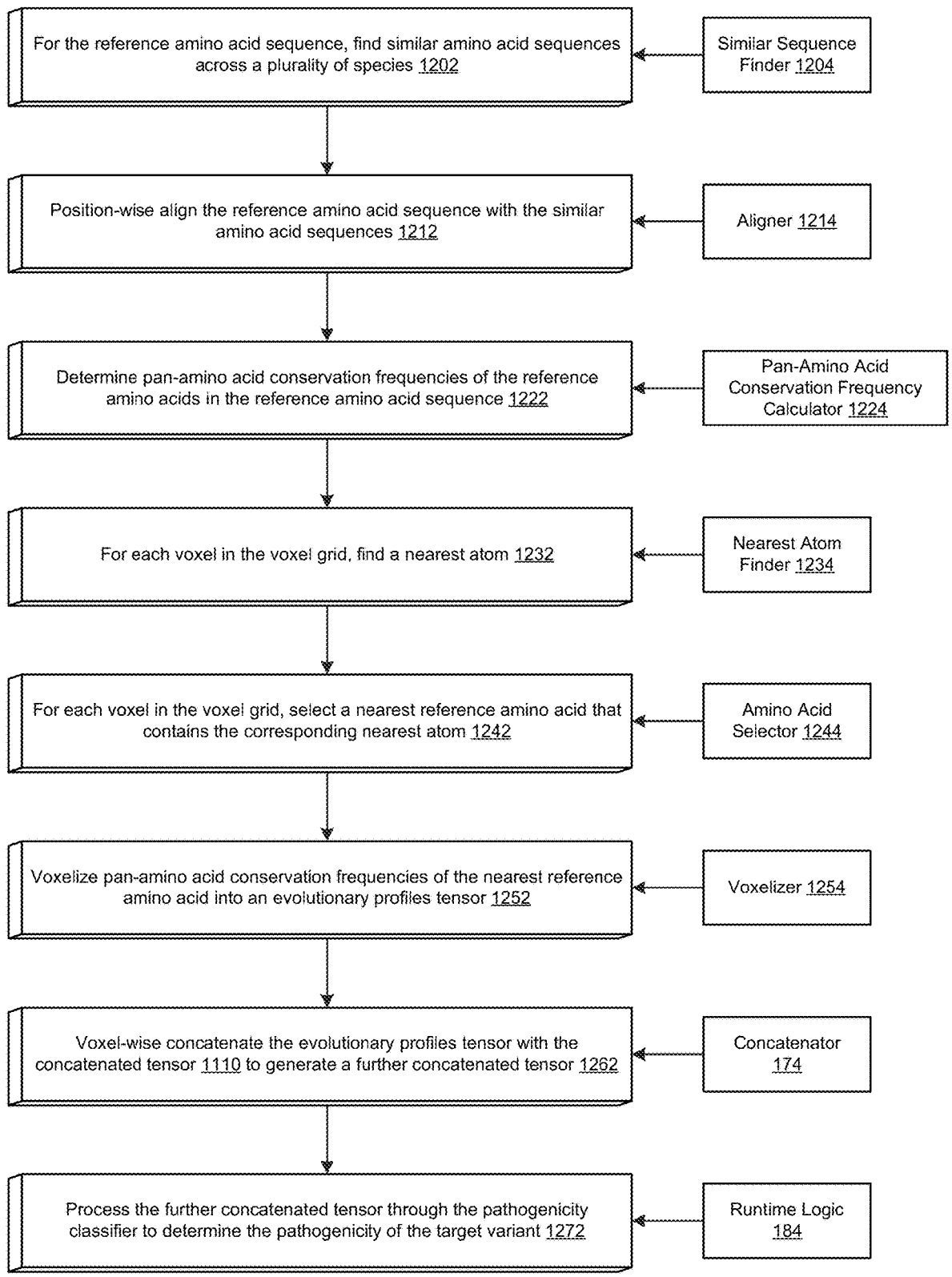
FIG. 12 is a flow diagram that illustrates a process of a system for determining and assigning pan-amino acid conservation frequencies of nearest atoms to voxels (voxelizing), in accordance with one implementation of the technology disclosed.

FIG. 12 is a flow diagram that illustrates a process 1200 of a system for determining and assigning pan-amino acid conservation frequencies of nearest atoms to voxels (voxelizing), in accordance with one implementation of the technology disclosed. FIGS. 12, 13, 14, 15, 16, 17, and 18 are discussed in tandem.

At step 1202, a similar sequence finder 1204 of the system retrieves amino acid sequences that are similar (homologous) to the reference amino acid sequence 202. The similar amino acid sequences can be selected from multiple species like primates, mammals, and vertebrates.

Figure 14:
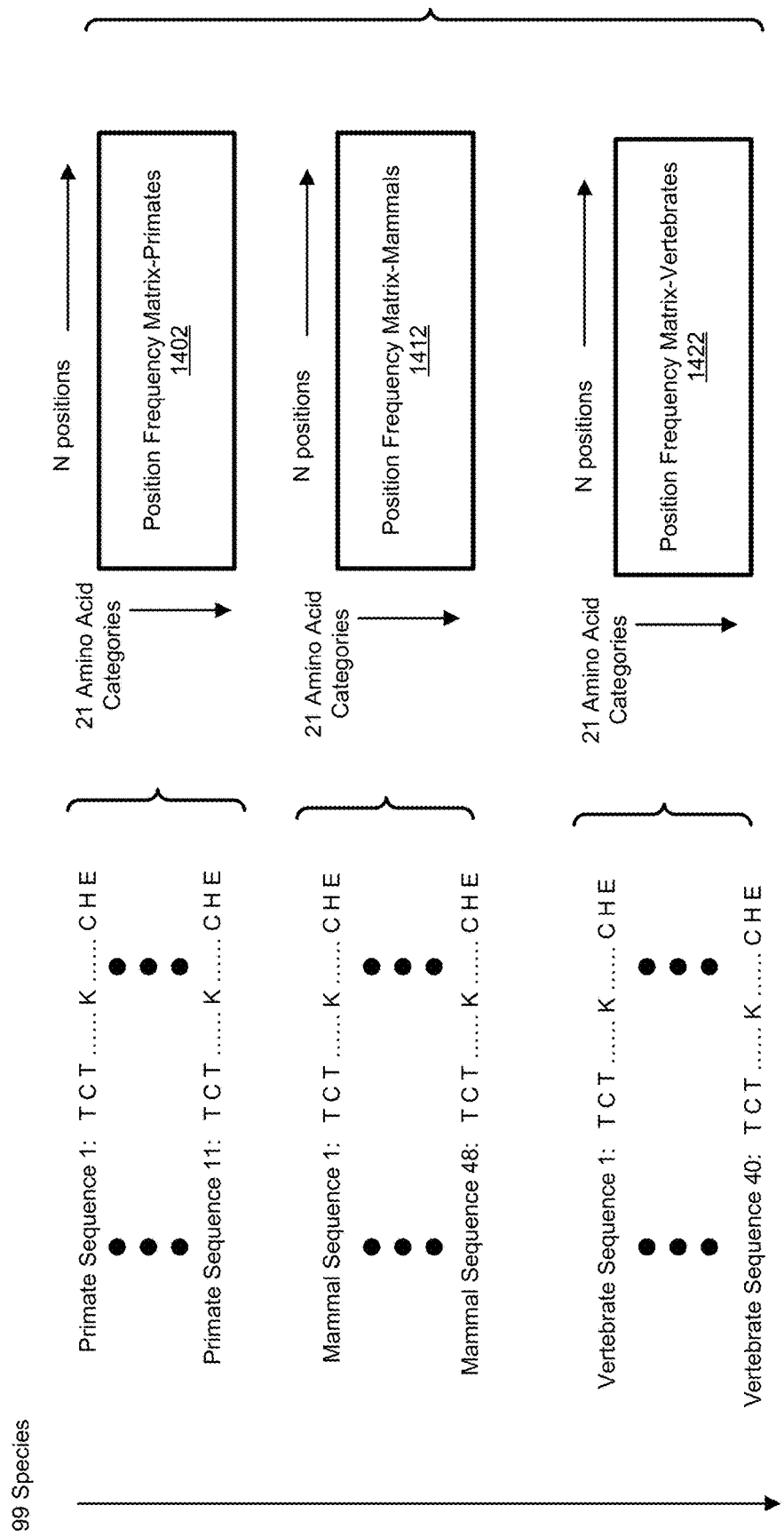
FIG. 14 shows an example multi-sequence alignment of the reference amino acid sequence across a ninety-nine species, in accordance with one implementation of the technology disclosed.

At step 1212, an aligner 1214 of the system position-wise aligns the reference amino acid sequence 202 with the similar amino acid sequences, i.e., the aligner 1214 performs a multi-sequence alignment. FIG. 14 shows an example multi-sequence alignment 1400 of the reference amino acid sequence 202 across a ninety-nine species. In some implementations, the multi-sequence alignment 1400 can be partitioned, for example, to generate a first position frequency matrix 1402 for primates, a second position frequency matrix 1412 for mammals, and a third position frequency matrix 1422 for primates. In other implementations, a single position frequency matrix is generated across the ninety-nine species.

At step 1222, a pan-amino acid conservation frequency calculator 1224 of the system uses the multi-sequence alignment to determine pan-amino acid conservation frequencies of the reference amino acids in the reference amino acid sequence 202.

At step 1232, a nearest atom finder 1234 of the system finds nearest atoms to the voxels 514 in the voxel grid 522. In some implementations, the search for the voxel-wise nearest atoms may not be confined to any particular amino acid category or atom type. That is, the voxel-wise nearest atoms can be selected across the amino acid categories and the amino acid types, as long as they are the most proximate atoms to the respective voxel centers. In other implementations, the search for the voxel-wise nearest atoms may be confined to only a particular atom category, such as only to a particular atomic element like oxygen, nitrogen, and hydrogen, or only to alpha-carbon atoms, or only to beta-carbon atoms, or only to sidechain atoms, or only to backbone atoms.

At step 1242, an amino acid selector 1244 of the system selects those reference amino acids in the reference amino acid sequence 202 that contain the nearest atoms identified at the step 1232. Such reference amino acids can be called nearest reference amino acids. FIG. 13 shows an example of locating nearest atoms 1302 to the voxels 514 in the voxel grid 522 and respectively mapping nearest reference amino acids 1312 that contain the nearest atoms 1302 to the voxels 514 in the voxel grid 522. This is identified in FIG. 13 as "voxels-to-nearest amino acids mapping 1300."

Figure 15:
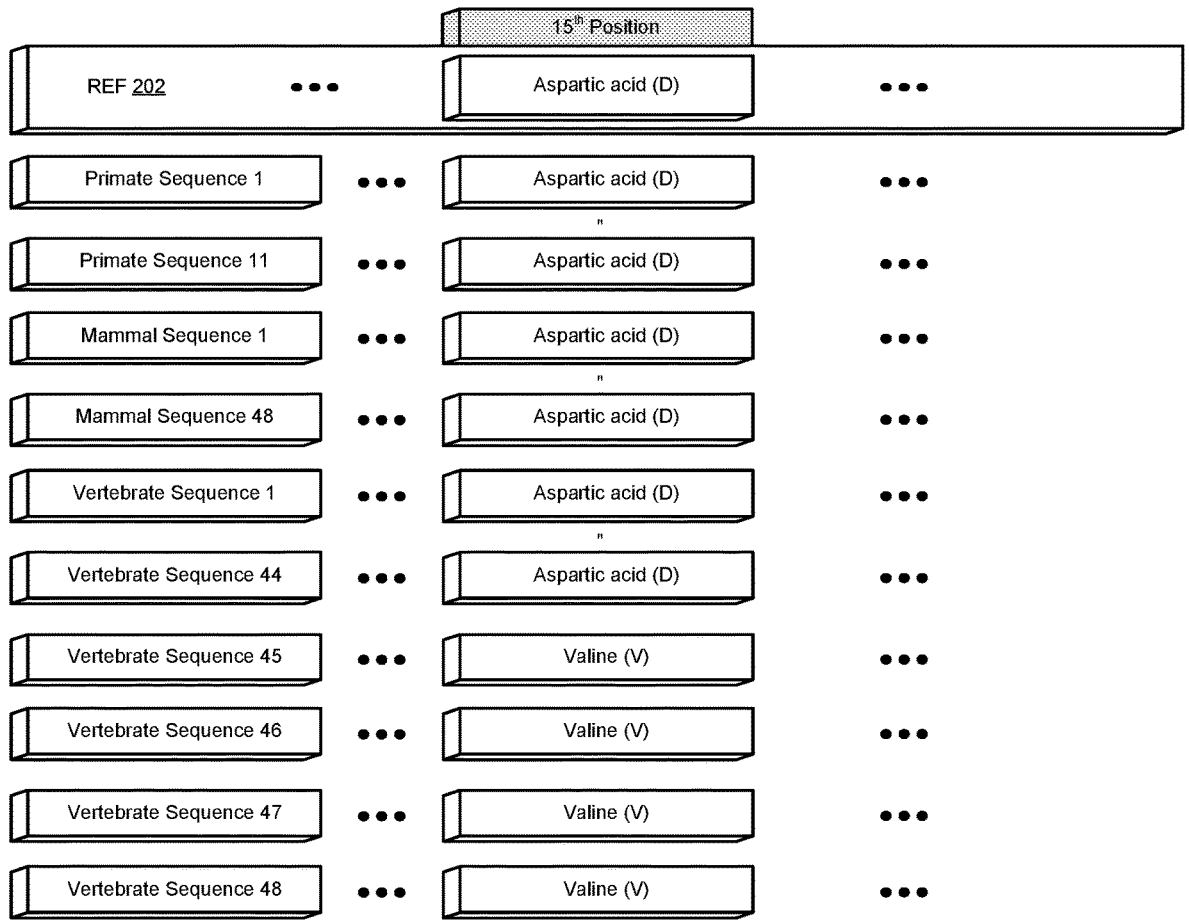
FIG. 15 shows an example of determining a pan-amino acid conservation frequencies sequence for a particular voxel, in accordance with one implementation of the technology disclosed.

At step 1252, a voxelizer 1254 of the system voxelizes pan-amino acid conservation frequencies of the nearest reference amino acids. FIG. 15 shows an example of determining a pan-amino acid conservation frequencies sequence for the first voxel (1, 1) in the voxel grid 522, also referred to herein as "per-voxel evolutionary profile determination 1500."

Turning to FIG. 13, the nearest reference amino acid that was mapped to the first voxel (1, 1) is Aspartic acid (D) amino acid at position 15 in the reference amino acid sequence 202. Then, the multi-sequence alignment of the reference amino acid sequence 202 with, for example, ninety-nine homologous amino acid sequences of the ninety-nine species is analyzed at position 15. Such a position-specific and cross-species analysis reveals how many instances of amino acids from each of the twenty-one amino acid categories are found at position 15 across the hundred aligned amino acid sequences (i.e., the reference amino acid sequence 202 plus the ninety-nine homologous amino acid sequences).

In the example illustrated in FIG. 15, the Aspartic acid (D) amino acid is found at position 15 in ninety-six out of the hundred aligned amino acid sequences. So, the Aspartic acid amino acid category 1504 is assigned a pan-amino acid conservation frequency of 0.96. Similarly, in the illustrated example, the Valine (V) acid amino acid is found at position 15 in four out of the hundred aligned amino acid sequences. So, the Valine acid amino acid category 1514 is assigned a pan-amino acid conservation frequency of 0.04. Since no instances of amino acids from other amino acid categories are detected at position 15, the remaining amino acid categories are assigned a pan-amino acid conservation frequency of zero. This way, each of the twenty-one amino acid categories is assigned a respective pan-amino acid conservation frequency, which can be encoded in the pan-amino acid conservation frequencies sequence 1502 for the first voxel (1, 1).

FIG. 16 shows respective pan-amino acid conservation frequencies 1612-1692 determined for respective ones of the voxels 514 in the voxel grid 522 using the position frequency logic described in FIG. 15, also referred to herein as "voxels-to-evolutionary profiles mapping 1600."

Figure 17:
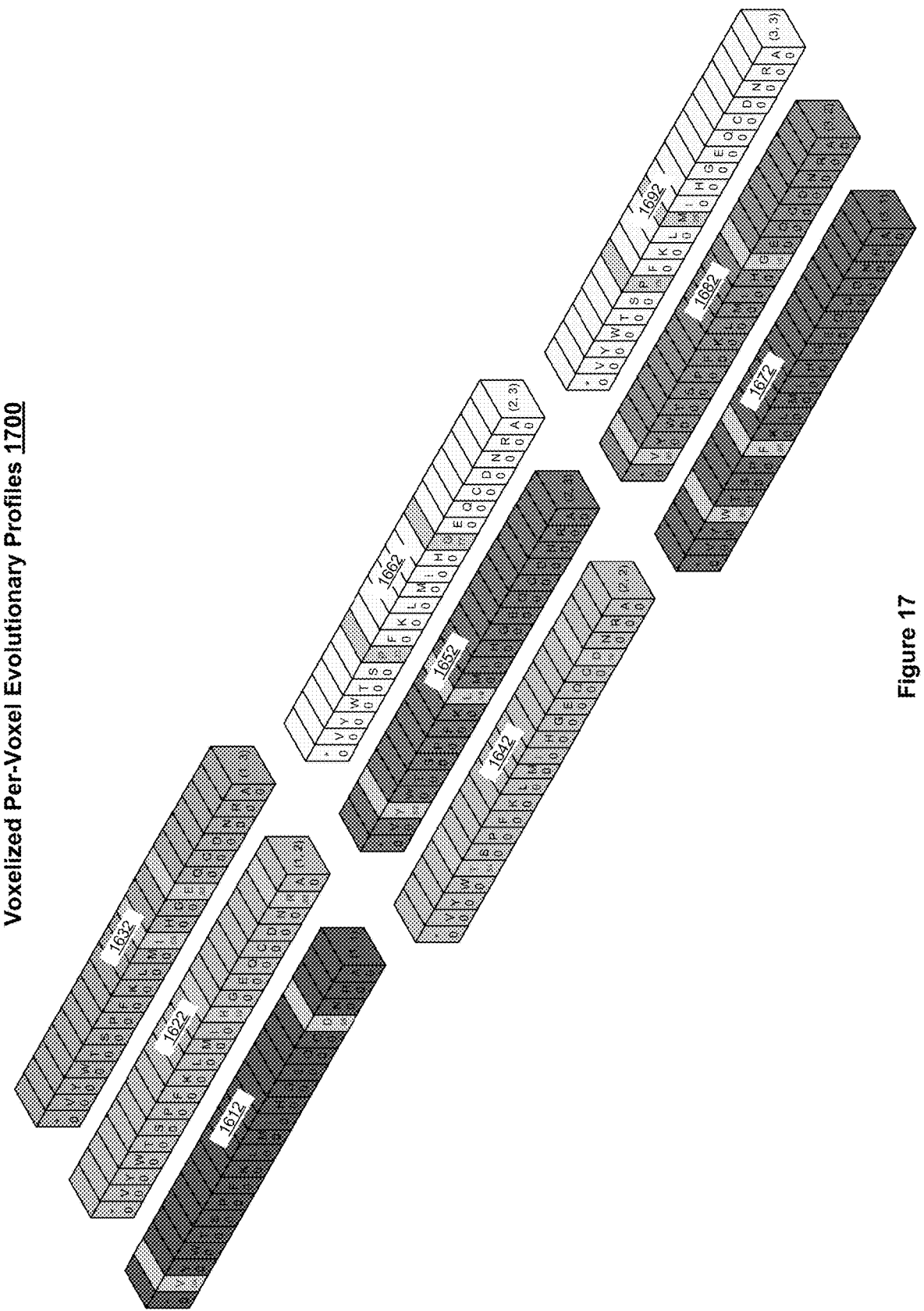
FIG. 17 illustrates voxelized per-voxel evolutionary profiles, in accordance with one implementation of the technology disclosed.

Per-voxel evolutionary profiles 1602 are then used by the voxelizer 1254 to generate voxelized per-voxel evolutionary profiles 1700, illustrated in FIG. 17. Often, each of the voxels 514 in the voxel grid 522 has a different pan-amino acid conservation frequencies sequence and therefore a different voxelized per-voxel evolutionary profile because the voxels are regularly mapped to different nearest atoms and therefore to different nearest reference amino acids. Of course, when two or more voxels have a same nearest atom and thereby a same nearest reference amino acid, a same pan-amino acid conservation frequencies sequence and a same voxelized per-voxel evolutionary profile is assigned to each of the two or more voxels.

Figure 18:
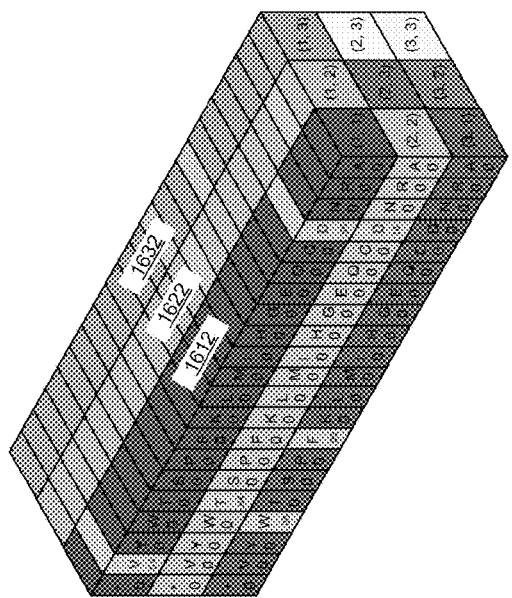
FIG. 18 depicts an example of an evolutionary profiles tensor, in accordance with one implementation of the technology disclosed.

FIG. 18 depicts an example of an evolutionary profiles tensor 1800 in which the voxelized per-voxel evolutionary profiles 1700 are voxel-wise concatenated with each other according to the spatial arrangement of the voxels 514 in the voxel grid 522. The voxelized dimensionality of the evolutionary profiles tensor 1800 is 21×3×3×3 (where 21 denotes the twenty-one amino acid categories and 3×3×3 denotes the 3D voxel grid with twenty-seven voxels); although FIG. 18 is a 2D depiction of the evolutionary profiles tensor 1800 having dimensionality 21×3×3.

At step 1262, the concatenator 174 voxel-wise concatenates the evolutionary profiles tensor 1800 with the distance channel tensor 700. In some implementations, the evolutionary profiles tensor 1800 is voxel-wise concatenated with the concatenator tensor 1110 to generate a further concatenated tensor of dimensionality 84×3×3×3 (not shown).

At step 1272, the runtime logic 184 processes the further concatenated tensor of dimensionality 84×3×3×3 through the pathogenicity classifier to determine the pathogenicity of the target variant, which is in turn inferred as a pathogenicity determination of the underlying nucleotide variant that creates the target variant at the amino acid level.

Per-Amino Acid Evolutionary Profiles

Figure 19:
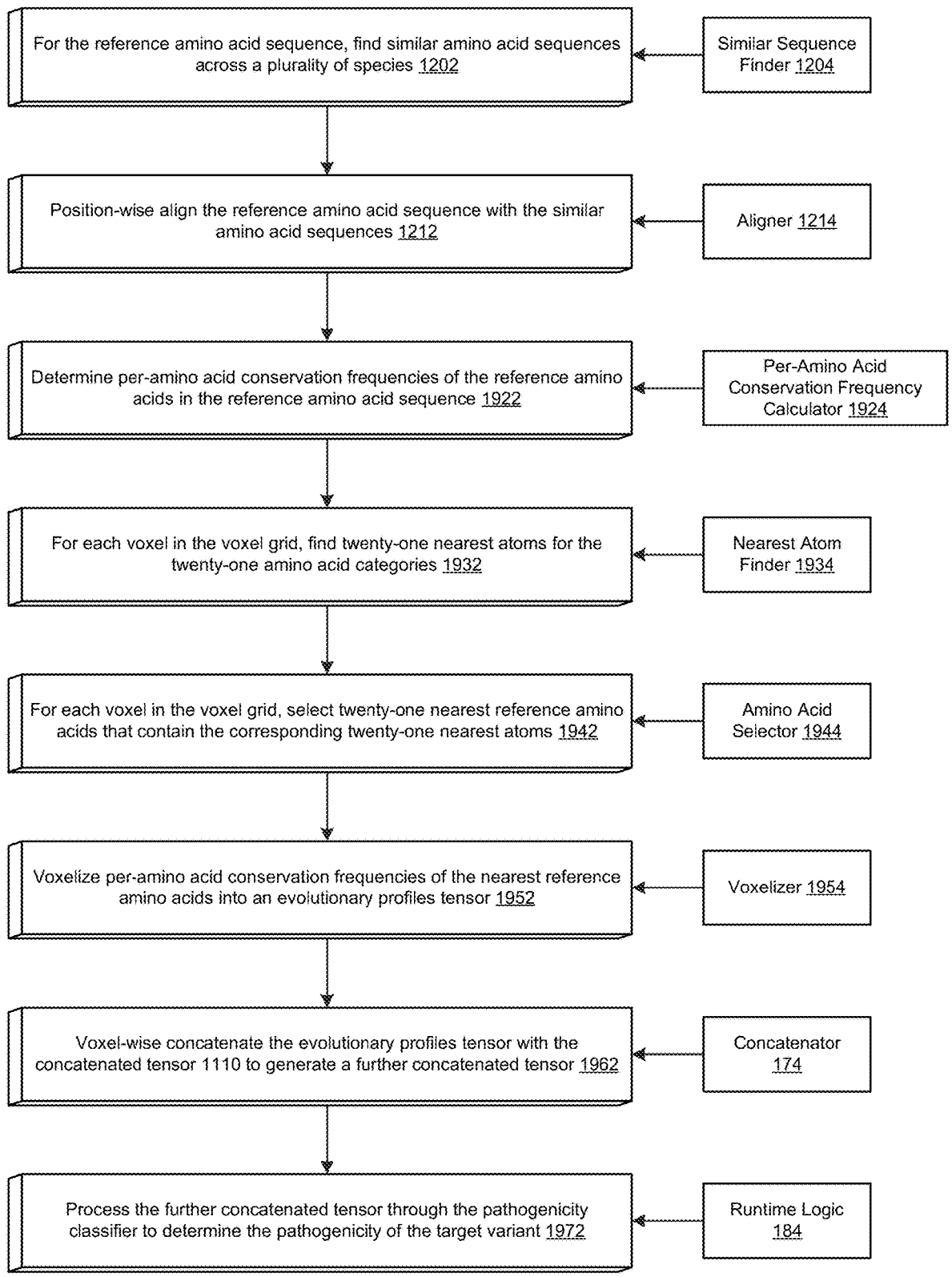
FIG. 19 is a flow diagram that illustrates a process of a system for determining and assigning per-amino acid conservation frequencies of nearest atoms to voxels (voxelizing), in accordance with one implementation of the technology disclosed.

FIG. 19 is a flow diagram that illustrates a process 1900 of a system for determining and assigning per-amino acid conservation frequencies of nearest atoms to voxels (voxelizing). In FIG. 19, the steps 1202 and 1212 are the same as FIG. 12.

At step 1922, a per-amino acid conservation frequency calculator 1924 of the system uses the multi-sequence alignment to determine per-amino acid conservation frequencies of the reference amino acids in the reference amino acid sequence 202.

At step 1932, a nearest atom finder 1934 of the system finds, for each of the voxels 514 in the voxel grid 522, twenty-one nearest atoms across each of the twenty-one amino acid categories. Each of the twenty-one nearest atoms is different from each other because they are selected from different amino acid categories. This leads to the selection of twenty-one unique nearest reference amino acids for a particular voxel, which in turn leads to generation of twenty-one unique position frequency matrices for the particular voxel, and which in turn leads to determination of twenty-one unique per-amino acid conservation frequencies for the particular voxel.

At step 1942, an amino acid selector 1944 of the system selects, for each of the voxels 514 in the voxel grid 522, twenty-one reference amino acids in the reference amino acid sequence 202 that contain the twenty-one nearest atoms identified at the step 1932. Such reference amino acids can be called nearest reference amino acids.

At step 1952, a voxelizer 1954 of the system voxelizes pen-amino acid conservation frequencies of the twenty-one nearest reference amino acids identified for the particular voxel at the step 1942. The twenty-one nearest reference amino acids are necessarily located at twenty-one different positions in the reference amino acid sequence 202 because they correspond to different underlying nearest atoms. Accordingly, for the particular voxel, twenty-one position frequency matrices can be generated for the twenty-one nearest reference amino acids. The twenty-one position frequency matrices can be generated across multiple species whose homologous amino acid sequences are position-wise aligned with the reference amino acid sequence 202, as discussed above with respect to FIGS. 12 to 15.

Then, using the twenty-one position frequency matrices, twenty-one position-specific conservation scores can be calculated for the twenty-one nearest reference amino acids identified for the particular voxel. These twenty-one position-specific conservation scores form the pen-amino acid conservation frequencies for the particular voxel, similar to the pan-amino acid conservation frequencies sequence 1502 in FIG. 12; except the sequence 1502 has many zero entries, whereas each element (feature) in a per-amino acid conservation frequencies sequence has a value (e.g., a floating point number) because the twenty-one nearest reference amino acids across the twenty-one amino acid categories necessarily have different positions that yield different position frequency matrices and thereby different per-amino acid conservation frequencies.

The above process is executed for each of the voxels 514 in the voxel grid 522, and the resulting voxel-wise per-amino acid conservation frequencies voxelized, tensorized, concatenated, and processed for pathogenicity determination similar to the pan-amino acid conservation frequencies discussed with respect to FIGS. 12 to 18.

Annotation Channels

FIG. 20 shows various examples of voxelized annotation channels 2000 that are concatenated with the distance channel tensor 700. In some implementations, the voxelized annotation channels are one-hot indicators for different protein annotations, for example whether an amino acid (residue) is part of a transmembrane region, a signal peptide, an active site, or any other binding site, or whether the residue is subject to posttranslational modifications, Path-Ratio (See Pei P, Zhang A: A Topological Measurement for Weighted Protein Interaction Network. *CSB* 2005, 268-278.), etc. Additional examples of the annotation channels can be found below in the Particular Implementations section and in the Claims The voxelized annotation channels are arranged voxel-wise such that the voxels can have a same annotation sequence like the voxelized reference allele and alternative allele sequences (e.g., annotation channels 2002, 2004, 2006), or the voxels can have respective annotation sequences like the voxelized per-voxel evolutionary profiles 1700 (e.g., annotation channels 2012, 2014, 2016 (as indicated by different colors)).

The annotation channels are voxelized, tensorized, concatenated, and processed for pathogenicity determination similar to the pan-amino acid conservation frequencies discussed with respect to FIGS. 12 to 18.

Structural Confidence Channels

The technology disclosed can also concatenate various voxelized structural confidence channels with the distance channel tensor 700. Some examples of the structure confidence channels include GMQE score (provided by Swiss-Model); B-factor; temperature factor column of homology models (indicates how well a residue satisfies (physical) constraints in the protein structure); normalized number of aligning template proteins for the residue nearest to the center of a voxel (alignments provided by HHpred, e.g., voxel is nearest to a residue at which 3 of 6 template structures align, signifying that the feature has value 3/6=0 5; minimum, maximum, and mean TM-scores; and predicted TM-scores of the template protein structures that align to the residue that is nearest to a voxel (continuing the example above, assume the 3 template structure has TM-scores 0.5, 0.5 and 1.5, then the minimum is 0.5, the mean is 2/3, and the maximum is 1.5). The TM-scores can be provided per protein template by HHpred. Additional examples of the structural confidence channels can be found below in the Particular Implementations section and in the Claims The voxelized structural confidence channels are arranged voxel-wise such that the voxels can have a same structural confidence sequence like the voxelized reference allele and alternative allele sequences, or the voxels can have respective structural confidence sequences like the voxelized per-voxel evolutionary profiles 1700.

The structural confidence channels are voxelized, tensorized, concatenated, and processed for pathogenicity determination similar to the pan-amino acid conservation frequencies discussed with respect to FIGS. 12 to 18.

Pathogenicity Classifier

Figure 21:
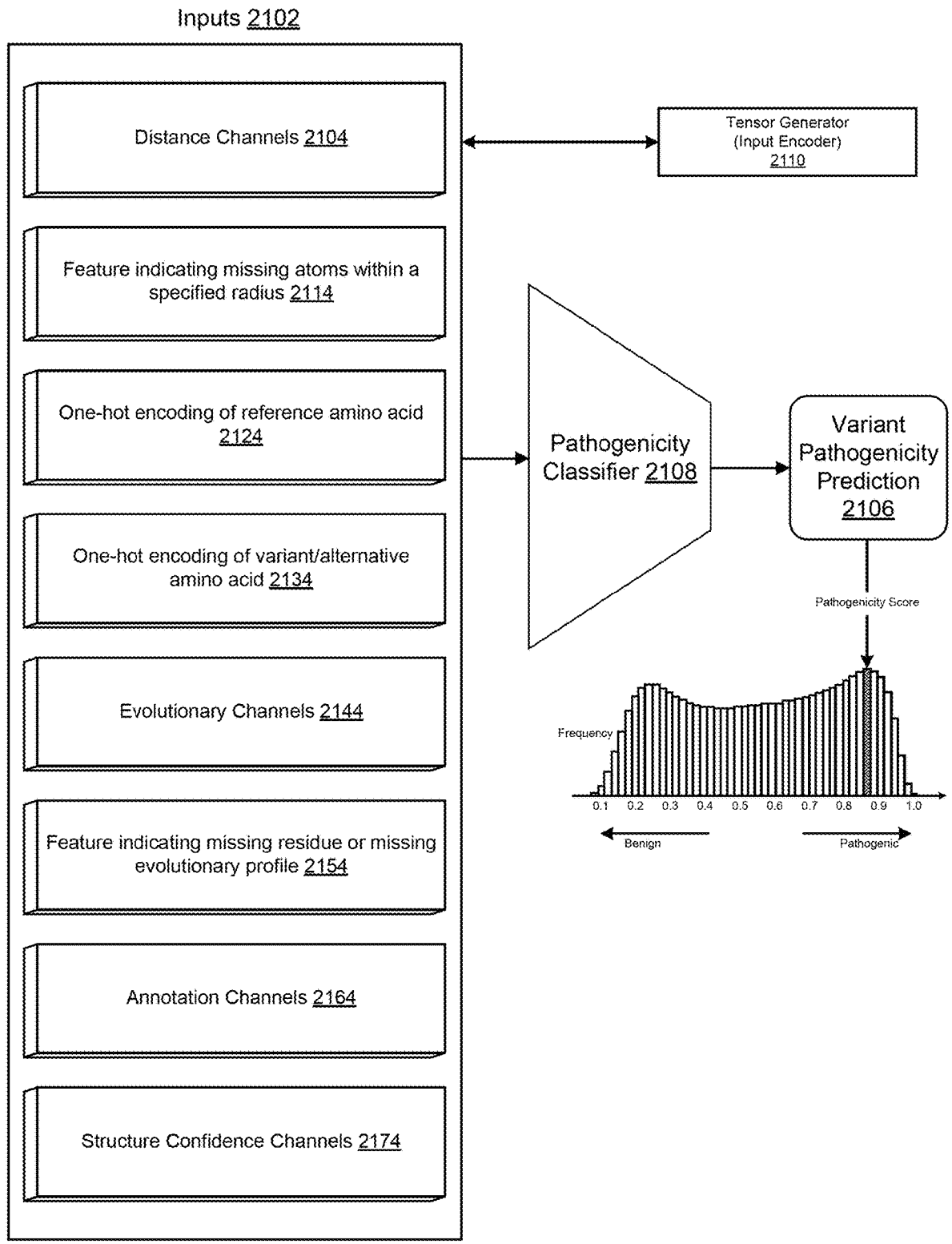
FIG. 21 illustrates different combinations and permutations of input channels that can be provided as inputs to a pathogenicity classifier for pathogenicity determination of a target variant, in accordance with one implementation of the technology disclosed.
Figure 22:
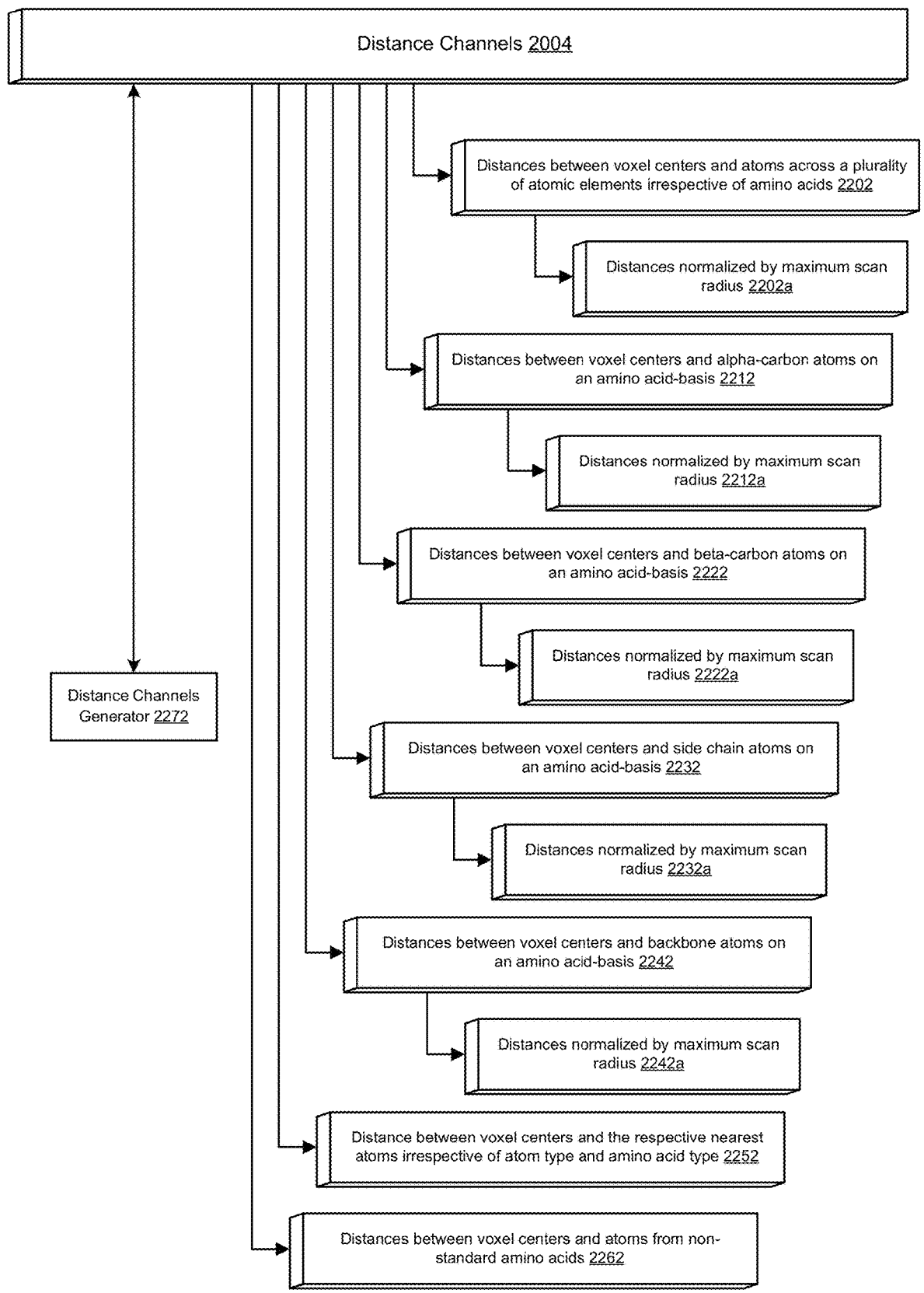
FIG. 22 shows different methods of calculating the disclosed distance channels, in accordance with various implementations of the technology disclosed.

FIG. 21 illustrates different combinations and permutations of input channels that can be provided as inputs 2102 to a pathogenicity classifier 2108 for a pathogenicity determination 2106 of a target variant. One of the inputs 2102 can be distance channels 2104 generated by a distance channels generator 2272. FIG. 22 shows different methods of calculating the distance channels 2104. In one implementation, the distance channels 2104 are generated based on distances 2202 between voxel centers and atoms across a plurality of atomic elements irrespective of amino acids. In some implementations, the distances 2202 are normalized by a maximum scan radius to generate normalized distances 2202*a*. In another implementation, the distance channels 2104 are generated based on distances 2212 between voxel centers and alpha-carbon atoms on an amino acid-basis. In some implementations, the distances 2212 are normalized by the maximum scan radius to generate normalized distances 2212*a*. In yet another implementation, the distance channels 2104 are generated based on distances 2222 between voxel centers and beta-carbon atoms on an amino acid-basis. In some implementations, the distances 2222 are normalized by the maximum scan radius to generate normalized distances 2222*a*. In yet another implementation, the distance channels 2104 are generated based on distances 2232 between voxel centers and side chain atoms on an amino acid-basis. In some implementations, the distances 2232 are normalized by the maximum scan radius to generate normalized distances 2232*a*. In yet another implementation, the distance channels 2104 are generated based on distances 2242 between voxel centers and backbone atoms on an amino acid-basis. In some implementations, the distances 2242 are normalized by the maximum scan radius to generate normalized distances 2242a. In yet another implementation, the distance channels 2104 are generated based on distances 2252 (one feature) between voxel centers and the respective nearest atoms irrespective of atom type and amino acid type. In yet another implementation, the distance channels 2104 are generated based on distances 2262 (one feature) between voxel centers and atoms from non-standard amino acids. In some implementations, the distances between the voxels and the atoms are calculated based on polar coordinates of the voxels and the atoms. The polar coordinates are parameterized by angles between the voxels and the atoms. In one implementation, this angel information is used to generate an angle channel for the voxels (i.e., independent of the distance channels). In some implementations, angles between a nearest atom and neighboring atoms (e.g., backbone atoms) can be used as features that are encoded with the voxels.

Another one of the inputs 2102 can be a feature 2114 indicating missing atoms within a specified radius.

Another one of the inputs 2102 can be one-hot encoding 2124 of the reference amino acid. Another one of the inputs 2102 can be one-hot encoding 2134 of the variant/alternative amino acid.

Figure 23:
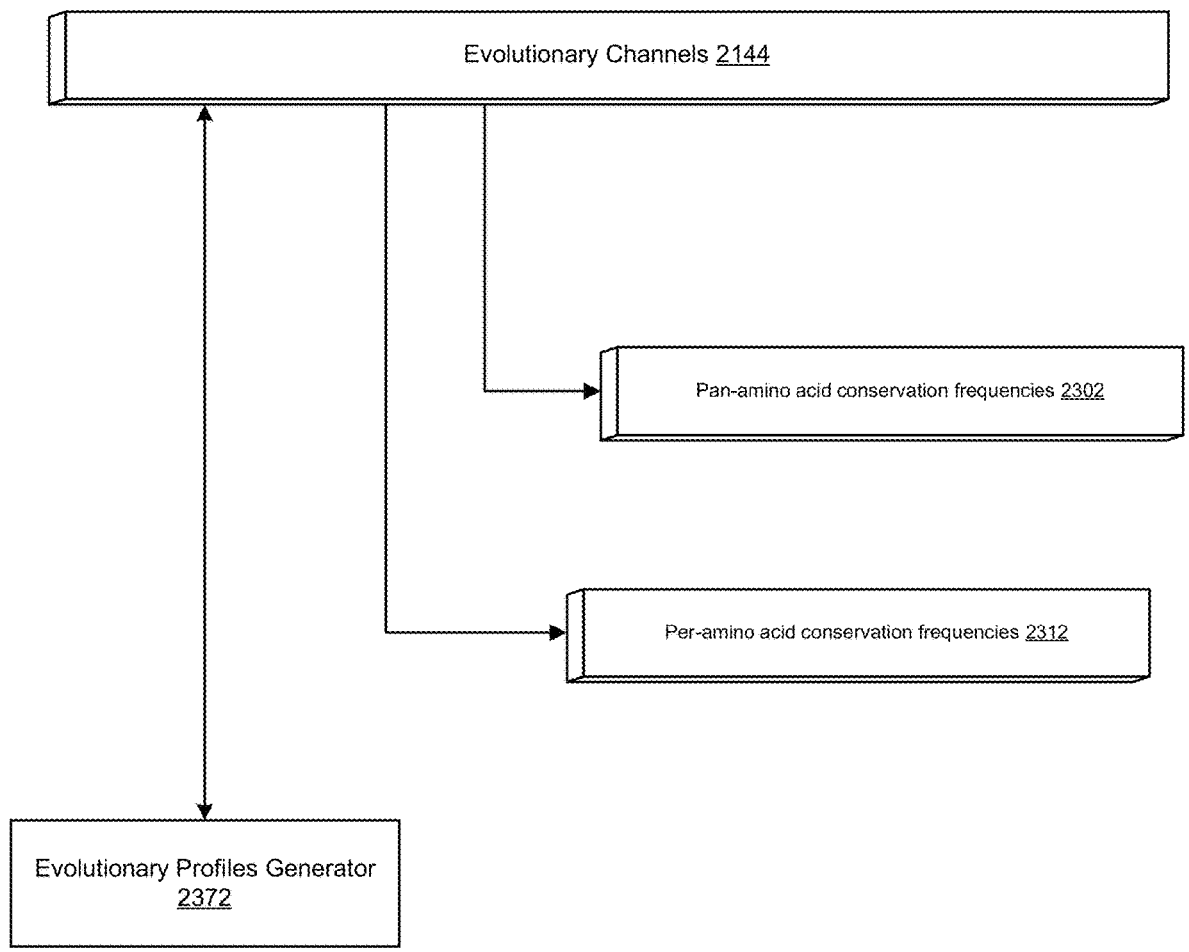
FIG. 23 shows different examples of the evolutionary channels, in accordance with various implementations of the technology disclosed.

Another one of the inputs 2102 can be evolutionary channels 2144 generated by an evolutionary profiles generator 2372, shown in FIG. 23. In one implementation, the evolutionary channels 2144 can be generated based on pan-amino acid conservation frequencies 2302. In another implementation, the evolutionary channels 2144 can be generated based on pan-amino acid conservation frequencies 2312.

Another one of the inputs 2102 can be a feature 2154 indicating missing residue or missing evolutionary profile.

Figure 24:
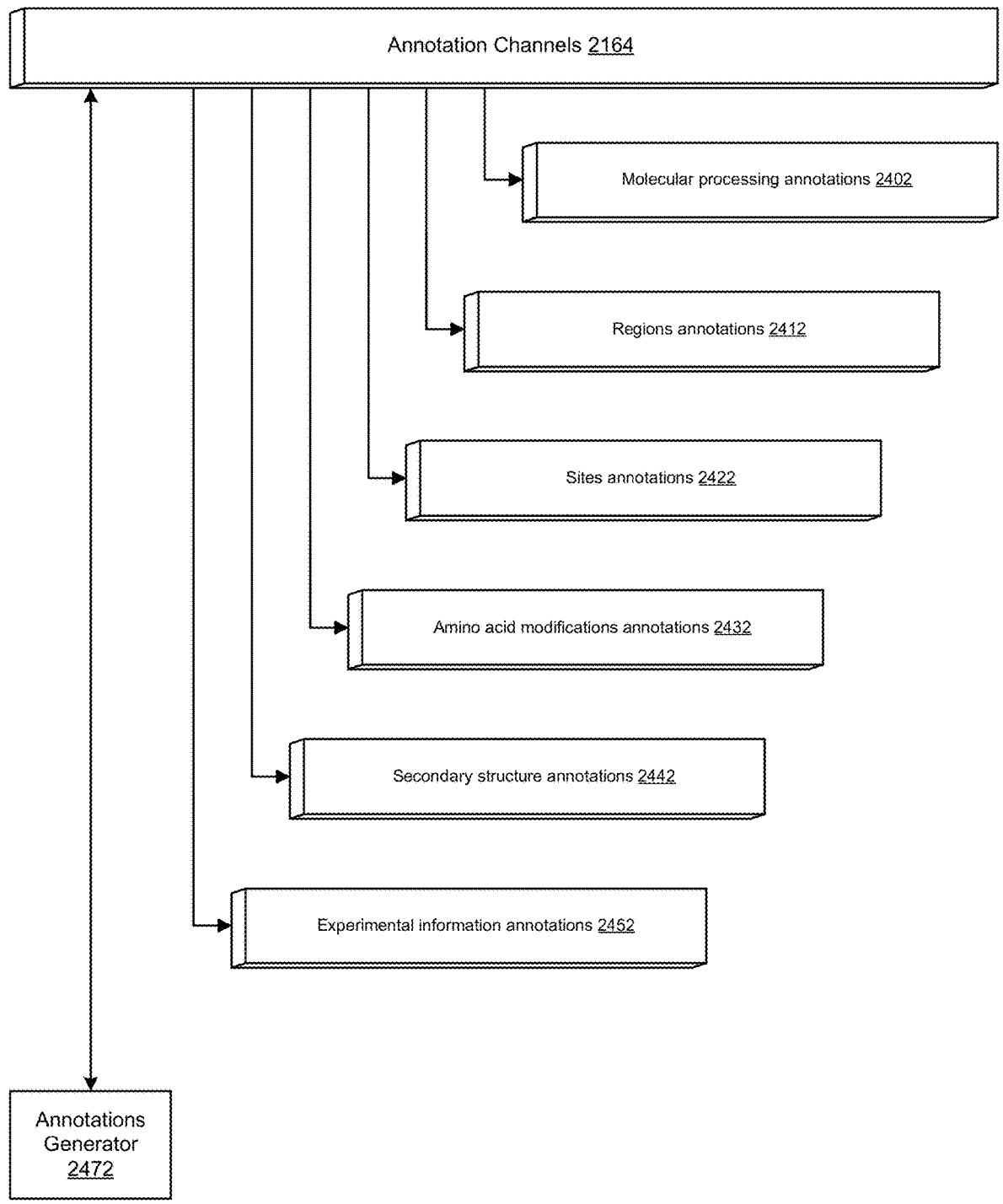
FIG. 24 shows different examples of the annotations channels, in accordance with various implementations of the technology disclosed.

Another one of the inputs 2102 can be annotations channels 2164 generated by an annotations generator 2472, shown in FIG. 24. In one implementation, the annotations channels 2154 can be generated based on molecular processing annotations 2402. In another implementation, the annotations channels 2154 can be generated based on regions annotations 2412. In yet another implementation, the annotations channels 2154 can be generated based on sites annotations 2422. In yet another implementation, the annotations channels 2154 can be generated based on Amino acid modifications annotations 2432. In yet another implementation, the annotations channels 2154 can be generated based on secondary structure annotations 2442. In yet another implementation, the annotations channels 2154 can be generated based on experimental information annotations 2452.

Figure 25:
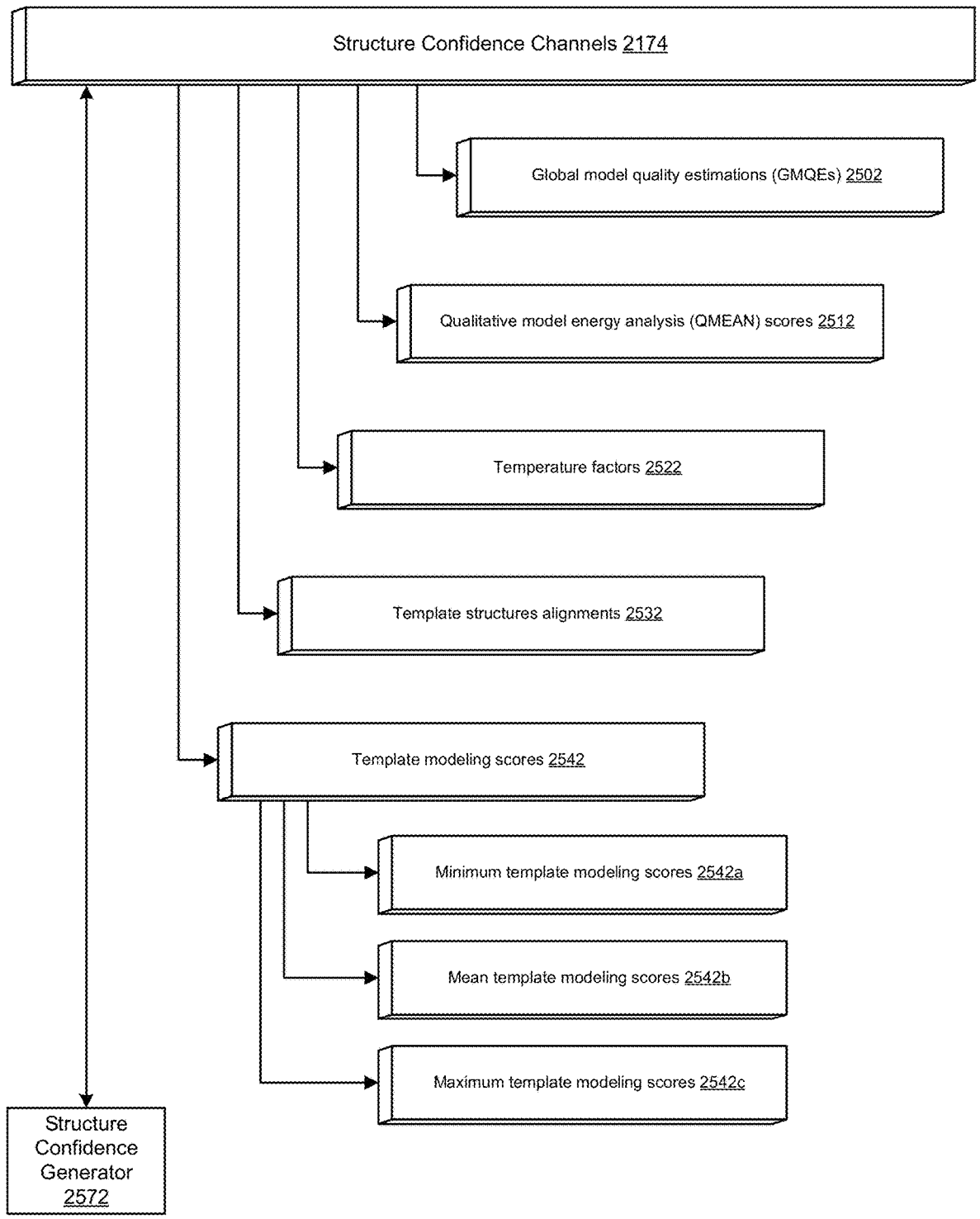
FIG. 25 shows different examples of the structure confidence channels, in accordance with various implementations of the technology disclosed.

Another one of the inputs 2102 can be structure confidence channels 2174 generated by a structure confidence generator 2572, shown in FIG. 25. In one implementation, the structure confidence 2174 can be generated based on global model quality estimations (GMQEs) 2502. In another implementation, the structure confidence 2174 can be generated based on qualitative model energy analysis (QMEAN) scores 2512. In yet another implementation, the structure confidence 2174 can be generated based on temperature factors 2522. In yet another implementation, the structure confidence 2174 can be generated based on template modeling scores 2542. Examples of the template modeling scores 2542 include minimum template modeling scores 2542a, mean template modeling scores 2542b, and maximum template modeling scores 2542c.

A person skilled in the art will appreciate that any permutation and combination of the input channels can be concatenated into an input for processing through the pathogenicity classifier 2108 for the pathogenicity determination 2106 of the target variant. In some implementations, only a subset of the input channels may be concatenated. The input channels can be concatenated in any order. In one implementation, the input channels can be concatenated into a single tensor by a tensor generator (input encoder) 2110. This single tensor can then be provided as input to the pathogenicity classifier 2108 for the pathogenicity determination 2106 of the target variant.

In one implementation, the pathogenicity classifier 2108 uses convolutional neural networks (CNNs) with a plurality of convolution layers. In another implementation, the pathogenicity classifier 2108 uses recurrent neural networks (RNNs) such as a long short-term memory networks (LSTMs), bi-directional LSTMs (Bi-LSTMs), and gated recurrent units (GRU)s. In yet another implementation, the pathogenicity classifier 2108 uses both the CNNs and the RNNs. In yet another implementation, the pathogenicity classifier 2108 uses graph-convolutional neural networks that model dependencies in graph-structured data. In yet another implementation, the pathogenicity classifier 2108 uses variational autoencoders (VAEs). In yet another implementation, the pathogenicity classifier 2108 uses generative adversarial networks (GANs). In yet another implementation, the pathogenicity classifier 2108 can also be a language model based, for example, on self-attention such as the one implemented by Transformers and BERTs.

In yet other implementations, the pathogenicity classifier 2108 can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous stochastic gradient descent (SGD). It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, attention mechanisms, and gaussian error linear unit.

The pathogenicity classifier 2108 is trained using backpropagation-based gradient update techniques. Example gradient descent techniques that can be used for training the pathogenicity classifier 2108 include stochastic gradient descent, batch gradient descent, and mini-batch gradient descent. Some examples of gradient descent optimization algorithms that can be used to train the pathogenicity classifier 2108 are Momentum, Nesterov accelerated gradient, Adagrad, Adadelta, RMSprop, Adam, AdaMax, Nadam, and AMSGrad. In other implementations, the pathogenicity classifier 2108 can be trained by unsupervised learning, semi-supervised learning, self-learning, reinforcement learning, multitask learning, multimodal learning, transfer learning, knowledge distillation, and so on.

Figure 26:
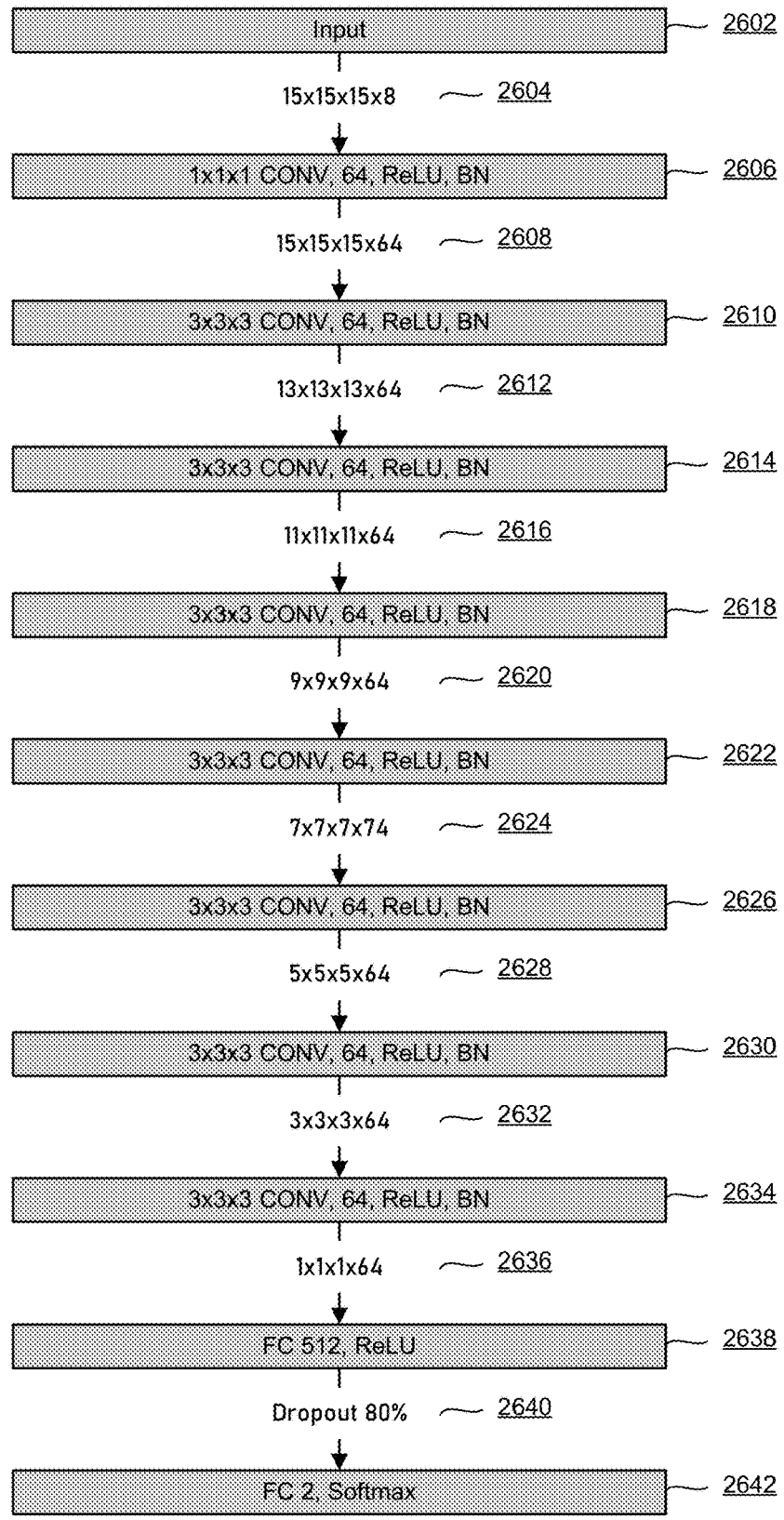
FIG. 26 shows an example processing architecture of the pathogenicity classifier, in accordance with one implementation of the technology disclosed.

FIG. 26 shows an example processing architecture 2600 of the pathogenicity classifier 2108, in accordance with one implementation of the technology disclosed. The processing architecture 2600 includes a cascade of processing modules 2606, 2610, 2614, 2618, 2622, 2626, 2630, 2634, 2638, and 2642 each of which can include 1D convolutions (1×1×1 CONV), 3D convolutions (3×3×3 CONV), ReLU non-linearity, and batch normalization (BN). Other examples of the processing modules include fully-connected (FC) layers, a dropout layer, a flattening layer, and a final softmax layer that produces exponentially normalized scores for the target variant belonging to a benign class and a pathogenic class. In FIG. 26, "64" denotes a number of convolution filters applied by a particular processing module. In FIG. 26, the size of an input voxel 2602 is 15×15×15×8. FIG. 26 also shows respective volumetric dimensionalities of the intermediate inputs 2604, 2608, 2612, 2616, 2620, 2624, 2628, 2632, 2636, and 2640 generated by the processing architecture 2600.

Figure 27:
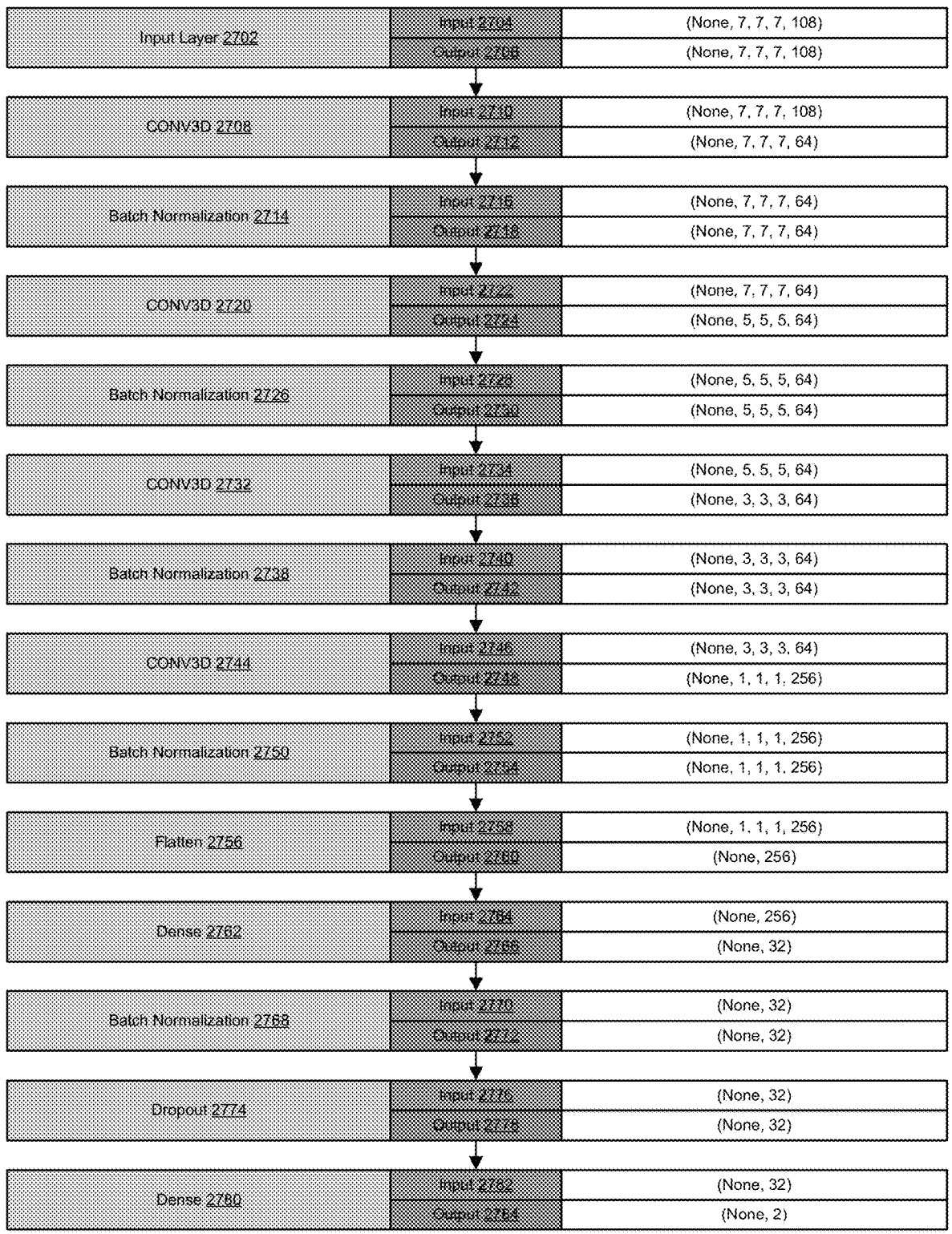
FIG. 27 shows an example processing architecture of the pathogenicity classifier, in accordance with one implementation of the technology disclosed.

FIG. 27 shows an example processing architecture 2700 of the pathogenicity classifier 2108, in accordance with one implementation of the technology disclosed. The processing architecture 2700 includes a cascade of processing modules 2708, 2714, 2720, 2726, 2732, 2738, 2744, 2750, 2756, 2762, 2768, 2774, and 2780 such as 1D convolutions (CONV 1D), 3D convolutions (CONV 3D), ReLU non-linearity, and batch normalization (BN). Other examples of the processing modules include fully-connected (dense) layers, a dropout layer, a flattening layer, and a final softmax layer that produces exponentially normalized scores for the target variant belonging to a benign class and a pathogenic class. In FIG. 27, "64" and "32" denote a number of convolution filters applied by a particular processing module. In FIG. 27, the size of an input voxel 2704 supplied by an input layer 2702 is 7×7×7×108. FIG. 27 also shows respective volumetric dimensionalities of the intermediate inputs 2710, 2716, 2722, 2728, 2734, 2740, 2746, 2752, 2758, 2764, 2770, 2776, and 2782 and the resulting intermediate outputs 2706, 2712, 2718, 2724, 2730, 2736, 2742, 2748, 2754, 2760, 2766, 2772, 2778, and 2784 generated by the processing architecture 2700.

A person skilled in the art will appreciate that other current and future artificial intelligence, machine learning, and deep learning models, datasets, and training techniques can be incorporated in the disclosed variant pathogenicity classifier without deviating from the spirit of the technology disclosed.

Performance Results as Objective Indicia of Inventiveness and Non-Obviousness

The variant pathogenicity classifier disclosed herein makes pathogenicity predictions based on 3D protein structures and is referred to as "PrimateAI 3D." "Primate AI" is a commonly owned and previously disclosed variant pathogenicity classifier that makes pathogenicity predictions based protein sequences. Additional details about PrimateAI can be found in commonly owned U.S. patent application Ser. Nos. 16/160,903; 16/160,986; 16/160,968; and 16/407,149 and in Sundaram, L et al. Predicting the clinical impact of human mutation with deep neural networks. *Nat. Genet.* 50, 1161-1170 (2018).

FIGS. 28, 29, 30, and 31 use PrimateAI as a benchmark model to demonstrate PrimateAI 3D's classification superiority over PrimateAI. The performance results in FIGS. 28, 29, 30, and 31 are generated on the classification task of accurately distinguishing benign variants from pathogenic variants across a plurality of validation sets. PrimateAI 3D is trained on training sets that are different from the plurality of validation sets. PrimateAI 3D is trained on common human variants and variants from primates used as benign dataset while simulated variants based on trinucleotide context used as unlabeled or pseudo-pathogenic dataset.

New developmental delay disorder (new DDD) is one example of a validation set used to compare the classification accuracy of Primate AI 3D against Primate AI. The new DDD validation set labels variants from individuals with DDD as pathogenic and labels the same variants from healthy relatives of the individuals with the DDD as benign. A similar labelling scheme is used with an autism spectrum disorder (ASD) validation set shown in FIG. 31.

BRCA1 is another example of a validation set used to compare the classification accuracy of Primate AI 3D against Primate AI. The BRCA1 validation set labels synthetically generated reference amino acid sequences simulating proteins of the BRCA1 gene as benign variants and labels synthetically altered allele amino acid sequences simulating proteins of the BRCA1 gene as pathogenic variants. A similar labelling scheme is used with different validation sets of the TP53 gene, TP53S3 gene and its variants, and other genes and their variants shown in FIG. 31.

Figure 28:
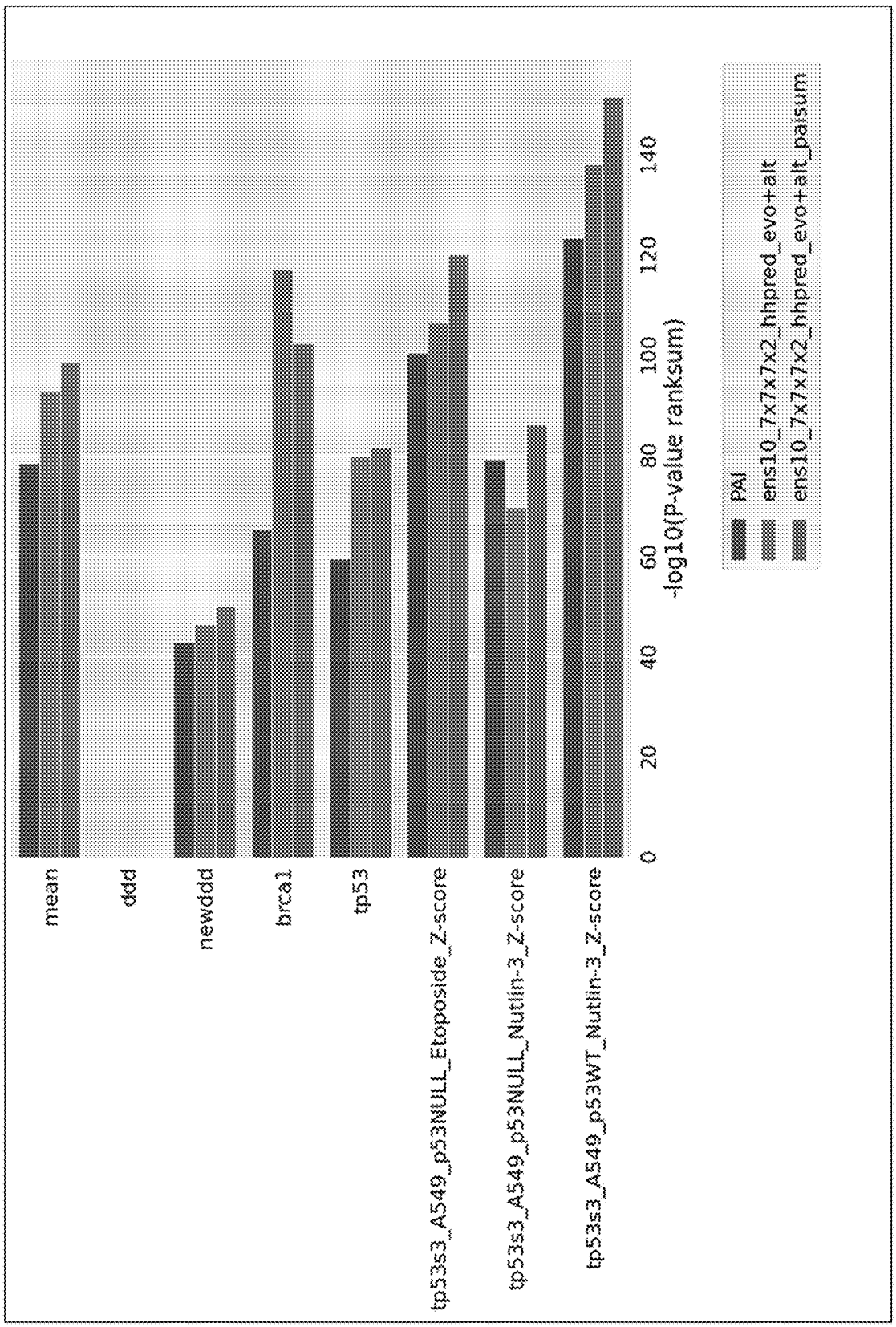
FIGS. 28, 29, 30, and 31 use PrimateAI as a benchmark model to demonstrate the disclosed PrimateAI 3D's classification superiority over PrimateAI.

FIG. 28 identifies performance of the benchmark PrimateAI model with blue horizontal bars and performance of the disclosed PrimateAI 3D model with orange horizontal bars. Green horizontal bars depict pathogenicity predictions derived by combining respective pathogenicity predictions of the disclosed PrimateAI 3D model and the benchmark PrimateAI model. In the legend, "ens10" denotes an ensemble of ten PrimateAI 3D models, each trained with a different seed training dataset and randomly initialized with different weights and biases. Also, "7×7×7×2" depicts the size of the voxel grid used to encode the input channels during the training of the ensemble of ten PrimateAI 3D models. For a given variant, the ensemble of ten PrimateAI 3D models respectively generates ten pathogenicity predictions, which are subsequently combined (e.g., by averaging) to generate a final pathogenicity prediction for the given variant. This logic analogous applies to ensembles of different group sizes.

Also, in FIG. 28, the y-axis has the different validation sets and the x-axis has p-values. Greater p-values, i.e., longer horizontal bars denote greater accuracy in differentiating benign variants from pathogenic variants. As demonstrated by the p-values in FIG. 28, PrimateAI 3D outperforms PrimateAI across most of the validation sets (only exception being the tp53s3_A549 validation set). That is, the orange horizontal bars for PrimateAI 3D are consistently longer than the blue horizontal bars for PrimateAI.

Also, in FIG. 28, a "mean" category along the y-axis calculates the mean of the p-values determined for each of the validation sets. In the mean category as well, PrimateAI 3D outperforms PrimateAI.

Figure 29:
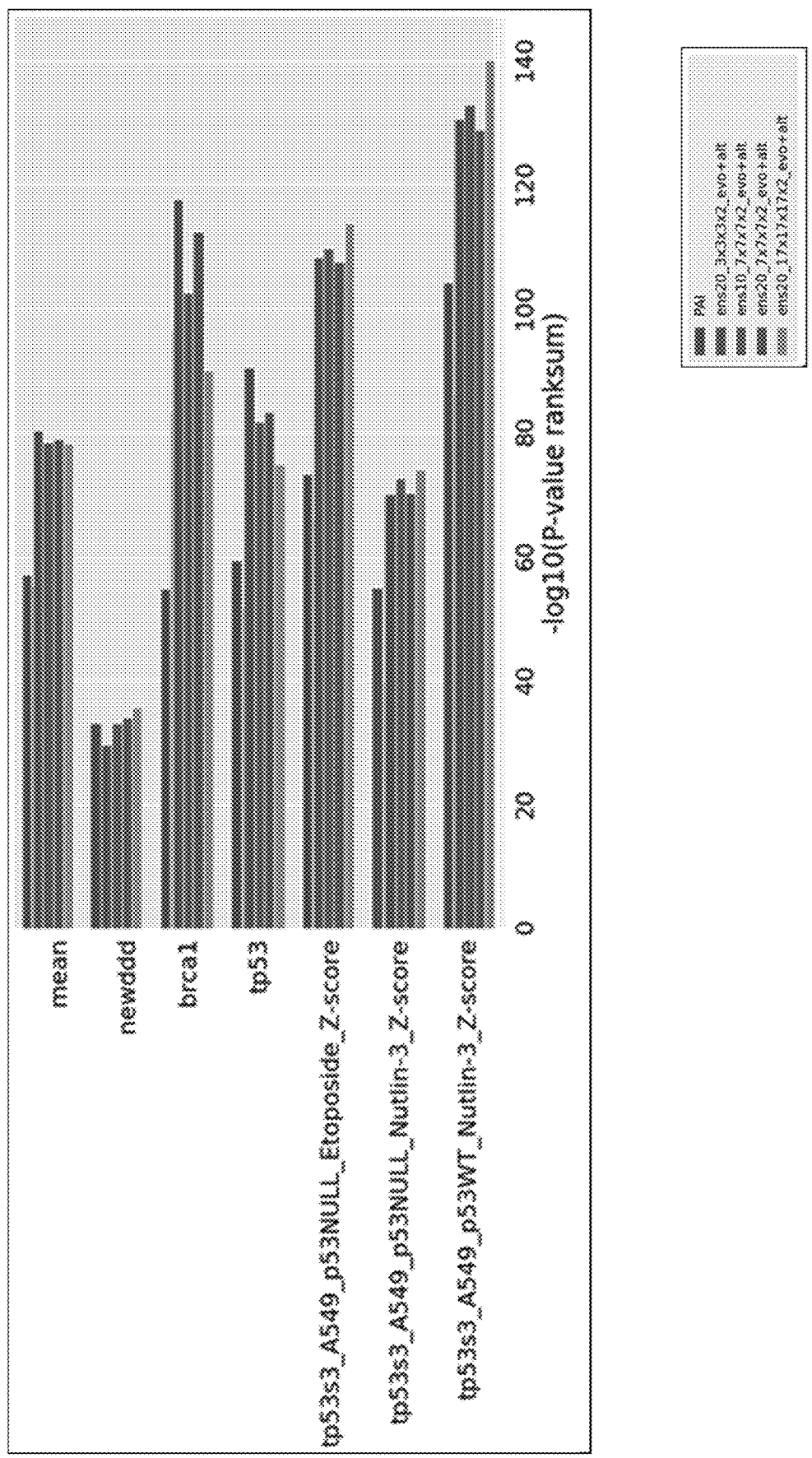

In FIG. 29, PrimateAI is represented by blue horizontal bars, an ensemble of twenty PrimateAI 3D models trained with a voxel grid of size 3×3×3 is represented by red horizontal bars, an ensemble of ten PrimateAI 3D models trained with a voxel grid of size 7×7×7×2 is represented by purple horizontal bars, an ensemble of twenty PrimateAI 3D models trained with a voxel grid of size 7×7×7×2 is represented by brown horizontal bars, and an ensemble of twenty PrimateAI 3D models trained with a voxel grid of size 17×17×17×2 is represented by purple horizontal bars.

Also, in FIG. 29, the y-axis has the different validation sets and the x-axis has p-values. As before, greater p-values, i.e., longer horizontal bars denote greater accuracy in differentiating benign variants from pathogenic variants. As demonstrated by the p-values in FIG. 20, different configurations of PrimateAI 3D outperform PrimateAI across most of the validation sets. That is, the red, purple, brown, and pink horizontal bars for PrimateAI 3D are mostly longer than the blue horizontal bars for PrimateAI.

Also, in FIG. 29, a "mean" category along the y-axis calculates the mean of the p-values determined for each of the validation sets. In the mean category as well, the different configurations of PrimateAI 3D outperform PrimateAI.

Figure 30:
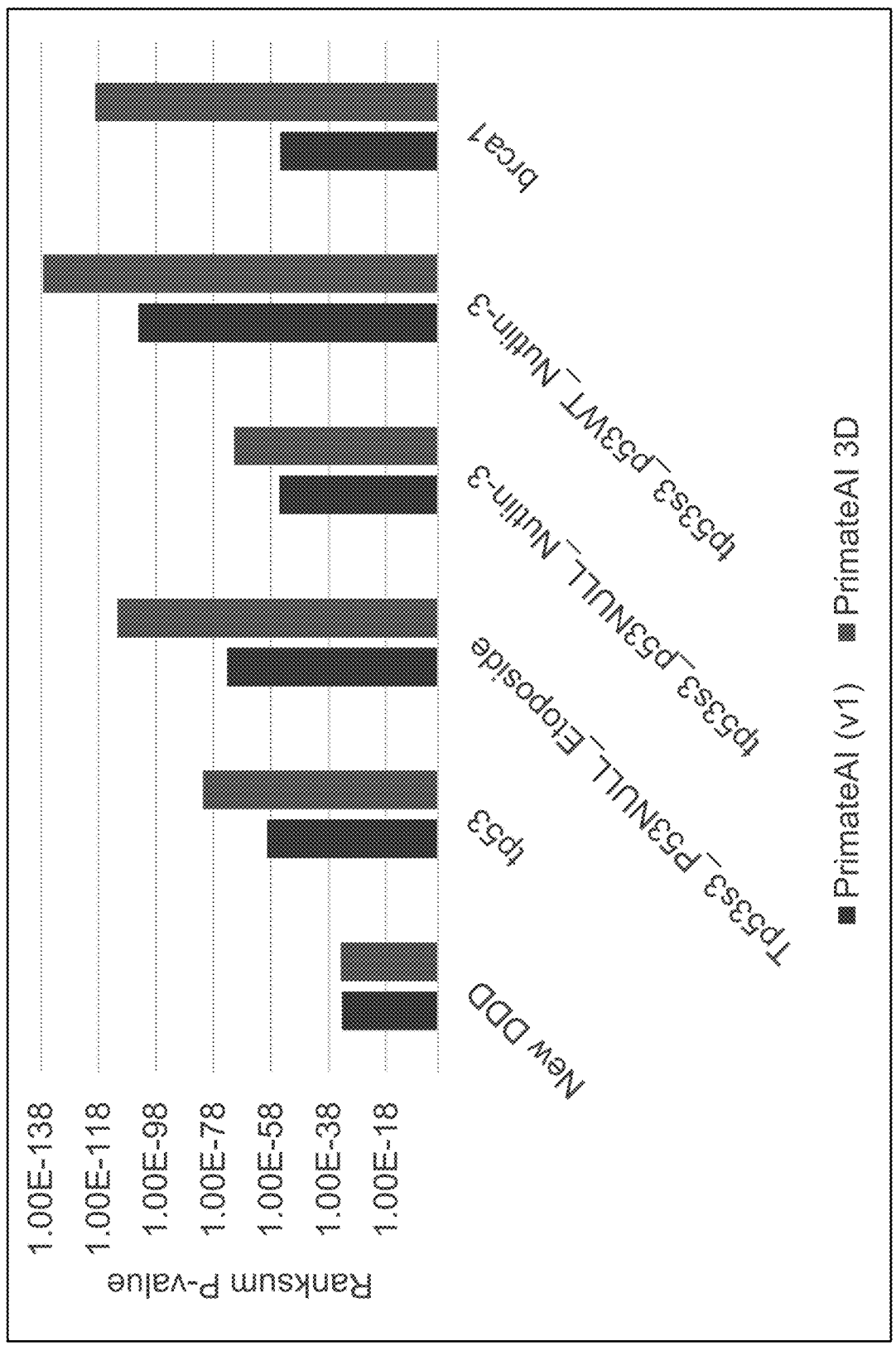

In FIG. 30, the red vertical bars represent PrimateAI, and the cyan vertical bars represent PrimateAI 3D. In FIG. 30, the y-axis has p-values, and the x-axis has the different validation sets. In FIG. 30, without exceptions, PrimateAI 3D consistently outperforms PrimateAI across all of the validation sets. That is, the cyan vertical bars for PrimateAI 3D are always longer than the red vertical bars for PrimateAI.

Figure 31:
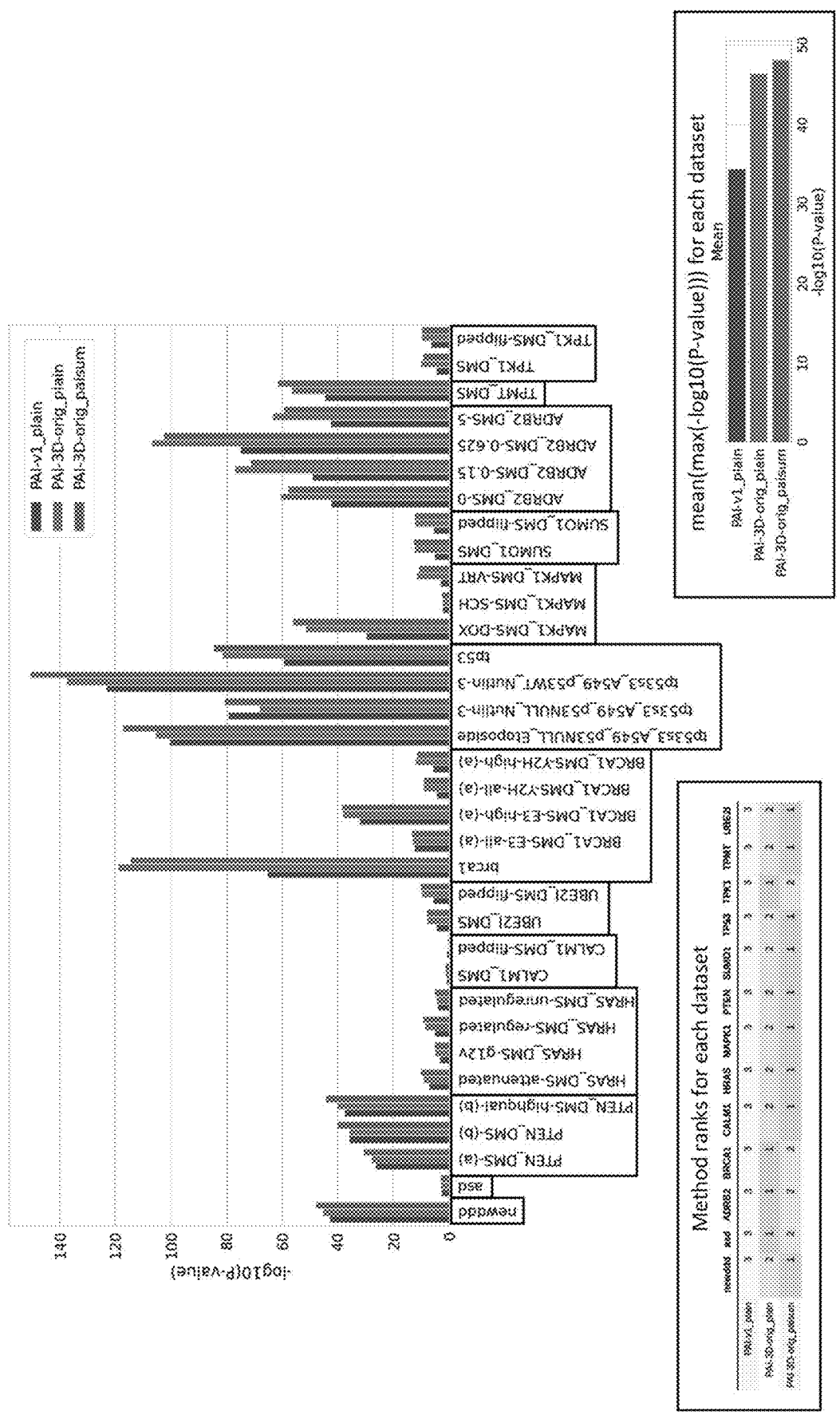

FIG. 31 identifies performance of the benchmark PrimateAI model with blue vertical bars and performance of the disclosed PrimateAI 3D model with orange vertical bars. Green vertical bars depict pathogenicity predictions derived by combining respective pathogenicity predictions of the disclosed PrimateAI 3D model and the benchmark PrimateAI model. In FIG. 31, the y-axis has p-values, and the x-axis has the different validation sets.

As demonstrated by the p-values in FIG. 31, PrimateAI 3D outperforms PrimateAI across most of the validation sets (only exception being the tp53s3_A549p53NULL_Nutlin-3 validation set). That is, the orange vertical bars for PrimateAI 3D are consistently longer than the blue vertical bars for PrimateAI.

Also, in FIG. 31, a separate "mean" chart calculates the mean of the p-values determined for each of the validation sets. In the mean chart as well, PrimateAI 3D outperforms PrimateAI.

The mean statistics may be biased by outliers. To address this, a separate "method ranks" chart is also depicted in FIG. 31. Higher rank denotes poorer classification accuracy. In the method ranks chart as well, PrimateAI 3D outperforms PrimateAI by having more counts of lower ranks 1 and 2 versus Primate AI having all 3s.

In FIGS. 28 to 31, it is also evident that combining PrimateAI 3D with PrimateAI produces superior classification accuracy. That is, a protein can be fed as an amino acid sequence to PrimateAI to generate a first output, and the same protein can be fed as a 3D, voxelized protein structure to PrimateAI 3D to generate a second output, and the first and second outputs can be combined or analyzed in aggregate to produce a final pathogenicity prediction for a variant experienced by the protein.

Efficient Voxelization

FIG. 32 is a flowchart illustrating an efficient voxelization process 3200 that efficiently identifies nearest atoms on a voxel-by-voxel basis.

The discussion now revisits the distance channels. As discussed above, the reference amino acid sequence 202 can contain different types of atoms, such as alpha-carbon atoms, beta-carbon atoms, oxygen atoms, nitrogen atoms, hydrogen atoms, and so on. Accordingly, as discussed above, the distance channels can be arranged by nearest alpha-carbon atoms, nearest beta-carbon atoms, nearest oxygen atoms, nearest nitrogen atoms, nearest hydrogen atoms, and so on. For example, in FIG. 6, each of the nine voxels 514 has twenty-one amino acid-wise distance channels for nearest alpha-carbon atoms. FIG. 6 can be further expanded for each of the nine voxels 514 to also have twenty-one amino acid-wise distance channels for nearest beta-carbon atoms, and for each of the nine voxels 514 to also have a nearest generic atom distance channel for a nearest atom irrespective of the type of the atom and the type of the amino acid. This way, each of the nine voxels 514 can have forty-three distance channels.

The discussion now turns to the number of distance calculations required to identify the nearest atoms on a voxel-by-voxel basis for inclusion in the distance channels. Consider the example in FIG. 3 that depicts a total of eight hundred and twenty-eight alpha-carbon atoms distributed across the twenty-one amino acid categories. To calculate the amino acid-wise distance channels 602-642 in FIG. 6, i.e., to determine the one hundred and eighty-nine distance values, distances are measured from each of the nine voxels 514 to each of the eight hundred and twenty-eight alpha-carbon atoms, resulting in 9*828=7,452 distance calculations. In the 3D case of twenty-seven voxels, this results in 828*27=22,356 distance calculations. When the eight hundred and twenty-eight beta-carbon atoms are also included, this number increases to 27*1656=44,712 distance calculations.

Figure 35A:
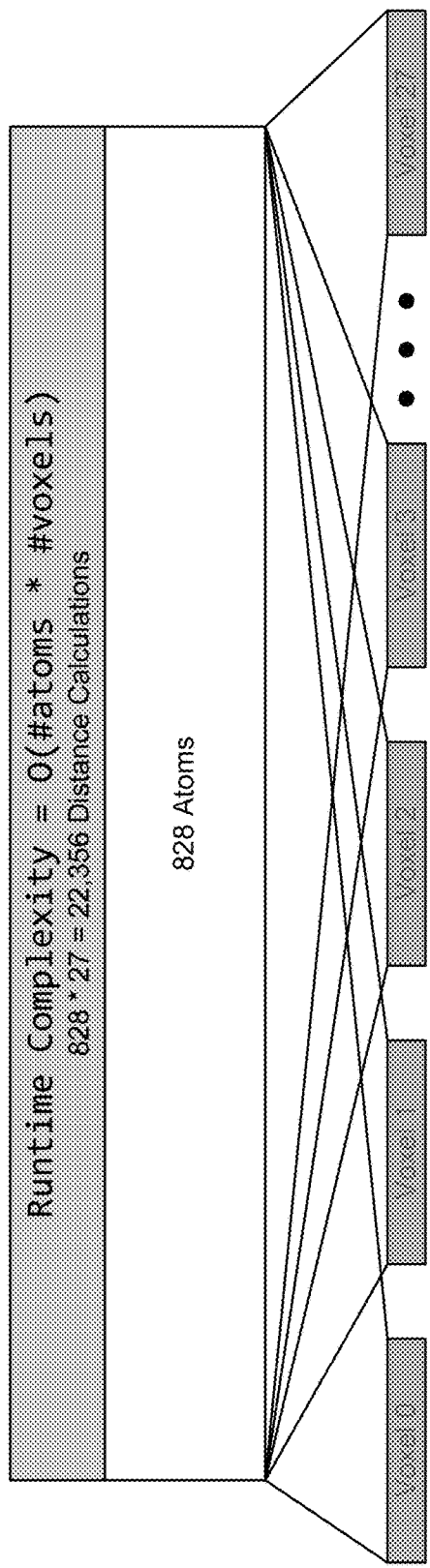
FIGS. 35A and 35B illustrate how the disclosed efficient voxelization has a runtime complexity of O(#atoms) versus the runtime complexity of O(#atoms*#voxels) without the use of disclosed efficient voxelization

This means that the runtime complexity of identifying the nearest atoms on a voxel-by-voxel basis for a single protein voxelization is O(#atoms*#voxels), as illustrated by FIG. 35A. Furthermore, the runtime complexity for a single protein voxelization increases to O(#atoms*#voxels*#attributes) when the distance channels are calculated across a variety of attributes (e.g., different features or channels per voxel like annotation channels and structural confidence channels).

Consequently, the distance calculations can become the most compute-consuming part of the voxelization process, taking valuable compute resources away from critical runtime tasks like model training and model inference. Consider, for example, the case of model training with a training dataset of 7,000 proteins. Generating distance channels for a plurality of voxels across a plurality of amino acids, atoms, and attributes can involve more than 100 voxelizations per protein, resulting in about 800,000 voxelizations in a single training iteration (epoch). A training run of 20-40 epochs, with rotation of atomic coordinates in each epoch, can result in as many as 32 million voxelizations.

In addition to the high compute cost, the size of the data for 32 million voxelizations is too big to fit in main memory (e.g., >20 TB for a 15×15×15 voxel grid). Considering repeated training runs for parameter optimization and ensemble learning, the memory footprint of the voxelization process gets too big to be stored on disk, making the voxelization process a part of the model training and not a precomputation step.

The technology disclosed provides an efficient voxelization process that achieves up to ~100× speedup over the runtime complexity of O(#atoms*#voxels). The disclosed efficient voxelization process reduces the runtime complexity for a single protein voxelization to O(#atoms). In the case of different features or channels per voxel, the disclosed efficient voxelization process reduces the runtime complexity for a single protein voxelization to O(#atoms*#attributes). As a result, the voxelization process becomes as fast as model training, shifting the computational bottleneck from voxelization back to computing neural network weights on processors such as GPUs, ASICs, TPUs, FPGAs, CGRAs, etc.

In some implementations of the disclosed efficient voxelization process involving large voxel grids, the runtime complexity for a single protein voxelization is O(#atoms+ voxels) and O(#atoms*#attributes+voxels) for the case of different features or channels per voxel. The "+voxels" complexity is observed when the number of atoms is minuscule compared to the number of voxels, for example, when there is one atom in a 100×100×100 voxel grid (i.e., one million voxels per atom). In such a scenario, the runtime is dominated by the overhead of the huge number of voxels, for example, for allocating the memory for one million voxels, initialization one million voxels to zero, etc.

The discussion now turns to details of the disclosed efficient voxelization process. FIGS. 32A, 32B, 33, 34, and 35B are discussed in tandem.

Starting with FIG. 32A, at step 3202, each atom (e.g., each of the 828 alpha-carbon atoms and each of the 828 beta-carbon atoms) is associated with a voxel that contains the atom (e.g., one of the nine voxels 514). The term "contains" refers to the 3D atomic coordinates of the atom being located in the voxel. The voxel that contains the atom is also referred to herein as "the atom-containing voxel."

FIGS. 32B and 33 describe how a voxel that contains a particular atom is selected. FIG. 33 uses 2D atomic coordinates as representative of 3D atomic coordinates. Note that the voxel grid 522 is regularly spaced with each of the voxels 514 having a same step size (e.g., 1 angstrom (Å) or 2 Å).

Also, in FIG. 33, the voxel grid 522 has magenta indices [0, 1, 2] along a first dimension (e.g., x-axis) and cyan indices [0, 1, 2] along a second dimension (e.g., y-axis). Also, in FIG. 33, the respective voxels 514 in the voxel 512 are identified by green voxel indices [Voxel 0, Voxel 1, . . . , Voxel 8] and by black voxel center indices [(1, 1), (1, 2), . . . , (3, 3)].

Also, in FIG. 33, center coordinates of the voxel centers along the first dimension, i.e., first dimension voxel coordinates, are identified in orange. Also, in FIG. 33, center coordinates of the voxel centers along the second dimension, i.e., second dimension voxel coordinates, are identified in red.

First, at step 3202a (Step 1 in FIG. 33), 3D atomic coordinates (1.7456, 2.14323) of the particular atom are quantized to generated quantized 3D atomic coordinates (1.7, 2.1). The quantization can be achieved by rounding or truncation of bits.

Then, at step 3202b (Step 2 in FIG. 33), voxel coordinates (or voxel centers or voxel center coordinates) of the voxels 514 are assigned to the quantized 3D atomic coordinates on a dimension-basis. For the first dimension, the quantized atomic coordinate 1.7 is assigned to Voxel 1 because it covers first dimension voxel coordinates ranging from 1 to 2 and is centered at 1.5 in the first dimension. Note that Voxel 1 has index 1 along the first dimension, in contrast to having index 0 along the second dimension.

For the second dimension, starting from Voxel 1, the voxel grid 522 is traversed along the second dimension. This results in the quantized atomic coordinate 2.5 being assigned to Voxel 7 because it covers second dimension voxel coordinates ranging from 2 to 3 and is centered at 2.5 in the second dimension. Note that Voxel 7 has index 2 along the second dimension, in contrast to having index 1 along the first dimension.

Then, at step 3202c (Step 3 in FIG. 33), dimension indices corresponding to the assigned voxel coordinates are selected. That is, for Voxel 1, index 1 is selected along the first dimension, and, for Voxel 7, index 2 is selected along the second dimension. A person skilled in the art will appreciate that the above steps can be analogously executed for a third dimension to select a dimension index along the third dimension.

Then, at step 3202d (Step 4 in FIG. 33), an accumulated sum is generated based on position-wise weighting the selected dimension indices by powers of a radix. The general idea behind positional numbering systems is that a numeric value is represented through increasing powers of the radix (or base), for example, binary is base two, ternary is base three, octal is base eight, and hexadecimal is base sixteen. This is often referred to as a weighted numbering system because each position is weighted by a power of the radix. The set of valid numericals for a positional numbering system is equal in size to the radix of that system. For example, there are ten digits in the decimal system, zero through nine, and three digits in the ternary system, zero, one, and two. The largest valid number in a radix system is one smaller than the radix (so eight is not a valid numerical in any radix system smaller than nine). Any decimal integer can be expressed exactly in any other integral base system, and vice-versa.

Returning to the example in FIG. 33, the selected dimension indices 1 and 2 are converted to a single integer by position-wise multiplying them with respective powers of base three and summing the results of the position-wise multiplications. Base three is selected here because the 3D atomic coordinates have three dimensions (although FIG. 33 shows only 2D atomic coordinates along two dimensions for simplicity's sake).

Since index 2 is positioned at the rightmost bit (i.e., the least significant bit), it is multiplied by three to the power of zero to yield two. Since index 1 is positioned at the second rightmost bit (i.e., the second least significant bit), it is multiplied by three to the power of one to yield three. This results in the accumulated sum being five.

Then, at step 3202e (Step 5 in FIG. 33), based on the accumulated sum, a voxel index of the voxel containing the particular atom is selected. That is, the accumulated sum is interpreted as the voxel index of the voxel containing the particular atom.

At step 3212, after each atom is associated with the atom-containing voxel, each atom is further associated with one or more voxels that are in a neighborhood of the atom-containing voxel, also referred to herein as "neighborhood voxels." The neighborhood voxels can be selected based on being within a predefined radius of the atom-containing voxel (e.g., 5 angstrom (Å)). In other implementations, the neighborhood voxels can be selected based on being contiguously adjacent to the atom-containing voxel (e.g., top, bottom, right, left adjacent voxels). The resulting association that associates each atom with the atom-containing voxel and the neighborhood voxels is encoded in an atom-to-voxels mapping 3402, also referred to herein as element-to-cells mapping. In one example, a first alpha-carbon atom is associated with a first subset of voxels 3404 that includes an atom-containing voxel and neighborhood voxels for the first alpha-carbon atom. In another example, a second alpha-carbon atom is associated with a second subset of voxels 3406 that includes an atom-containing voxel and neighborhood voxels for the second alpha-carbon atom.

Note that no distance calculations are made to determine the atom-containing voxel and the neighborhood voxels. The atom-containing voxel is selected by virtue of the spatial arrangement of the voxels that allows assignment of quantized 3D atomic coordinates to corresponding regularly spaced voxel centers in the voxel grid (without using any distance calculations). Also, the neighborhood voxels are selected by virtue of being spatially contiguous to the atom-containing voxel in the voxel grid (again without using any distance calculations).

At step 3222, each voxel is mapped to atoms to which it was associated at steps 3202 and 3212. In one implementation, this mapping is encoded in a voxel-to-atoms mapping 3412, which is generated based on the atom-to-voxels mapping 3402 (e.g., by applying a voxel-based sorting key on the atom-to-voxels mapping 3402). The voxel-to-atoms mapping 3412 is also referred to herein as "cell-to-elements mapping." In one example, a first voxel is mapped to a first subset of alpha-carbon atoms 3414 that includes alpha-carbon atoms associated with the first voxel at steps 3202 and 3212. In another example, a second voxel is mapped to a second subset of alpha-carbon atoms 3416 that includes alpha-carbon atoms associated with the second voxel at steps 3202 and 3212.

At step 3232, for each voxel, distances are calculated between the voxel and atoms mapped to the voxel at step 3222. Step 3232 has a runtime complexity of O(#atoms) because distance to a particular atom is measured only once from a respective voxel to which the particular atom is uniquely mapped in the voxel-to-atoms mapping 3412. This is true when no neighboring voxels are considered. Without neighbors, the constant factor that is implied in the big-O notation is 1. With neighbors, the big-O notation is equal to the number of neighbors+1 since the number of neighbors is constant for each voxel, and therefore the runtime complexity of O(#atoms) remains true. In contrast, in FIG. 35A, distances to a particular atom are redundantly measured as many times as the number of voxels (e.g., 27 distances for a particular atom due to 27 voxels).

Figure 35B:
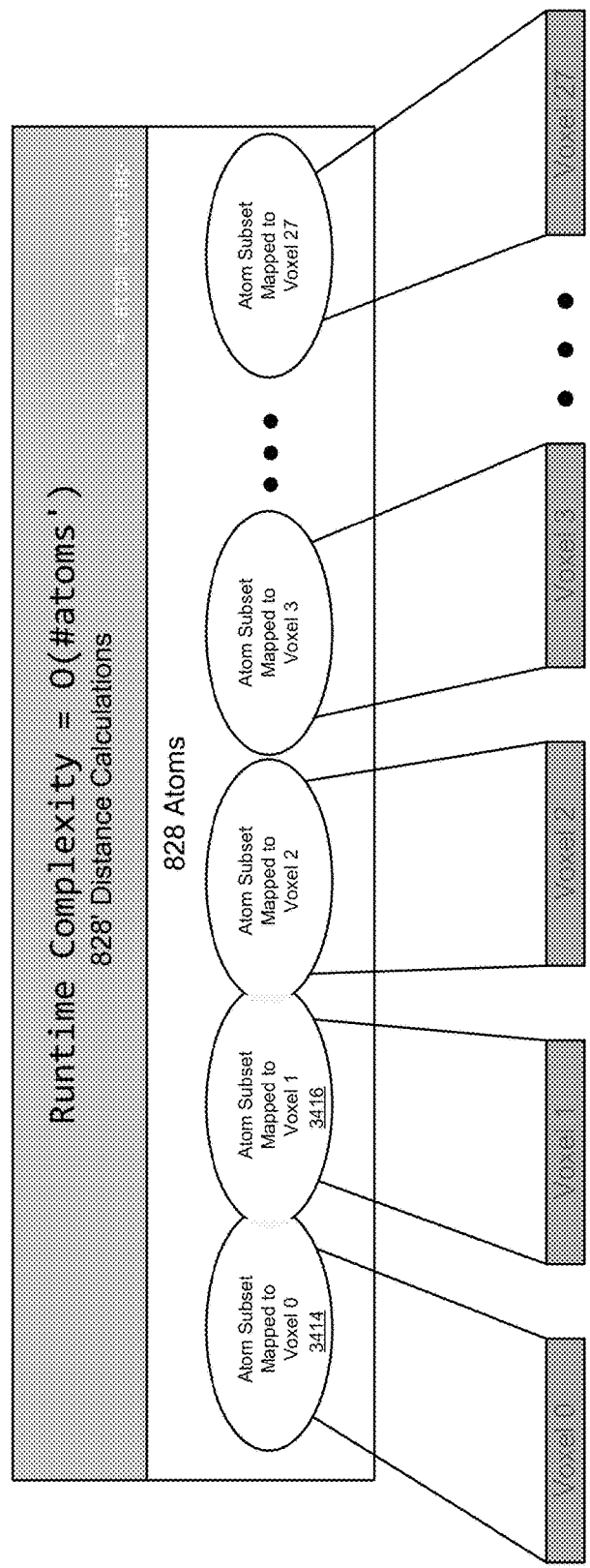

In FIG. 35B, based on the voxel-to-atoms mapping 3412, each voxel is mapped to a respective subset of the 828 atoms (not including distance calculations to neighborhood voxels), as illustrated by respective ovals for respective voxels. The respective subsets are largely non-overlapping, with some exceptions. Insignificant overlap exists due to some instances when multiple atoms are mapped to a same voxel, as indicated in FIG. 35B by the prime symbol "'" and the yellow overlap between the ovals. This minimal overlap has an additive effect on the runtime complexity of O(#atoms) and not a multiplicative effect. This overlap is a result of considering neighboring voxels, after determining the voxel that contains the atom. Without neighboring voxels, there can be no overlap, because an atom is only associated with one voxel. Considering neighbors, however, each neighbor could potentially be associated with the same atom (as long as there is no other atom of the same amino acid that is closer).

At step 3242, for each voxel, based on the distances calculated at step 3232, a nearest atom to the voxel is identified. In one implementation, this identification is encoded in a voxel-to-nearest atom mapping 3422, also referred to herein as "cell-to-nearest element mapping." In one example, the first voxel is mapped to a second alpha-carbon atom as its nearest alpha-carbon atom 3424. In another example, the second voxel is mapped to a thirty-first alpha-carbon atom as its nearest alpha-carbon atom 3426.

Furthermore, as the voxel-wise distances are calculated using the technique discussed above, the atom-type and amino acid-type categorization of the atoms and the corresponding distance values are stored to generate categorized distance channels.

Once the distances to nearest atoms are identified using the technique discussed above, these distances can be encoded in the distance channels for voxelization and subsequent processing by the pathogenicity classifier 2108.

Computer System

Figure 36:
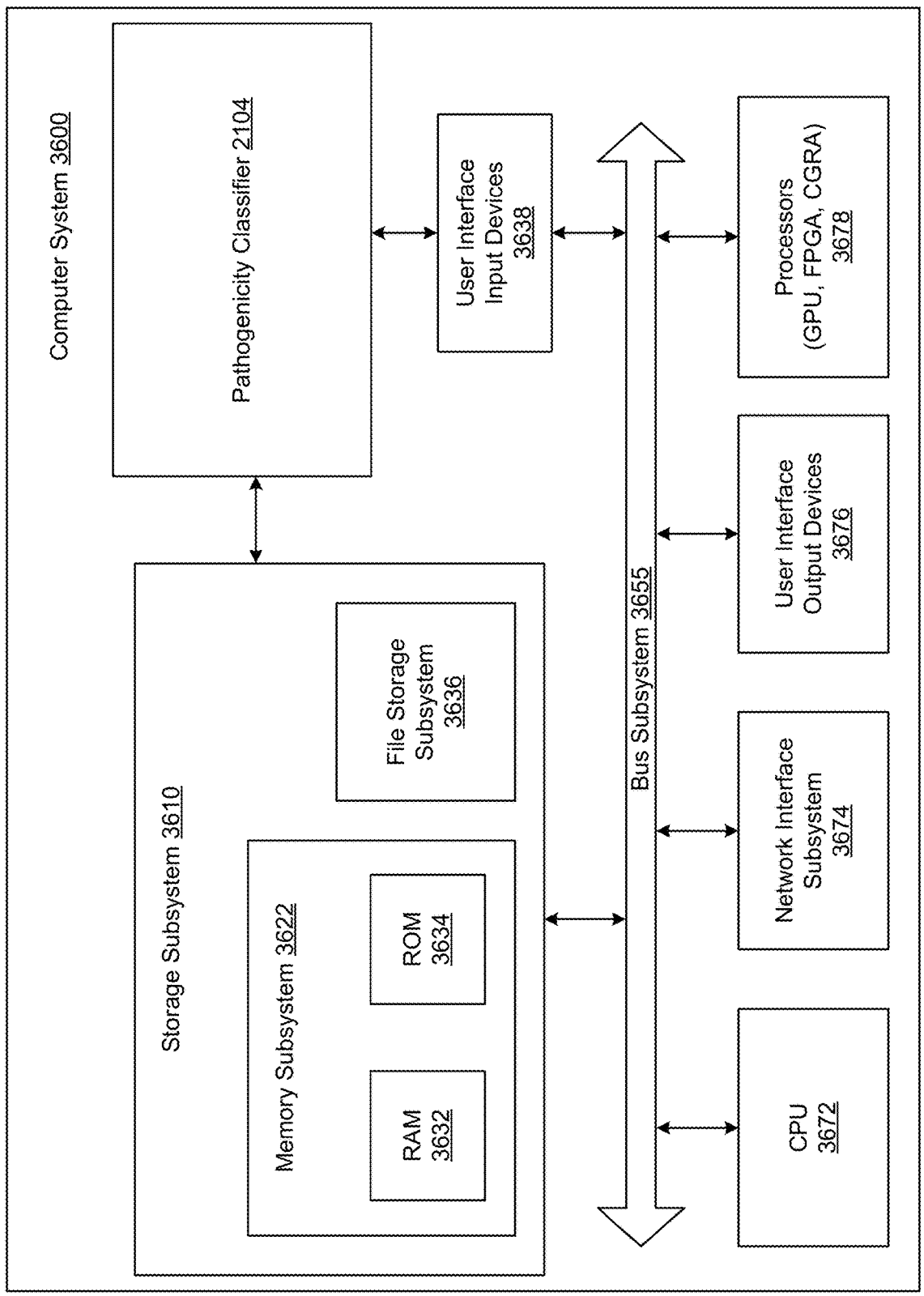
FIG. 36 shows an example computer system that can be used to implement the technology disclosed.

FIG. 36 shows an example computer system 3600 that can be used to implement the technology disclosed. Computer system 3600 includes at least one central processing unit (CPU) 3672 that communicates with a number of peripheral devices via bus subsystem 3655. These peripheral devices can include a storage subsystem 3610 including, for example, memory devices and a file storage subsystem 3636, user interface input devices 3638, user interface output devices 3676, and a network interface subsystem 3674. The input and output devices allow user interaction with computer system 3600. Network interface subsystem 3674 provides an interface to outside networks, including an interface to corresponding interface devices in other computer systems.

In one implementation, the pathogenicity classifier 2108 is communicably linked to the storage subsystem 3610 and the user interface input devices 3638.

User interface input devices 3638 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 3600.

User interface output devices 3676 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 3600 to the user or to another machine or computer system.

Storage subsystem 3610 stores programming and data constructs that provide the functionality of some or all of the modules and methods described herein. These software modules are generally executed by processors 3678.

Processors 3678 can be graphics processing units (GPUs), field-programmable gate arrays (FPGAs), application-specific integrated circuits (ASICs), and/or coarse-grained reconfigurable architectures (CGRAs). Processors 3678 can be hosted by a deep learning cloud platform such as Google Cloud Platform™ Xilinx™ and Cirrascale™. Examples of processors 3678 include Google's Tensor Processing Unit (TPU)™, rackmount solutions like GX4 Rackmount Series™, GX36 Rackmount Series™, NVIDIA DGX-1™, Microsoft' Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, Lambda GPU Server with Testa V100s™, and others.

Memory subsystem 3622 used in the storage subsystem 3610 can include a number of memories including a main random access memory (RAM) 3632 for storage of instructions and data during program execution and a read only memory (ROM) 3634 in which fixed instructions are stored. A file storage subsystem 3636 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 3636 in the storage subsystem 3610, or in other machines accessible by the processor.

Bus subsystem 3655 provides a mechanism for letting the various components and subsystems of computer system 3600 communicate with each other as intended. Although bus subsystem 3655 is shown schematically as a single bus, alternative implementations of the bus subsystem can use multiple busses.

Computer system 3600 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 3600 depicted in FIG. 36 is intended only as a specific example for purposes of illustrating the preferred implementations of the present invention. Many other configurations of computer system 3600 are possible having more or less components than the computer system depicted in FIG. 36.

Amino Acid Prediction

Protein language models trained with the masked language modeling objective are supervised to output the probability that an amino acid occurs at a position in a protein given the surrounding context. Proteins are linear polymers that fold into various specific conformations to function. The incredible variety of three-dimensional (3D) structures determined by the combination and order in which 20 amino acids thread the protein polymer chain (sequence of the protein) enables the sophisticated functionality of proteins responsible for most biological activities. Hence, obtaining the structures of proteins is of paramount importance in both understanding the fundamental biology of health and disease and developing therapeutic molecules. While protein structure is primarily determined by sophisticated experimental techniques, such as X-ray crystallography, NMR spectroscopy and, increasingly, cryo-electron microscopy, computational structure prediction from the genetically encoded amino acid sequence of a protein has been used as an alternative when experimental approaches are limited.

Computational methods have been used to predict the structure of proteins, to illustrate the mechanism of biological processes, and to determine the properties of proteins. Furthermore, all naturally occurring proteins are a result of an evolutionary process of random variants arising under various selective pressures. Through this process, nature has explored only a small subset of theoretically possible protein sequence space. Advances in machine learning, especially deep learning, are catalyzing a revolution in the paradigm of scientific research. Some deep learning-based approaches, especially in structure prediction, now outperform conventional methods, often in combination with higher-resolution physical modeling. Challenges remain in experimental validation, benchmarking, leveraging known physics and interpreting models, and extending to other biomolecules and contexts.

Protein sites are microenvironments within a protein structure, distinguished by their structural or functional role. A site can be defined by a three-dimensional location and a local neighborhood around this location in which the structure or function exists. Central to rational protein engineering is the understanding of how the structural arrangement of amino acids creates functional characteristics within protein sites. Determination of the structural and functional roles of individual amino acids within a protein provides information to help engineer and alter protein functions. Identifying functionally or structurally important amino acids allows focused engineering efforts such as site-directed mutagenesis for altering targeted protein functional properties. In one implementation, the technology disclosed relates to predicting spatial tolerability of amino acid substitutes. In such an implementation, the technology disclosed includes a gapping logic and a substitution logic. The gapping logic is configured to remove, from a protein, a particular amino acid at a particular position, and create an amino acid vacancy at the particular position in the protein. The substitution logic is configured to process the protein with the amino acid vacancy, and score tolerability of substitute amino acids that are candidates for filling/fitting the amino acid vacancy. The substitution logic is further configured to score the tolerability of the substitute amino acids based at least in part on structural (or spatial) compatibility between the substitute amino acids and adjacent amino acids in a neighborhood of the amino acid vacancy (e.g., the right and left flanking amino acids). The substitution logic evaluates the extent to which an amino acid "fits" its surrounding protein environment and shows that mutations that disrupt strong amino acid preferences are more likely to be deleterious. When the substitution logic is a convolutional neural network, during the training process, the weights of the convolutional filters are optimized to detect local spatial patterns that best capture the local biochemical features to separate the 20 amino acid microenvironments. After the training process, filters in convolution layers of the convolutional neural network are activated when the desired features are present at some spatial position in the input. The structural (or spatial) compatibility can be defined by changes to or impact on protein functionality. When a substitute amino acid, after substitution at a specific location within a protein structure, causes changes in the functionality of a protein, then the substitute amino acid is considered structurally (or spatially) incompatible. When a substitute amino acid, after substitution at the specific location within the protein structure, does not cause changes in the functionality of a protein, then the substitute amino acid is considered structurally (or spatially) compatible. The structural (or spatial) compatibility can be defined by a spatial deviation measured by a distance metric. First, a pre-insertion spatial measurement of a protein structure can be determined, for example, by measuring distances between amino acids in the protein structure prior to the amino acid substitution at a particular position. The distances can be atomic distances based on atomic coordinates of the atoms of the amino acids. The distances can be measured between pairs of amino acids. Then, a post-insertion spatial measure of the protein structure be determined, for example, by remeasuring the distances between the amino acids in the protein structure after the amino acid substitution at the particular position. When the spatial deviation between the pre-insertion spatial measurement and the post-insertion spatial measure exceeds a threshold, then the substitute amino acid is considered structurally (or spatially) incompatible. When the spatial deviation between the pre-insertion spatial measurement and the post-insertion spatial measure does not exceed the threshold, then the substitute amino acid is considered structurally (or spatially) compatible.

In another implementation, the technology disclosed relates to predicting evolutionary conservation of amino acid substitutes. In such an implementation, the technology disclosed includes a gapping logic and a substitution logic. The gapping logic is configured to remove, from a protein, a particular amino acid at a particular position, and create an amino acid vacancy at the particular position in the protein. The substitution logic is configured to process the protein with the amino acid vacancy, and score evolutionary conservation of substitute amino acids that are candidates for filling the amino acid vacancy. The substitution logic is further configured to score the evolutionary conservation of the substitute amino acids based at least in part on structural (or spatial) compatibility between the substitute amino acids and adjacent amino acids in a neighborhood of the amino acid vacancy (e.g., the right and left flanking amino acids). In some implementations, the evolutionary conservation is scored using evolutionary conservation frequencies. In one implementation, the evolutionary conservation frequencies are based on a position-specific frequency matrix (PSFM). In another implementation, the evolutionary conservation frequencies are based on a position-specific scoring matrix (PSSM). In one implementation, evolutionary conservation scores of the substitute amino acids are rank-ordered by magnitude.

In yet another implementation, the technology disclosed relates to predicting evolutionary conservation of amino acid substitutes. In such an implementation, the technology disclosed includes a gapping logic and an evolutionary conservation prediction logic. The gapping logic is configured to remove, from a protein, a particular amino acid at a particular position, and create an amino acid vacancy at the particular position in the protein. The evolutionary conservation prediction logic is configured to process the protein with the amino acid vacancy, and rank evolutionary conservation of substitute amino acids that are candidates for filling the amino acid vacancy.

Figure 37:
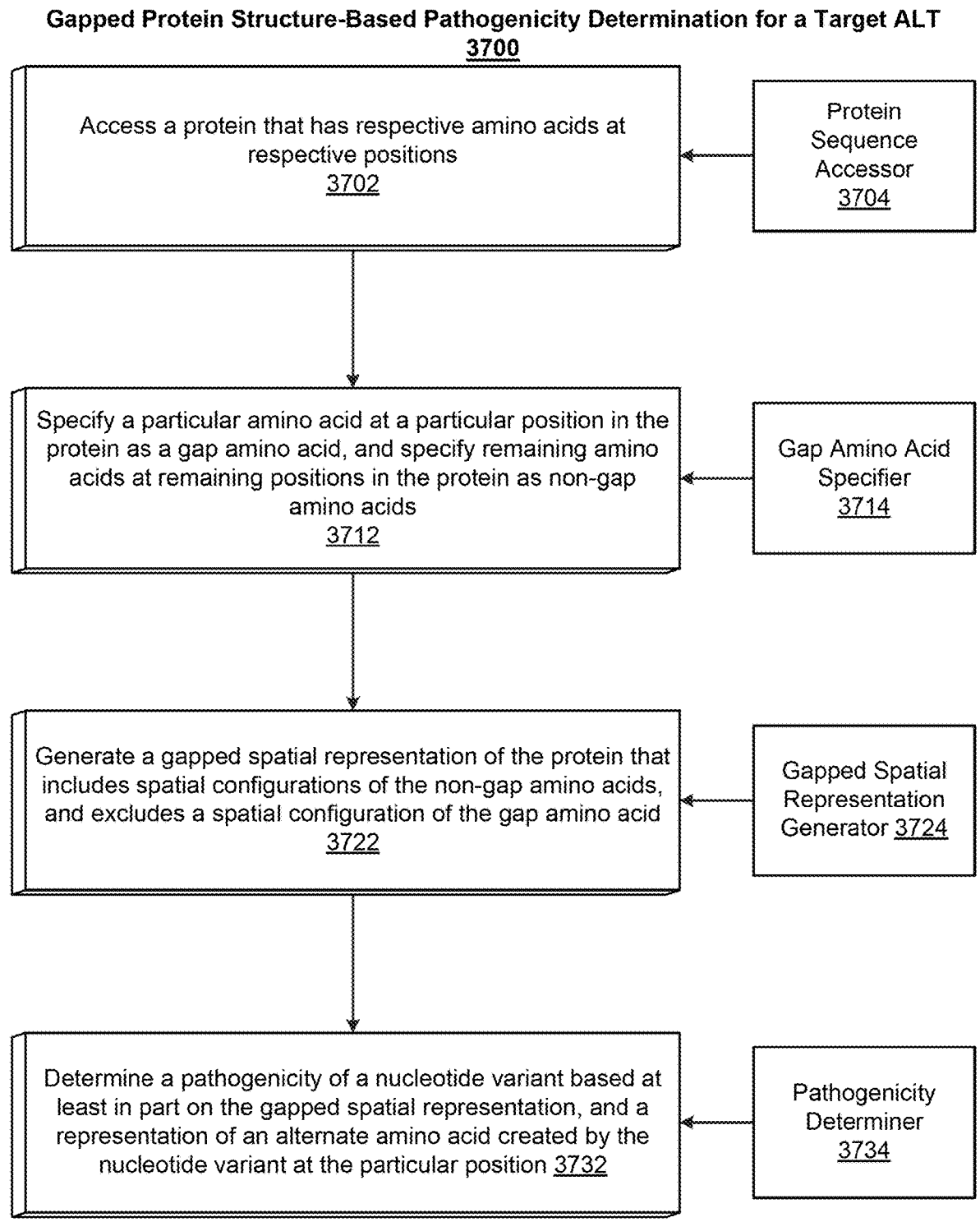
FIG. 37 illustrates one implementation of determining variant pathogenicity for a target alternate amino acid based on processing a gapped protein spatial representation.

Gapped Protein Spatial Representation-Based Pathogenicity Determination for a Target Alternate Amino Acid FIG. 37 illustrates one implementation of determining 3700 variant pathogenicity for a target alternate amino acid based on processing a gapped protein spatial representation. A protein is a sequence of amino acids. A particular amino acid in the protein that is removed or masked from the protein is called a "gap amino acid." The resulting protein that lacks the gap amino acid is called a "gapped protein" or a "vacancy-containing protein."

A "spatial representation" of a protein characterizes structural information about amino acids in the protein. The spatial representation of the protein can be based on shape, location, position, patterns, and/or arrangement of the amino acids in the protein. The spatial representation of the protein can be one-dimensional (1D), two-dimensional (2D), three-dimensional (3D), or n-dimensional (nD) information.

In one implementation, the spatial representation of the protein includes the amino acid-wise distance channels discussed above, for example, the amino acid-wise distance channels 600 described above with respect to FIG. 6. In another implementation, the spatial representation of the protein includes the distance channel tensor discussed above, for example, the distance channel tensor 700 described above with respect to FIG. 7. In yet another implementation, the spatial representation of the protein includes the evolutionary profiles tensor discussed above, for example, the evolutionary profiles tensor 1800 described above with respect to FIG. 18. In yet another implementation, the spatial representation of the protein includes the voxelized annotation channels discussed above, for example, the voxelized annotation channels 2000 described above with respect to FIG. 20. In yet another implementation, the spatial representation of the protein includes the structure confidence channels discussed above. In other implementations, the spatial representation can include other channels as well.

A "gapped spatial representation" of a protein is such a spatial representation of the protein that excludes at least one gap amino acid in the protein. In one implementation, a gap amino acid is excluded by excluding (or not considering or ignoring) one or more atoms or atom-types of the gap amino acid when generating the gapped spatial representation. For example, the atoms of the gap amino acid can be excluded from the calculations (or selections or computations) that produce the distance channels, the evolutionary profiles, the annotation channels, and/or the structure confidence channels. In other implementations, the gapped spatial representation can be generated by excluding the gap amino acid from other feature channels as well.

Consider the following example of generating a gapped spatial representation of a protein by excluding atoms of a gap amino acid from calculations of the amino acid-wise distance channels. In FIG. 5, the $C\alpha^{45}$ atom belongs to the Alanine amino acid at position five in the protein. Now assume that this Alanine amino acid at the fifth position is selected as the gap amino acid. Then the gapped spatial representation is generated by calculating the distance channel by not accounting for the distance 512 between the center of voxel (1, 1) of voxel grid 522 and the nearest alpha-carbon ($C_\alpha$) atom, which is the $C\alpha^{45}$ atom of the gap amino acid, i.e., the Alanine amino acid at the fifth position.

Also note that this Application uses "spatial representation of a protein" and "protein structure" interchangeably. Also note that this Application uses "gapped spatial representation of a protein" and "gapped protein structure" interchangeably.

Turning to FIG. 37, at action 3702, a protein sequence accessor 3704 accesses a protein that has respective amino acids at respective positions.

At action 3712, a gap amino acid specifier 3714 specifies a particular amino acid at a particular position in the protein as a gap amino acid, and specifies remaining amino acids at remaining positions in the protein as non-gap amino acids. In one implementation, the particular amino acid is a reference amino acid that is a major allele of the protein.

At action 3722, a gapped spatial representation generator 3724 generates a gapped spatial representation of the protein that includes spatial configurations of the non-gap amino acids, and excludes a spatial configuration of the gap amino acid. The spatial configurations of the non-gap amino acids are encoded as amino acid class-wise distance channels. Each of the amino acid class-wise distance channels has voxel-wise distance values for voxels in a plurality of voxels. The voxel-wise distance values specify distances from corresponding voxels in the plurality of voxels to atoms of the non-gap amino acids. The spatial configurations of the non-gap amino acids are determined based on spatial proximity between the corresponding voxels and the atoms of the non-gap amino acids. The spatial configuration of the gap amino acid is excluded from the gapped spatial representation by disregarding distances from the corresponding voxels to atoms of the gap amino acid when determining the voxel-wise distance values. The spatial configuration of the gap amino acid is excluded from the gapped spatial representation by disregarding spatial proximity between the corresponding voxels and the atoms of the gap amino acid.

The spatial configurations of the non-gap amino acids are encoded as evolutionary profile channels based on pan-amino acid conservation frequencies of amino acids with nearest atoms to the voxels. In one implementation, the spatial configuration of the gap amino acid is excluded from the gapped spatial representation by disregarding nearest atoms of the gap amino acid when determining the pan-amino acid conservation frequencies. The spatial configurations of the non-gap amino acids are encoded as evolutionary profile channels based on per-amino acid conservation frequencies of respective amino acids with respective nearest atoms to the voxels. In one implementation, the spatial configuration of the gap amino acid is excluded from the gapped spatial representation by disregarding respective nearest atoms of the gap amino acid when determining the per-amino acid conservation frequencies. The spatial configurations of the non-gap amino acids are encoded as annotation channels. In one implementation, the spatial configuration of the gap amino acid is excluded from the gapped spatial representation by disregarding atoms of the gap amino acid when determining the annotation channels. The spatial configurations of the non-gap amino acids are encoded as structural confidence channels. In one implementation, the spatial configuration of the gap amino acid is excluded from the gapped spatial representation by disregarding atoms of the gap amino acid when determining the structural confidence channels. The spatial configurations of the non-gap amino acids are encoded as additional input channels. In one implementation, the spatial configuration of the gap amino acid is excluded from the gapped spatial representation by disregarding atoms of the gap amino acid when determining the additional input channels.

At action 3732, a pathogenicity determiner 3734, determines a pathogenicity of a nucleotide variant based at least in part on the gapped spatial representation, and a representation of an alternate amino acid created by the nucleotide variant at the particular position. The representation of the alternate amino acid can be a one-hot encoding of the alternate amino acid (e.g., see FIG. 8). In some implementations, the alternate amino acid is an amino acid that is same as the reference amino acid. In other implementations, the alternate amino acid is an amino acid that is different from the reference amino acid.

Figure 38:
FIG. 38 shows an example of a spatial representation of a protein.
Figure 39:
FIG. 39 shows an example of a gapped spatial representation of the protein illustrated in FIG. 38.

FIG. 38 shows an example of a spatial representation 3800 of a protein. The protein contains an amino acid sequence 3804. An Aspartic acid (D) amino acid at a $22^{nd}$ position in the amino acid sequence 3804 is selected as a gap amino acid 3802. FIG. 39 shows an example of a gapped spatial representation 3900 of the protein illustrated in FIG. 38. In FIG. 39, the gap amino acid 3802 is removed from the gapped spatial representation 3900. Also in FIG. 39, the absence of the gap amino acid 3802 is illustrated as a missing gap amino acid 3902.

Figure 40:
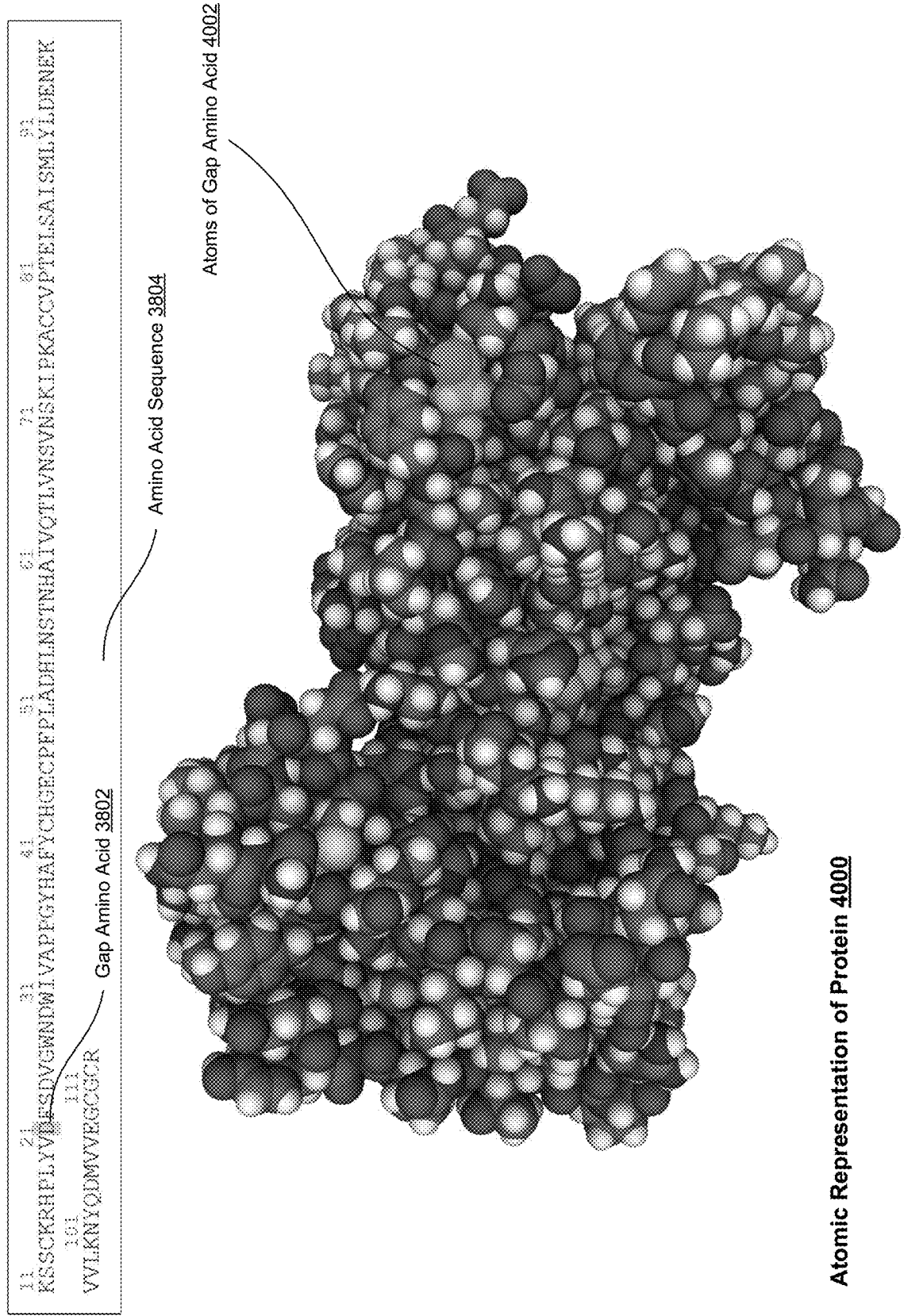
FIG. 40 shows an example of an atomic spatial representation of the protein illustrated in FIG. 38.
Figure 41:
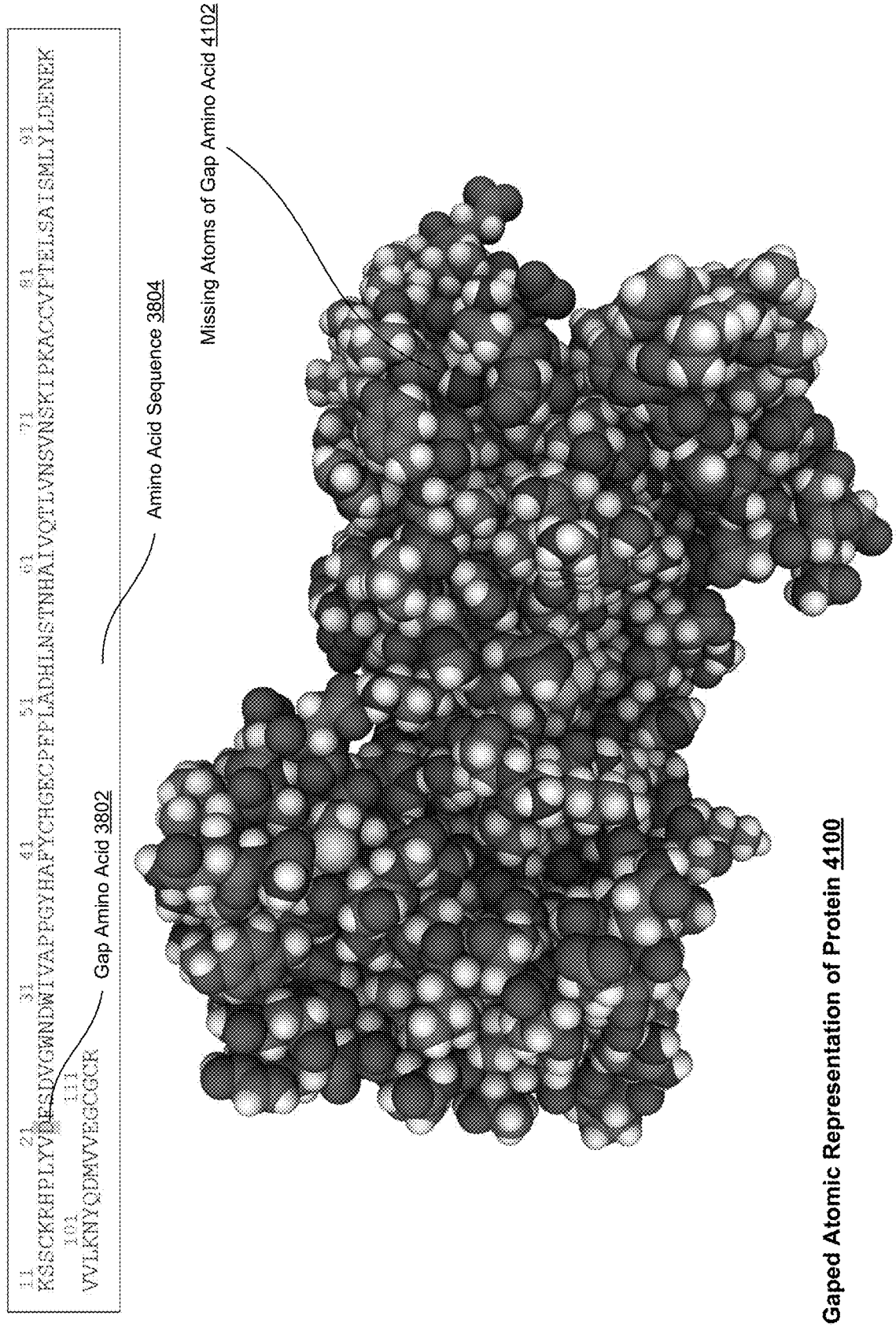
FIG. 41 shows an example of a gapped atomic spatial representation of the protein illustrated in FIG. 38.

FIG. 40 shows an example of an atomic spatial representation 4000 of the protein illustrated in FIG. 38. FIG. 40 also depicts atoms 4002 of the gap amino acid 3802. FIG. 41 shows an example of a gapped atomic spatial representation 4100 of the protein illustrated in FIG. 38. In FIG. 41, the atoms 4002 of the gap amino acid 3802 are removed from the gapped atomic spatial representation 4100. Also in FIG. 41, the absence of the atoms 4002 of the gap amino acid 3802 is illustrated as missing atoms 4102 of the gap amino acid 3802.

Also note that this Application uses "pathogenicity determiner," "pathogenicity predictor," "pathogenicity classifier," "variant pathogenicity classifier," "evolutionary conservation predictor," and "evolutionary conservation determiner" interchangeably.

Figure 42:
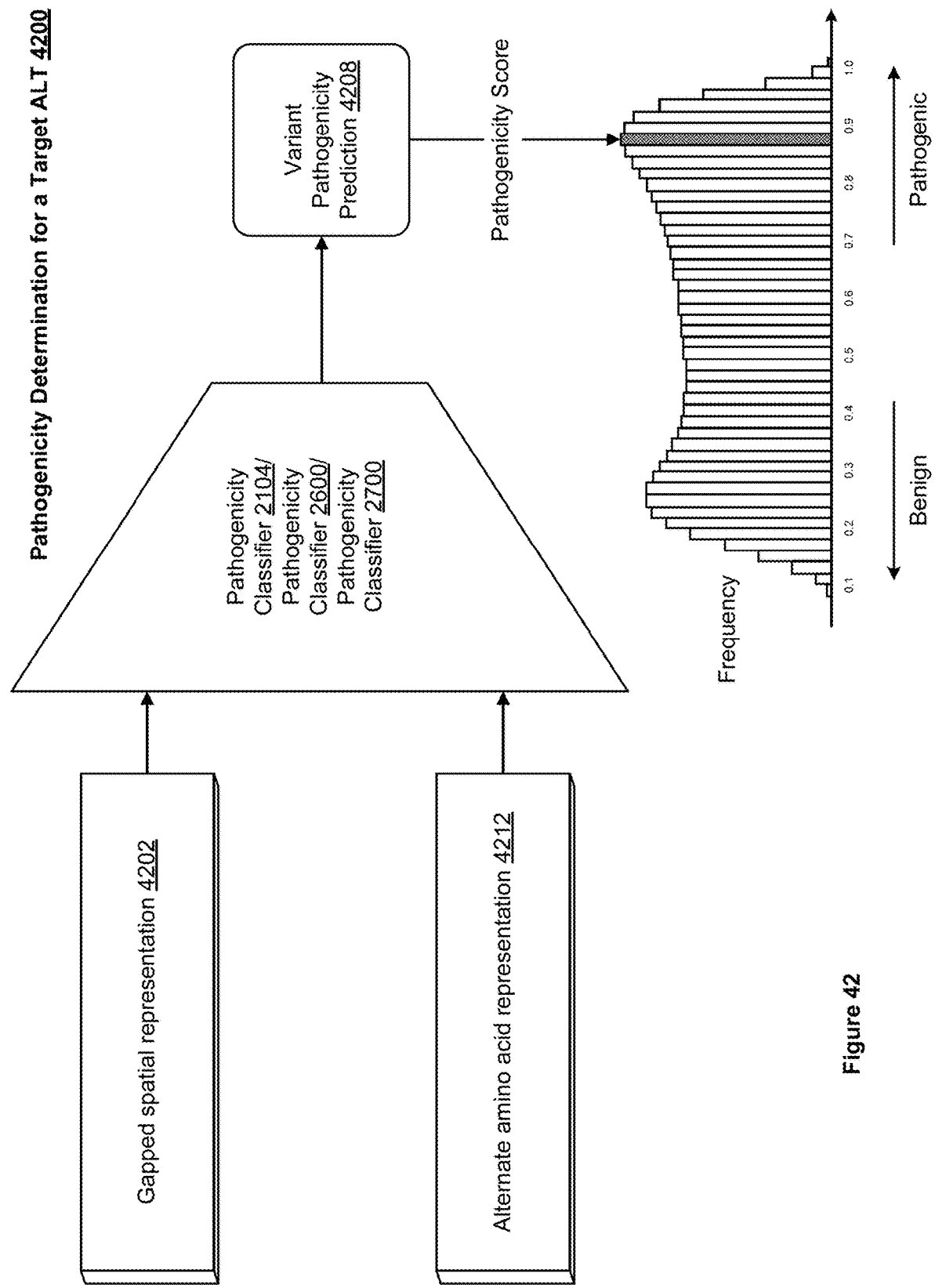
FIG. 42 illustrates one implementation of a pathogenicity classifier determining variant pathogenicity for a target alternate amino acid based on processing a gapped protein spatial representation and an alternate amino acid representation of the target alternate amino acid.

FIG. 42 illustrates one implementation of a pathogenicity classifier 2108/2600/2700 determining 4200 variant pathogenicity for a target alternate amino acid based on processing a gapped protein spatial representation 4202 and an alternate amino acid representation 4212 of the target alternate amino acid.

The pathogenicity classifier 2108/2600/2700 determines the pathogenicity of the nucleotide variant by processing, as input, the gapped spatial representation 4202, and the representation of the alternate amino acid 3212, and generating, as output, a pathogenicity score 4208 for the alternate amino acid.

Figure 43:
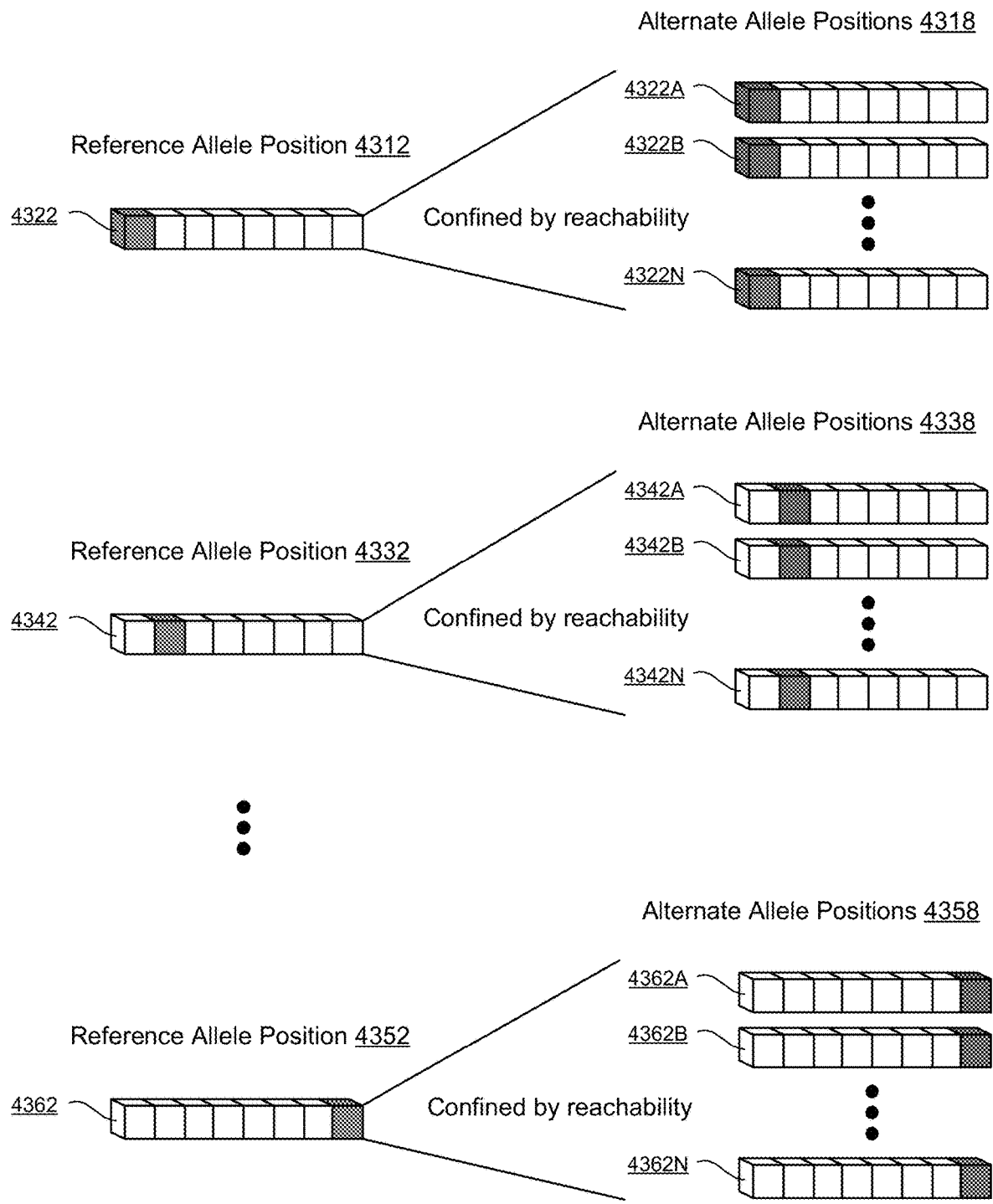
FIG. 43 depicts one implementation of training data used to train the pathogenicity classifier.

FIG. 43 depicts one implementation of training data 4300 used to train the pathogenicity classifier 2108/2600/2700. The pathogenicity classifier 2108/2600/2700 is trained on a benign training set 4302. The benign training set 4302 has respective benign protein samples 4322, 4342, and 4362 for respective reference amino acids at respective positions 4312, 4332, and 4352 in a proteome. The reference amino acids are major allele amino acids of the proteome. In one implementation, the proteome has ten million positions, and therefore the benign training set 4302 has ten million benign protein samples. The respective benign protein samples have respective gapped spatial representations generated by using the respective reference amino acids as respective gap amino acids. The respective benign protein samples have respective representations of the respective reference amino acids as respective alternate amino acids. In various implementations, the proteome includes human proteome and non-human proteome, including non-human primate proteome.

Figure 44:
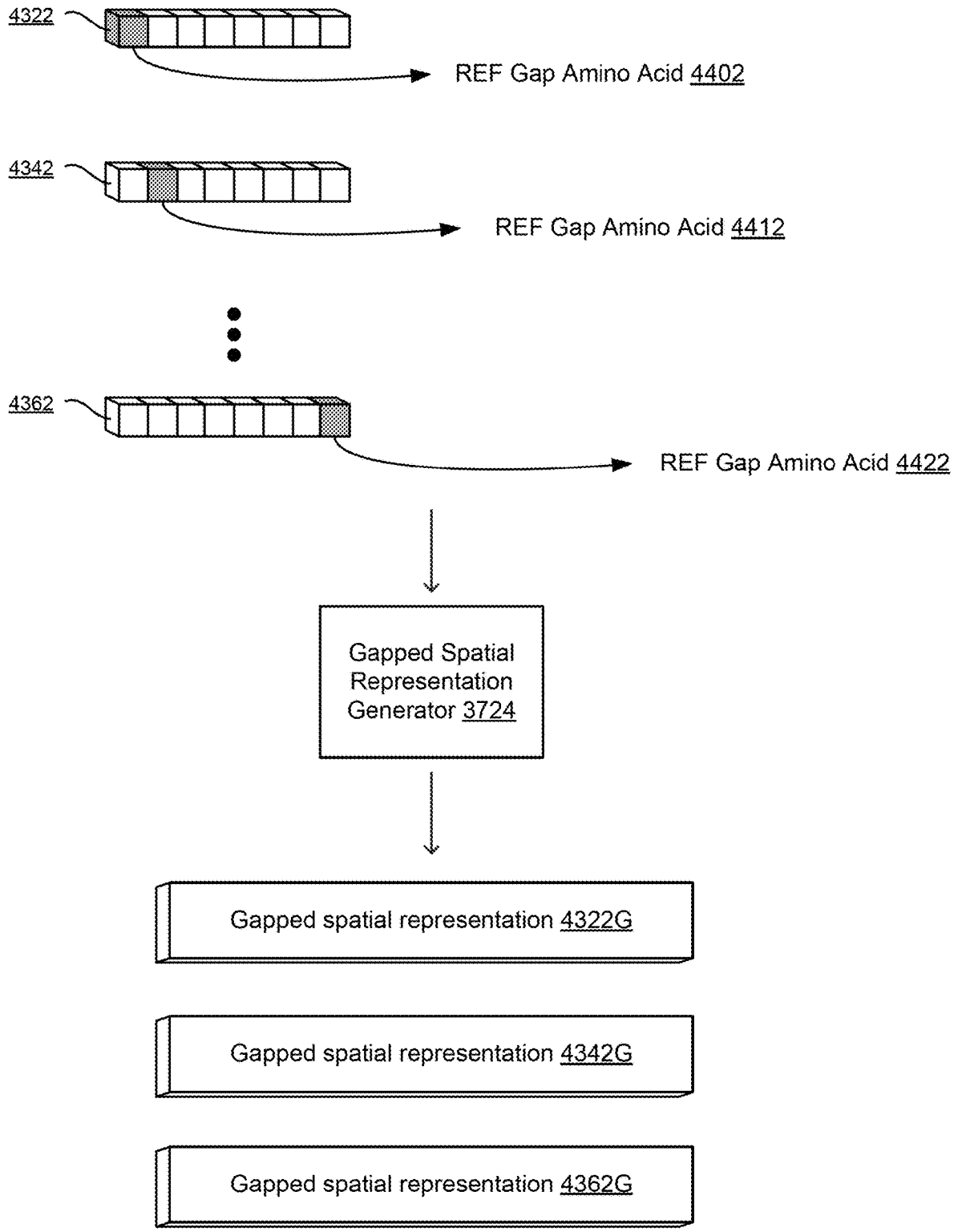
FIG. 44 illustrates one implementation of generating gapped spatial representations for reference proteins samples by using reference amino acids as gap amino acids.
Figure 45:
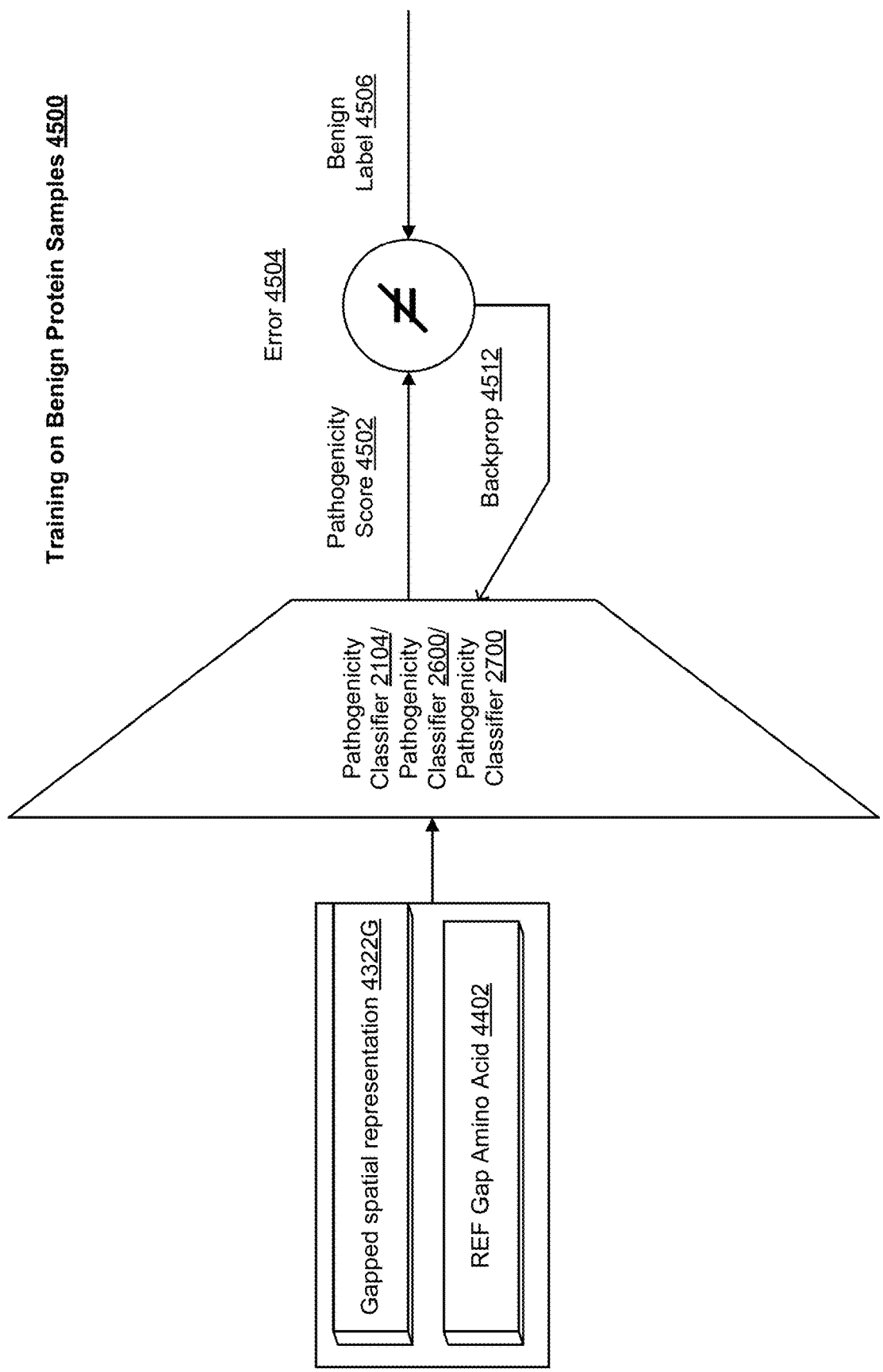
FIG. 45 shows one implementation of training the pathogenicity classifier on benign protein samples.

FIG. 44 illustrates one implementation of generating 4400 gapped spatial representations 4322G, 4342G, and 4362G for reference proteins samples 4322, 4342, and 4362 by using reference amino acids 4402, 4412, and 4422 as gap amino acids, respectively. FIG. 45 shows one implementation of training the pathogenicity classifier 2108/2600/2700 on benign protein samples 4500.

The pathogenicity classifier 2108/2600/2700 trains on a particular benign protein sample and estimates a pathogenicity of a particular reference amino acid at a particular position in the particular benign protein sample by processing, as input, (i) a particular gapped spatial representation 4322G of the particular benign protein sample, and (ii) a representation 4402 (e.g., a one-hot encoding) of the particular reference amino acid as a particular alternate amino acid, and generating, as output, a pathogenicity score for the particular reference amino acid. The particular gapped spatial representation is generated by using the particular reference amino acid as a gap amino acid, and by using remaining amino acids at remaining positions in the particular benign protein sample as non-gap amino acids.

Each of the benign protein samples has a ground truth benignness label 4506 that indicates absolute benignness of the benign protein samples. In one implementation, the ground truth benignness label is zero, one, or minus one. The pathogenicity score 4502 for the particular reference amino acid is compared against the ground truth benignness label to determine an error 4504, and to improve coefficients of the pathogenicity classifier 2108/2600/2700 based on the error using a training technique (e.g., backpropagation 4512).

The pathogenicity classifier 2108/2600/2700 is trained on a pathogenic training set 4308. The pathogenic training set 4308 has respective pathogenic protein samples 4322A-N, 4342A-N, and 4362A-N for respective combinatorically generated amino acid substitutions for each of the reference amino acids 4312, 4332, and 4352 at each of the respective positions 4318, 4338, and 4358 in the proteome. In one implementation, the respective combinatorically generated amino acid substitutions are confined by reachability of single nucleotide polymorphisms (SNPs) to transform a reference codon of a reference amino acid into alternate amino acids of unreachable alternate amino acid classes. The combinatorically generated amino acid substitutions for a particular reference amino acid of a particular amino acid class at a particular position in the proteome include respective alternate amino acids of respective amino acid classes that are different from the particular amino acid class.

In one implementation, the proteome has the ten million positions, wherein there are nineteen combinatorically generated amino acid substitutions for each of the ten million positions, and therefore the pathogenic training set 4308 has one hundred and ninety million pathogenic protein samples.

The respective pathogenic protein samples have respective gapped spatial representations generated by using the respective reference amino acids as respective gap amino acids. The respective pathogenic protein samples have respective representations of the respective combinatorically generated amino acid substitutions as respective alternate amino acids created by respective combinatorically generated nucleotide variants at the respective positions in the proteome.

Figure 46:
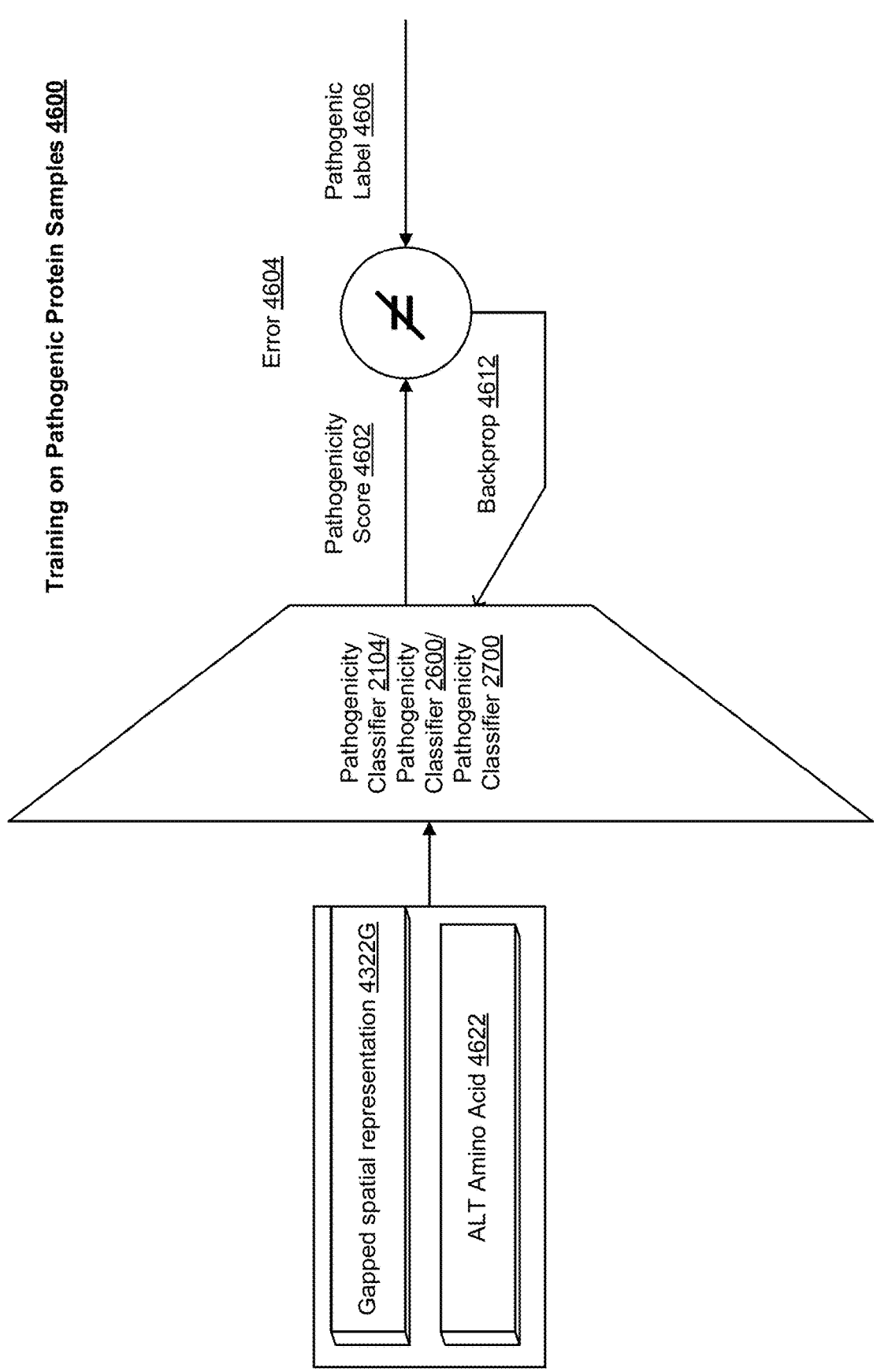
FIG. 46 shows one implementation of training the pathogenicity classifier on pathogenic protein samples.

FIG. 46 shows one implementation of training the pathogenicity classifier 2108/2600/2700 on pathogenic protein samples 4600. The pathogenicity classifier 2108/2600/2700 trains on a particular pathogenic protein sample and estimates a pathogenicity of a particular combinatorically generated amino acid substitution for a particular reference amino acid at a particular position in the particular pathogenic protein sample by processing, as input, (i) a particular gapped spatial representation 4322G of the particular pathogenic protein sample, and (ii) a representation 4622 (e.g., a one-hot encoding) of the particular combinatorically generated amino acid substitution as a particular alternate amino acid, and generating, as output, a pathogenicity score for the particular combinatorically generated amino acid substitution. The particular gapped spatial representation is generated by using the particular reference amino acid as a gap amino acid, and by using remaining amino acids at remaining positions in the particular pathogenic protein sample as non-gap amino acids.

Each of the pathogenic protein samples has a ground truth pathogenicity label that indicates absolute pathogenicity of the pathogenic protein samples. In one implementation, the ground truth pathogenicity label is one, zero, or minus one, as long as it is different (e.g., opposite) than the ground truth benignness label. The pathogenicity score 4602 for the particular combinatorically generated amino acid substitution is compared against the ground truth pathogenicity label 4606 to determine an error 4604, and to improve the coefficients of the pathogenicity classifier 2108/2600/2700 based on the error using the training technique (e.g., backpropagation 4612).

In one implementation, the pathogenicity classifier 2108/2600/2700 is trained on two hundred million training iterations. In such an implementation, the two hundred million training iterations include ten million training iterations with the ten million benign protein samples, and one hundred and ninety million iterations with the one hundred and ninety million pathogenic protein samples. In one implementation, the proteome has one million to ten million positions, and therefore the benign training set has one million to ten million benign protein samples. In such an implementation, there are nineteen combinatorically generated amino acid substitutions for each of the one million to ten million positions, and therefore the pathogenic training set has nineteen million to one hundred and ninety million pathogenic protein samples.

In one implementation, the pathogenicity classifier 2108/2600/2700 is trained on twenty million to two hundred million training iterations. In such an implementation, the twenty million to two hundred million training iterations include one million to ten million training iterations with the one million to ten million benign protein samples, and nineteen million to one hundred and ninety million iterations with the nineteen million to one hundred and ninety million pathogenic protein samples.

FIG. 47 shows how certain unreachable amino acid classes are masked 4700 during training. At action 4702, those unreachable alternate amino acid classes that are confined by reachability of single nucleotide polymorphisms (SNPs) to transform a reference codon of a reference amino acid into alternate amino acids of the unreachable alternate amino acid classes are masked in ground truth labels. At action 4712, the masked amino acid classes result in zero loss and do not contribute to gradient updates. At action 4722, the masked amino acid classes are identified in a lookup table. At action 4732, the lookup table identifies a set of masked amino acids classes for each reference amino acid position.

FIG. 48 illustrates one implementation of determining a final pathogenicity score. At action 4802, in one implementation, the pathogenicity classifier 2108/2600/2700 generates a first pathogenicity score for a first alternate amino acid that is same as a first reference amino acid. At action 4812, in one implementation, the pathogenicity classifier 2108/2600/2700 generates a second pathogenicity score for a second alternate amino acid that is different from the first reference amino acid. At action 4822, in one implementation, a final pathogenicity score for the second alternate amino acid is the second pathogenicity score for the second alternate amino acid.

In other alternatives, the final pathogenicity score for the second alternate amino acid is based on a combination of the first pathogenicity score and the second pathogenicity score. In a first alternative at 4822a, in one implementation, the final pathogenicity score for the second alternate amino acid is a ratio of the second pathogenicity score over a sum of the first pathogenicity score and the second pathogenicity score. In a second alternative at 4822b, in one implementation, the final pathogenicity score for the second alternate amino acid is determined by subtracting the first pathogenicity score from the second pathogenicity score.

Figures 49A, 49B:
FIG. 49A shows that a variant pathogenicity determination is made for a target alternate amino acid filling a vacancy created by a reference gap amino acid at a given position in a protein.
FIG. 49B shows that respective variant pathogenicity determinations are made for amino acids of respective amino acid classes filing the vacancy created by the reference gap amino acid at the given position in the protein.

The discussion so far covered what is depicted in FIG. 49A. FIG. 49A shows that a variant pathogenicity determination is made for a target alternate amino acid 4922 filling a vacancy created by a reference gap amino acid 4902 at a given position in a protein 4912. In particular, this analysis is done by spatially representing the protein 4912 and the vacancy in a 3D format, for example, by using voxelized amino acid category-wise distance calculations that exclude the reference gap amino acid 4902 (or atoms thereof).

The discussion now turns to FIG. 49B. FIG. 49B shows that respective variant pathogenicity determinations are made for amino acids of respective amino acid classes 4916 filing the vacancy created by the reference gap amino acid 4902 at the given position in the protein 4912. The inputs in FIGS. 49A and 49B are the same; only the output is different, and so are the spatial representations of the protein 4912 and the vacancy in the 3D format. In FIG. 49A only one pathogenicity score is generated; whereas in FIG. 49B a pathogenicity score is generated for each of the twenty amino acid classes/categories (e.g., by using a 20-way softmax classification).

Figure 50:
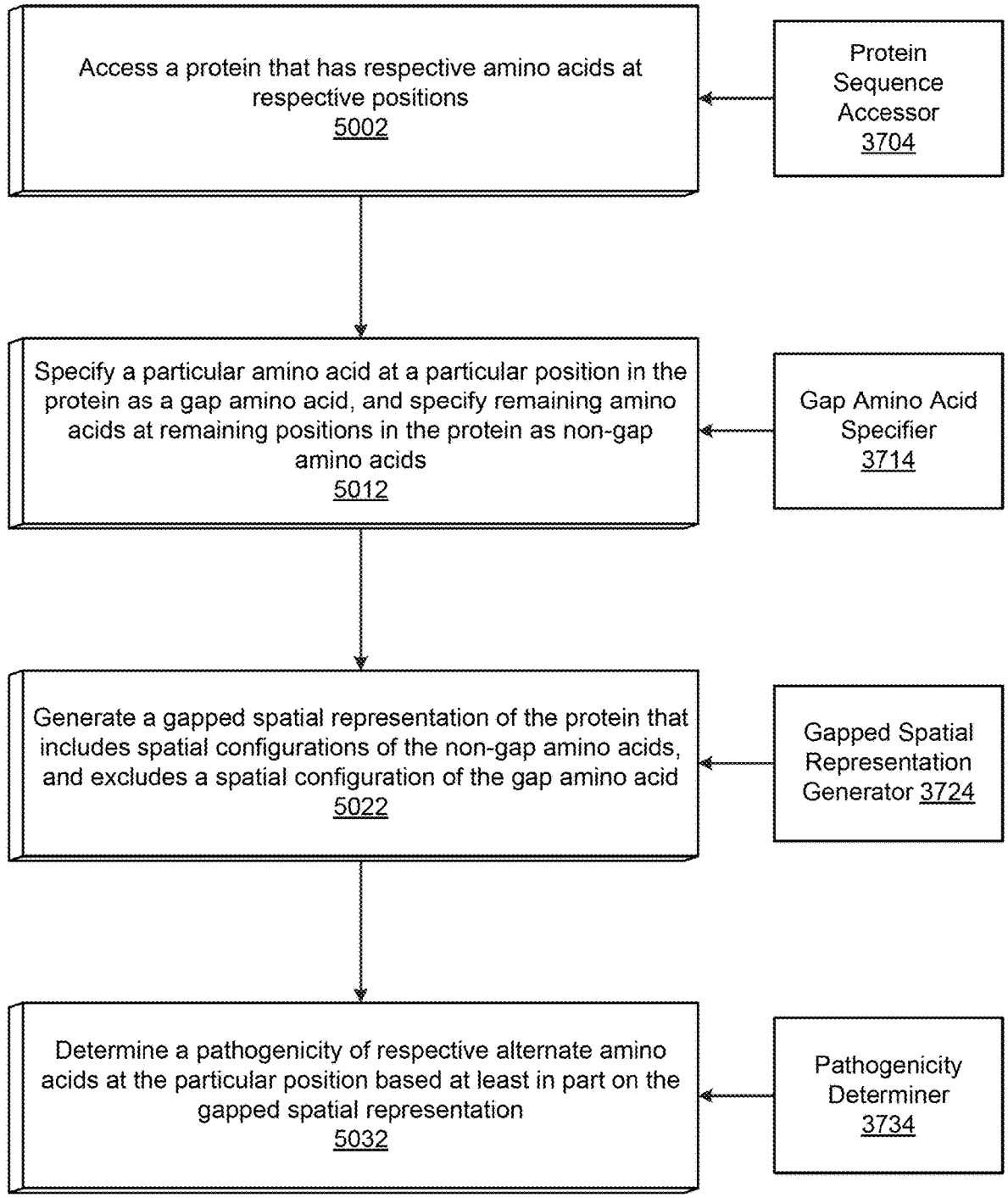
FIG. 50 illustrates one implementation of determining variant pathogenicity for multiple alternate amino acids based on processing a gapped protein spatial representation.

Gapped Protein Spatial Representation-Based Pathogenicity Determination for Multiple Alternate Amino Acids FIG. 50 illustrates one implementation of determining 5000 variant pathogenicity for multiple alternate amino acids based on processing a gapped protein spatial representation. At action 5002, the protein sequence accessor 3704 accesses a protein that has respective amino acids at respective positions.

At action 5012, the gap amino acid specifier 3714 specifies a particular amino acid at a particular position in the protein as a gap amino acid, and specifies remaining amino acids at remaining positions in the protein as non-gap amino acids. In one implementation, the particular amino acid is a reference amino acid that is a major allele of the protein.

At action 5022, the gapped spatial representation generator 3724 generates a gapped spatial representation of the protein that includes spatial configurations of the non-gap amino acids, and excludes a spatial configuration of the gap amino acid. The spatial configurations of the non-gap amino acids are encoded as amino acid class-wise distance channels. Each of the amino acid class-wise distance channels has voxel-wise distance values for voxels in a plurality of voxels. The voxel-wise distance values specify distances from corresponding voxels in the plurality of voxels to atoms of the non-gap amino acids. The spatial configurations of the non-gap amino acids are determined based on spatial proximity between the corresponding voxels and the atoms of the non-gap amino acids. The spatial configuration of the gap amino acid is excluded from the gapped spatial representation by disregarding distances from the corresponding voxels to atoms of the gap amino acid when determining the voxel-wise distance values. The spatial configuration of the gap amino acid is excluded from the gapped spatial representation by disregarding spatial proximity between the corresponding voxels and the atoms of the gap amino acid.

The spatial configurations of the non-gap amino acids are encoded as evolutionary profile channels based on pan-amino acid conservation frequencies of amino acids with nearest atoms to the voxels. In one implementation, the spatial configuration of the gap amino acid is excluded from the gapped spatial representation by disregarding nearest atoms of the gap amino acid when determining the pan-amino acid conservation frequencies. The spatial configurations of the non-gap amino acids are encoded as evolutionary profile channels based on per-amino acid conservation frequencies of respective amino acids with respective nearest atoms to the voxels. In one implementation, the spatial configuration of the gap amino acid is excluded from the gapped spatial representation by disregarding respective nearest atoms of the gap amino acid when determining the per-amino acid conservation frequencies. The spatial configurations of the non-gap amino acids are encoded as annotation channels. In one implementation, the spatial configuration of the gap amino acid is excluded from the gapped spatial representation by disregarding atoms of the gap amino acid when determining the annotation channels. The spatial configurations of the non-gap amino acids are encoded as structural confidence channels. In one implementation, the spatial configuration of the gap amino acid is excluded from the gapped spatial representation by disregarding atoms of the gap amino acid when determining the structural confidence channels. The spatial configurations of the non-gap amino acids are encoded as additional input channels. In one implementation, the spatial configuration of the gap amino acid is excluded from the gapped spatial representation by disregarding atoms of the gap amino acid when determining the additional input channels.

At action 5032, the pathogenicity determiner 3734, determines, based at least in part on the gapped spatial representation, a pathogenicity of respective alternate amino acids at the particular position. The respective alternate amino acids are respective combinatorically generated alternate amino acids created by respective combinatorically generated nucleotide variants at the particular position.

Figure 51:
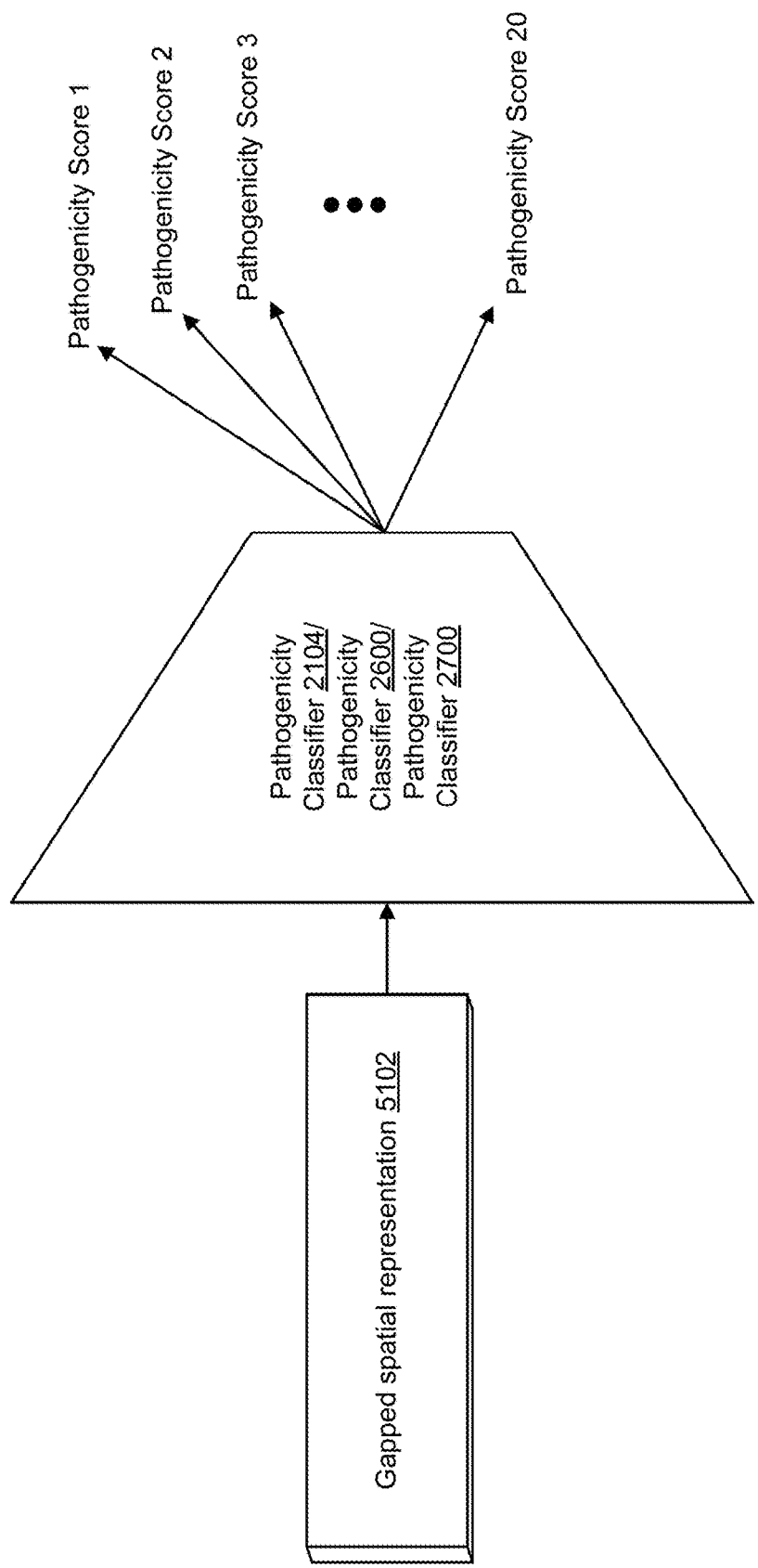
FIG. 51 illustrates one implementation of the pathogenicity classifier determining variant pathogenicity for multiple alternate amino acids based on processing a gapped protein spatial representation.

FIG. 51 illustrates one implementation of the pathogenicity classifier 2108/2600/2700 determining 5100 variant pathogenicity for multiple alternate amino acids based on processing a gapped protein spatial representation 5102. The pathogenicity classifier 2108/2600/2700 determines the pathogenicity of the respective alternate amino acids by processing, as input, the gapped spatial representation 5102, and generating, as output, respective pathogenicity scores 1-20 for respective amino acid classes. In some implementations, the respective amino acid classes correspond to respective twenty naturally-occurring amino acids. In other implementations, the respective amino acid classes correspond to respective naturally-occurring amino acids from a subset of the twenty naturally-occurring amino acids. In one implementation, the output is displayed with the respective rankings of the respective pathogenicity scores 1-20 for respective amino acid classes.

Figure 52:
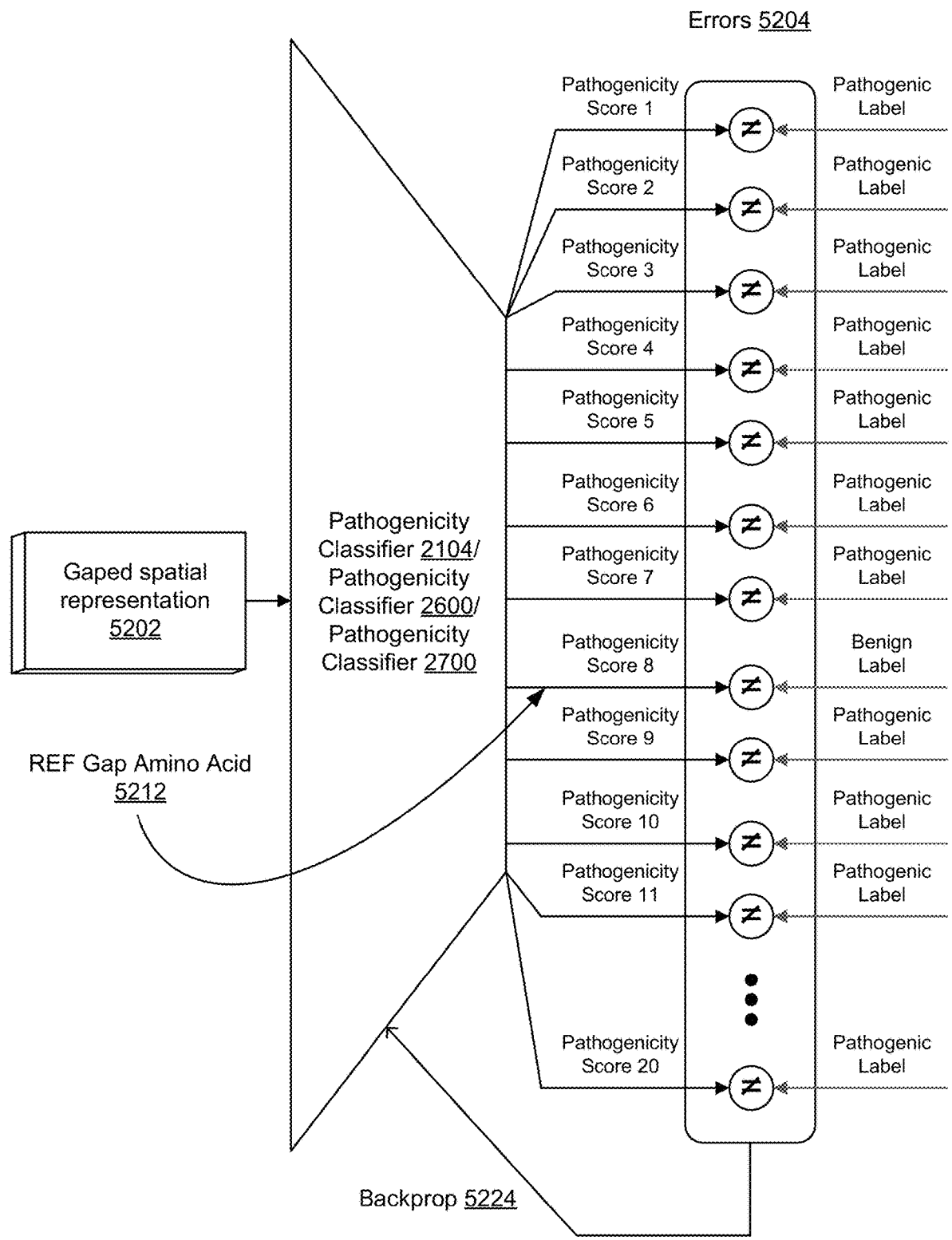
FIG. 52 illustrates one implementation of concurrently training the pathogenicity classifier on benign and pathogenic protein samples.

FIG. 52 illustrates one implementation of concurrently training 5200 the pathogenicity classifier 2108/2600/2700 on benign and pathogenic protein samples. The pathogenicity classifier 2108/2600/2700 is trained on a training set. The training set has respective protein samples for respective positions in the proteome. The proteome has ten million positions, and therefore the training set has ten million protein samples. The respective protein samples have respective gapped spatial representations generated by using respective reference amino acids at the respective positions in proteome as respective gap amino acids. The reference amino acids are major allele amino acids of the proteome.

The pathogenicity classifier 2108/2600/2700 trains on a particular protein sample and estimates a pathogenicity of respective alternate amino acids for a particular reference amino acid at a particular position in the particular protein sample by processing, as input, a particular gapped spatial representation 5202 of the particular protein sample, and generating, as output, respective pathogenicity scores 1-20 for the respective amino acid classes. The particular gapped spatial representation is generated by using the particular reference amino acid as a gap amino acid, and by using remaining amino acids at remaining positions in the particular protein sample as non-gap amino acids.

Each of the protein samples has respective ground truth labels for the respective amino acid classes. The respective ground truth labels include an absolute benignness label for a reference amino acid class in the respective amino acid classes, and include respective absolute pathogenicity labels for respective alternate amino acid classes in the respective amino acid classes. In one implementation, the absolute benignness label is zero. The absolute pathogenicity labels are same across the respective alternate amino acid classes. In one implementation, the absolute pathogenicity labels are one.

In one implementation, an error 5204 is determined based on a comparison of a pathogenicity score for the reference amino acid class against the absolute benignness label (e.g., pathogenicity score 8 for reference gap amino acid 5212 in FIG. 52), and respective comparisons of respective pathogenicity scores for the respective alternate amino acid classes against the respective absolute pathogenicity labels (e.g., pathogenicity scores 1-7 and 9-20 in FIG. 52). In one implementation, coefficients of the pathogenicity classifier 2108/2600/2700 are improved based on the error using a training technique (e.g., backpropagation 5224).

In one implementation, the pathogenicity classifier 2108/2600/2700 is trained on ten million training iterations with the ten million protein samples. In some implementations, the proteome has one million to ten million positions, and therefore the training set has one million to ten million protein samples. In one implementation, the pathogenicity classifier 2108/2600/2700 is trained on one million to ten million training iterations with the one million to ten million protein samples.

In one implementation, the pathogenicity classifier 2108/2600/2700 generates a reference pathogenicity score for a first alternate amino acid of the reference amino acid class. In one implementation, the pathogenicity classifier 2108/2600/2700 generates respective alternate pathogenicity scores for respective alternate amino acids of the respective alternate amino acid classes.

In one implementation, respective final alternate pathogenicity scores for the respective alternate amino acids are the respective alternate pathogenicity scores. In one implementation, respective final alternate pathogenicity scores for the respective alternate amino acids are based on respective combinations of the reference pathogenicity score and the respective alternate pathogenicity scores. In one implementation, respective final alternate pathogenicity scores for the respective alternate amino acids are respective ratios of the respective alternate pathogenicity scores over a sum of the reference pathogenicity score and the respective alternate pathogenicity scores. In one implementation, respective final alternate pathogenicity scores for the respective alternate amino acids are determined by respectively subtracting the reference pathogenicity score from the respective alternate pathogenicity scores.

In one implementation, the pathogenicity classifier 2108/2600/2700 has an output layer that generates the respective pathogenicity scores. In some implementations, the output layer is a normalization layer. In such implementations, the respective pathogenicity scores are normalized. In one implementation, the output layer is a softmax layer. In such an implementation, the respective pathogenicity scores are exponentially normalized. In another implementation, the output layer has respective sigmoid units that respectively generate the respective pathogenicity scores. In yet another implementation, the respective pathogenicity scores are unnormalized.

Figure 53:
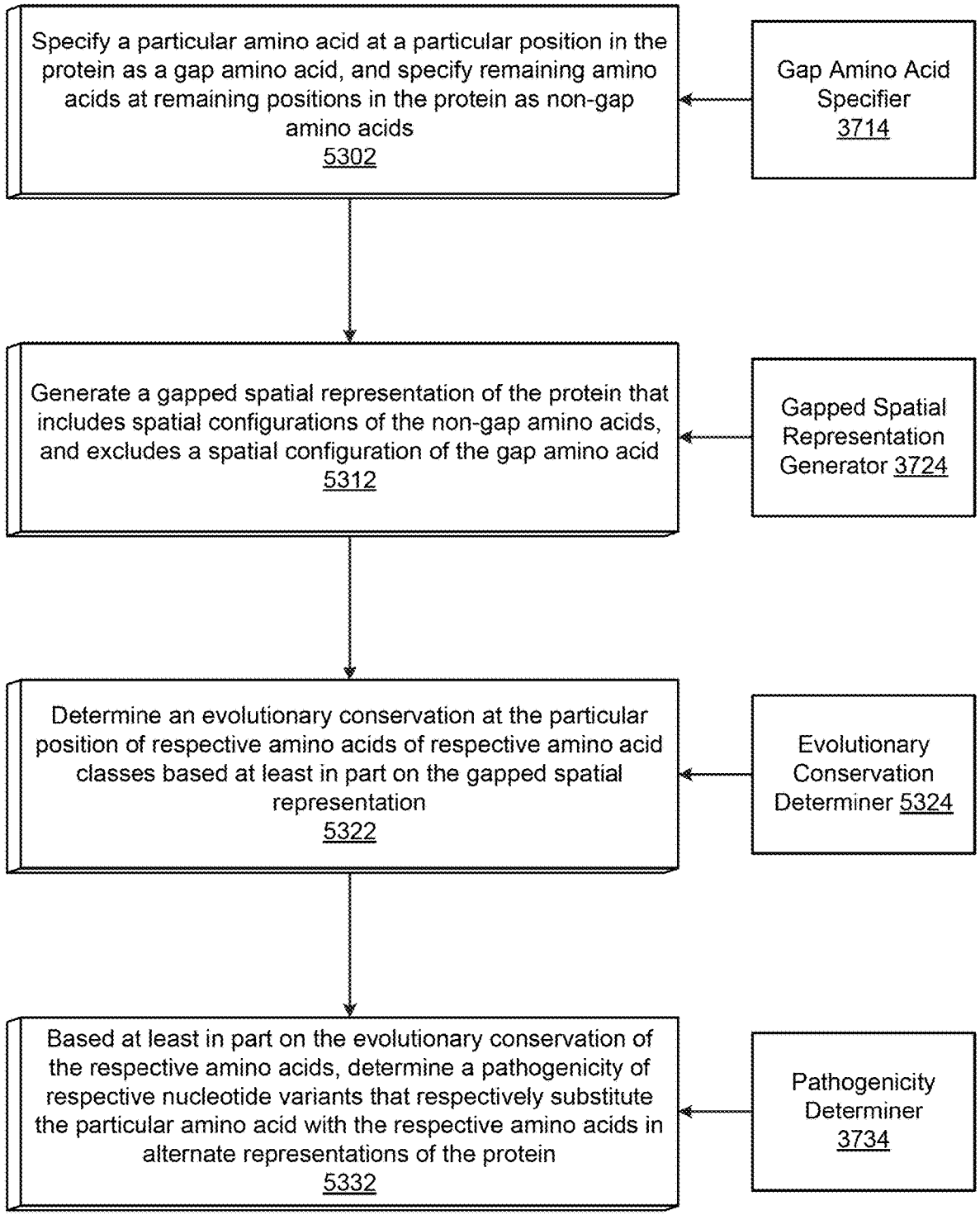
FIG. 53 illustrates one implementation of determining variant pathogenicity for multiple alternate amino acids based on processing a gapped protein spatial representation and, in response, generating evolutionary conservation scores for the multiple alternate amino acids.

Gapped Protein Spatial Representation- and Evolutionary Conservation-Based Pathogenicity Determination for Multiple Alternate Amino Acids Evolutionary conservation refers to the presence of similar genes, portions of genes, or chromosome segments in different species, reflecting both the common origin of species and an important functional property of the conserved element. Mutations occur spontaneously in each generation, randomly changing an amino acid here and there in a protein. Individuals with mutations that impair critical functions of proteins may have resulting problems that make them less able to reproduce. Harmful mutations are lost from the gene pool because the individuals carrying them reproduce less effectively. Since the harmful mutations are lost, the amino acids critical for the function of a protein are conserved in the gene pool. In contrast, harmless (or very rare beneficial) mutations are kept in the gene pool, producing variability in non-critical amino acids. Evolutionary conservation in proteins is identified by aligning the amino acid sequences of proteins with the same function from different taxa (orthologs). Predicting the functional consequences of variants relies at least in part on the assumption that crucial amino acids for protein families are conserved through evolution due to negative selection (i.e., amino acid changes at these sites were deleterious in the past), and that mutations at these sites have an increased likelihood of being pathogenic (causing disease) in humans. In general, homologous sequences of a target protein are collected and aligned, and a metric of conservation is computed based on the weighted frequencies of different amino acids observed in the target position in the alignment. FIG. 53 illustrates one implementation of determining 5300 variant pathogenicity for multiple alternate amino acids based on processing a gapped protein spatial representation and, in response, generating evolutionary conservation scores for the multiple alternate amino acids. At action 5302, the gap amino acid specifier 3714 specifies a particular amino acid at a particular position in a protein as a gap amino acid, and specifies remaining amino acids at remaining positions in the protein as non-gap amino acids. In one implementation, the particular amino acid is a reference amino acid that is a major allele of the protein.

At action 5312, the gapped spatial representation generator 3724 generates a gapped spatial representation of the protein that includes spatial configurations of the non-gap amino acids, and excludes a spatial configuration of the gap amino acid. The spatial configurations of the non-gap amino acids are encoded as amino acid class-wise distance channels. Each of the amino acid class-wise distance channels has voxel-wise distance values for voxels in a plurality of voxels. The voxel-wise distance values specify distances from corresponding voxels in the plurality of voxels to atoms of the non-gap amino acids. The spatial configurations of the non-gap amino acids are determined based on spatial proximity between the corresponding voxels and the atoms of the non-gap amino acids. The spatial configuration of the gap amino acid is excluded from the gapped spatial representation by disregarding distances from the corresponding voxels to atoms of the gap amino acid when determining the voxel-wise distance values. The spatial configuration of the gap amino acid is excluded from the gapped spatial representation by disregarding spatial proximity between the corresponding voxels and the atoms of the gap amino acid.

The spatial configurations of the non-gap amino acids are encoded as evolutionary profile channels based on pan-amino acid conservation frequencies of amino acids with nearest atoms to the voxels. In one implementation, the spatial configuration of the gap amino acid is excluded from the gapped spatial representation by disregarding nearest atoms of the gap amino acid when determining the pan-amino acid conservation frequencies. The spatial configurations of the non-gap amino acids are encoded as evolutionary profile channels based on per-amino acid conservation frequencies of respective amino acids with respective nearest atoms to the voxels. In one implementation, the spatial configuration of the gap amino acid is excluded from the gapped spatial representation by disregarding respective nearest atoms of the gap amino acid when determining the per-amino acid conservation frequencies. The spatial configurations of the non-gap amino acids are encoded as annotation channels. In one implementation, the spatial configuration of the gap amino acid is excluded from the gapped spatial representation by disregarding atoms of the gap amino acid when determining the annotation channels. The spatial configurations of the non-gap amino acids are encoded as structural confidence channels. In one implementation, the spatial configuration of the gap amino acid is excluded from the gapped spatial representation by disregarding atoms of the gap amino acid when determining the structural confidence channels. The spatial configurations of the non-gap amino acids are encoded as additional input channels. In one implementation, the spatial configuration of the gap amino acid is excluded from the gapped spatial representation by disregarding atoms of the gap amino acid when determining the additional input channels.

At action 5322, an evolutionary conservation determiner 5324 determines an evolutionary conservation at the particular position of respective amino acids of respective amino acid classes based at least in part on the gapped spatial representation.

Figure 54:
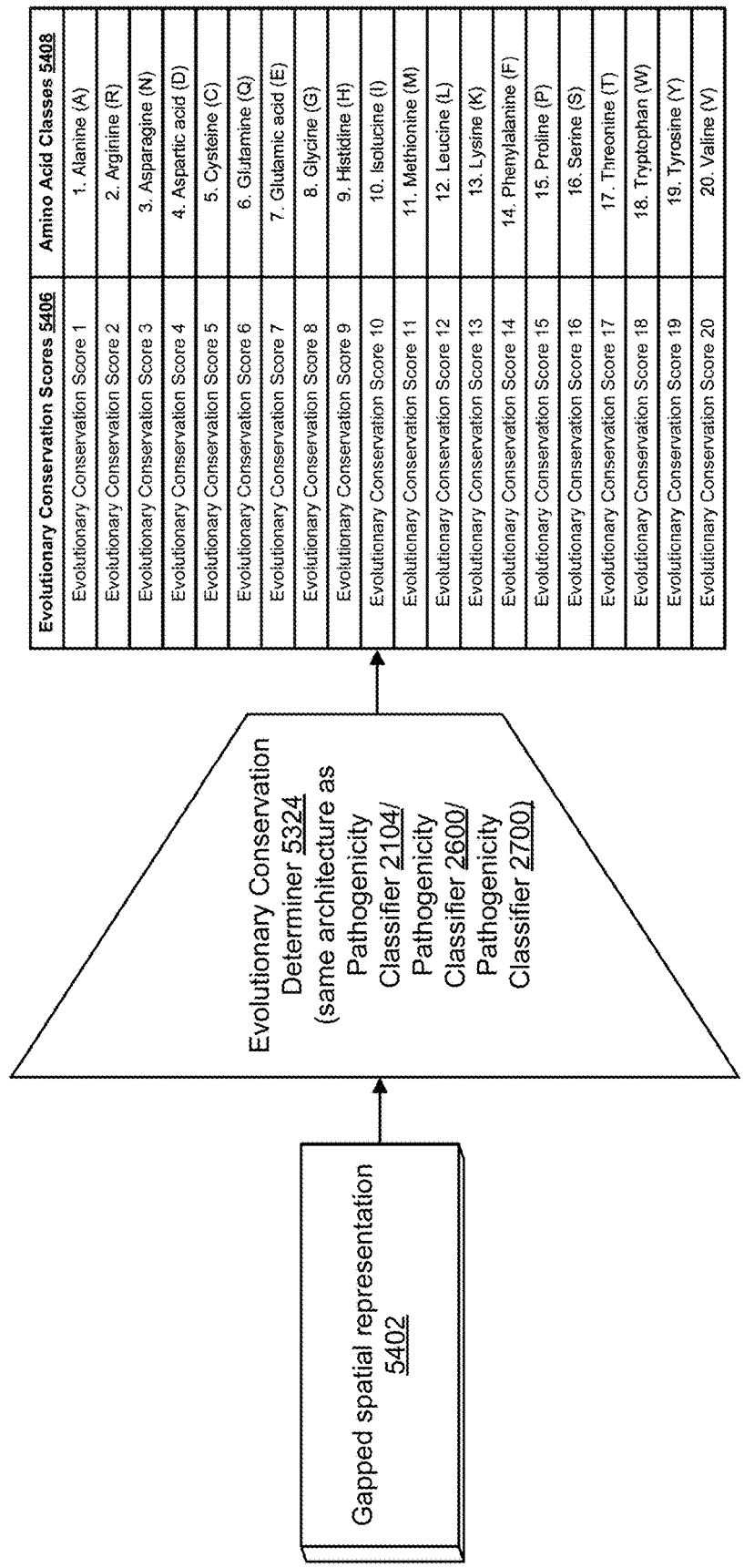
FIG. 54 shows the evolutionary conservation determiner in operation, in accordance with one implementation.

FIG. 54 shows the evolutionary conservation determiner 5324 in operation 5400, in accordance with one implementation. The evolutionary conservation determiner 5324, in some implementations, has the same architecture as the pathogenicity classifier 2108/2600/2700. The evolutionary conservation determiner 5324 determines the evolutionary conservation by processing, as input, the gapped spatial representation 5402, and generating, as output, respective evolutionary conservation scores 5406 for the respective amino acids 5408. The respective evolutionary conservation scores are rankable by magnitude. For purposes of the present disclosure, a "classifier", "determiner", "insert term here" can include one or more software modules, one or more hardware modules, or any combination thereof.

At action 5332, the pathogenicity determiner 3734, based at least in part on the evolutionary conservation of the respective amino acids 5408, determines a pathogenicity of respective nucleotide variants that respectively substitute the particular amino acid with the respective amino acids 5408 in alternate representations of the protein.

Figure 55:
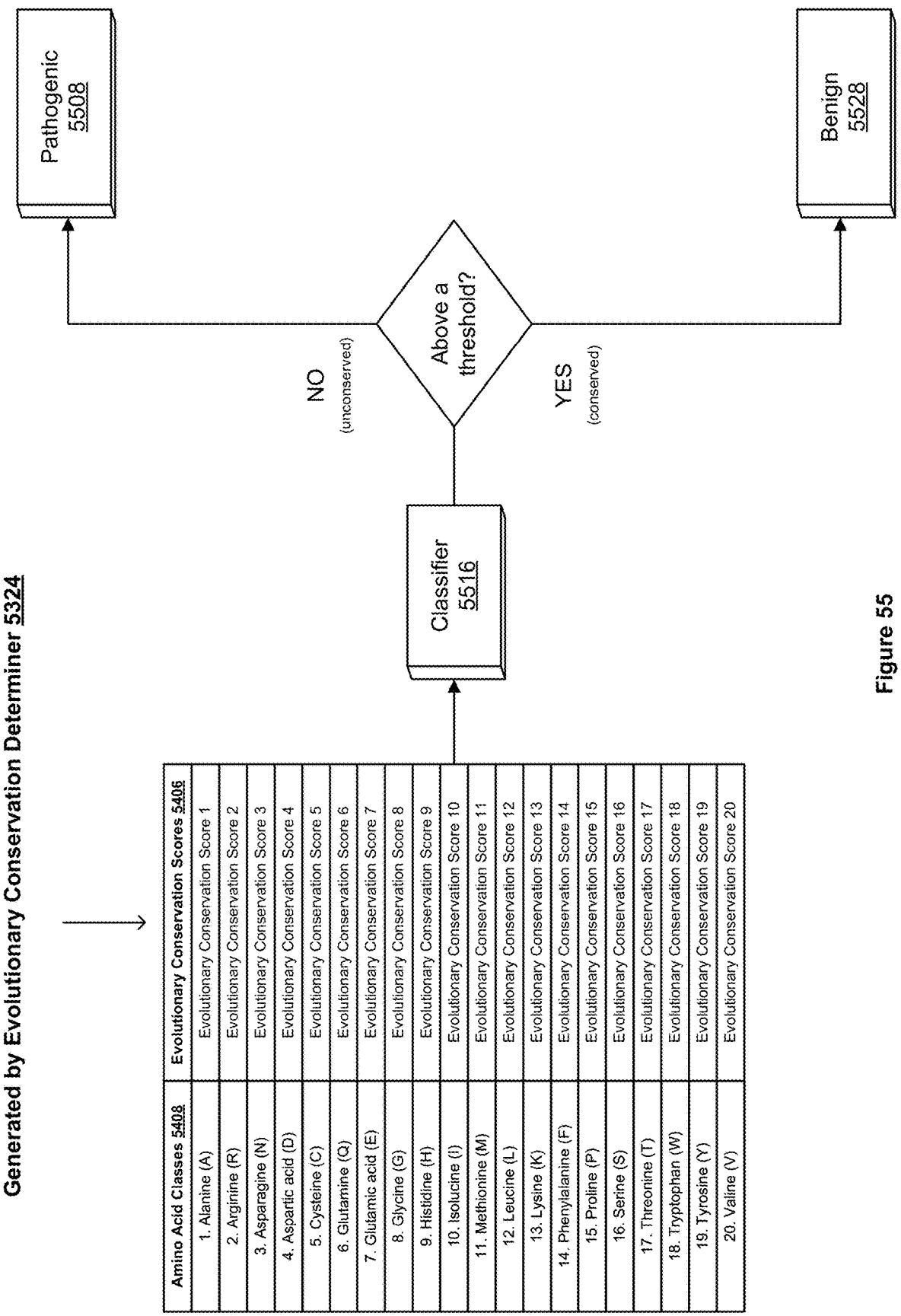
FIG. 55 illustrates one implementation of determining pathogenicity based on predicted evolutionary scores.

FIG. 55 illustrates one implementation of determining pathogenicity based on predicted evolutionary scores. A classifier 5516 classifies a nucleotide variant as pathogenic 5508 when an evolutionary conservation score generated by the evolutionary conservation determiner 5324 for a corresponding amino acid substitution is below a threshold. In one implementation, the classifier 5516 classifies a nucleotide variant as pathogenic 5508 when an evolutionary conservation score generated by the evolutionary conservation determiner 5324 for a corresponding amino acid substitution is zero (i.e., indication of non-conservation).

The classifier 5516 classifies a nucleotide variant as benign 5528 when an evolutionary conservation score generated by the evolutionary conservation determiner 5324 for a corresponding amino acid substitution is above a threshold. In one implementation, the classifier 5516 classifies a nucleotide variant as benign 5528 when an evolutionary conservation score generated by the evolutionary conservation determiner 5324 for a corresponding amino acid substitution is non-zero (i.e., indication of conservation).

Figure 56:
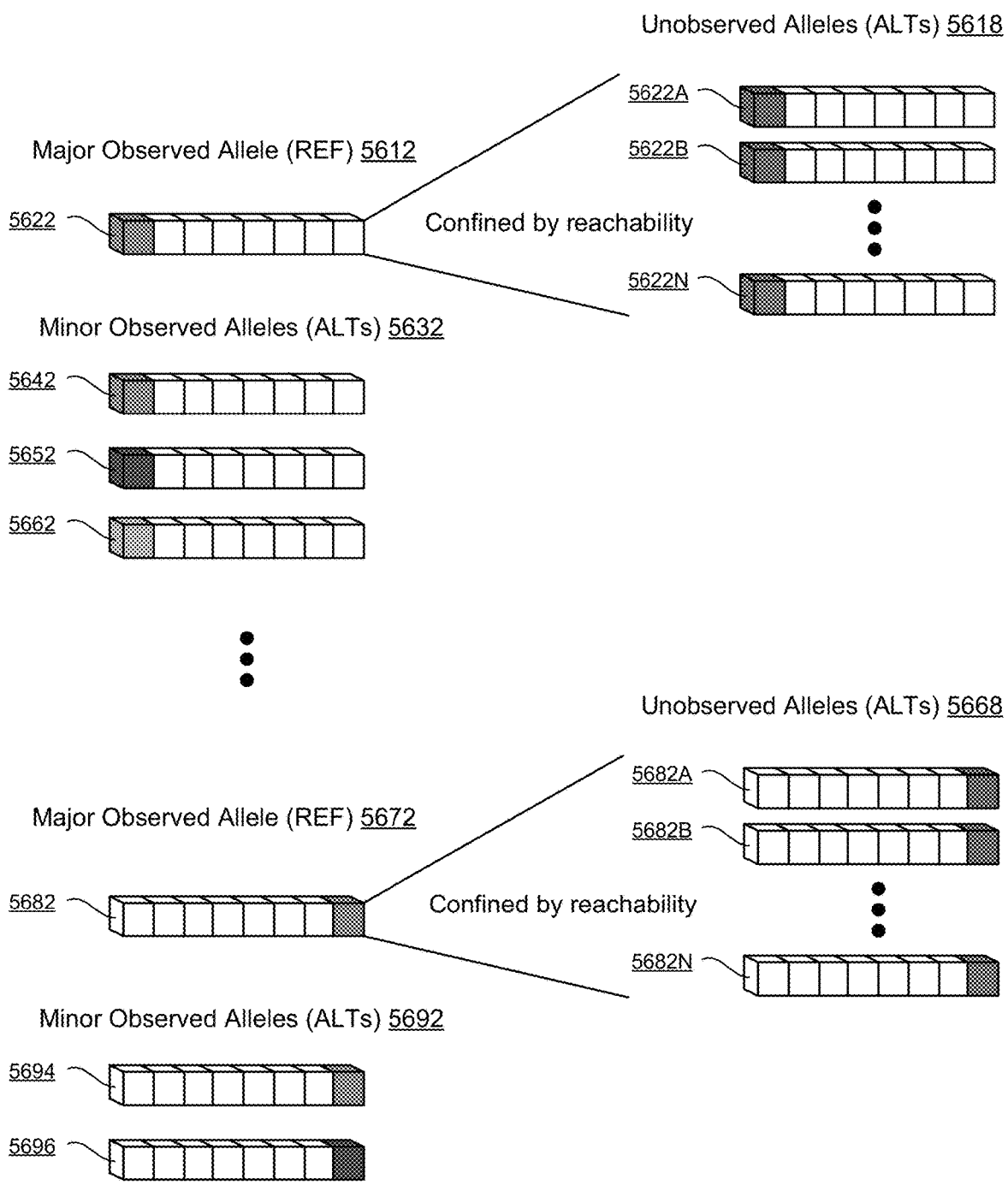
FIG. 56 illustrates one implementation of training data used to train the evolutionary conservation determiner.

FIG. 56 illustrates one implementation of training data 5600 used to train the evolutionary conservation determiner 5324. The evolutionary conservation determiner 5324 is trained on a conserved training set and a non-conserved training set. The conserved training set has respective conserved protein samples 5602 for respective conserved amino acids at respective positions in a proteome. The non-conserved training set has respective non-conserved (or unconserved) protein samples 5608 for respective non-conserved amino acids at the respective positions. In various implementations, the proteome includes human proteome and non-human proteome, including non-human primate proteome.

Each of the respective positions has a set of conserved amino acids and a set of non-conserved amino acids. A particular set of conserved amino acids for a particular position in a particular protein in the proteome includes at least one major allele amino acid observed at the particular position across a plurality of species. In one implementation, the major allele amino acid is a reference amino acid (e.g., REF allele 5612 spanning benign protein sample 5622, and REF allele 5662 spanning benign protein sample 5682). The particular set of conserved amino acids includes one or more minor allele amino acids observed at the particular position across the plurality of species (e.g., observed ALT alleles 5632 spanning benign protein samples 5642, 5652, 5662, and observed ALT alleles 5692 spanning benign protein samples 5695, 5696).

A particular set of non-conserved amino acids for the particular position includes amino acids not in the particular set of conserved amino acids (e.g., unobserved ALT alleles 5618 spanning pathogenic protein samples 5622A-N, and unobserved ALT alleles 5668 spanning pathogenic protein samples 5682A-N).

In one implementation, each of the respective positions has C conserved amino acids in the set of conserved amino acids. In such an implementation, each of the respective positions has NC non-conserved amino acids in the set of non-conserved amino acids, where NC=20−C. The conserved training set has CP conserved protein samples, where CP=a number of the respective positions*C. The non-conserved training set has NCP non-conserved protein samples, where NCP=the number of the respective positions*(20−C). In one implementation, the C ranges from one to ten. In another implementation, the C varies across the respective positions. In yet another implementation, the C is same for some of the respective positions.

In one implementation, the proteome has one to ten million positions. In such an implementation, each of the one to ten million positions has the C conserved amino acids in the set of conserved amino acids. Each of the one to ten million positions has the NC non-conserved amino acids in the set of non-conserved amino acids, where NC=20−C. The conserved training set has the CP conserved protein samples, where CP=one to ten million*C. The non-conserved training set has the NCP non-conserved protein samples, where NCP=one to ten million*(20−C).

In one implementation, the evolutionary conservation determiner 5324 is trained on twenty million to two hundred million training iterations. In such an implementation, the twenty million to two hundred million training iterations include one million to ten million training iterations with the one million to ten million conserved protein samples, and nineteen million to one hundred and ninety million iterations with the nineteen million to one hundred and ninety million non-conserved protein samples.

In another implementation, the proteome has one million to ten million positions, and therefore the training set has one million to ten million protein samples. In such an implementation, the evolutionary conservation determiner 5324 is trained on one million to ten million training iterations with the one million to ten million protein samples.

The respective conserved and non-conserved protein samples have respective gapped spatial representations generated by using respective reference amino acids at the respective positions as respective gap amino acids. The evolutionary conservation determiner 5324 trains on a particular conserved protein sample and estimates an evolutionary conservation of a particular conserved amino acid at a particular position in the particular conserved protein sample by processing, as input, a particular gapped spatial representation of the particular conserved protein sample, and generating, as output, an evolutionary conservation score for the particular conserved amino acid. The particular gapped spatial representation is generated by using a particular reference amino acid at the particular position as a gap amino acid, and by using remaining amino acids at remaining positions in the particular conserved protein sample as non-gap amino acids.

Each of the conserved protein samples has a ground truth conserved label. The ground truth conserved label is an evolutionary conservation frequency. In one implementation, the ground truth conserved label is one. The evolutionary conservation for the particular conserved amino acid is compared against the ground truth conserved label to determine an error, and to improve coefficients of the evolutionary conservation determiner 5324 based on the error using a training technique. In one implementation, the training technique is a loss function-based gradient update technique (e.g., backpropagation).

In some implementations, the ground truth conserved label is masked and not used to determine the error when the particular conserved amino acid is the particular reference amino acid. In such implementations, the masking causes the evolutionary conservation determiner 5324 to not overfit on the particular reference amino acid.

The evolutionary conservation determiner 5324 trains on a particular non-conserved protein sample and estimates an evolutionary conservation of a particular non-conserved amino acid at a particular position in the particular non-conserved protein sample by processing, as input, a particular gapped spatial representation of the particular non-conserved protein sample, and generating, as output, an evolutionary conservation score for the particular non-conserved amino acid. The particular gapped spatial representation is generated by using a particular reference amino acid at the particular position as a gap amino acid, and by using remaining amino acids at remaining positions in the particular non-conserved protein sample as non-gap amino acids.

Each of the non-conserved protein samples has a ground truth non-conserved label. The ground truth non-conserved label is an evolutionary conservation frequency. In one implementation, the ground truth non-conserved label is zero. The evolutionary conservation score for the particular non-conserved amino acid is compared against the ground truth non-conserved label to determine an error, and to improve the coefficients of the evolutionary conservation determiner 5324 based on the error using the training technique (e.g., backpropagation).

The evolutionary conservation determiner 5324 is trained on a training set. The training set has respective protein samples for the respective positions in the proteome. The respective protein samples have respective gapped spatial representations generated by using the respective reference amino acids at the respective positions as the respective gap amino acids.

Figure 57:
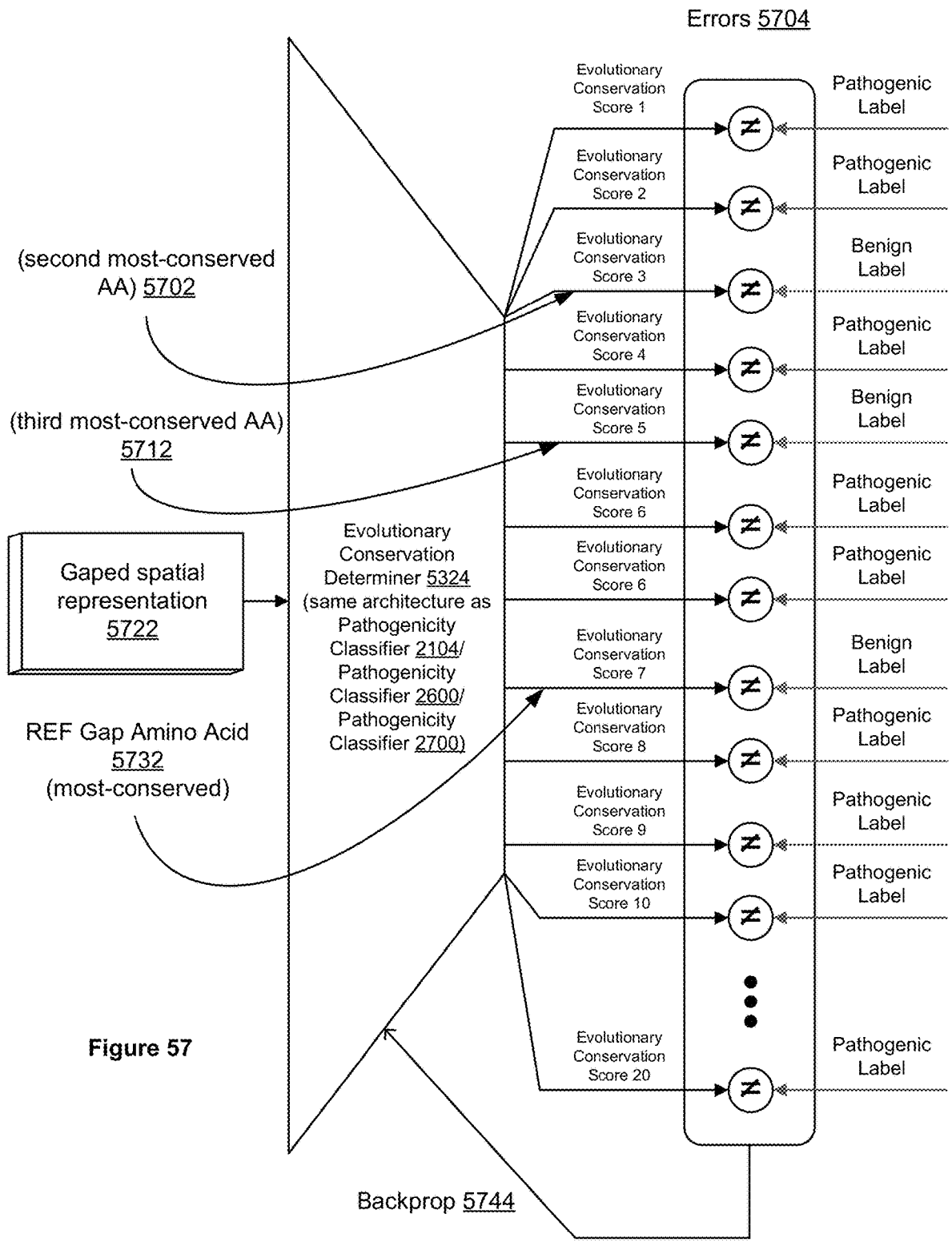
FIG. 57 illustrates one implementation of concurrently training the evolutionary conservation determiner on benign and pathogenic protein samples.

FIG. 57 illustrates one implementation of concurrently training 5700 the evolutionary conservation determiner on benign and pathogenic protein samples. The evolutionary conservation determiner 5324 trains on a particular protein sample and estimates an evolutionary conservation of respective amino acids of respective amino acid classes at a particular position in the particular protein sample by processing, as input, a particular gapped spatial representation 5722 of the particular protein sample, and generating, as output, respective evolutionary conservation scores 1-20 for the respective amino acids. The particular gapped spatial representation 5722 is generated by using a particular reference amino acid at the particular position as a gap amino acid, and by using remaining amino acids at remaining positions in the particular protein sample as non-gap amino acids.

Each of the protein samples has respective ground truth labels for the respective amino acids. The respective ground truth labels include one or more conserved (benign) labels for one or more conserved amino acids 5732, 5702, 5712, in the respective amino acids, and include one or more non-conserved (pathogenic) labels for one or more non-conserved amino acids in the respective amino acids. The conserved labels and the non-conserved labels have respective evolutionary conservation frequencies. The respective evolutionary conservation frequencies are rankable according to magnitude. In one implementation, the conserved labels are ones, and the non-conserved labels are zeros.

In one implementation, an error 5704 is determined based on respective comparisons of respective evolutionary conservation scores for the respective conserved amino acids against the respective conserved amino acids, and respective comparisons of respective evolutionary conservation scores for the respective non-conserved amino acids against the respective non-conserved amino acids. The coefficients of the evolutionary conservation determiner 5324 are improved based on the error using the training technique (e.g., backpropagation 5744).

In one implementation, the conserved amino acids include the particular reference amino acid, and a conserved label for the particular reference amino acid is masked and not used to determine the error. The masking causes the evolutionary conservation determiner 5324 to not overfit on the particular reference amino acid.

Synonymous mutations are point mutations, meaning they are just a miscopied DNA nucleotide that only changes one base pair in the RNA copy of the DNA. A codon in RNA is a set of three nucleotides that encode a specific amino acid. Most amino acids have several RNA codons that translate into that particular amino acid. Most of the time, if the third nucleotide is the one with the mutation, it will result in coding for the same amino acid. This is called a synonymous mutation because, like a synonym in grammar, the mutated codon has the same meaning as the original codon and therefore does not change the amino acid. If the amino acid does not change, then the protein is also unaffected. Synonymous mutations do not change anything, and no changes are made. That means they have no real role in the evolution of species since the gene or protein is not changed in any way. Synonymous mutations are actually fairly common, but since they have no effect, then they are not noticed.

Nonsynonymous mutations have a much greater effect on an individual than a synonymous mutation. In a nonsynonymous mutation, there is usually an insertion or deletion of a single nucleotide in the sequence during transcription when the messenger RNA is copying the DNA. This single missing or added nucleotide causes a frameshift mutation which throws off the entire reading frame of the amino acid sequence and mixes up the codons. This usually does affect the amino acids that are coded for and change the resulting protein that is expressed. The severity of this kind of mutation depends on how early in the amino acid sequence it happens. If it happens near the beginning and the entire protein is changed, this could become a lethal mutation. Another way a nonsynonymous mutation can occur is if the point mutation changes the single nucleotide into a codon that does not translate into the same amino acid. A lot of times, the single amino acid change does not affect the protein very much and is still viable. If it happens early in the sequence and the codon is changed to translate into a stop signal, then the protein will not be made, and it could cause serious consequences. Sometimes nonsynonymous mutations are actually positive changes. Natural selection may favor this new expression of the gene and the individual may have developed a favorable adaptation from the mutation. If that mutation occurs in the gametes, this adaptation will be passed down to the next generation of offspring. Nonsynonymous mutations increase the diversity in the gene pool for natural selection to work on and drive evolution on a microevolutionary level.

The nucleotide triplet that encodes an amino acid is called a codon. Each group of three nucleotides encodes one amino acid. Since there are 64 combinations of 4 nucleotides taken three at a time and only 20 amino acids, the code is degenerate (more than one codon per amino acid, in most cases). One example of the unreachable alternate amino acid classes are those alternate amino acid classes that are not coded by synonymous SNPs. Another example of the unreachable alternate amino acid classes are those alternate amino acid classes that are restricted by the number of triplet nucleotide mutant combinations deviated away by single nucleotide polymorphisms (SNPs) at the triplet nucleotide positions from an initial codon.

In one implementation, those unreachable alternate amino acid classes that are confined by reachability of SNPs to transform a reference codon of a reference amino acid into alternate amino acids of the unreachable alternate amino acid classes are masked in ground truth labels. In such an implementation, masked amino acid classes result in zero loss and do not contribute to gradient updates. In one implementation, the masked amino acid classes are identified in a lookup table. In one implementation, the lookup table identifies a set of masked amino acids classes for each reference amino acid position.

The particular set of conserved amino acids and the particular set of non-conserved amino acids are identified based on evolutionary conservation profiles of homologous proteins of the plurality of species. In one implementation, the evolutionary conservation profiles of the homologous proteins are determined using a position-specific frequency matrix (PSFM). In another implementation, the evolutionary conservation profiles of the homologous proteins are determined using a position-specific scoring matrix (PSSM).

FIG. 58 depicts different implementations of ground truth label encodings used to train the evolutionary conservation determiner 5324. Ground truth label encoding 5802 uses evolutionary conservation frequencies (e.g., PSFM or PSSM) to label the conserved amino acid classes A, C, F, and uses a "zero value" to label the remaining non-conserved amino acid classes. Ground truth label encoding 5812 is the same as the ground truth label encoding 5802 except that the ground truth label encoding 5812 "masks out" the REF major allele/most-conserved amino acid class F such that the REF major allele/most-conserved amino acid class F does not contribute to the training of the evolutionary conservation determiner 5324 (e.g., by zeroing-out the loss calculated by the loss function for the REF major allele/most-conserved amino acid class F).

Ground truth label encoding 5822 uses a "one value" to label the conserved amino acid classes A, C, F, and uses a "zero value" to label the remaining non-conserved amino acid classes. Ground truth label encoding 5832 is the same as the ground truth label encoding 5822 except that the ground truth label encoding 5832 "masks out" the REF major allele/most-conserved amino acid class F such that the REF major allele/most-conserved amino acid class F does not contribute to the training of the evolutionary conservation determiner 5324 (e.g., by zeroing-out the loss calculated by the loss function for the REF major allele/most-conserved amino acid class F).

Figure 61:
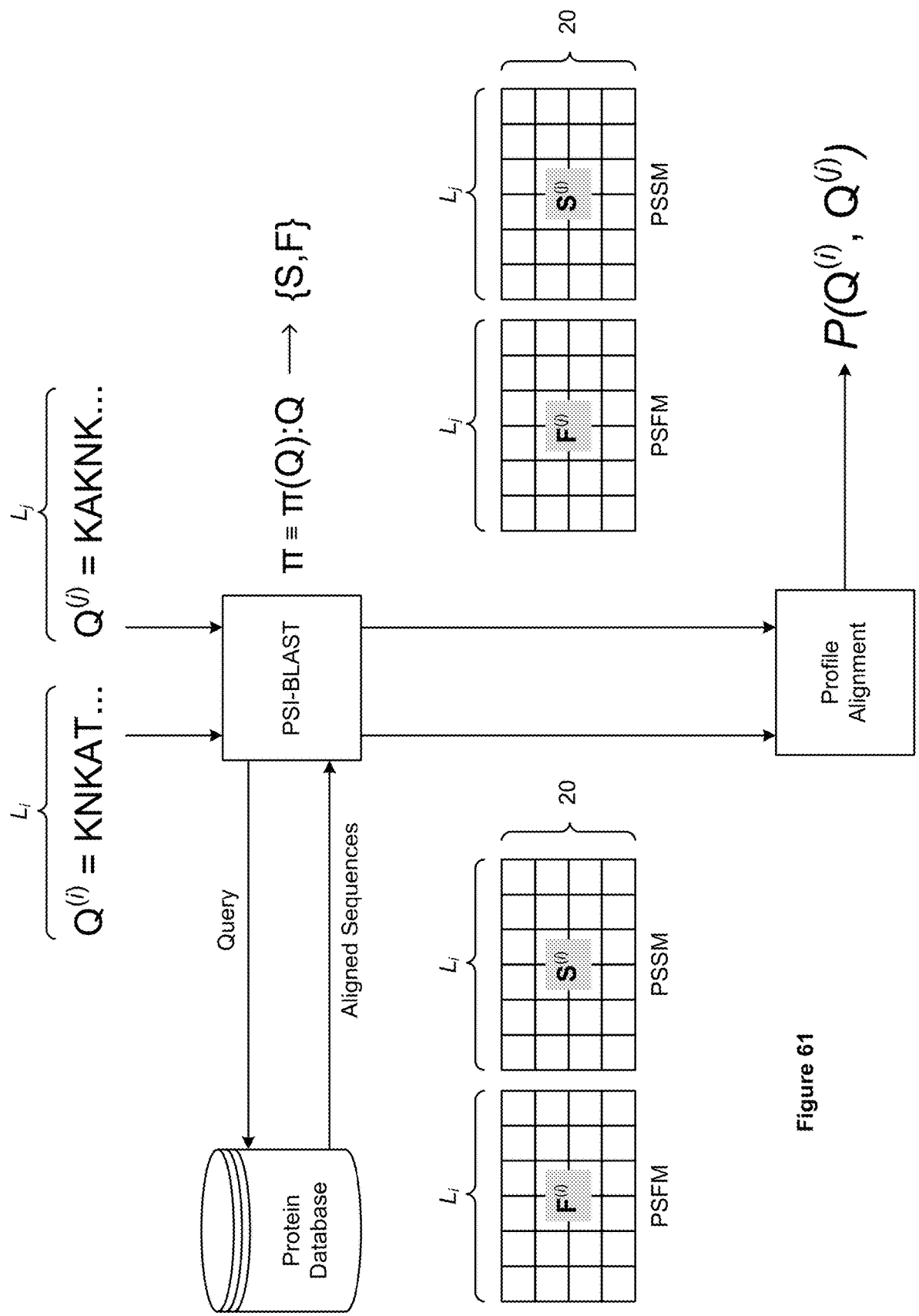
FIG. 61 shows one implementation of generating the PSFM and the PSSM.
Figure 62:
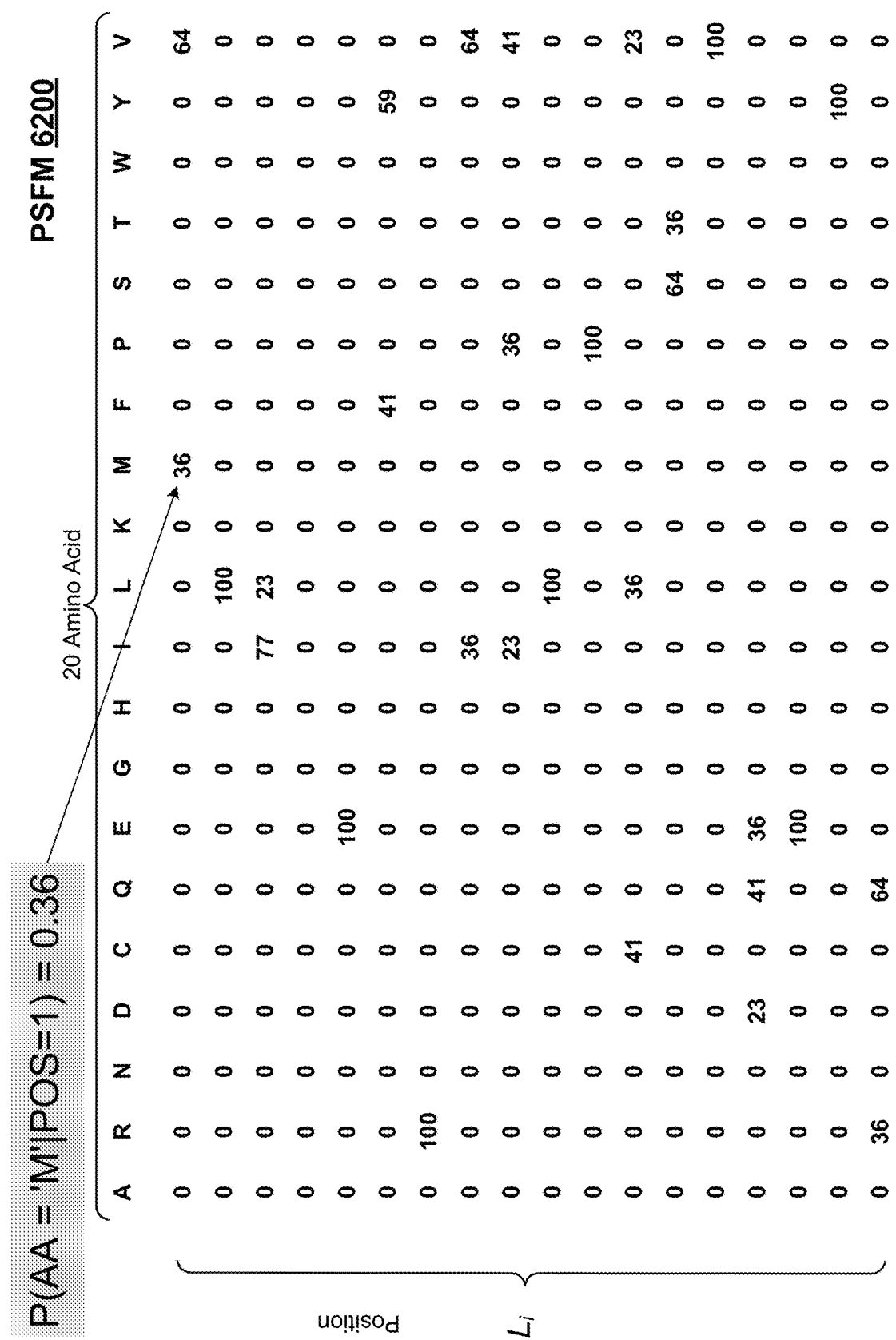
FIG. 62 illustrates an example PSFM encoding.

FIG. 59 illustrates an example PSFM 5900. FIG. 60 depicts an example PSSM 6000. FIG. 61 shows one implementation of generating the PSFM and the PSSM. FIG. 62 illustrates an example PSFM 6200 encoding. FIG. 63 depicts an example PSSM 6300 encoding.

Multiple sequence alignment (MSA) is a sequence alignment of multiple homologous protein sequences to a target protein. MSA is an important step in comparative analyses and property prediction of biological sequences since a lot of information, for example, evolution and coevolution clusters, are generated from the MSA and can be mapped to the target sequence of choice or on the protein structure.

Sequence profiles of a protein sequence X of length L are a L×20 matrix, either in the form of a PSSM or a PSFM. The columns of a PSSM and a PSFM are indexed by the alphabet of amino acids and each row corresponds to a position in the protein sequence. PSSMs and PSFMs contain the substitution scores and the frequencies, respectively, of the amino acids at different positions in the protein sequence. Each row of a PSFM is normalized to sum to 1. The sequence profiles of the protein sequence X are computed by aligning X with multiple sequences in a protein database that have statistically significant sequence similarities with X. Therefore, the sequence profiles contain more general evolutionary and structural information of the protein family that protein sequence X belongs to, and thus, provide valuable information for remote homology detection and fold recognition.

A protein sequence (called query sequence, e.g., a reference amino acid sequence of a protein) can be used as a seed to search and align homogenous sequences from a protein database (e.g., SWISSPROT) using, for example, a PSI-BLAST program. The aligned sequences share some homogenous segments and belong to the same protein family. The aligned sequences are further converted into two profiles to express their homogeneous information: PSSM and PSFM. Both PSSM and PSFM are matrices with 20 rows and L columns, where L is the total number of amino acids in the query sequence. Each column of a PSSM represents the log-likelihood of the residue substitutions at the corresponding positions in the query sequence. The (i, j)-th entry of the PSSM matrix represents the chance of the amino acid in the j-th position of the query sequence being mutated to amino acid type i during the evolution process. A PSFM contains the weighted observation frequencies of each position of the aligned sequences. Specifically, the (i, j)-th entry of the PSFM matrix represents the possibility of having amino acid type i in position j of the query sequence.

Given a query sequence, we first obtain its sequence profile by presenting it to PSI-BLAST to search and align homologous protein sequences from a protein database (e.g., Swiss-Prot Database). FIG. 61 shows the procedures of obtaining the sequence profile by using the PSI-BLAST program. The parameters h and j for PSI-BLAST are usually set to 0.001 and 3, respectively. The sequence profile of a protein encapsulates its homolog information pertaining to a query protein sequence. In PSI-BLAST, the homolog information is represented by two matrices: the PSFM and the PSSM. Examples of the PSFM and the PSSM are shown in FIGS. 62 and 63, respectively.

In FIG. 62, the (l, u)-th element ($l \in \{1, 2, \ldots, Li\}$, $u \in \{1, 2, \ldots, 20\}$) represents the chance of having the u-th amino acid in the l-th position of the query protein. For example, the chance of having the amino acid M in the 1st position of the query protein is 0.36.

In FIG. 63, the (l, u)-th element ($l \in \{1, 2, \ldots, Li\}$, $u \in \{1, 2, \ldots, 20\}$) represents the likelihood score of the amino acid in the l-th position of the query protein being mutated to the u-th amino acid during the evolution process. For example, the score for the amino acid V in the 1st position of the query protein being mutated to H during the evolution process is −3, while that in the 8th position is −4.

Combined Learning and Transfer Learning

FIG. 64 illustrates two datasets on which the models disclosed herein can be trained, for example, by way of combined learning (FIGS. 65A-B), or by way of transfer learning (FIGS. 66A-B). The first training dataset is called JigsawAI dataset 6406. The second training dataset is called PrimateAI dataset 6408. The JigsawAI dataset 6406 is characterized by a voxel input 6412 with a missing central residue identified as a gap amino acid, as discussed above. The PrimateAI dataset 6408 is characterized by the voxel input 6412 with no missing residues and complete input.

For the JigsawAI dataset 6406, ground truth labels 6422 have a missing or masked label 6426 for the gap amino acid (e.g., the REF amino acid). For the PrimateAI dataset 6408, the ground truth labels 6422 have nineteen missing or masked labels 6436 for those remaining amino acids that are different from the alternate amino acid-under-analysis (benign or pathogenic). In one implementation, the number of samples 6432 in the JigsawAI dataset 6406 are 10 million 6436, and 1 million 6438 in the PrimateAI dataset 6408.

FIGS. 65A-B illustrate one implementation of combined learning 6500 of the models disclosed herein. At action 6502, a gapped training set is accessed. The gapped training set is also referred to herein as the JigsawAI dataset 6406. The gapped training set includes respective gapped protein samples for respective positions in a proteome. The respective gapped protein samples are labelled with respective gapped ground truth sequences. A particular gapped ground truth sequence for a particular gapped protein sample has a benign label for a particular amino acid class that corresponds to a reference amino acid at a particular position in the particular gapped protein, and has respective pathogenic labels for respective remaining amino acid classes that correspond to alternate amino acids at the particular position.

At action 6512, a non-gapped training set is accessed. The non-gapped training set is also referred to herein as the PrimateAI dataset 6408. The non-gapped training set includes non-gapped benign protein samples and non-gapped pathogenic protein samples. A particular non-gapped benign protein sample includes a benign alternate amino acid at a particular position substituted by a benign nucleotide variant. A particular non-gapped pathogenic protein sample includes a pathogenic alternate amino acid at a particular position substituted by a pathogenic nucleotide variant. The particular non-gapped benign protein sample is labelled with a benign ground truth sequence that has a benign label for a particular amino acid class that corresponds to the benign alternate amino acid, and respective masked labels for respective remaining amino acid classes that correspond to amino acids that are different from the benign alternate amino acid. The particular non-gapped pathogenic protein sample is labelled with a pathogenic ground truth sequence that has a pathogenic label for a particular amino acid class that corresponds to the pathogenic alternate amino acid, and respective masked labels for respective remaining amino acid classes that correspond to amino acids that are different from the pathogenic alternate amino acid.

In one implementation, the benign label for the particular amino acid class that corresponds to the reference amino acid at the particular position in the particular gapped protein is masked. In one implementation, the non-gapped benign protein samples are derived from common human and non-human primate nucleotide variants. In one implementation, the non-gapped pathogenic protein samples are derived from combinatorically simulated nucleotide variants.

At action 6522, respective gapped spatial representations for the gapped protein samples are generated, and respective non-gapped spatial representations for the non-gapped benign protein samples and the non-gapped pathogenic protein samples are generated.

At action 6532, the pathogenicity classifier 2108/2600/2700 is trained over one or more training cycles, and a trained pathogenicity classifier 2108/2600/2700 is generated as a result of parameters/coefficients/weights of the trained pathogenicity classifier 2108/2600/2700 being optimized Each of the training cycles uses as training examples gapped spatial representations from the respective gapped spatial representations, and non-gapped spatial representations from the respective non-gapped spatial representations.

At action 6542, the trained pathogenicity classifier 2108/2600/2700 is used to determine pathogenicity of variants.

In one implementation, a sample indicator is used to indicate to the pathogenicity classifier 2108/2600/2700 whether a current training example is a gapped spatial representation for a gapped protein sample, or a non-gapped spatial representation for a non-gapped protein sample.

In one implementation, the pathogenicity classifier 2108/2600/2700 generates an amino acid class-wise output sequence in response to processing a training example. The amino acid class-wise output sequence has amino acid class-wise pathogenicity scores.

In one implementation, a performance of the trained pathogenicity classifier 2108/2600/2700 is measured between training cycles over a validation set. In some implementations, the validation set includes a pair of gapped and non-gapped spatial representations for each held-out protein sample.

In one implementation, the trained pathogenicity classifier 2108/2600/2700 generates a first amino acid class-wise output sequence for the gapped spatial representation in the pair, and a second amino acid class-wise output sequence for the non-gapped spatial representation in the pair. In some implementations, a final pathogenicity score for a nucleotide variant that causes an amino acid substitution in a held-out protein sample is determined based on a combination of first and second pathogenicity scores for the amino acid substitution in the first and second amino acid class-wise output sequences. In other implementations, the final pathogenicity score is based on an average of the first and second pathogenicity scores.

In some implementations, at least some of the training cycles use a same of number of gapped spatial representations and non-gapped spatial representations. In other implementations, at least some of the training cycles use batches of training examples that have a same of number of gapped spatial representations and non-gapped spatial representations.

In one implementation, a masked label does not contribute to error determination, and therefore does not contribute to training of the pathogenicity classifier 2108/2600/2700. In some implementations, the masked label is zeroed-out.

In some implementations, the gapped spatial representations are weighted differently from the non-gapped spatial representations, such that a contribution of the gapped spatial representations to gradient updates applied to parameters of the pathogenicity classifier 2108/2600/2700 in response to the pathogenicity classifier 2108/2600/2700 processing the non-gapped spatial representations varies from a contribution of the non-gapped spatial representations to gradient updates applied to the parameters of the pathogenicity classifier 2108/2600/2700 in response to the pathogenicity classifier 2108/2600/2700 processing the non-gapped spatial representations. In one implementation, the variation is determined by pre-defined weights.

FIGS. 66A-B illustrate one implementation of using transfer learning 6600 to train the models disclosed herein using the two datasets shown in FIG. 64. At action 6602, the pathogenicity classifier 2108/2600/2700 is first trained on the gapped training set (i.e., the JigsawAI data set 6406) to generate the trained pathogenicity classifier 2108/2600/2700.

At action 6612, the trained pathogenicity classifier 2108/2600/2700 is further trained on the non-gapped training set (i.e., the PrimateAI data set 6408) to generate a retrained pathogenicity classifier 2108/2600/2700.

At action 6622, the retrained pathogenicity classifier 2108/2600/2700 is used to determine pathogenicity of variants.

At action 6632, performance of the trained pathogenicity classifier 2108/2600/2700 is measured between training cycles over a first validation set that includes only non-gapped spatial representations of held-out protein samples. In another implementation, performance of the retrained pathogenicity classifier 2108/2600/2700 is measured between training cycles over a second validation set that includes gapped spatial representations and non-gapped spatial representations of held-out protein samples.

At action 6642, the retrained pathogenicity classifier 2108/2600/2700 generates a first amino acid class-wise output sequence for the pair in response to processing the pair. In one implementation, a final pathogenicity score for a nucleotide variant that causes an amino acid substitution in a corresponding held-out protein sample is determined based on the first amino acid class-wise output sequence.

Generating Training Data and Training Labels

Figure 67:
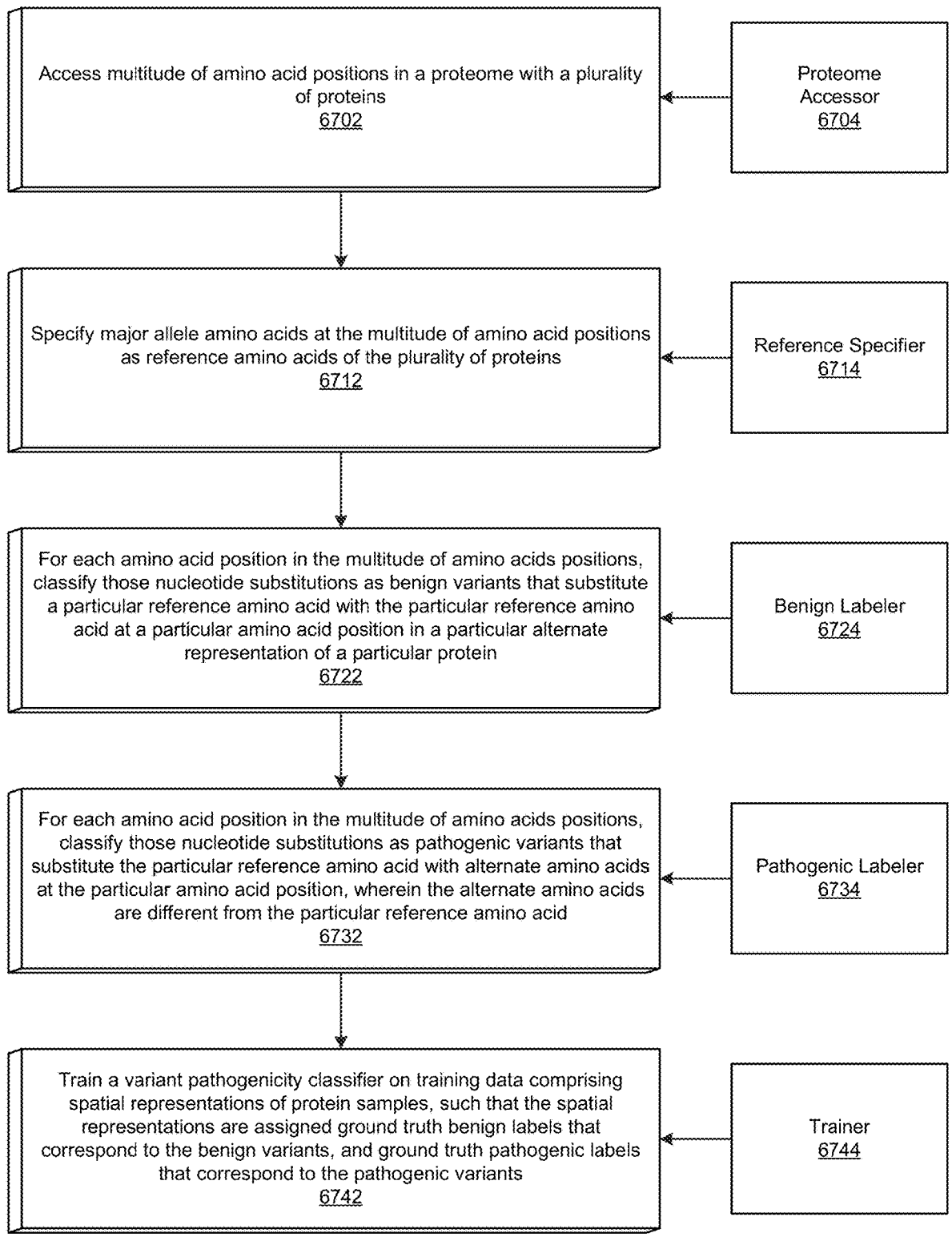
FIG. 67 shows one implementation of generating training data and labels to train the models disclosed herein.

FIG. 67 shows one implementation of generating 6700 training data and labels to train the models disclosed herein.

A proteome accessor 6704 accesses multitude of amino acid positions in a proteome with a plurality of proteins.

A reference specifier 6714 specifies major allele amino acids at the multitude of amino acid positions as reference amino acids of the plurality of proteins.

A benign labeler 6724, for each amino acid position in the multitude of amino acids positions, classifies those nucleotide substitutions as benign variants that substitute a particular reference amino acid with the particular reference amino acid at a particular amino acid position in a particular alternate representation of a particular protein.

A pathogenic labeler 6734, for each amino acid position in the multitude of amino acids positions, classifies those nucleotide substitutions as pathogenic variants that substitute the particular reference amino acid with alternate amino acids at the particular amino acid position. The alternate amino acids are different from the particular reference amino acid.

A trainer 6744 trains a variant pathogenicity classifier 2108/2600/2700 on training data comprising spatial representations of protein samples, such that the spatial representations are assigned ground truth benign labels that correspond to the benign variants, and ground truth pathogenic labels that correspond to the pathogenic variants.

In one implementation, the variant pathogenicity classifier 2108/2600/2700 is trained to determine whether a substitution of a first amino acid with a second amino acid at a given amino acid position in a protein is pathogenic or benign. In such an implementation, the variant pathogenicity classifier 2108/2600/2700 is trained to generate a pathogenicity score for the substitution. In one implementation, the variant pathogenicity classifier 2108/2600/2700 is trained to determine whether respective substitutions of a first amino acid with respective amino acids at a given amino acid position in a protein are pathogenic or benign. In such an implementation, the variant pathogenicity classifier 2108/2600/2700 is trained to generate respective pathogenicity scores for the respective substitutions. In some implementations, the respective amino acids correspond to respective twenty naturally-occurring amino acids. In other implementations, the respective amino acids correspond to respective naturally-occurring amino acids from a subset of the twenty naturally-occurring amino acids.

In one implementation, the variant pathogenicity classifier 2108/2600/2700 is trained to determine whether an insertion of an amino acid at a given vacant amino acid position in a protein is pathogenic or benign. In such an implementation, the variant pathogenicity classifier 2108/2600/2700 is trained to generate a pathogenicity score for the insertion. In one implementation, the variant pathogenicity classifier 2108/2600/2700 is trained to determine whether respective insertions of respective amino acids at a given vacant amino acid position in a protein are pathogenic or benign. In such an implementation, the variant pathogenicity classifier 2108/2600/2700 is trained to generate respective pathogenicity scores for the respective insertions. In some implementations, the respective amino acids correspond to respective twenty naturally-occurring amino acids. In other implementations, the respective amino acids correspond to respective naturally-occurring amino acids from a subset of the twenty naturally-occurring amino acids.

In one implementation, the variant pathogenicity classifier 2108/2600/2700 is trained to determine whether a substitution of a first amino acid with a second amino acid at a given amino acid position in a protein is spatially tolerated by other amino acids of the protein or not. In such an implementation, the variant pathogenicity classifier 2108/2600/2700 is trained to generate a spatial tolerance score for the substitution. In one implementation, the variant pathogenicity classifier 2108/2600/2700 is trained to determine whether respective substitutions of a first amino acid with respective amino acids at a given amino acid position in a protein are spatially tolerated by other amino acids of the protein or not. In such an implementation, the variant pathogenicity classifier 2108/2600/2700 is trained to generate respective spatial tolerance scores for the respective substitutions. In some implementations, the respective amino acids correspond to respective twenty naturally-occurring amino acids. In other implementations, the respective amino acids correspond to respective naturally-occurring amino acids from a subset of the twenty naturally-occurring amino acids.

In one implementation, the variant pathogenicity classifier 2108/2600/2700 is trained to determine whether an insertion of an amino acid at a given vacant amino acid position in a protein is spatially tolerated by other amino acids of the protein or not. In such an implementation, the variant pathogenicity classifier 2108/2600/2700 is trained to generate a spatial tolerance score for the insertion. In one implementation, the variant pathogenicity classifier 2108/2600/2700 is trained to determine whether respective insertions of respective amino acids at a given vacant amino acid position in a protein are spatially tolerated by other amino acids of the protein or not. In such an implementation, the variant pathogenicity classifier 2108/2600/2700 is trained to generate respective spatial tolerance scores for the respective insertions. In some implementations, the respective amino acids correspond to respective twenty naturally-occurring amino acids. In other implementations, the respective amino acids correspond to respective naturally-occurring amino acids from a subset of the twenty naturally-occurring amino acids.

In one implementation, the variant pathogenicity classifier 2108/2600/2700 is trained to determine whether a substitution of a first amino acid with a second amino acid at a given amino acid position in a protein is evolutionary conserved or non-conserved. In such an implementation, the variant pathogenicity classifier 2108/2600/2700 is trained to generate an evolutionary conservation score for the substitution. In one implementation, the variant pathogenicity classifier 2108/2600/2700 is trained to determine whether respective substitutions of a first amino acid with respective amino acids at a given amino acid position in a protein are evolutionary conserved or non-conserved. In such an implementation, the variant pathogenicity classifier 2108/2600/2700 is trained to generate respective evolutionary conservation scores for the respective substitutions. In some implementations, the respective amino acids correspond to respective twenty naturally-occurring amino acids. In other implementations, the respective amino acids correspond to respective naturally-occurring amino acids from a subset of the twenty naturally-occurring amino acids.

In one implementation, the variant pathogenicity classifier 2108/2600/2700 is trained to determine whether an insertion of an amino acid at a given vacant amino acid position in a protein is evolutionary conserved or non-conserved. In such an implementation, the variant pathogenicity classifier 2108/2600/2700 is trained to generate an evolutionary conservation score for the insertion.

In one implementation, the variant pathogenicity classifier 2108/2600/2700 is trained to determine whether respective insertions of respective amino acids at a given vacant amino acid position in a protein are evolutionary conserved or non-conserved. In such an implementation, the variant pathogenicity classifier 2108/2600/2700 is trained to generate respective evolutionary conservation scores for the respective insertions. In some implementations, the respective amino acids correspond to respective twenty naturally-occurring amino acids. In other implementations, the respective amino acids correspond to respective naturally-occurring amino acids from a subset of the twenty naturally-occurring amino acids.

In different implementations, spatial tolerance corresponds to structural tolerance, and spatial intolerance corresponds to structural intolerance. In different implementations, the multitude of amino acids positions range from one million to ten million amino acid positions. In different implementations, the multitude of amino acids positions range from ten million to hundred million amino acid positions. In different implementations, the multitude of amino acids positions range from hundred million to a billion amino acid positions. In different implementations, the multitude of amino acids positions range from one to a million amino acid positions.

In one implementation, those unreachable alternate amino acid classes that are confined by reachability of single nucleotide polymorphisms (SNPs) to transform a reference codon of a reference amino acid into alternate amino acids of the unreachable alternate amino acid classes are masked in ground truth labels. In such an implementation, masked amino acid classes result in zero loss and do not contribute to gradient updates. In such an implementation, the masked amino acid classes are identified in a lookup table. In such an implementation, the lookup table identifies a set of masked amino acids classes for each reference amino acid position.

In different implementations, the spatial representations are structural representations of protein structures of the protein samples. In different implementations, the spatial representations are encoded using voxelization Pathogenicity Determination FIG. 68 illustrates one implementation of a method 6800 of determining pathogenicity of nucleotide variants. The method includes, at action 6802, accessing a spatial representation of a protein. The spatial representation of the protein specifies respective spatial configurations of respective amino acids at respective positions in the protein.

The method includes, at action 6812, removing, from the spatial representation of the protein, a particular spatial configuration of a particular amino acid at a particular position, thereby generating a gapped spatial representation of the protein. In one implementation, the removal of the particular spatial configuration is implemented (or automated) by a script.

The method includes, at action 6822, determining a pathogenicity of a nucleotide variant based at least in part on the gapped spatial representation, and a representation of an alternate amino acid created by the nucleotide variant at the particular position.

Structural Tolerability Prediction

Figure 69:
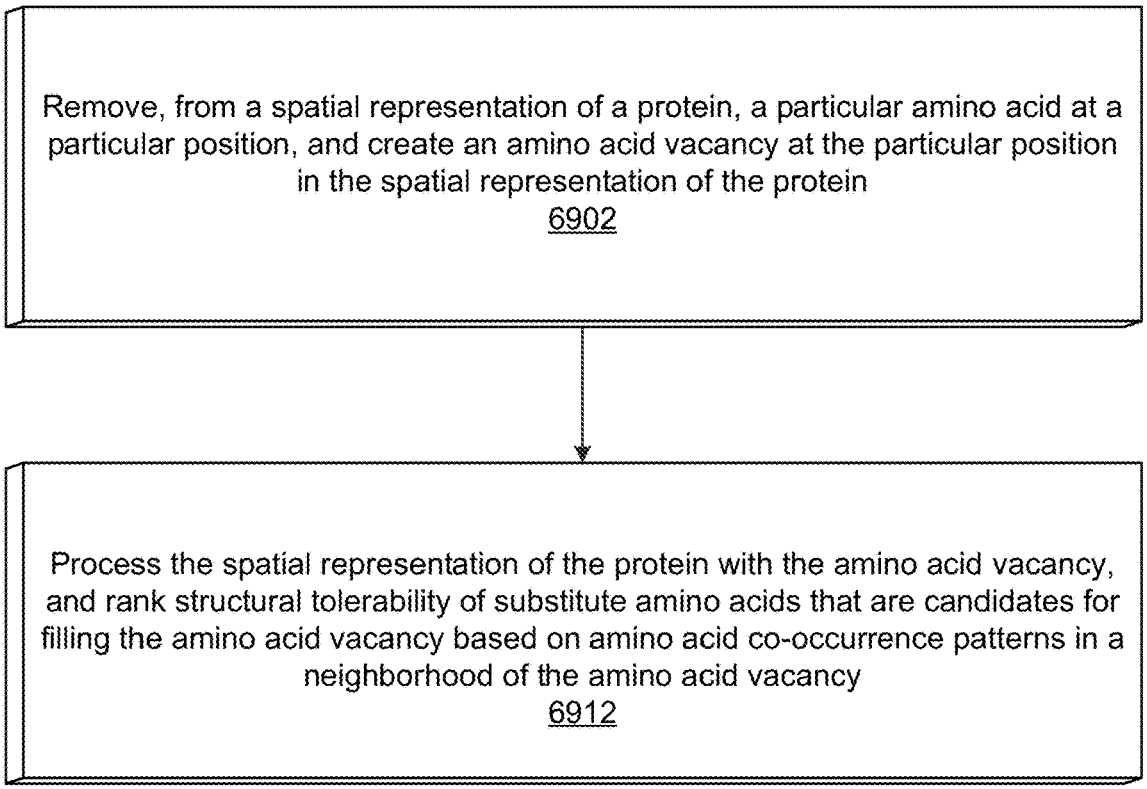
FIG. 69 illustrates one implementation of a system to predict structural tolerability of amino acid substitutes.

FIG. 69 illustrates one implementation of a system 6900 to predict structural tolerability of amino acid substitutes. At action 6902, a gapping logic is configured to remove, from a spatial representation of a protein, a particular amino acid at a particular position, and create an amino acid vacancy at the particular position in the spatial representation of the protein.

At action 6912, a structural tolerability prediction logic is configured to process the spatial representation of the protein with the amino acid vacancy, and rank structural tolerability of substitute amino acids that are candidates for filling the amino acid vacancy based on amino acid co-occurrence patterns in a neighborhood of the amino acid vacancy.

Performance Results as Objective Indicia of Inventiveness and Non-Obviousness

The variant pathogenicity classifier disclosed herein makes pathogenicity predictions based on 3D protein structures and is referred to as "PrimateAI 3D." "Primate AI" is a commonly owned and previously disclosed variant pathogenicity classifier that makes pathogenicity predictions based protein sequences. Additional details about PrimateAI can be found in commonly owned U.S. patent application Ser. Nos. 16/160,903; 16/160,986; 16/160,968; and 16/407, 149 and in Sundaram, L et al. Predicting the clinical impact of human mutation with deep neural networks. *Nat. Genet.* 50, 1161-1170 (2018).

The variant pathogenicity classifier trained using the transfer learning technique disclosed herein (FIGS. 66A-B) is referred to as "Transfer Learning." The variant pathogenicity classifier trained using the combined learning technique disclosed herein (FIGS. 65A-B) is referred to as "Combined Learning."

The performance results in FIG. 70 are generated on the classification task of accurately distinguishing benign variants from pathogenic variants across a plurality of validation sets. New developmental delay disorder (new DDD) is one example of a validation set used to compare the classification accuracy of Transfer Learning against Combined Learning again Primate AI 3D against Primate AI. The new DDD validation set labels variants from individuals with DDD as pathogenic and labels the same variants from healthy relatives of the individuals with the DDD as benign. A similar labelling scheme is used with an autism spectrum disorder (ASD) validation set.

BRCA1 is another example of a validation set used to compare the classification accuracy of Transfer Learning against Combined Learning again Primate AI 3D against Primate AI. The BRCA1 validation set labels synthetically generated reference amino acid sequences simulating proteins of the BRCA1 gene as benign variants and labels synthetically altered allele amino acid sequences simulating proteins of the BRCA1 gene as pathogenic variants. A similar labelling scheme is used with different validation sets of the TP53 gene, TP53S3 gene and its variants, and other genes and their variants shown in FIG. 70.

In FIG. 70, the y-axis has p-values, and the x-axis has the different validation sets. As demonstrated by the p-values in FIG. 70, Combined Learning generally outperforms other approaches, followed by Transfer Learning, which is in turn followed by PrimateAI 3D. Greater p-values, i.e., longer vertical bars denote greater accuracy in differentiating benign variants from pathogenic variants. In FIG. 70, the vertical bars for Combined Learning are consistently longer than the vertical bars for other approaches.

Also, in FIG. 70, a separate "mean" chart calculates the mean of the p-values determined for each of the validation sets. In the mean chart as well, Combined Learning generally outperforms other approaches, followed by Transfer Learning, which is in turn followed by PrimateAI 3D, as indicated by the horizontal bars for Combined Learning being consistently longer than the horizontal bars for other approaches.

The mean statistics may be biased by outliers. To address this, a separate "method ranks" chart is also depicted in FIG. 70. Higher rank denotes poorer classification accuracy. In the method ranks chart as well, Combined Learning generally outperforms other approaches, followed by Transfer Learning, which is in turn followed by PrimateAI 3D. In the method ranks chart, having more counts of lower ranks 1 and 2 is better than having higher ranks of 3s.

Clauses

The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

One or more implementations and clauses of the technology disclosed or elements thereof can be implemented in the form of a computer product, including a non-transitory computer readable storage medium with computer usable program code for performing the method steps indicated. Furthermore, one or more implementations and clauses of the technology disclosed or elements thereof can be implemented in the form of an apparatus including a memory and at least one processor that is coupled to the memory and operative to perform exemplary method steps. Yet further, in another aspect, one or more implementations and clauses of the technology disclosed or elements thereof can be implemented in the form of means for carrying out one or more of the method steps described herein; the means can include (i) hardware module(s), (ii) software module(s) executing on one or more hardware processors, or (iii) a combination of hardware and software modules; any of (i)-(iii) implement the specific techniques set forth herein, and the software modules are stored in a computer readable storage medium (or multiple such media).

The clauses described in this section can be combined as features. In the interest of conciseness, the combinations of features are not individually enumerated and are not repeated with each base set of features. The reader will understand how features identified in the clauses described in this section can readily be combined with sets of base features identified as implementations in other sections of this application. These clauses are not meant to be mutually exclusive, exhaustive, or restrictive; and the technology disclosed is not limited to these clauses but rather encompasses all possible combinations, modifications, and variations within the scope of the claimed technology and its equivalents.

Other implementations of the clauses described in this section can include a non-transitory computer readable storage medium storing instructions executable by a processor to perform any of the clauses described in this section. Yet another implementation of the clauses described in this section can include a system including memory and one or more processors operable to execute instructions, stored in the memory, to perform any of the clauses described in this section.

We disclose the following clauses:

Clauses Set 1 (ILLM 1050-2)

1. A computer-implemented method of determining pathogenicity of nucleotide variants, including:

accessing a protein that has respective amino acids at respective positions;

specifying a particular amino acid at a particular position in the protein as a gap amino acid, and specifying remaining amino acids at remaining positions in the protein as non-gap amino acids;

generating a gapped spatial representation of the protein that includes spatial configurations of the non-gap amino acids, and excludes a spatial configuration of the gap amino acid; and determining a pathogenicity of a nucleotide variant based at least in part on
  the gapped spatial representation, and
  a representation of an alternate amino acid created by the nucleotide variant at the particular position.

2. The computer-implemented method of clause 1, wherein the spatial configurations of the non-gap amino acids are encoded as amino acid class-wise distance channels,
  wherein each of the amino acid class-wise distance channels has voxel-wise distance values for voxels in a plurality of voxels, and
  wherein the voxel-wise distance values specify distances from corresponding voxels in the plurality of voxels to atoms of the non-gap amino acids.

3. The computer-implemented method of clause 2, wherein the spatial configurations of the non-gap amino acids are determined based on spatial proximity between the corresponding voxels and the atoms of the non-gap amino acids.

4. The computer-implemented method of clause 2, wherein the spatial configuration of the gap amino acid is excluded from the gapped spatial representation by disregarding distances from the corresponding voxels to atoms of the gap amino acid when determining the voxel-wise distance values.

5. The computer-implemented method of clause 4, wherein the spatial configuration of the gap amino acid is excluded from the gapped spatial representation by disregarding spatial proximity between the corresponding voxels and the atoms of the gap amino acid.

6. The computer-implemented method of clause 1, wherein the particular amino acid is a reference amino acid that is a major allele of the protein.

7. The computer-implemented method of clause 1, wherein a pathogenicity predictor determines the pathogenicity of the nucleotide variant by
  processing, as input,
    the gapped spatial representation, and
    the representation of the alternate amino acid; and
  generating, as output, a pathogenicity score for the alternate amino acid.

8. The computer-implemented method of clause 7, wherein the pathogenicity predictor is trained on a benign training set.

9. The computer-implemented method of clause 8, wherein the benign training set has respective benign protein samples for respective reference amino acids at respective positions in a proteome.

10. The computer-implemented method of clause 9, wherein the reference amino acids are major allele amino acids of the proteome.

11. The computer-implemented method of clause 10, wherein the proteome has ten million positions, and therefore the benign training set has ten million benign protein samples.

12. The computer-implemented method of clause 11, wherein the respective benign protein samples have respective gapped spatial representations generated by using the respective reference amino acids as respective gap amino acids.

13. The computer-implemented method of clause 12, wherein the respective benign protein samples have respective representations of the respective reference amino acids as respective alternate amino acids.

14. The computer-implemented method of clause 13, wherein the pathogenicity predictor trains on a particular benign protein sample and estimates a pathogenicity of a particular reference amino acid at a particular position in the particular benign protein sample by
  processing, as input,
    (i) a particular gapped spatial representation of the particular benign protein sample,
      wherein the particular gapped spatial representation is generated
        by using the particular reference amino acid as a gap amino acid, and
        by using remaining amino acids at remaining positions in the particular benign protein sample as non-gap amino acids, and
    (ii) a representation of the particular reference amino acid as a particular alternate amino acid; and
  generating, as output, a pathogenicity score for the particular reference amino acid.

15. The computer-implemented method of clause 14, wherein each of the benign protein samples has a ground truth benignness label that indicates absolute benignness of the benign protein samples.

16. The computer-implemented method of clause 15, wherein the ground truth benignness label is zero.

17. The computer-implemented method of clause 16, wherein the pathogenicity score for the particular reference amino acid is compared against the ground truth benignness label to determine an error, and to improve coefficients of the pathogenicity predictor based on the error using a training technique.

18. The computer-implemented method of clause 1, wherein the pathogenicity predictor is trained on a pathogenic training set.

19. The computer-implemented method of clause 18, wherein the pathogenic training set has respective pathogenic protein samples for respective combinatorically generated amino acid substitutions for each of the reference amino acids at each of the respective positions in the proteome.

20. The computer-implemented method of clause 19, wherein the combinatorically generated amino acid substitutions for a particular reference amino acid of a particular amino acid class at a particular position in the proteome include respective alternate amino acids of respective amino acid classes that are different from the particular amino acid class.

21. The computer-implemented method of clause 20, wherein the proteome has the ten million positions, wherein there are nineteen combinatorically generated amino acid substitutions for each of the ten million positions, and therefore the pathogenic training set has one hundred and ninety million pathogenic protein samples.

22. The computer-implemented method of clause 21, wherein the respective pathogenic protein samples have respective gapped spatial representations generated by using the respective reference amino acids as respective gap amino acids.

23. The computer-implemented method of clause 22, wherein the respective pathogenic protein samples have respective representations of the respective combinatorically generated amino acid substitutions as respective alternate amino acids created by respective combinatorically generated nucleotide variants at the respective positions in the proteome.

24. The computer-implemented method of clause 23, wherein the pathogenicity predictor trains on a particular pathogenic protein sample and estimates a pathogenicity of a particular combinatorically generated amino acid substitution for a particular reference amino acid at a particular position in the particular pathogenic protein sample by
processing, as input,
(i) a particular gapped spatial representation of the particular pathogenic protein sample,
wherein the particular gapped spatial representation is generated
by using the particular reference amino acid as a gap amino acid, and
by using remaining amino acids at remaining positions in the particular pathogenic protein sample as non-gap amino acids, and
(ii) a representation of the particular combinatorically generated amino acid substitution as a particular alternate amino acid; and
generating, as output, a pathogenicity score for the particular combinatorically generated amino acid substitution.

25. The computer-implemented method of clause 24, wherein each of the pathogenic protein samples has a ground truth pathogenicity label that indicates absolute pathogenicity of the pathogenic protein samples.

26. The computer-implemented method of clause 25, wherein the ground truth pathogenicity label is one.

27. The computer-implemented method of clause 26, wherein the pathogenicity score for the particular combinatorically generated amino acid substitution is compared against the ground truth pathogenicity label to determine an error, and to improve the coefficients of the pathogenicity predictor based on the error using the training technique.

28. The computer-implemented method of clause 27, wherein the pathogenicity predictor is trained on two hundred million training iterations,
wherein the two hundred million training iterations include
ten million training iterations with the ten million benign protein samples, and
one hundred and ninety million iterations with the one hundred and ninety million pathogenic protein samples.

29. The computer-implemented method of clause 10, wherein the proteome has one million to ten million positions, and therefore the benign training set has one million to ten million benign protein samples,
wherein there are nineteen combinatorically generated amino acid substitutions for each of the one million to ten million positions, and therefore the pathogenic training set has nineteen million to one hundred and ninety million pathogenic protein samples.

30. The computer-implemented method of clause 29, wherein the pathogenicity predictor is trained on twenty million to two hundred million training iterations,
wherein the twenty million to two hundred million training iterations include
one million to ten million training iterations with the one million to ten million benign protein samples, and
nineteen million to one hundred and ninety million iterations with the nineteen million to one hundred and ninety million pathogenic protein samples.

31. The computer-implemented method of clause 6, wherein the alternate amino acid is an amino acid that is same as the reference amino acid.

32. The computer-implemented method of clause 31, wherein the alternate amino acid is an amino acid that is different from the reference amino acid.

33. The computer-implemented method of clause 32, wherein the pathogenicity predictor generates a first pathogenicity score for a first alternate amino acid that is same as a first reference amino acid,
wherein the pathogenicity predictor generates a second pathogenicity score for a second alternate amino acid that is different from the first reference amino acid.

34. The computer-implemented method of clause 33, wherein a final pathogenicity score for the second alternate amino acid is the second pathogenicity score.

35. The computer-implemented method of clause 34, wherein the final pathogenicity score for the second alternate amino acid is based on a combination of the first pathogenicity score and the second pathogenicity score.

36. The computer-implemented method of clause 35, wherein the final pathogenicity score for the second alternate amino acid is a ratio of the second pathogenicity score over a sum of the first pathogenicity score and the second pathogenicity score.

37. The computer-implemented method of clause 36, wherein the final pathogenicity score for the second alternate amino acid is determined by subtracting the first pathogenicity score from the second pathogenicity score.

38. The computer-implemented method of clause 1, wherein the spatial configurations of the non-gap amino acids are encoded as evolutionary profile channels based on pan-amino acid conservation frequencies of amino acids with nearest atoms to the voxels.

39. The computer-implemented method of clause 38, wherein the spatial configuration of the gap amino acid is excluded from the gapped spatial representation by disregarding nearest atoms of the gap amino acid when determining the pan-amino acid conservation frequencies.

40. The computer-implemented method of clause 1, wherein the spatial configurations of the non-gap amino acids are encoded as evolutionary profile channels based on per-amino acid conservation frequencies of respective amino acids with respective nearest atoms to the voxels.

41. The computer-implemented method of clause 40, wherein the spatial configuration of the gap amino acid is excluded from the gapped spatial representation by disregarding respective nearest atoms of the gap amino acid when determining the per-amino acid conservation frequencies.

42. The computer-implemented method of clause 1, wherein the spatial configurations of the non-gap amino acids are encoded as annotation channels.

43. The computer-implemented method of clause 42, wherein the spatial configuration of the gap amino acid is excluded from the gapped spatial representation by disregarding atoms of the gap amino acid when determining the annotation channels.

44. The computer-implemented method of clause 1, wherein the spatial configurations of the non-gap amino acids are encoded as structural confidence channels.

45. The computer-implemented method of clause 44, wherein the spatial configuration of the gap amino acid is excluded from the gapped spatial representation by disregarding atoms of the gap amino acid when determining the structural confidence channels.

46. The computer-implemented method of clause 1, wherein the spatial configurations of the non-gap amino acids are encoded as additional input channels.

47. The computer-implemented method of clause 46, wherein the spatial configuration of the gap amino acid is excluded from the gapped spatial representation by disregarding atoms of the gap amino acid when determining the additional input channels.

48. The computer-implemented method of clause 9, wherein the proteome includes human proteome and non-human proteome, including non-human primate proteome.

49. The computer-implemented method of clause 7, wherein those unreachable alternate amino acid classes that are confined by reachability of single nucleotide polymorphisms (SNPs) to transform a reference codon of a reference amino acid into alternate amino acids of the unreachable alternate amino acid classes are masked in ground truth labels.

50. The computer-implemented method of clause 1, wherein masked amino acid classes result in zero loss and do not contribute to gradient updates.

51. The computer-implemented method of clause 50, wherein the masked amino acid classes are identified in a lookup table.

52. The computer-implemented method of clause 51, wherein the lookup table identifies a set of masked amino acids classes for each reference amino acid position.

Clauses Set 2

1. A computer-implemented method of determining pathogenicity of nucleotide variants, including:
   accessing a protein that has respective amino acids at respective positions;
   specifying a particular amino acid of a particular amino acid class at a particular position in the protein as a gap amino acid, and specifying remaining amino acids at remaining positions in the protein as non-gap amino acids;
   generating a gapped spatial representation of the protein that
   includes spatial configurations of the non-gap amino acids, and
   excludes a spatial configuration of the gap amino acid; and
   based at least in part on the gapped spatial representation, determining a pathogenicity of respective alternate amino acids at the particular position.

2. The computer-implemented method of clause 1, wherein the spatial configurations of the non-gap amino acids are encoded as amino acid class-wise distance channels,
   wherein each of the amino acid class-wise distance channels has voxel-wise distance values for voxels in a plurality of voxels, and
   wherein the voxel-wise distance values specify distances from corresponding voxels in the plurality of voxels to atoms of the non-gap amino acids.

3. The computer-implemented method of clause 2, wherein the spatial configurations of the non-gap amino acids are determined based on spatial proximity between the corresponding voxels and the atoms of the non-gap amino acids.

4. The computer-implemented method of clause 2, wherein the spatial configuration of the gap amino acid is excluded from the gapped spatial representation by disregarding distances from the corresponding voxels to atoms of the gap amino acid when determining the voxel-wise distance values.

5. The computer-implemented method of clause 4, wherein the spatial configuration of the gap amino acid is excluded from the gapped spatial representation by disregarding spatial proximity between the corresponding voxels and the atoms of the gap amino acid.

6. The computer-implemented method of clause 1, wherein the particular amino acid is a reference amino acid that is a major allele of the protein.

7. The computer-implemented method of clause 1, wherein the respective alternate amino acids are respective combinatorically generated alternate amino acids created by respective combinatorically generated nucleotide variants at the particular position.

8. The computer-implemented method of clause 1, wherein a pathogenicity predictor determines the pathogenicity of the respective alternate amino acids by
   processing, as input, the gapped spatial representation; and
   generating, as output, respective pathogenicity scores for respective amino acid classes.

9. The computer-implemented method of clause 8, wherein the pathogenicity predictor is trained on a training set.

10. The computer-implemented method of clause 9, wherein the training set has respective protein samples for respective positions in a proteome.

11. The computer-implemented method of clause 10, wherein the proteome has ten million positions, and therefore the training set has ten million protein samples.

12. The computer-implemented method of clause 11, wherein the respective protein samples have respective gapped spatial representations generated by using respective reference amino acids at the respective positions in proteome as respective gap amino acids.

13. The computer-implemented method of clause 12, wherein the reference amino acids are major allele amino acids of the proteome.

14. The computer-implemented method of clause 13, wherein the pathogenicity predictor trains on a particular protein sample and estimates a pathogenicity of respective alternate amino acids for a particular reference amino acid at a particular position in the particular protein sample by
   processing, as input,
     a particular gapped spatial representation of the particular protein sample,
       wherein the particular gapped spatial representation is generated
         by using the particular reference amino acid as a gap amino acid, and
         by using remaining amino acids at remaining positions in the particular protein sample as non-gap amino acids; and
   generating, as output, respective pathogenicity scores for the respective amino acid classes.

15. The computer-implemented method of clause 14, wherein each of the protein samples has respective ground truth labels for the respective amino acid classes.

16. The computer-implemented method of clause 15, wherein the respective ground truth labels include an absolute benignness label for a reference amino acid class in the respective amino acid classes, and include respective absolute pathogenicity labels for respective alternate amino acid classes in the respective amino acid classes.

17. The computer-implemented method of clause 16, wherein the absolute benignness label is zero.

18. The computer-implemented method of clause 17, wherein the absolute pathogenicity labels are same across the respective alternate amino acid classes.

19. The computer-implemented method of clause 18, wherein the absolute pathogenicity labels are one.

20. The computer-implemented method of clause 1, wherein an error is determined based on
   a comparison of a pathogenicity score for the reference amino acid class against the absolute benignness label, and
   respective comparisons of respective pathogenicity scores for the respective alternate amino acid classes against the respective absolute pathogenicity labels.

21. The computer-implemented method of clause 20, wherein coefficients of the pathogenicity predictor are improved based on the error using a training technique.

22. The computer-implemented method of clause 21, wherein the pathogenicity predictor is trained on ten million training iterations with the ten million protein samples.

23. The computer-implemented method of clause 8, wherein the respective amino acid classes correspond to respective twenty naturally-occurring amino acids.

24. The computer-implemented method of clause 23, wherein the respective amino acid classes correspond to respective naturally-occurring amino acids from a subset of the twenty naturally-occurring amino acids.

25. The computer-implemented method of clause 11, wherein the proteome has one million to ten million positions, and therefore the training set has one million to ten million protein samples,
wherein the pathogenicity predictor is trained on one million to ten million training iterations with the one million to ten million protein samples.

26. The computer-implemented method of clause 8, wherein the pathogenicity predictor generates a reference pathogenicity score for a first alternate amino acid of the reference amino acid class,
wherein the pathogenicity predictor generates respective alternate pathogenicity scores for respective alternate amino acids of the respective alternate amino acid classes.

27. The computer-implemented method of clause 26, wherein respective final alternate pathogenicity scores for the respective alternate amino acids are the respective alternate pathogenicity scores.

28. The computer-implemented method of clause 27, wherein the respective final alternate pathogenicity scores for the respective alternate amino acids are based on respective combinations of the reference pathogenicity score and the respective alternate pathogenicity scores.

29. The computer-implemented method of clause 28, wherein the respective final alternate pathogenicity scores for the respective alternate amino acids are respective ratios of the respective alternate pathogenicity scores over a sum of the reference pathogenicity score and the respective alternate pathogenicity scores.

30. The computer-implemented method of clause 29, wherein the respective final alternate pathogenicity scores for the respective alternate amino acids are determined by respectively subtracting the reference pathogenicity score from the respective alternate pathogenicity scores.

31. The computer-implemented method of clause 8, wherein the pathogenicity predictor has an output layer that generates the respective pathogenicity scores.

32. The computer-implemented method of clause 31, wherein the output layer is a normalization layer.

33. The computer-implemented method of clause 32, wherein the respective pathogenicity scores are normalized.

34. The computer-implemented method of clause 31, wherein the output layer is a softmax layer.

35. The computer-implemented method of clause 34, wherein the respective pathogenicity scores are exponentially normalized.

36. The computer-implemented method of clause 31, wherein the output layer has respective sigmoid units that respectively generate the respective pathogenicity scores.

37. The computer-implemented method of clause 31, wherein the respective pathogenicity scores are unnormalized.

38. The computer-implemented method of clause 1, wherein the spatial configurations of the non-gap amino acids are encoded as evolutionary profile channels based on pan-amino acid conservation frequencies of amino acids with nearest atoms to the voxels.

39. The computer-implemented method of clause 38, wherein the spatial configuration of the gap amino acid is excluded from the gapped spatial representation by disregarding nearest atoms of the gap amino acid when determining the pan-amino acid conservation frequencies.

40. The computer-implemented method of clause 1, wherein the spatial configurations of the non-gap amino acids are encoded as evolutionary profile channels based on per-amino acid conservation frequencies of respective amino acids with respective nearest atoms to the voxels.

41. The computer-implemented method of clause 40, wherein the spatial configuration of the gap amino acid is excluded from the gapped spatial representation by disregarding respective nearest atoms of the gap amino acid when determining the per-amino acid conservation frequencies.

42. The computer-implemented method of clause 1, wherein the spatial configurations of the non-gap amino acids are encoded as annotation channels.

43. The computer-implemented method of clause 42, wherein the spatial configuration of the gap amino acid is excluded from the gapped spatial representation by disregarding atoms of the gap amino acid when determining the annotation channels.

44. The computer-implemented method of clause 1, wherein the spatial configurations of the non-gap amino acids are encoded as structural confidence channels.

45. The computer-implemented method of clause 44, wherein the spatial configuration of the gap amino acid is excluded from the gapped spatial representation by disregarding atoms of the gap amino acid when determining the structural confidence channels.

46. The computer-implemented method of clause 1, wherein the spatial configurations of the non-gap amino acids are encoded as additional input channels.

47. The computer-implemented method of clause 46, wherein the spatial configuration of the gap amino acid is excluded from the gapped spatial representation by disregarding atoms of the gap amino acid when determining the additional input channels.

48. The computer-implemented method of clause 10, wherein the proteome includes human proteome and non-human proteome, including non-human primate proteome.

49. The computer-implemented method of clause 8, wherein those unreachable alternate amino acid classes that are confined by reachability of single nucleotide polymorphisms (SNPs) to transform a reference codon of a reference amino acid into alternate amino acids of the unreachable alternate amino acid classes are masked in ground truth labels.

50. The computer-implemented method of clause 1, wherein masked amino acid classes result in zero loss and do not contribute to gradient updates.

51. The computer-implemented method of clause 50, wherein the masked amino acid classes are identified in a lookup table.

52. The computer-implemented method of clause 51, wherein the lookup table identifies a set of masked amino acids classes for each reference amino acid position.

Clauses Set 3

1. A computer-implemented method of generating training data for training a variant pathogenicity classifier, including:
accessing multitude of amino acid positions in a proteome with a plurality of proteins;
specifying major allele amino acids at the multitude of amino acid positions as reference amino acids of the plurality of proteins;
for each amino acid position in the multitude of amino acids positions, classifying those nucleotide substitutions as benign variants that substitute a particular reference amino acid with the particular reference amino acid at a particular amino acid position in a particular alternate representation of a particular protein, and classifying those nucleotide substitutions as pathogenic variants that substitute the particular reference amino acid with alternate amino acids at the particular amino acid position, wherein the alternate amino acids are different from the particular reference amino acid; and training a variant pathogenicity classifier using the benign variants and the pathogenic variants as training data.

2. The computer-implemented method of clause 1, wherein the variant pathogenicity classifier is trained to determine whether a substitution of a first amino acid with a second amino acid at a given amino acid position in a protein is pathogenic or benign.

3. The computer-implemented method of clause 2, wherein the variant pathogenicity classifier is trained to generate a pathogenicity score for the substitution.

4. The computer-implemented method of clause 1, wherein the variant pathogenicity classifier is trained to determine whether respective substitutions of a first amino acid with respective amino acids at a given amino acid position in a protein are pathogenic or benign.

5. The computer-implemented method of clause 4, wherein the variant pathogenicity classifier is trained to generate respective pathogenicity scores for the respective substitutions.

6. The computer-implemented method of clause 5, wherein the respective amino acids correspond to respective twenty naturally-occurring amino acids.

7. The computer-implemented method of clause 6, wherein the respective amino acids correspond to respective naturally-occurring amino acids from a subset of the twenty naturally-occurring amino acids.

8. The computer-implemented method of clause 1, wherein the variant pathogenicity classifier is trained to determine whether an insertion of an amino acid at a given vacant amino acid position in a protein is pathogenic or benign.

9. The computer-implemented method of clause 8, wherein the variant pathogenicity classifier is trained to generate a pathogenicity score for the insertion.

10. The computer-implemented method of clause 1, wherein the variant pathogenicity classifier is trained to determine whether respective insertions of respective amino acids at a given vacant amino acid position in a protein are pathogenic or benign.

11. The computer-implemented method of clause 10, wherein the variant pathogenicity classifier is trained to generate respective pathogenicity scores for the respective insertions.

12. The computer-implemented method of clause 11, wherein the respective amino acids correspond to respective twenty naturally-occurring amino acids.

13. The computer-implemented method of clause 12, wherein the respective amino acids correspond to respective naturally-occurring amino acids from a subset of the twenty naturally-occurring amino acids.

14. The computer-implemented method of clause 1, wherein the variant pathogenicity classifier is trained to determine whether a substitution of a first amino acid with a second amino acid at a given amino acid position in a protein is spatially tolerated by other amino acids of the protein or not.

15. The computer-implemented method of clause 14, wherein the variant pathogenicity classifier is trained to generate a spatial tolerance score for the substitution.

16. The computer-implemented method of clause 1, wherein the variant pathogenicity classifier is trained to determine whether respective substitutions of a first amino acid with respective amino acids at a given amino acid position in a protein are spatially tolerated by other amino acids of the protein or not.

17. The computer-implemented method of clause 16, wherein the variant pathogenicity classifier is trained to generate respective spatial tolerance scores for the respective substitutions.

18. The computer-implemented method of clause 17, wherein the respective amino acids correspond to respective twenty naturally-occurring amino acids.

19. The computer-implemented method of clause 18, wherein the respective amino acids correspond to respective naturally-occurring amino acids from a subset of the twenty naturally-occurring amino acids.

20. The computer-implemented method of clause 1, wherein the variant pathogenicity classifier is trained to determine whether an insertion of an amino acid at a given vacant amino acid position in a protein is spatially tolerated by other amino acids of the protein or not.

21. The computer-implemented method of clause 20, wherein the variant pathogenicity classifier is trained to generate a spatial tolerance score for the insertion.

22. The computer-implemented method of clause 1, wherein the variant pathogenicity classifier is trained to determine whether respective insertions of respective amino acids at a given vacant amino acid position in a protein are spatially tolerated by other amino acids of the protein or not.

23. The computer-implemented method of clause 22, wherein the variant pathogenicity classifier is trained to generate respective spatial tolerance scores for the respective insertions.

24. The computer-implemented method of clause 23, wherein the respective amino acids correspond to respective twenty naturally-occurring amino acids.

25. The computer-implemented method of clause 24, wherein the respective amino acids correspond to respective naturally-occurring amino acids from a subset of the twenty naturally-occurring amino acids.

26. The computer-implemented method of clause 1, wherein the variant pathogenicity classifier is trained to determine whether a substitution of a first amino acid with a second amino acid at a given amino acid position in a protein is evolutionary conserved or non-conserved.

27. The computer-implemented method of clause 26, wherein the variant pathogenicity classifier is trained to generate an evolutionary conservation score for the substitution.

28. The computer-implemented method of clause 1, wherein the variant pathogenicity classifier is trained to determine whether respective substitutions of a first amino acid with respective amino acids at a given amino acid position in a protein are evolutionary conserved or non-conserved.

29. The computer-implemented method of clause 28, wherein the variant pathogenicity classifier is trained to generate respective evolutionary conservation scores for the respective substitutions.

30. The computer-implemented method of clause 29, wherein the respective amino acids correspond to respective twenty naturally-occurring amino acids.

31. The computer-implemented method of clause 30, wherein the respective amino acids correspond to respective naturally-occurring amino acids from a subset of the twenty naturally-occurring amino acids.

32. The computer-implemented method of clause 1, wherein the variant pathogenicity classifier is trained to determine whether an insertion of an amino acid at a given vacant amino acid position in a protein is evolutionary conserved or non-conserved.

33. The computer-implemented method of clause 32, wherein the variant pathogenicity classifier is trained to generate an evolutionary conservation score for the insertion.

34. The computer-implemented method of clause 1, wherein the variant pathogenicity classifier is trained to determine whether respective insertions of respective amino acids at a given vacant amino acid position in a protein are evolutionary conserved or non-conserved.

35. The computer-implemented method of clause 34, wherein the variant pathogenicity classifier is trained to generate respective evolutionary conservation scores for the respective insertions.

36. The computer-implemented method of clause 35, wherein the respective amino acids correspond to respective twenty naturally-occurring amino acids.

37. The computer-implemented method of clause 36, wherein the respective amino acids correspond to respective naturally-occurring amino acids from a subset of the twenty naturally-occurring amino acids.

38. The computer-implemented method of clause 14, wherein spatial tolerance corresponds to structural tolerance, and spatial intolerance corresponds to structural intolerance.

39. The computer-implemented method of clause 1, wherein the multitude of amino acids positions range from one million to ten million amino acid positions.

40. The computer-implemented method of clause 1, wherein the multitude of amino acids positions range from ten million to hundred million amino acid positions.

41. The computer-implemented method of clause 1, wherein the multitude of amino acids positions range from hundred million to a billion amino acid positions.

42. The computer-implemented method of clause 1, wherein the multitude of amino acids positions range from one to a million amino acid positions.

43. The computer-implemented method of clause 1, wherein those unreachable alternate amino acid classes that are confined by reachability of single nucleotide polymorphisms (SNPs) to transform a reference codon of a reference amino acid into alternate amino acids of the unreachable alternate amino acid classes are masked in ground truth labels.

44. The computer-implemented method of clause 1, wherein masked amino acid classes result in zero loss and do not contribute to gradient updates.

45. The computer-implemented method of clause 44, wherein the masked amino acid classes are identified in a lookup table.

46. The computer-implemented method of clause 45, wherein the lookup table identifies a set of masked amino acids classes for each reference amino acid position.

Clauses Set 4 (ILLM 1060-1)

1. A computer-implemented method of determining pathogenicity of nucleotide variants, including:
    specifying a particular amino acid at a particular position in a protein as a gap amino acid, and specifying remaining amino acids at remaining positions in the protein as non-gap amino acids;
    generating a gapped spatial representation of the protein that
        includes spatial configurations of the non-gap amino acids, and
        excludes a spatial configuration of the gap amino acid;
    determining an evolutionary conservation at the particular position of respective amino acids of respective amino acid classes based at least in part on the gapped spatial representation; and
    based at least in part on the evolutionary conservation of the respective amino acids, determining a pathogenicity of respective nucleotide variants that respectively substitute the particular amino acid with the respective amino acids in alternate representations of the protein.

2. The computer-implemented method of clause 1, wherein the spatial configurations of the non-gap amino acids are encoded as amino acid class-wise distance channels,
    wherein each of the amino acid class-wise distance channels has voxel-wise distance values for voxels in a plurality of voxels, and
    wherein the voxel-wise distance values specify distances from corresponding voxels in the plurality of voxels to atoms of the non-gap amino acids.

3. The computer-implemented method of clause 2, wherein the spatial configurations of the non-gap amino acids are determined based on spatial proximity between the corresponding voxels and the atoms of the non-gap amino acids.

4. The computer-implemented method of clause 2, wherein the spatial configuration of the gap amino acid is excluded from the gapped spatial representation by disregarding distances from the corresponding voxels to atoms of the gap amino acid when determining the voxel-wise distance values.

5. The computer-implemented method of clause 4, wherein the spatial configuration of the gap amino acid is excluded from the gapped spatial representation by disregarding spatial proximity between the corresponding voxels and the atoms of the gap amino acid.

6. The computer-implemented method of clause 1, wherein the particular amino acid is a reference amino acid that is a major allele of the protein.

7. The computer-implemented method of clause 1, wherein an evolutionary conservation predictor determines the evolutionary conservation by
    processing, as input, the gapped spatial representation; and
    generating, as output, respective evolutionary conservation scores for the respective amino acids.

8. The computer-implemented method of clause 7, wherein the respective evolutionary conservation scores are rankable by magnitude.

9. The computer-implemented method of clause 7, further including classifying a nucleotide variant as pathogenic when an evolutionary conservation score generated by the evolutionary conservation predictor for a corresponding amino acid substitution is below a threshold.

10. The computer-implemented method of clause 7, further including classifying a nucleotide variant as pathogenic when an evolutionary conservation score generated by the evolutionary conservation predictor for a corresponding amino acid substitution is zero.

11. The computer-implemented method of clause 7, further including classifying a nucleotide variant as benign when an evolutionary conservation score generated by the evolutionary conservation predictor for a corresponding amino acid substitution is above a threshold.

12. The computer-implemented method of clause 7, further including classifying a nucleotide variant as benign when an evolutionary conservation score generated by the evolutionary conservation predictor for a corresponding amino acid substitution is non-zero.

13. The computer-implemented method of clause 7, wherein the evolutionary conservation predictor is trained on a conserved training set and a non-conserved training set.

14. The computer-implemented method of clause 13, wherein the conserved training set has respective conserved protein samples for respective conserved amino acids at respective positions in a proteome, wherein the non-conserved training set has respective non-conserved protein samples for respective non-conserved amino acids at the respective positions.

15. The computer-implemented method of clause 14, wherein each of the respective positions has a set of conserved amino acids and a set of non-conserved amino acids.

16. The computer-implemented method of clause 15, wherein a particular set of conserved amino acids for a particular position in a particular protein in the proteome includes at least one major allele amino acid observed at the particular position across a plurality of species.

17. The computer-implemented method of clause 16, wherein the particular set of conserved amino acids includes one or more minor allele amino acids observed at the particular position across the plurality of species.

18. The computer-implemented method of clause 17, wherein a particular set of non-conserved amino acids for the particular position includes amino acids not in the particular set of conserved amino acids.

19. The computer-implemented method of clause 18, wherein the particular set of conserved amino acids and the particular set of non-conserved amino acids are identified based on evolutionary conservation profiles of homologous proteins of the plurality of species.

20. The computer-implemented method of clause 18, wherein the evolutionary conservation profiles of the homologous proteins are determined using a position-specific frequency matrix (PSFM).

21. The computer-implemented method of clause 18, wherein the evolutionary conservation profiles of the homologous proteins are determined using a position-specific scoring matrix (PSSM).

22. The computer-implemented method of clause 16, wherein the major allele amino acid is a reference amino acid.

23. The computer-implemented method of clause 14, wherein each of the respective positions has C conserved amino acids in the set of conserved amino acids, wherein each of the respective positions has NC non-conserved amino acids in the set of non-conserved amino acids, where NC=20−C, wherein the conserved training set has CP conserved protein samples, where CP=a number of the respective positions*C, and wherein the non-conserved training set has NCP non-conserved protein samples, where NCP=the number of the respective positions*(20−C).

24. The computer-implemented method of clause 23, wherein the C ranges from one to ten.

25. The computer-implemented method of clause 24, wherein the C varies across the respective positions.

26. The computer-implemented method of clause 25, wherein the C is same for some of the respective positions.

27. The computer-implemented method of clause 14, wherein the respective conserved and non-conserved protein samples have respective gapped spatial representations generated by using respective reference amino acids at the respective positions as respective gap amino acids.

28. The computer-implemented method of clause 27, wherein the evolutionary conservation predictor trains on a particular conserved protein sample and estimates an evolutionary conservation of a particular conserved amino acid at a particular position in the particular conserved protein sample by processing, as input,
a particular gapped spatial representation of the particular conserved protein sample,
wherein the particular gapped spatial representation is generated
by using a particular reference amino acid at the particular position as a gap amino acid, and
by using remaining amino acids at remaining positions in the particular conserved protein sample as non-gap amino acids; and
generating, as output, an evolutionary conservation score for the particular conserved amino acid.

29. The computer-implemented method of clause 28, wherein each of the conserved protein samples has a ground truth conserved label.

30. The computer-implemented method of clause 29, wherein the ground truth conserved label is an evolutionary conservation frequency.

31. The computer-implemented method of clause 29, wherein the ground truth conserved label is one.

32. The computer-implemented method of clause 29, wherein the evolutionary conservation for the particular conserved amino acid is compared against the ground truth conserved label to determine an error, and to improve coefficients of the evolutionary conservation predictor based on the error using a training technique.

33. The computer-implemented method of clause 32, wherein the ground truth conserved label is masked and not used to determine the error when the particular conserved amino acid is the particular reference amino acid, wherein the masking causes the evolutionary conservation predictor to not overfit on the particular reference amino acid.

34. The computer-implemented method of clause 32, wherein the training technique is a loss function-based gradient update technique.

35. The computer-implemented method of clause 27, wherein the evolutionary conservation predictor trains on a particular non-conserved protein sample and estimates an evolutionary conservation of a particular non-conserved amino acid at a particular position in the particular non-conserved protein sample by processing, as input,
a particular gapped spatial representation of the particular non-conserved protein sample,
wherein the particular gapped spatial representation is generated
by using a particular reference amino acid at the particular position as a gap amino acid, and
by using remaining amino acids at remaining positions in the particular non-conserved protein sample as non-gap amino acids; and
generating, as output, an evolutionary conservation score for the particular non-conserved amino acid.

36. The computer-implemented method of clause 35, wherein each of the non-conserved protein samples has a ground truth non-conserved label.

37. The computer-implemented method of clause 35, wherein the ground truth non-conserved label is an evolutionary conservation frequency.

38. The computer-implemented method of clause 35, wherein the ground truth non-conserved label is zero.

39. The computer-implemented method of clause 35, wherein the evolutionary conservation score for the particular non-conserved amino acid is compared against the ground truth non-conserved label to determine an error, and to improve the coefficients of the evolutionary conservation predictor based on the error using the training technique.

40. The computer-implemented method of clause 7, wherein the evolutionary conservation predictor is trained on a training set.

41. The computer-implemented method of clause 40, wherein the training set has respective protein samples for the respective positions in the proteome.

42. The computer-implemented method of clause 41, wherein the respective protein samples have respective gapped spatial representations generated by using the respective reference amino acids at the respective positions as the respective gap amino acids.

43. The computer-implemented method of clause 42, wherein the evolutionary conservation predictor trains on a particular protein sample and estimates an evolutionary conservation of respective amino acids of respective amino acid classes at a particular position in the particular protein sample by
   processing, as input,
      a particular gapped spatial representation of the particular protein sample,
         wherein the particular gapped spatial representation is generated
            by using a particular reference amino acid at the particular position as a gap amino acid, and
            by using remaining amino acids at remaining positions in the particular protein sample as non-gap amino acids; and
   generating, as output, respective evolutionary conservation scores for the respective amino acids.

44. The computer-implemented method of clause 43, wherein each of the protein samples has respective ground truth labels for the respective amino acids.

45. The computer-implemented method of clause 44, wherein the respective ground truth labels include one or more conserved labels for one or more conserved amino acids in the respective amino acids, and include one or more non-conserved labels for one or more non-conserved amino acids in the respective amino acids.

46. The computer-implemented method of clause 45, wherein the conserved labels and the non-conserved labels have respective evolutionary conservation frequencies.

47. The computer-implemented method of clause 46, wherein the respective evolutionary conservation frequencies are rankable according to magnitude.

48. The computer-implemented method of clause 46, wherein the conserved labels are ones, and the non-conserved labels are zeros.

49. The computer-implemented method of clause 46, wherein an error is determined based on
   respective comparisons of respective evolutionary conservation scores for the respective conserved amino acids against the respective conserved amino acids, and
   respective comparisons of respective evolutionary conservation scores for the respective non-conserved amino acids against the respective non-conserved amino acids.

50. The computer-implemented method of clause 49, wherein coefficients of the evolutionary conservation predictor are improved based on the error using the training technique.

51. The computer-implemented method of clause 50, wherein the conserved amino acids include the particular reference amino acid, and a conserved label for the particular reference amino acid is masked and not used to determine the error,
   wherein the masking causes the evolutionary conservation predictor to not overfit on the particular reference amino acid.

52. The computer-implemented method of clause 14, wherein the proteome has one to ten million positions,
   wherein each of the one to ten million positions has the C conserved amino acids in the set of conserved amino acids,
   wherein each of the one to ten million positions has the NC non-conserved amino acids in the set of non-conserved amino acids, where NC=20−C,
   wherein the conserved training set has the CP conserved protein samples, where CP=one to ten million*C, and
   wherein the non-conserved training set has the NCP non-conserved protein samples, where NCP=one to ten million*(20−C).

53. The computer-implemented method of clause 14, wherein the evolutionary conservation predictor is trained on twenty million to two hundred million training iterations,
   wherein the twenty million to two hundred million training iterations include
      one million to ten million training iterations with the one million to ten million conserved protein samples, and
      nineteen million to one hundred and ninety million iterations with the nineteen million to one hundred and ninety million non-conserved protein samples.

54. The computer-implemented method of clause 14, wherein the proteome has one million to ten million positions, and therefore the training set has one million to ten million protein samples,
   wherein the evolutionary conservation predictor is trained on one million to ten million training iterations with the one million to ten million protein samples.

55. The computer-implemented method of clause 1, wherein the spatial configurations of the non-gap amino acids are encoded as evolutionary profile channels based on pan-amino acid conservation frequencies of amino acids with nearest atoms to the voxels.

56. The computer-implemented method of clause 55, wherein the spatial configuration of the gap amino acid is excluded from the gapped spatial representation by disregarding nearest atoms of the gap amino acid when determining the pan-amino acid conservation frequencies.

57. The computer-implemented method of clause 1, wherein the spatial configurations of the non-gap amino acids are encoded as evolutionary profile channels based on per-amino acid conservation frequencies of respective amino acids with respective nearest atoms to the voxels.

58. The computer-implemented method of clause 57, wherein the spatial configuration of the gap amino acid is excluded from the gapped spatial representation by disregarding respective nearest atoms of the gap amino acid when determining the per-amino acid conservation frequencies.

59. The computer-implemented method of clause 1, wherein the spatial configurations of the non-gap amino acids are encoded as annotation channels.

60. The computer-implemented method of clause 59, wherein the spatial configuration of the gap amino acid is excluded from the gapped spatial representation by disregarding atoms of the gap amino acid when determining the annotation channels.

61. The computer-implemented method of clause 1, wherein the spatial configurations of the non-gap amino acids are encoded as structural confidence channels.

62. The computer-implemented method of clause 61, wherein the spatial configuration of the gap amino acid is excluded from the gapped spatial representation by disregarding atoms of the gap amino acid when determining the structural confidence channels.

63. The computer-implemented method of clause 1, wherein the spatial configurations of the non-gap amino acids are encoded as structural confidence channels.

64. The computer-implemented method of clause 63, wherein the spatial configuration of the gap amino acid is excluded from the gapped spatial representation by disregarding atoms of the gap amino acid when determining the structural confidence channels.

65. The computer-implemented method of clause 1, wherein the spatial configurations of the non-gap amino acids are encoded as additional input channels.

66. The computer-implemented method of clause 65, wherein the spatial configuration of the gap amino acid is excluded from the gapped spatial representation by disregarding atoms of the gap amino acid when determining the additional input channels.

67. The computer-implemented method of clause 14, wherein the proteome includes human proteome and non-human proteome, including non-human primate proteome.

68. The computer-implemented method of clause 1, wherein those unreachable alternate amino acid classes that are confined by reachability of single nucleotide polymorphisms (SNPs) to transform a reference codon of a reference amino acid into alternate amino acids of the unreachable alternate amino acid classes are masked in ground truth labels.

69. The computer-implemented method of clause 1, wherein masked amino acid classes result in zero loss and do not contribute to gradient updates.

70. The computer-implemented method of clause 69, wherein the masked amino acid classes are identified in a lookup table.

71. The computer-implemented method of clause 70, wherein the lookup table identifies a set of masked amino acids classes for each reference amino acid position.

Clauses Set 5 (ILLM 1061-1)

1. A computer-implemented method of training a pathogenicity predictor, including:
    accessing a gapped training set that includes respective gapped protein samples for respective positions in a proteome;
    accessing a non-gapped training set that includes non-gapped benign protein samples and non-gapped pathogenic protein samples;
    generating respective gapped spatial representations for the gapped protein samples, and generating respective non-gapped spatial representations for the non-gapped benign protein samples and the non-gapped pathogenic protein samples;
    training a pathogenicity predictor over one or more training cycles and generating a trained pathogenicity predictor, wherein each of the training cycles uses as training examples gapped spatial representations from the respective gapped spatial representations and non-gapped spatial representations from the respective non-gapped spatial representations; and
    using the trained pathogenicity classifier to determine pathogenicity of variants.

2. The computer-implemented method of clause 1, wherein the respective gapped protein samples are labelled with respective gapped ground truth sequences.

3. The computer-implemented method of clause 2, wherein a particular gapped ground truth sequence for a particular gapped protein sample has a benign label for a particular amino acid class that corresponds to a reference amino acid at a particular position in the particular gapped protein.

4. The computer-implemented method of clause 3, wherein the particular gapped protein sample has respective pathogenic labels for respective remaining amino acid classes that correspond to alternate amino acids at the particular position.

5. The computer-implemented method of clause 1, wherein a particular non-gapped benign protein sample includes a benign alternate amino acid at a particular position substituted by a benign nucleotide variant.

6. The computer-implemented method of clause 5, wherein a particular non-gapped pathogenic protein sample includes a pathogenic alternate amino acid at a particular position substituted by a pathogenic nucleotide variant.

7. The computer-implemented method of clause 6, wherein the particular non-gapped benign protein sample is labelled with a benign ground truth sequence that has a benign label for a particular amino acid class that corresponds to the benign alternate amino acid.

8. The computer-implemented method of clause 7, wherein the benign ground truth sequence respective masked labels for respective remaining amino acid classes that correspond to amino acids that are different from the benign alternate amino acid.

9. The computer-implemented method of clause 8, wherein the particular non-gapped pathogenic protein sample is labelled with a pathogenic ground truth sequence that has a pathogenic label for a particular amino acid class that corresponds to the pathogenic alternate amino acid.

10. The computer-implemented method of clause 9, wherein the pathogenic ground truth sequence has respective masked labels for respective remaining amino acid classes that correspond to amino acids that are different from the pathogenic alternate amino acid.

11. The computer-implemented method of clause 1, further including using a sample indicator to indicate to the pathogenicity predictor whether a current training example is a gapped spatial representation for a gapped protein sample, or a non-gapped spatial representation for a non-gapped protein sample.

12. The computer-implemented method of clause 1, further including masking the benign label for the particular amino acid class that corresponds to the reference amino acid at the particular position in the particular gapped protein.

13. The computer-implemented method of clause 1, wherein the non-gapped benign protein samples are derived from common human and non-human primate nucleotide variants.

14. The computer-implemented method of clause 1, wherein the non-gapped pathogenic protein samples are derived from combinatorically simulated nucleotide variants.

15. The computer-implemented method of clause 1, wherein the pathogenicity predictor generates an amino acid class-wise output sequence in response to processing a training example,
    wherein the amino acid class-wise output sequence has amino acid class-wise pathogenicity scores.

16. The computer-implemented method of clause 1, further including measuring performance of the trained pathogenicity predictor between training cycles over a validation set.

17. The computer-implemented method of clause 16, wherein the validation set includes a pair of gapped and non-gapped spatial representations for each held-out protein sample.

18. The computer-implemented method of clause 1, wherein the trained pathogenicity predictor generates a first amino acid class-wise output sequence for the gapped spatial representation in the pair, and a second amino acid class-wise output sequence for the non-gapped spatial representation in the pair, wherein a final pathogenicity score for a nucleotide variant that causes an amino acid substitution in a held-out protein sample is determined based on a combination of first and second pathogenicity scores for the amino acid substitution in the first and second amino acid class-wise output sequences.

19. The computer-implemented method of clause 18, wherein the final pathogenicity score is based on an average of the first and second pathogenicity scores.

20. The computer-implemented method of clause 1, wherein at least some of the training cycles use a same of number of gapped spatial representations and non-gapped spatial representations.

21. The computer-implemented method of clause 1, wherein at least some of the training cycles use batches of training examples that have a same of number of gapped spatial representations and non-gapped spatial representations.

22. The computer-implemented method of clause 1, wherein a masked label does not contribute to error determination, and therefore does not contribute to training of the pathogenicity predictor.

23. The computer-implemented method of clause 22, wherein the masked label is zeroed-out.

24. The computer-implemented method of clause 1, wherein the gapped spatial representations are weighted differently from the non-gapped spatial representations, such that a contribution of the gapped spatial representations to gradient updates applied to parameters of the pathogenicity predictor in response to the pathogenicity predictor processing the non-gapped spatial representations varies from a contribution of the non-gapped spatial representations to gradient updates applied to the parameters of the pathogenicity predictor in response to the pathogenicity predictor processing the non-gapped spatial representations.

25. The computer-implemented method of clause 24, wherein the variation is determined by pre-defined weights.

26. A computer-implemented method of training a pathogenicity predictor, including:

starting with training a pathogenicity classifier on a gapped training set and generating a trained pathogenicity classifier;

further training the trained pathogenicity classifier on a non-gapped training set and generating a retrained pathogenicity classifier; and using the retrained pathogenicity classifier to determine pathogenicity of variants.

27. The computer-implemented method of clause 26, further including measuring performance of the trained pathogenicity predictor between training cycles over a first validation set that includes only non-gapped spatial representations of held-out protein samples.

28. The computer-implemented method of clause 27, further including measuring performance of the retrained pathogenicity predictor between training cycles over a second validation set that includes gapped spatial representations and non-gapped spatial representations of held-out protein samples.

29. The computer-implemented method of clause 28, wherein the retrained pathogenicity predictor generates a first amino acid class-wise output sequence for the pair in response to processing the pair, wherein a final pathogenicity score for a nucleotide variant that causes an amino acid substitution in a corresponding held-out protein sample is determined based on the first amino acid class-wise output sequence.

30. A computer-implemented method of training a pathogenicity predictor, including:

accessing a gapped training set that includes respective gapped protein samples for respective positions in a proteome, wherein the respective gapped protein samples are labelled with respective gapped ground truth sequences, wherein a particular gapped ground truth sequence for a particular gapped protein sample has a benign label for a particular amino acid class that corresponds to a reference amino acid at a particular position in the particular gapped protein, and has respective pathogenic labels for respective remaining amino acid classes that correspond to alternate amino acids at the particular position;

accessing a non-gapped training set that includes non-gapped benign protein samples and non-gapped pathogenic protein samples, wherein a particular non-gapped benign protein sample includes a benign alternate amino acid at a particular position substituted by a benign nucleotide variant, wherein a particular non-gapped pathogenic protein sample includes a pathogenic alternate amino acid at a particular position substituted by a pathogenic nucleotide variant, wherein the particular non-gapped benign protein sample is labelled with a benign ground truth sequence that has a benign label for a particular amino acid class that corresponds to the benign alternate amino acid, and respective masked labels for respective remaining amino acid classes that correspond to amino acids that are different from the benign alternate amino acid, and wherein the particular non-gapped pathogenic protein sample is labelled with a pathogenic ground truth sequence that has a pathogenic label for a particular amino acid class that corresponds to the pathogenic alternate amino acid, and respective masked labels for respective remaining amino acid classes that correspond to amino acids that are different from the pathogenic alternate amino acid;

generating respective gapped spatial representations for the gapped protein samples, and generating respective non-gapped spatial representations for the non-gapped benign protein samples and the non-gapped pathogenic protein samples;

training a pathogenicity predictor over one or more training cycles, and generating a trained pathogenicity predictor, wherein each of the training cycles uses as training examples gapped spatial representations from the respective gapped spatial representations, and non-gapped spatial representations from the respective non-gapped spatial representations; and using the trained pathogenicity classifier to determine pathogenicity of variants.

Clauses Set 6

1. A computer-implemented method of generating training data for training a variant pathogenicity classifier, including:

accessing multitude of amino acid positions in a proteome with a plurality of proteins;

specifying major allele amino acids at the multitude of amino acid positions as reference amino acids of the plurality of proteins;

for each amino acid position in the multitude of amino acids positions, classifying those nucleotide substitutions as benign variants that substitute a particular reference amino acid with the particular reference amino acid at a particular amino acid position in a particular alternate representation of a particular protein, and classifying those nucleotide substitutions as pathogenic variants that substitute the particular reference amino acid with alternate amino acids at the particular amino acid position, wherein the alternate amino acids are different from the particular reference amino acid; and training a variant pathogenicity classifier on training data comprising spatial representations of protein samples, such that the spatial representations are assigned ground truth benign labels that correspond to the benign variants, and ground truth pathogenic labels that correspond to the pathogenic variants.

2. The computer-implemented method of clause 1, wherein the variant pathogenicity classifier is trained to determine whether a substitution of a first amino acid with a second amino acid at a given amino acid position in a protein is pathogenic or benign.

3. The computer-implemented method of clause 2, wherein the variant pathogenicity classifier is trained to generate a pathogenicity score for the substitution.

4. The computer-implemented method of clause 1, wherein the variant pathogenicity classifier is trained to determine whether respective substitutions of a first amino acid with respective amino acids at a given amino acid position in a protein are pathogenic or benign.

5. The computer-implemented method of clause 4, wherein the variant pathogenicity classifier is trained to generate respective pathogenicity scores for the respective substitutions.

6. The computer-implemented method of clause 5, wherein the respective amino acids correspond to respective twenty naturally-occurring amino acids.

7. The computer-implemented method of clause 6, wherein the respective amino acids correspond to respective naturally-occurring amino acids from a subset of the twenty naturally-occurring amino acids.

8. The computer-implemented method of clause 1, wherein the variant pathogenicity classifier is trained to determine whether an insertion of an amino acid at a given vacant amino acid position in a protein is pathogenic or benign.

9. The computer-implemented method of clause 8, wherein the variant pathogenicity classifier is trained to generate a pathogenicity score for the insertion.

10. The computer-implemented method of clause 1, wherein the variant pathogenicity classifier is trained to determine whether respective insertions of respective amino acids at a given vacant amino acid position in a protein are pathogenic or benign.

11. The computer-implemented method of clause 10, wherein the variant pathogenicity classifier is trained to generate respective pathogenicity scores for the respective insertions.

12. The computer-implemented method of clause 11, wherein the respective amino acids correspond to respective twenty naturally-occurring amino acids.

13. The computer-implemented method of clause 12, wherein the respective amino acids correspond to respective naturally-occurring amino acids from a subset of the twenty naturally-occurring amino acids.

14. The computer-implemented method of clause 1, wherein the variant pathogenicity classifier is trained to determine whether a substitution of a first amino acid with a second amino acid at a given amino acid position in a protein is spatially tolerated by other amino acids of the protein or not.

15. The computer-implemented method of clause 14, wherein the variant pathogenicity classifier is trained to generate a spatial tolerance score for the substitution.

16. The computer-implemented method of clause 1, wherein the variant pathogenicity classifier is trained to determine whether respective substitutions of a first amino acid with respective amino acids at a given amino acid position in a protein are spatially tolerated by other amino acids of the protein or not.

17. The computer-implemented method of clause 16, wherein the variant pathogenicity classifier is trained to generate respective spatial tolerance scores for the respective substitutions.

18. The computer-implemented method of clause 17, wherein the respective amino acids correspond to respective twenty naturally-occurring amino acids.

19. The computer-implemented method of clause 18, wherein the respective amino acids correspond to respective naturally-occurring amino acids from a subset of the twenty naturally-occurring amino acids.

20. The computer-implemented method of clause 1, wherein the variant pathogenicity classifier is trained to determine whether an insertion of an amino acid at a given vacant amino acid position in a protein is spatially tolerated by other amino acids of the protein or not.

21. The computer-implemented method of clause 20, wherein the variant pathogenicity classifier is trained to generate a spatial tolerance score for the insertion.

22. The computer-implemented method of clause 1, wherein the variant pathogenicity classifier is trained to determine whether respective insertions of respective amino acids at a given vacant amino acid position in a protein are spatially tolerated by other amino acids of the protein or not.

23. The computer-implemented method of clause 22, wherein the variant pathogenicity classifier is trained to generate respective spatial tolerance scores for the respective insertions.

24. The computer-implemented method of clause 23, wherein the respective amino acids correspond to respective twenty naturally-occurring amino acids.

25. The computer-implemented method of clause 24, wherein the respective amino acids correspond to respective naturally-occurring amino acids from a subset of the twenty naturally-occurring amino acids.

26. The computer-implemented method of clause 1, wherein the variant pathogenicity classifier is trained to determine whether a substitution of a first amino acid with a second amino acid at a given amino acid position in a protein is evolutionary conserved or non-conserved.

27. The computer-implemented method of clause 26, wherein the variant pathogenicity classifier is trained to generate an evolutionary conservation score for the substitution.

28. The computer-implemented method of clause 1, wherein the variant pathogenicity classifier is trained to determine whether respective substitutions of a first amino acid with respective amino acids at a given amino acid position in a protein are evolutionary conserved or non-conserved.

29. The computer-implemented method of clause 28, wherein the variant pathogenicity classifier is trained to generate respective evolutionary conservation scores for the respective substitutions.

30. The computer-implemented method of clause 29, wherein the respective amino acids correspond to respective twenty naturally-occurring amino acids.

31. The computer-implemented method of clause 30, wherein the respective amino acids correspond to respective naturally-occurring amino acids from a subset of the twenty naturally-occurring amino acids.

32. The computer-implemented method of clause 1, wherein the variant pathogenicity classifier is trained to determine whether an insertion of an amino acid at a given vacant amino acid position in a protein is evolutionary conserved or non-conserved.

33. The computer-implemented method of clause 32, wherein the variant pathogenicity classifier is trained to generate an evolutionary conservation score for the insertion.

34. The computer-implemented method of clause 1, wherein the variant pathogenicity classifier is trained to determine whether respective insertions of respective amino acids at a given vacant amino acid position in a protein are evolutionary conserved or non-conserved.

35. The computer-implemented method of clause 34, wherein the variant pathogenicity classifier is trained to generate respective evolutionary conservation scores for the respective insertions.

36. The computer-implemented method of clause 35, wherein the respective amino acids correspond to respective twenty naturally-occurring amino acids.

37. The computer-implemented method of clause 36, wherein the respective amino acids correspond to respective naturally-occurring amino acids from a subset of the twenty naturally-occurring amino acids.

38. The computer-implemented method of clause 14, wherein spatial tolerance corresponds to structural tolerance, and spatial intolerance corresponds to structural intolerance.

39. The computer-implemented method of clause 1, wherein the multitude of amino acids positions range from one million to ten million amino acid positions.

40. The computer-implemented method of clause 1, wherein the multitude of amino acids positions range from ten million to hundred million amino acid positions.

41. The computer-implemented method of clause 1, wherein the multitude of amino acids positions range from hundred million to a billion amino acid positions.

42. The computer-implemented method of clause 1, wherein the multitude of amino acids positions range from one to a million amino acid positions.

43. The computer-implemented method of clause 1, wherein those unreachable alternate amino acid classes that are confined by reachability of single nucleotide polymorphisms (SNPs) to transform a reference codon of a reference amino acid into alternate amino acids of the unreachable alternate amino acid classes are masked in ground truth labels.

44. The computer-implemented method of clause 1, wherein masked amino acid classes result in zero loss and do not contribute to gradient updates.

45. The computer-implemented method of clause 44, wherein the masked amino acid classes are identified in a lookup table.

46. The computer-implemented method of clause 45, wherein the lookup table identifies a set of masked amino acids classes for each reference amino acid position.

47. The computer-implemented method of clause 1, wherein the spatial representations are structural representations of protein structures of the protein samples.

48. The computer-implemented method of clause 1, wherein the spatial representations are encoded using voxelization Clauses Set 7

1. A computer-implemented method of determining pathogenicity of nucleotide variants, including:

accessing a spatial representation of a protein, wherein the spatial representation of the protein specifies respective spatial configurations of respective amino acids at respective positions in the protein;

removing, from the spatial representation of the protein, a particular spatial configuration of a particular amino acid at a particular position, thereby generating a gapped spatial representation of the protein; and determining a pathogenicity of a nucleotide variant based at least in part on
   the gapped spatial representation, and
   a representation of an alternate amino acid created by the nucleotide variant at the particular position.

2. The computer-implemented method of clause 1, wherein the removal of the particular spatial configuration is implemented by a script.

3. A computer-implemented method of determining pathogenicity of nucleotide variants, including:

removing, from a protein, a particular amino acid at a particular position, thereby generating a gapped protein; and determining a pathogenicity of a nucleotide variant based at least in part on the gapped protein and an alternate amino acid created by the nucleotide variant at the particular position.

4. The computer-implemented method of clause 3, wherein the removal of the particular amino acids is implemented by a script.

5. A system to predict spatial tolerability of amino acid substitutes, comprising:

gapping logic configured to remove, from a protein, a particular amino acid at a particular position, and create an amino acid vacancy at the particular position in the protein; and substitution logic configured to process the protein with the amino acid vacancy, and score tolerability of substitute amino acids that are candidates for filling the amino acid vacancy.

6. The system of clause 5, wherein the substitution logic is further configured to score the tolerability of the substitute amino acids based at least in part on structural compatibility between the substitute amino acids and adjacent amino acids in a neighborhood of the amino acid vacancy.

7. A computer-implemented method of determining pathogenicity of nucleotide variants, including:

accessing a protein that has respective amino acids at respective positions;

specifying a particular amino acid of a particular amino acid class at a particular position in the protein as a gap amino acid, and specifying remaining amino acids at remaining positions in the protein as non-gap amino acids;

generating a gapped spatial representation of the protein that
   includes spatial configurations of the non-gap amino acids, and
   excludes a spatial configuration of the gap amino acid; and based at least in part on the gapped spatial representation, determining a pathogenicity of respective alternate amino acids at the particular position,
   wherein the respective alternate amino acids have respective amino acid classes that are different from the particular amino acid class.

8. A system to predict evolutionary conservation of amino acid substitutes, comprising:

gapping logic configured to remove, from a protein, a particular amino acid at a particular position, and create an amino acid vacancy at the particular position in the protein; and substitution logic configured to process the protein with the amino acid vacancy, and score evolutionary conservation of substitute amino acids that are candidates for filling the amino acid vacancy.

9. The system of clause 8, wherein the substitution logic is further configured to score the evolutionary conservation of the substitute amino acids based at least in part on structural compatibility between the substitute amino acids and adjacent amino acids in a neighborhood of the amino acid vacancy.

10. The system of clause 8, wherein the evolutionary conservation is scored using evolutionary conservation frequencies.

11. The system of clause 10, wherein the evolutionary conservation frequencies are based on a position-specific frequency matrix (PSFM).

12. The system of clause 10, wherein the evolutionary conservation frequencies are based on a position-specific scoring matrix (PSSM).

13. The system of clause 8, wherein evolutionary conservation scores of the substitute amino acids are rank-ordered by magnitude.

14. A system to predict evolutionary conservation of amino acid substitutes, comprising:

gapping logic configured to remove, from a protein, a particular amino acid at a particular position, and create an amino acid vacancy at the particular position in the protein; and evolutionary conservation prediction logic configured to process the protein with the amino acid vacancy, and rank evolutionary conservation of substitute amino acids that are candidates for filling the amino acid vacancy.

15. A system to predict structural tolerability of amino acid substitutes, comprising:

gapping logic configured to remove, from a protein, a particular amino acid at a particular position, and create an amino acid vacancy at the particular position in the protein; and structural tolerability prediction logic configured to process the protein with the amino acid vacancy, and rank structural tolerability of substitute amino acids that are candidates for filling the amino acid vacancy based on amino acid co-occurrence patterns in a neighborhood of the amino acid vacancy.

16. A computer-implemented method of determining pathogenicity of nucleotide variants, including:

accessing a protein that has respective amino acids at respective positions;

specifying a particular amino acid at a particular position in the protein as a gap amino acid, and specifying remaining amino acids at remaining positions in the protein as non-gap amino acids;

generating a gapped spatial representation of the protein that includes spatial configurations of the non-gap amino acids, and excludes a spatial configuration of the gap amino acid;

determining an evolutionary conservation of an alternate amino acid at the particular position based at least in part on the gapped spatial representation, and a representation of the alternate amino acid; and determining a pathogenicity of a nucleotide variant that creates the alternate amino acid based at least in part on the evolutionary conservation.

Clauses Set 8

1. A computer-implemented method of determining pathogenicity of nucleotide variants, including:

accessing a spatial representation of a protein, wherein the spatial representation of the protein specifies respective spatial configurations of respective amino acids at respective positions in the protein;

removing, from the spatial representation of the protein, a particular spatial configuration of a particular amino acid at a particular position, thereby generating a gapped spatial representation of the protein; and determining a pathogenicity of a nucleotide variant based at least in part on the gapped spatial representation, and a representation of an alternate amino acid created by the nucleotide variant at the particular position.

2. The computer-implemented method of clause 1, wherein the removal of the particular spatial configuration is implemented by a script.

3. A computer-implemented method of determining pathogenicity of nucleotide variants, including:

removing, from a spatial representation of protein, a particular amino acid at a particular position, thereby generating a gapped spatial representation of the protein; and determining a pathogenicity of a nucleotide variant based at least in part on the gapped spatial representation of the protein and an alternate amino acid created by the nucleotide variant at the particular position.

4. The computer-implemented method of clause 3, wherein the removal of the particular amino acids is implemented by a script.

5. A system to predict spatial tolerability of amino acid substitutes, comprising:

gapping logic configured to remove, from a spatial representation of a protein, a particular amino acid at a particular position, and create an amino acid vacancy at the particular position in the spatial representation of the protein; and substitution logic configured to process the spatial representation of the protein with the amino acid vacancy, and score tolerability of substitute amino acids that are candidates for filling the amino acid vacancy.

6. The system of clause 5, wherein the substitution logic is further configured to score the tolerability of the substitute amino acids based at least in part on structural compatibility between the substitute amino acids and adjacent amino acids in a neighborhood of the amino acid vacancy.

7. A computer-implemented method of determining pathogenicity of nucleotide variants, including:

accessing a protein that has respective amino acids at respective positions;

specifying a particular amino acid of a particular amino acid class at a particular position in the protein as a gap amino acid, and specifying remaining amino acids at remaining positions in the protein as non-gap amino acids;

generating a gapped spatial representation of the protein that includes spatial configurations of the non-gap amino acids, and excludes a spatial configuration of the gap amino acid; and based at least in part on the gapped spatial representation, determining a pathogenicity of respective alternate amino acids at the particular position, wherein the respective alternate amino acids have respective amino acid classes that are different from the particular amino acid class.

8. A system to predict evolutionary conservation of amino acid substitutes, comprising:
gapping logic configured to remove, from a spatial representation of a protein, a particular amino acid at a particular position, and create an amino acid vacancy at the particular position in the spatial representation of the protein; and
substitution logic configured to process the spatial representation of the protein with the amino acid vacancy, and score evolutionary conservation of substitute amino acids that are candidates for filling the amino acid vacancy.

9. The system of clause 8, wherein the substitution logic is further configured to score the evolutionary conservation of the substitute amino acids based at least in part on structural compatibility between the substitute amino acids and adjacent amino acids in a neighborhood of the amino acid vacancy.

10. The system of clause 8, wherein the evolutionary conservation is scored using evolutionary conservation frequencies.

11. The system of clause 10, wherein the evolutionary conservation frequencies are based on a position-specific frequency matrix (PSFM).

12. The system of clause 10, wherein the evolutionary conservation frequencies are based on a position-specific scoring matrix (PSSM).

13. The system of clause 8, wherein evolutionary conservation scores of the substitute amino acids are rank-ordered by magnitude.

14. A system to predict evolutionary conservation of amino acid substitutes, comprising:
gapping logic configured to remove, from a spatial representation of a protein, a particular amino acid at a particular position, and create an amino acid vacancy at the particular position in the spatial representation of the protein; and
evolutionary conservation prediction logic configured to process the spatial representation of the protein with the amino acid vacancy, and rank evolutionary conservation of substitute amino acids that are candidates for filling the amino acid vacancy.

15. A system to predict structural tolerability of amino acid substitutes, comprising:
gapping logic configured to remove, from a spatial representation of a protein, a particular amino acid at a particular position, and create an amino acid vacancy at the particular position in the spatial representation of the protein; and
structural tolerability prediction logic configured to process the spatial representation of the protein with the amino acid vacancy, and rank structural tolerability of substitute amino acids that are candidates for filling the amino acid vacancy based on amino acid co-occurrence patterns in a neighborhood of the amino acid vacancy.

16. A computer-implemented method of determining pathogenicity of nucleotide variants, including:
accessing a protein that has respective amino acids at respective positions;
specifying a particular amino acid at a particular position in the protein as a gap amino acid, and specifying remaining amino acids at remaining positions in the protein as non-gap amino acids;
generating a gapped spatial representation of the protein that
includes spatial configurations of the non-gap amino acids, and
excludes a spatial configuration of the gap amino acid;
determining an evolutionary conservation of an alternate amino acid at the particular position based at least in part on the gapped spatial representation, and
a representation of the alternate amino acid; and
determining a pathogenicity of a nucleotide variant that creates the alternate amino acid based at least in part on the evolutionary conservation.

While the present invention is disclosed by reference to the preferred implementations and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following

What is claimed is:

1. A computer-implemented method of scoring nucleotide variants as benign or pathogenic, including:
accessing a protein that has respective amino acids at respective positions;
specifying a particular amino acid at a particular position in the protein as a gap amino acid, and specifying remaining amino acids at remaining positions in the protein as non-gap amino acids;
generating a gapped spatial representation of the protein that
includes spatial configurations of the non-gap amino acids, and
excludes a spatial configuration of the gap amino acid; and
using a neural network pathogenicity predictor to score a nucleotide variant as benign or pathogenic based at least on
the gapped spatial representation, and
a representation of an alternate amino acid created by the nucleotide variant at the particular position.

2. The computer-implemented method of claim 1, wherein the spatial configurations of the non-gap amino acids are encoded as amino acid class-wise distance channels,
wherein each of the amino acid class-wise distance channels has voxel-wise distance values for voxels in a plurality of voxels, and
wherein the voxel-wise distance values specify distances from corresponding voxels in the plurality of voxels to atoms of the non-gap amino acids.

3. The computer-implemented method of claim 2, wherein the spatial configurations of the non-gap amino acids are determined based on spatial proximity between the corresponding voxels and the atoms of the non-gap amino acids.

4. The computer-implemented method of claim 2, wherein the spatial configuration of the gap amino acid is excluded from the gapped spatial representation by disregarding distances from the corresponding voxels to atoms of the gap amino acid when determining the voxel-wise distance values.

5. The computer-implemented method of claim 4, wherein the spatial configuration of the gap amino acid is excluded from the gapped spatial representation by disregarding spatial proximity between the corresponding voxels and the atoms of the gap amino acid.

6. The computer-implemented method of claim 1, wherein the particular amino acid is a reference amino acid that is a major allele of the protein.

7. The computer-implemented method of claim 1, wherein using the neural network pathogenicity predictor to score the nucleotide variant as benign or pathogenic comprises processing, as input,
the gapped spatial representation, and
the representation of the alternate amino acid; and
generating, as output, a pathogenicity score for the alternate amino acid.

8. The computer-implemented method of claim 7, wherein the neural network pathogenicity predictor is trained on a benign training set.

9. The computer-implemented method of claim 8, wherein the benign training set has respective benign protein samples for respective reference amino acids at respective positions in a proteome.

10. The computer-implemented method of claim 9, wherein the respective reference amino acids are major allele amino acids of the proteome.

11. The computer-implemented method of claim 10, wherein the proteome has ten million positions, and therefore the benign training set has ten million benign protein samples.

12. The computer-implemented method of claim 11, wherein the respective benign protein samples have respective gapped spatial representations generated by using the respective reference amino acids as respective gap amino acids.

13. The computer-implemented method of claim 12, wherein the respective benign protein samples have respective representations of the respective reference amino acids as respective alternate amino acids.

14. The computer-implemented method of claim 13, wherein the neural network pathogenicity predictor trains on a particular benign protein sample and scores a particular reference amino acid at a particular position in the particular benign protein sample as benign or pathogenic by:
processing, as input,
(i) a particular gapped spatial representation of the particular benign protein sample, wherein the particular gapped spatial representation is generated
by using the particular reference amino acid as a gap amino acid, and
by using remaining amino acids at remaining positions in the particular benign protein sample as non-gap amino acids, and
(ii) a representation of the particular reference amino acid as a particular alternate amino acid; and
generating, as output, a pathogenicity score for the particular reference amino acid.

15. The computer-implemented method of claim 14, wherein each of the respective benign protein samples has a ground truth benignness label that indicates absolute benignness of the respective benign protein samples.

16. The computer-implemented method of claim 15, wherein the ground truth benignness label is zero.

17. The computer-implemented method of claim 16, wherein the pathogenicity score for the particular reference amino acid is compared against the ground truth benignness label to determine an error, and to improve coefficients of the pathogenicity predictor based on the error using a training technique.

18. The computer-implemented method of claim 17, wherein the neural network pathogenicity predictor is trained on a pathogenic training set.

19. The computer-implemented method of claim 18, wherein the pathogenic training set has respective pathogenic protein samples for respective combinatorically generated amino acid substitutions for each of the reference amino acids at each of the respective positions in a proteome.

20. The computer-implemented method of claim 19, wherein the combinatorically generated amino acid substitutions for a particular reference amino acid of a particular amino acid class at a particular position in the proteome include respective alternate amino acids of respective amino acid classes that are different from the particular amino acid class.

21. The computer-implemented method of claim 20, wherein the proteome has ten million positions, wherein there are nineteen combinatorically generated amino acid substitutions for each of the ten million positions, and therefore the pathogenic training set has one hundred and ninety million pathogenic protein samples.

22. The computer-implemented method of claim 21, wherein the respective pathogenic protein samples have respective gapped spatial representations generated by using the respective reference amino acids as respective gap amino acids.

23. The computer-implemented method of claim 22, wherein the respective pathogenic protein samples have respective representations of the respective combinatorically generated amino acid substitutions as respective alternate amino acids created by respective combinatorically generated nucleotide variants at the respective positions in the proteome.

24. The computer-implemented method of claim 23, wherein the neural network pathogenicity predictor trains on a particular pathogenic protein sample and scores a particular combinatorically generated amino acid substitution for a particular reference amino acid at a particular position in the particular pathogenic protein sample as benign or pathogenic by:
processing, as input,
(i) a particular gapped spatial representation of the particular pathogenic protein sample, wherein the particular gapped spatial representation is generated
by using the particular reference amino acid as a gap amino acid, and
by using remaining amino acids at remaining positions in the particular pathogenic protein sample as non-gap amino acids, and
(ii) a representation of the particular combinatorically generated amino acid substitution as a particular alternate amino acid; and
generating, as output, a pathogenicity score for the particular combinatorically generated amino acid substitution.

25. The computer-implemented method of claim 24, wherein each of the pathogenic protein samples has a ground truth pathogenicity label that indicates absolute pathogenicity of the respective pathogenic protein samples.

26. The computer-implemented method of claim 25, wherein the ground truth pathogenicity label is one.

27. The computer-implemented method of claim 26, wherein the pathogenicity score for the particular combinatorically generated amino acid substitution is compared against the ground truth pathogenicity label to determine an error, and to improve coefficients of the pathogenicity predictor based on the error using a training technique.

28. The computer-implemented method of claim 27, wherein the pathogenicity predictor is trained on two hundred million training iterations,
   wherein the two hundred million training iterations include
      ten million training iterations with the ten million benign protein samples, and
      one hundred and ninety million iterations with the one hundred and ninety million pathogenic protein samples.

29. A non-transitory computer readable storage medium impressed with computer program instructions to score nucleotide variants as benign or pathogenic, the instructions, when executed on a processor, implement a method comprising: accessing a protein that has respective amino acids at respective positions;
   specifying a particular amino acid at a particular position in the protein as a gap amino acid, and specifying remaining amino acids at remaining positions in the protein as non-gap amino acids;
   generating a gapped spatial representation of the protein that
      includes spatial configurations of the non-gap amino acids, and
      excludes a spatial configuration of the gap amino acid; and
   using a neural network pathogenicity predictor to score a nucleotide variant as benign or using a based at least on the gapped spatial representation, and
      a representation of an alternate amino acid created by the nucleotide variant at the particular position.

30. A system including one or more processors coupled to memory, the memory loaded with computer instructions to score nucleotide variants as benign or pathogenic, the computer instructions, when executed on the one or more processors, implement actions comprising:
   accessing a protein that has respective amino acids at respective positions;
   specifying a particular amino acid at a particular position in the protein as a gap amino acid, and specifying remaining amino acids at remaining positions in the protein as non-gap amino acids;
   generating a gapped spatial representation of the protein that
      includes spatial configurations of the non-gap amino acids, and
      excludes a spatial configuration of the gap amino acid; and
   using a neural network pathogenicity predictor to score a nucleotide variant as benign or using a based at least on the gapped spatial representation, and
      a representation of an alternate amino acid created by the nucleotide variant at the particular position.

* * * * *

UNITED STATES PATENT AND TRADEMARK OFFICE
CERTIFICATE OF CORRECTION

| | | |
|---|---|---|
| PATENT NO. | : 11,538,555 B1 | Page 1 of 1 |
| APPLICATION NO. | : 17/533091 | |
| DATED | : December 27, 2022 | |
| INVENTOR(S) | : Tobias Hamp, Hong Gao and Kai-How Farh | |

It is certified that error appears in the above-identified patent and that said Letters Patent is hereby corrected as shown below:

In the Claims

Column 91, Line 27, replace "using a" with -- pathogenic -- in Claim 29

Column 92, Line 23, replace "using a" with -- pathogenic -- in Claim 30

Signed and Sealed this
Thirty-first Day of January, 2023

*Katherine Kelly Vidal*

Katherine Kelly Vidal
*Director of the United States Patent and Trademark Office*